(12) United States Patent
Groneberg et al.

(10) Patent No.: US 7,199,244 B2
(45) Date of Patent: Apr. 3, 2007

(54) CYCLIC AMINE DERIVATIVES AND METHODS OF USE

(75) Inventors: Robert D. Groneberg, Boulder, CO (US); James Zhan, Shanghai (CN); Benny C. Askew, Jr., Newbury Park, CA (US); Derin C. D'Amico, Newbury Park, CA (US); Nianhe Han, Thousand Oaks, CA (US); Christopher H. Fotsch, Thousand Oaks, CA (US); Qingyian Liu, Camarillo, CA (US); Babak Riahi, Woodland Hills, CA (US); Jiawang Zhu, Simi Valley, CA (US); Kevin Yang, San Gabriel, CA (US); Jian Jeffrey Chen, Newbury Park, CA (US); Rana Nomak, Istanbul (TR)

(73) Assignees: Amgen, Boulder, CO (US); Array Biopharma Inc., Boulder, CO (US)

( * ) Notice: Subject to any disclaimer, the term of this patent is extended or adjusted under 35 U.S.C. 154(b) by 199 days.

(21) Appl. No.: 10/823,372

(22) Filed: Apr. 12, 2004

(65) Prior Publication Data

US 2005/0234044 A1 Oct. 20, 2005

Related U.S. Application Data

(60) Provisional application No. 60/461,673, filed on Apr. 10, 2003.

(51) Int. Cl.
C07D 211/08 (2006.01)
C07D 405/00 (2006.01)

(52) U.S. Cl. .................. 546/192; 548/517; 514/317; 514/318; 514/326

(58) Field of Classification Search ........... 514/317, 514/318, 326; 546/192; 548/517
See application file for complete search history.

(56) References Cited

U.S. PATENT DOCUMENTS 6,384,222 B1 5/2002 Barth et al.
6,479,515 B1 11/2002 Barth et al.

FOREIGN PATENT DOCUMENTS

| EP | 1213289 A1 | 6/2002 |
| WO | WO 92/12140 | 7/1992 |
| WO | WO 97/25315 A | 7/1997 |
| WO | WO 00/43415 A1 | 7/2000 |
| WO | WO 00/75107 A | 12/2000 |
| WO | WO 02/06222 A1 | 1/2002 |
| WO | WO 03007958 | 1/2003 |
| WO | WO 2004/033436 | 4/2004 |
| WO | WO 2004/054584 A1 | 7/2004 |
| WO | WO 2004/083173 A3 | 9/2004 |

OTHER PUBLICATIONS

Jessell et al., "Pain and Analgesia" in *Principles of Neural Science*, 3rd Edition, 1991, E.R. Kandel, J.H. Schwartz, T.M. Jessell, editors, pp. 385-399.
M.J. Millan, "The Induction of Pain: An Integrative Review," *Prog. Neurobiol.*, 1999, 57:1-164.
Regoli et al., "Pharmacology of Bradykinin and Related Kinins," *Pharmacological Rev.*, 1980, 32(1):1-46.
Menke et al., "Expression Cloning of a Human $B_1$ Bradykinin Receptor," *J. Biol. Chem.*, 1994, 269:21583-21586.
Hess et al., "Cloning and Pharmacological Characterization of a Human Bradykinin (BK-2) Receptor," *Biochem. Biophys. Res. Commun.*, 1992, 184:260-268.
F. Marceau et al., "Kinin $B_1$ receptors: a review," *Immunopharmacology*, 1995, 30:1-26.
E.J. Corey et al., "Highly Enantioselective Borane Reduction of Ketones Catalyzed by Chiral Oxazaborolidines. Mechanism and Synthetic Implications," *J. Am. Chem. Soc.*, 1987, v. 109, pp. 5551-5553.
T. Ohkuma et al., "Practical Enantioselective Hydrogenation of Aromatic Ketones," *J. Am. Chem Soc.*, 1995, v. 117, pp. 2675-2676.
Thompson et al., "Direct Conversion of Activated Alcohols to Azides Using Diphenyl Phosphoroazidate. A Practical Alternative to Mitsunobu Conditions," *J. Org. Chem.*, 1993, 58 (22):5886-5888.

*Primary Examiner*—D. Margaret Seaman
(74) *Attorney, Agent, or Firm*—McDonnell Boehnen Hulbert & Berghoff LLP

(57) ABSTRACT

Selected compounds are effective for treatment of pain and diseases, such as inflammation mediated diseases. The invention encompasses novel compounds, analogs, prodrugs and pharmaceutically acceptable derivatives thereof, pharmaceutical compositions and methods for prophylaxis and treatment of diseases and other maladies or conditions involving pain, inflammation, and the like. The subject invention also relates to processes for making such compounds as well as to intermediates useful in such processes.

48 Claims, No Drawings

CYCLIC AMINE DERIVATIVES AND METHODS OF USE

FIELD OF THE INVENTION

This invention is in the field of pharmaceutical agents and specifically relates to compounds, compositions, uses and methods for treating inflammation-related disorders, including pain.

BACKGROUND OF THE INVENTION

More than two million people in the United States alone are incapacitated by chronic pain on any given day (T. M. Jessell & D. D. Kelly, Pain and Analgesia in Principles of Neural Science, $3^{rd}$ edition (E. R. Kandel, J. H. Schwartz, T. M. Jessell, editors, (1991)). Unfortunately, current treatments for pain are only partially effective, and many cause life-style altering, debilitating, and/or dangerous side effects. For example, non-steroidal anti-inflammatory drugs ("NSAIDs") such as aspirin, ibuprofen, and indomethacin are moderately effective against inflammatory pain but they are also renally toxic, and high doses tend to cause gastrointestinal irritation, ulceration, bleeding, increased cardiovascular risk, and confusion. Patients treated with opioids frequently experience confusion and constipation, and long-term opioid use is associated with tolerance and dependence. Local anesthetics such as lidocaine and mixelitine simultaneously inhibit pain and cause loss of normal sensation. In addition, when used systemically, local anesthetics are associated with adverse cardiovascular effects. Thus, there is currently an unmet need in the treatment of chronic pain.

Pain is a perception based on signals received from the environment and transmitted and interpreted by the nervous system (for review, see Millan, M. J., Prog. Neurobiol. 57:1–164 (1999)). Noxious stimuli such as heat and touch cause specialized sensory receptors in the skin to send signals to the central nervous system ("CNS"). This process is called nociception, and the peripheral sensory neurons that mediate it are nociceptors. Depending on the strength of the signal from the nociceptor(s) and the abstraction and elaboration of that signal by the CNS, a person may or may not experience a noxious stimulus as painful. When one's perception of pain is properly calibrated to the intensity of the stimulus, pain serves its intended protective function. However, certain types of tissue damage cause a phenomenon, known as hyperalgesia or pronociception, in which relatively innocuous stimuli are perceived as intensely painful because the person's pain thresholds have been lowered. Both inflammation and nerve damage can induce hyperalgesia. Thus, persons afflicted with inflammatory conditions, such as sunburn, osteoarthritis, colitis, carditis, dermatitis, myositis, neuritis, inflammatory bowel disease, collagen vascular diseases (which include rheumatoid arthritis and lupus) and the like, often experience enhanced sensations of pain. Similarly, trauma, surgery, amputation, abscess, causalgia, collagen vascular diseases, demyelinating diseases, trigeminal neuralgia, cancer, chronic alcoholism, stroke, thalamic pain syndrome, diabetes, herpes infections, acquired immune deficiency syndrome ("AIDS"), toxins and chemotherapy cause nerve injuries that result in excessive pain.

As the mechanisms by which nociceptors transduce external signals under normal and hyperalgesic conditions become better understood, processes implicated in hyperalgesia can be targeted to inhibit the lowering of the pain threshold and thereby lessen the amount of pain experienced.

Bradykinin (BK) and the related peptide, kallidin (Lys-BK) mediate the physiological actions of kinins on the cardiovascular and renal systems. However, the active peptides, BK and kallidin, are quickly degraded by peptidases in the plasma and other biological fluids and by those released from a variety of cells, so that the half-life of BK in plasma is reported to be approximately 17 seconds (1). BK and kallidin are rapidly metabolized in the body by carboxypeptidase N, which removes the carboxyterminal arginine residue to generate des-Arg BK or des-Arg kallidin. Des-Arg-kallidin is among the predominant kinins in man and mediate the pathophysiological actions of kinins in man. In addition to being a very potent proinflammatory peptide, des-Arg-BK or des-Arg-kallidin is known to induce vasodilation, vascular permeability, and bronchoconstriction (for review, see Regoli and Barabe, Pharmacological Rev, 32(1), 1–46 (1980)). In addition, des-Arg-BK and des-Arg-kallidin appear to be particularly important mediators of inflammation and inflammatory pain as well as being involved in the maintenance thereof. There is also a considerable body of evidence implicating the overproduction of des-Arg-kallidin in conditions in which pain is a prominent feature such as septic shock, arthritis, angina, and migraine.

The membrane receptors that mediate the pleiotropic actions of kinins are of two distinct classes, designated B1 and B2. Both classes of receptors have been cloned and sequenced from a variety of species, including man (Menke, et al, J. Biol. Chem., 269:21583–21586 (1994); Hess et al, Biochem. Biophys. Res. Commun., 184:260–268 (1992)). They are typical G protein coupled receptors having seven putative membrane spanning regions. In various tissues, BK receptors are coupled to every known second messenger. B2 receptors, which have a higher affinity for BK, appear to be the most prevalent form of bradykinin receptor. Essentially all normal physiological responses and many pathophysiological responses to bradykinin are mediated by B2 receptors.

B1 receptors, on the other hand, have a higher affinity for des-Arg-BK compared with BK, whereas des-Arg-BK is inactive at B2 receptors. In addition, B1 receptors are not normally expressed in most tissues. Their expression is induced upon injury or tissue damage as well as in certain kinds of chronic inflammation or systemic insult (Marceau, F., et al., Immunopharmacology, 30:1–26 (1995)). Furthermore, responses mediated by B1 receptors are upregulated from a null level following administration of bacterial lipopolysaccharide (LPS) or inflammatory cytokines in rabbits, rats, and pigs.

The pain-inducing properties of kinins coupled with the inducible expression of B1 receptors make the B1 receptor an interesting target in the development of anti-inflammatory, antinociceptive, antihyperalgesic and analgesic agents that may be directed specifically at injured tissues with minimal actions in normal tissues.

Clearly, there is a need for new, safe and effective treatments for inflammation and pain. Such agents are provided in the present invention.

DETAILED DESCRIPTION OF THE INVENTION

A class of compounds useful in treating inflammation and pain is defined by Formula I

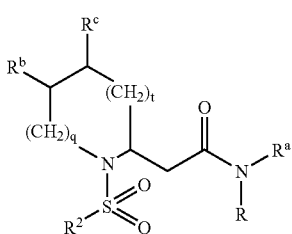

I wherein q is 0–3;

wherein t is 0–2, provided that when t is 2, q is not 3;

wherein R is a 9–11 membered fused bicyclic carbocyclic or heterocyclic ring substituted with one to three basic moieties, and optionally substituted with one to three groups independently selected from halo, —$NH_2$, —OH, —CN, —$CF_3$, ($C_1$–$C_6$)alkylamino, oxo, ($C_1$–$C_6$)alkoxy, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, —N$R^8$C(O)$R^{8'}$, and ($C_1$–$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, and —N$R^8$C(O)$R^{8'}$;

wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

wherein $R^2$ is selected from arylalkenyl, aryl, and heterocyclyl, wherein $R^2$ is optionally substituted with one to five groups independently selected from halo, —$NH_2$, —OH, —CN, —$CF_3$, ($C_1$–$C_6$)alkylamino, oxo, ($C_1$–$C_6$)alkoxy, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, —N$R^8$C(O)$R^{8'}$, and ($C_1$–$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, and —N$R^8$C(O)$R^{8'}$;

wherein $R^a$ is independently selected from H and $C_{1-4}$-alkyl, and aryl optionally substituted with one to three groups selected from halo, —$NH_2$, —OH, —CN, —$CF_3$, ($C_1$–$C_6$)alkylamino, haloalkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, and —N$R^8$C(O)$R^{8'}$;

wherein $R^b$ is independently selected from H and $C_{1-2}$-alkyl; and wherein $R^c$ is independently selected from H and $C_{1-2}$-alkyl; or wherein $R^b$ and $R^c$ may be joined to form a 6-membered aryl or heteroaryl ring optionally substituted with one to three groups independently selected from halo, —$NH_2$, —OH, —CN, —$CF_3$, ($C_1$–$C_6$)alkylamino, oxo, ($C_1$–$C_6$)alkoxy, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, —N$R^8$C(O)$R^{8'}$, and ($C_1$–$C_6$)alkyl, aryl, heteroaryl, cycloalkyl or heterocyclyl, each of which is optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, and —N$R^8$C(O)$R^{8'}$;

and pharmaceutically acceptable derivatives thereof;

provided the basic moiety is not 2-oxo-piperaziny-4-ylmethyl.

The invention also relates to compounds of Formula I wherein R is a partially unsaturated carbocyclic ring, such as 1,2,3,4-tetrahydronaphthyl or indanyl.

The invention also relates to compounds of Formula I wherein R is selected from 1,2,3,4-tetrahydronaphth-1-yl, 1,2,3,4-tetrahydronaphth-2-yl, indan-1-yl and indan-2-yl.

The invention also relates to compounds of Formula I wherein R is partially unsaturated heterocyclyl, such as chroman and 2,2-dioxo-3,4-dihydro-1H-2,1-benzothiazinyl.

The invention also relates to compounds of Formula I wherein R is chroman-4-yl, or 2,2-dioxo-3,4-dihydro-1H-2,1-benzothiazin-4-yl.

The invention also relates to compounds of Formula I wherein $R^2$ is selected from phenyl-CH=CH—, tetrahydronaphthyl, naphtho[2.3-d]dioxolyl, benzofuranyl, benzoxadiazolyl, benzothiadiazolyl, benzothiazolyl, 1H-pyrazolyl, thienyl, isoxazolthienyl, benzothienyl, thieno[3,2-c]pyridinyl, naphthyl, phenyl, pyridinyl, tetrahydroisoquinolinyl, quinolinyl and isoquinolinyl;

wherein $R^2$ is optionally substituted with one to five groups independently selected from halo, —$NH_2$, —OH, —CN, —$CF_3$, ($C_1$–$C_6$)alkylamino, oxo, ($C_1$–$C_6$)alkoxy, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, —N$R^8$C(O)$R^{8'}$, and ($C_1$–$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_8$)alkenyl, ($C_2$–$C_6$)alkynyl, di($C_1$–$C_6$)alkylamino, —C(O)$R^8$, —COO$R^8$, —C(O)N$R^8R^{8'}$, and —N$R^8$C(O)$R^{8'}$; and preferably with one or two groups independently selected from —Cl, —F or —$CF_3$.

The invention also relates to compounds of Formula I wherein $R^2$ is selected from phenyl-CH=CH—, tetrahydronaphthyl, naphtho[2.3-d]dioxol-6-yl, 1-benzofuran-2-yl, 2,1,3-benzoxadiazol-4-yl, 2,1,3-benzothiadiazol-4-yl, 1,3-benzothiazol-2-yl, 1H-pyrazol-4-yl, thien-2-yl, 5-isoxazolthien-2-yl, benzothien-2-yl, thieno[3,2-c]pyridin-2-yl, naphthyl, phenyl, 3-pyridinyl, tetrahydroisoquinolinyl, quinolinyl and isoquinolinyl;

wherein $R^2$ is optionally substituted with one to five groups independently selected from halo, —$NH_2$, —OH, —CN, —$CF_3$, ($C_1$–$C_6$)alkylamino, oxo, ($C_1$–$C_6$)alkoxy, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, —N$R^8$C(O)$R^{8'}$, and ($C_1$–$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, C(O)N$R^8R^{8'}$, and —N$R^8$C(O)$R^{8'}$; and preferably with one or two groups independently selected from —Cl, —F or —$CF_3$.

The invention also relates to compounds of Formula I wherein $R^a$ is selected from H; $C_{1-2}$-alkyl, such as methyl; or phenyl, optionally substituted with one to three groups selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, and —N$R^8$C(O)$R^{8'}$.

The invention also relates to compounds of Formula I wherein $R^b$ and $R^c$ are H.

The invention also relates to compounds of Formula I wherein q is 1 or 2, and t is 0 or 1.

The invention also relates to compounds of Formula I wherein $R^b$ and $R^c$ are joined to form a phenyl ring; and wherein q is 2, and t is 0 or 1.

The invention also relates to compounds of Formula I wherein the one to three basic moieties on R are independently selected from cycloalkylamino $C_{1-6}$-alkyl, cycloalkyl($C_1$–$C_6$)alkylamino $C_{1-6}$-alkyl, heteroarylamino $C_{1-6}$-alkyl, heteroaryl($C_1$–$C_6$)alkylamino $C_{1-6}$-alkyl, arylamino $C_{1-6}$-alkyl, aryl($C_1$–$C_6$)alkylamino $C_{1-6}$-alkyl, $C_{1-6}$-alkylamino–$C_{1-6}$-alkoxy, $C_{1-6}$-alkylamino–$C_{1-6}$-alkoxy–$C_{1-6}$-alkoxy, amino $C_{1-6}$-alkoxy, amino $C_{1-6}$-alkyl, alkylamino $C_{1-6}$-alkyl; or 5–6 membered heterocyclyloxy, 5–6 membered nitrogen-containing heterocyclyl or 5–7 membered nitrogen-containing heterocyclyl-$C_{1-6}$-alkyl, each of which is optionally substituted with one to three groups selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxyalkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, —N$R^8$C(O)$R^8$, =NCN; or ($C_1$–$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, and —N$R^8$C(O)$R^{8'}$.

The invention also relates to compounds of Formula I wherein the one to three basic moieties on R are independently selected from $NH_2$, mono–$C_{1-4}$-alkylamino–$C_{1-4}$-alkyl, di–$C_{1-4}$-alkylamino–$C_{1-4}$-alkyl; or 5–6 membered heterocyclyloxy, 5–6 membered nitrogen-containing heterocyclyl or 5–7 membered nitrogen-containing heterocyclyl-alkyl, each of which is optionally substituted with one to three groups selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$—C(O)N$R^8R^{8'}$, —N$R^8$C(O)$R^{8'}$, =NCN; or ($C_1$–$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, and —N$R^8$C(O)$R^{8'}$.

The invention also relates to compounds of Formula I wherein the one to three basic moieties on R are independently selected from $NH_2$, aminomethyl, isopropylaminomethyl, t-butylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, 1-piperidinylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl and 4-methylpiperazin-1-ylmethyl.

The invention also relates to compounds of Formula II

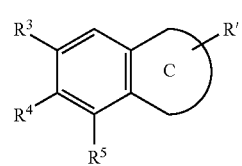

II wherein the C ring is a 4- to 7-membered saturated carbocyclic or heterocyclic moiety;

wherein R' is

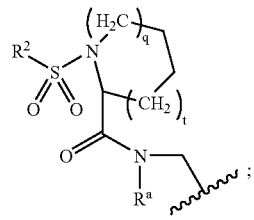

wherein q is 0–3;

wherein t is 0–2, provided that when t is 2, q is not 3;

wherein $R^2$ is selected from arylalkenyl, aryl, and heterocyclyl, wherein $R^2$ is optionally substituted with one to five groups independently selected from halo, —$NH_2$, —OH, —CN, —$CF_3$, ($C_1$–$C_6$)alkylamino, oxo, ($C_1$–$C_6$)alkoxy, ($C_2$–$C_8$)alkenyl, ($C_2$–$C_6$)alkynyl, di($C_1$–$C_6$)alkylamino, —C(O)$R^8$, —COO$R^8$, —C(O)N$R^8R^{8'}$, —N$R^8$C(O)$R^{8'}$, and ($C_1$–$C_6$)alkyl, aryl, heteroaryl, cycloalkyl or heterocyclyl, each of which is optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, and —N$R^8$C(O)$R^{8'}$;

wherein $R^a$ is independently selected from H and $C_{1-4}$-alkyl, or
aryl optionally substituted with one to three groups selected from halo, —$NH_2$, —OH, —CN, —$CF_3$, ($C_1$–$C_6$)alkylamino, halo($C_1$–$C_6$)alkyl, oxo, ($C_1$–$C_6$) alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$ —C(O)N$R^8R^{8'}$, and —$NR^8$C(O)$R^{8'}$;
wherein $R^3$, $R^4$ and $R^5$ are the same or different and represent H, halo, —$NH_2$, —OH, —CN, —$CF_3$, ($C_1$–$C_6$)alkylamino, oxo, ($C_1$–$C_6$)alkoxy, ($C_2$–$C_6$)alkenyl, ($C_2$–$C_6$) alkynyl, di($C_1$–$C_6$)alkylamino, —C(O)$R^8$, —COO$R^8$, —C(O)N$R^8R^{8'}$, —$NR^8$C(O)$R^{8'}$, a basic moiety, or
($C_1$–$C_2$)alkyl, aryl, heteroaryl, cycloalkyl or heterocyclyl, each of which is optionally substituted with one to three groups independently selected from halo, —$NH_2$, —OH, —CN, —$CF_3$, ($C_1$–$C_6$)alkylamino, halo ($C_1$–$C_6$)alkyl, oxo, ($C_1$–$C_6$)alkoxy, ($C_1$–$C_6$)alkoxy ($C_1$–$C_6$)alkyl, ($C_1$–$C_6$)alkyl, ($C_2$–$C_6$)alkenyl, ($C_2$–$C_6$) alkynyl, di($C_1$–$C_6$)alkylamino, —C(O)$R^8$, —COO$R^8$, —C(O)N$R^8R^{8'}$, and —$NR^8$C(O)$R^{8'}$; and
wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;
provided at least one of $R^3$, $R^4$ and $R^5$ is a basic moiety; and pharmaceutically acceptable derivatives thereof.

The invention also relates to compounds of Formula II wherein $R^3$ and $R^4$ are H; and wherein $R^4$ is selected from $NH_2$, aminomethyl, isopropylaminomethyl, t-butylaminomethyl, N-isopropyl-N-ethylaminomethyl, N-isopropyl-N-methylaminomethyl, N-t-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, 1-piperidinylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl and 4-methylpiperazin-1-ylmethyl.

The invention also relates to compounds of Formula II wherein $R^4$ and $R^5$ are H; and wherein $R^3$ is selected from $NH_2$, aminomethyl, isopropylaminomethyl, t-butylaminomethyl, N-isopropyl-N-ethylaminomethyl, N-isopropyl-N-methylaminomethyl, N-t-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, 1-piperidinylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl and 4-methylpiperazin-1-ylmethyl.

The invention also relates to compounds of Formula II wherein $R^3$ and $R^4$ are H; and wherein $R^5$ is selected from $NH_2$, aminomethyl, isopropylaminomethyl, t-butylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, 1-piperidinylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl and 4-methylpiperazin-1-ylmethyl.

The invention also relates to compounds of Formula II wherein the C ring is selected from

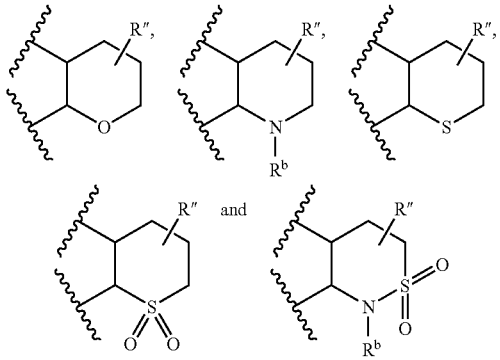

wherein R" is R' when $R^b$ is hydrogen or $C_{1-2}$alkyl, or R" is hydrogen when $R^b$ is R'.

The invention also relates to compounds of Formula II wherein q is 1 or 2, and t is 0 or 1.

The invention also relates to compounds of Formula II wherein q is 2, and t is 0 or 1.

The invention also relates to compounds of Formula II wherein $R^2$ is selected from phenyl-CH=CH—, tetrahydronaphthyl, naphtho[2.3-d]dioxol-6-yl, 1-benzofuran-2-yl, 2,1,3-benzoxadiazol-4-yl, 2,1,3-benzothiadiazol-4-yl, 1,3-benzothiazol-2-yl, 1H-pyrazol-4-yl, thien-2-yl, 5-isoxazolthien-2-yl, benzothien-2-yl, thieno[3,2-c]pyridin-2-yl, naphthyl, phenyl, 3-pyridinyl, tetrahydroisoquinolinyl, quinolinyl and isoquinolinyl; wherein $R^2$ is optionally substituted with one or more groups selected from halo, —$NH_2$, —OH, —$CO_2H$, ($C_1$–$C_2$)alkylamino, ($C_1$–$C_2$)alkoxy, ($C_1$–$C_2$)alkoxy-($C_1$–$C_2$)alkyl, ($C_1$–$C_2$)alkyl, halo($C_1$–$C_2$) alkyl, di($C_1$–$C_2$)alkylamino, and phenyl, and preferably with one or two groups independently selected from —Cl, —F or —$CF_3$.

The invention also relates to compounds of Formula II wherein $R^2$ is selected from 2-naphthyl, 1-naphthyl, phenyl, 3-chlorophenyl, 4-chlorophenyl, 3,5-dichlorophenyl, 3,4-dichlorophenyl, 2,4,6-trichlorophenyl, 3-fluorophenyl, 3-methoxyphenyl, 4-methoxyphenyl, 3-biphenyl, 4'chlorophenyl-3-phenyl, 3-methylphenyl, 3-trifluoromethylphenyl, and 3-pyridinyl; wherein $R^2$ is optionally substituted with one or more groups selected from halo, —$NH_2$, —OH, —$CO_2H$, ($C_1$–$C_2$)alkylamino, ($C_1$–$C_2$)alkoxy, ($C_1$–$C_2$) alkoxy-($C_1$–$C_2$)alkyl, ($C_1$–$C_2$)alkyl, halo($C_1$–$C_2$)alkyl, di($C_1$–$C_2$)alkylamino, and phenyl, and preferably with one or two groups independently selected from —Cl, —F or —$CF_3$.

The invention also relates to compounds of Formula II wherein $R^a$ is H.

The invention also relates to compounds of Formula II wherein $R^2$ is 2-naphthyl.

The invention also relates to compounds of Formula II wherein $R^2$ is 3,4-dichlorophenyl.

The invention also relates to compounds of Formula II wherein $R^2$ is 3-trifluoromethylphenyl.

The invention also relates to compounds of Formula III

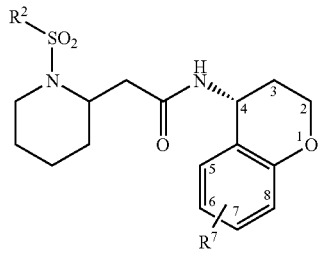

III wherein p is 1–2;
wherein $R^2$ is selected from naphthyl, phenyl, pyridinyl, quinolinyl and isoquinolinyl, and wherein each is optionally substituted with one to three substituents selected from chloro, fluoro, methoxy, methyl, trifluoromethyl, and phenyl; and
wherein $R^7$ is selected from amino-$(CH_2)_p$—, mono$(C_{1-4})$alkylamino-$(CH_2)_p$—, di$(C_{1-4})$alkylamino-$(CH_2)_p$—, and
a 5–7 membered nitrogen-containing heterocyclyl-$(CH_2)_p$— optionally substituted with one to three groups independently selected from halo, —$NH_2$, —OH, —CN, —$CF_3$, $(C_1-C_6)$alkylamino, oxo, $(C_1-C_6)$alkoxy, $(C_2-C_6)$alkenyl, $(C_2-C_6)$alkynyl, di$(C_1-C_6)$alkylamino, —$C(O)R^8$, —$COOR^8$, —$C(O)NR^8R^{8'}$, —$NR^8C(O)R^{8'}$, =NCN;

$(C_1-C_6)$alkyl, aryl, heteroaryl, cycloalkyl and heterocyclyl, each of which is optionally substituted with one to three groups independently selected from halo, —$NH_2$, —OH, —CN, —$CF_3$, $(C_1-C_6)$alkylamino, halo$(C_1-C_6)$alkyl, oxo, $(C_1-C_6)$alkoxy, $(C_1-C_6)$alkoxy$(C_1-C_6)$alkyl, $(C_1-C_6)$alkyl, $(C_2-C_6)$alkenyl, $(C_2-C_6)$alkynyl, di$(C_1-C_6)$alkylamino, —$C(O)R^8$, —$COOR^8$, —$C(O)NR^8R^{8'}$, and —$NR^8C(O)R^{8'}$; and wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;
wherein $R^7$ is at position 6, 7 or 8;

and pharmaceutically acceptable derivatives thereof.

The invention also relates to compounds of Formula III wherein $R^7$ is selected from aminomethyl, isopropylaminomethyl, t-butylaminomethyl, N-isopropyl-N-ethylaminomethyl, N-isopropyl-N-methylaminomethyl, N-t-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, 1-piperidinylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl and 4-methylpiperazin-1-ylmethyl.

The invention also relates to compounds of Formula III wherein $R^7$—$(CH_2)_p$— is substituted at position 7.

The invention also relates to compounds of Formula III wherein $R^2$ is 2-naphthyl, 3,4-dichlorophenyl or 3-trifluoromethylphenyl.

The invention also relates to compounds of Formula IV

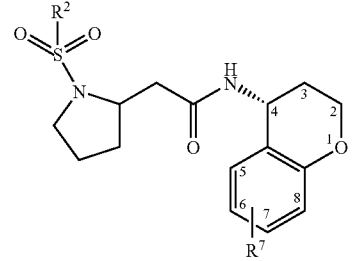

IV wherein p is 1–2;
wherein $R^2$ is selected from naphthyl, phenyl, pyridinyl, quinolinyl and isoquinolinyl, and wherein each is optionally substituted with one to three substituents selected from chloro, fluoro, methoxy, methyl, trifluoromethyl, and phenyl; and
wherein $R^7$ is selected from amino-$(CH_2)_p$—, mono$(C_{1-4})$alkylamino-$(CH_2)_p$—, di$(C_{1-4})$alkylamino-$(CH_2)_p$—, and
a 5–7 membered nitrogen-containing heterocyclyl-$(CH_2)_p$— optionally substituted with one to three groups independently selected from halo, —$NH_2$, —OH, —CN, —$CF_3$, $(C_1-C_6)$alkylamino, oxo, $(C_1-C_6)$alkoxy, $(C_2-C_6)$alkenyl, $(C_2-C_6)$alkynyl, di$(C_1-C_6)$alkylamino, —$C(O)R^8$, —$COOR^8$, —$C(O)NR^8R^{8'}$, —$NR^8C(O)R^{8'}$, =NCN; and $(C_1-C_6)$alkyl, aryl, heteroaryl, cycloalkyl and heterocyclyl, each of which is optionally substituted with one to three groups independently selected from halo, —$NH_2$, —OH, —CN, —$CF_3$, $(C_1-C_6)$alkylamino, halo$(C_1-C_6)$alkyl, oxo, $(C_1-C_6)$alkoxy, $(C_1-C_6)$alkoxy$(C_1-C_6)$alkyl, $(C_1-C_6)$alkyl, $(C_2-C_6)$alkenyl, $(C_2-C_6)$alkynyl, di$(C_1-C_6)$alkylamino, —$C(O)R^8$, —$COOR^8$, —$C(O)NR^8R^{8'}$, and —$NR^8C(O)R^{8'}$;

wherein $R^7$ is at position 6, 7 or 8; and
wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

and pharmaceutically acceptable derivatives thereof.

The invention also relates to compounds of Formula IV wherein $R^7$ is selected from aminomethyl, isopropylaminomethyl, t-butylaminomethyl, N-isopropyl-N-ethylaminomethyl, N-isopropyl-N-methylaminomethyl, N-t-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, 1-piperidinylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl and 4-methylpiperazin-1-ylmethyl.

The invention also relates to compounds of Formula IV wherein $R^7$ is substituted at position 7.

The invention also relates to compounds of Formula IV wherein $R^2$ is 2-naphthyl, 3,4-dichlorophenyl or 3-trifluoromethylphenyl.

The invention also relates to compounds of Formula V

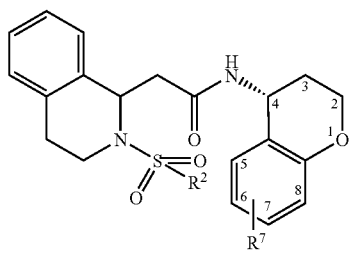

wherein p is 1–2;

wherein $R^2$ is selected from naphthyl, phenyl, pyridinyl, quinolinyl and isoquinolinyl, wherein each is optionally substituted with one to three substituents selected from chloro, fluoro, methoxy, methyl, trifluoromethyl, and phenyl; and optionally substitute wherein $R^7$ is selected from amino-$(CH_2)_p$—, mono$(C_{1-4})$alkylamino-$(CH_2)_p$—, di$(C_{1-4})$alkylamino-$(CH_2)_p$—, and a 5–7 membered nitrogen-containing heterocyclyl-$(CH_2)_p$— optionally substituted with one to three groups independently selected from halo, —$NH_2$, —OH, —CN, —$CF_3$, $(C_1-C_6)$alkylamino, oxo, $(C_1-C_6)$alkoxy, $(C_2-C_6)$alkenyl, $(C_2-C_6)$alkynyl, di$(C_1-C_6)$alkylamino, —C(O)$R^8$, —COO$R^8$, —C(O)N$R^8R^{8'}$, —N$R^8$C(O)$R^{8'}$, =NCN; and $(C_1-C_6)$alkyl, aryl, heteroaryl, cycloalkyl and heterocyclyl, each of which is optionally substituted with one to three groups independently selected from halo, —$NH_2$, —OH, —CN, —$CF_3$, $(C_1-C_6)$alkylamino, halo$(C_1-C_6)$alkyl, oxo, $(C_1-C_6)$alkoxy, $(C_1-C_6)$alkoxy$(C_1-C_6)$alkyl, $(C_1-C_6)$alkyl, $(C_2-C_6)$alkenyl, $(C_2-C_6)$alkynyl, di$(C_1-C_6)$alkylamino, —C(O)$R^8$, —COO$R^8$, —C(O)N$R^8R^{8'}$, and —N$R^8$C(O)$R^{8'}$;

wherein $R^7$ is at position 6, 7 or 8; and wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

and pharmaceutically acceptable derivatives thereof.

The invention also relates to compounds of Formula V wherein $R^7$ is selected from aminomethyl, isopropylaminomethyl, t-butylaminomethyl, N-isopropyl-N-ethylaminomethyl, N-isopropyl-N-methylaminomethyl, N-t-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, 1-piperidinylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl and 4-methylpiperazin-1-ylmethyl.

The invention also relates to compounds of Formula V wherein $R^7$ is substituted at position 7.

The invention also relates to compounds of Formula V wherein $R^2$ is 2-naphthyl, 3,4-dichlorophenyl or 3-trifluoromethylphenyl.

The invention also relates to compounds of Formula VI

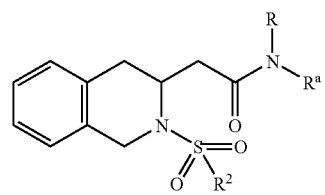

wherein R is a 9–11 membered fused bicyclic carbocyclic or heterocyclic ring substituted with one to three basic moieties, and optionally substituted with one to three groups independently selected from halo, —$NH_2$, —OH, —CN, —$CF_3$, $(C_1-C_6)$alkylamino, oxo, $(C_1-C_6)$alkoxy, $(C_2-C_6)$alkenyl, $(C_2-C_6)$alkynyl, di$(C_1-C_6)$alkylamino, —C(O)$R^8$, —COO$R^8$, —C(O)N$R^8R^{8'}$, —N$R^8$C(O)$R^{8'}$, and $(C_1-C_6)$alkyl, aryl, heteroaryl, cycloalkyl or heterocyclyl, each of which is optionally substituted with one to three groups independently selected from halo, —$NH_2$, —OH, —CN, —$CF_3$, $(C_1-C_6)$alkylamino, halo $(C_1-C_6)$alkyl, oxo, $(C_1-C_6)$alkoxy, $(C_1-C_6)$alkoxy $(C_1-C_6)$alkyl, $(C_1-C_6)$alkyl, $(C_2-C_6)$alkenyl, $(C_2-C_6)$alkynyl, di$(C_1-C_6)$alkylamino, —C(O)$R^8$, —COO$R^8$, —C(O)N$R^8R^{8'}$, and —N$R^8$C(O)$R^8$;

wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

wherein $R^2$ is selected from arylalkenyl, aryl, and heterocyclyl, wherein $R^2$ is optionally substituted with one to five groups independently selected from halo, —$NH_2$, —OH, —CN, —$CF_3$, $(C_1-C_6)$alkylamino, oxo, $(C_1-C_6)$alkoxy, $(C_2-C_6)$alkenyl, $(C_2-C_6)$alkynyl, di$(C_1-C_6)$alkylamino, —C(O)$R^8$, —COO$R^8$, —C(O)N$R^8R^{8'}$, —N$R^8$C(O)$R^{8'}$, and $(C_1-C_6)$alkyl, aryl, heteroaryl, cycloalkyl and heterocyclyl, each of which is optionally substituted with one to three groups independently selected from halo, —$NH_2$, —OH, —CN, —$CF_3$, $(C_1-C_6)$alkylamino, halo $(C_1-C_6)$alkyl, oxo, $(C_1-C_6)$alkoxy, $(C_1-C_6)$alkoxy $(C_1-C_6)$alkyl, $(C_1-C_6)$alkyl, $(C_2-C_6)$alkenyl, $(C_2-C_6)$alkynyl, di$(C_1-C_6)$alkylamino, —C(O)$R^8$, —COO$R^8$, —C(O)N$R^8R^{8'}$, and —N$R^8$C(O)$R^{8'}$; and wherein $R^a$ is independently selected from H and $C_{1-4}$-alkyl, and aryl optionally substituted with one to three groups independently selected from halo, —$NH_2$, —OH, —CN, —$CF_3$, $(C_1-C_6)$alkylamino, halo$(C_1-C_6)$alkyl, oxo, $(C_1-C_6)$alkoxy, $(C_1-C_6)$alkoxy$(C_1-C_6)$alkyl, $(C_1-C_6)$alkyl, $(C_2-C_6)$alkenyl, $(C_2-C_6)$alkynyl, di$(C_1-C_6)$alkylamino, —C(O)$R^8$, —COO$R^8$, —C(O)N$R^8R^{8'}$, and —N$R^8$C(O)$R^{8'}$.

The invention also relates to compounds of Formula VI wherein $R^2$ is selected from phenyl-CH=CH—, tetrahydronaphthyl, naphtho[2.3-d]dioxolyl, benzofuranyl, benzoxadiazolyl, benzothiadiazolyl, benzothiazolyl, 1H-pyrazolyl, thienyl, isoxazolthienyl, benzothienyl, thieno[3,2-c]pyridinyl, naphthyl, phenyl, pyridinyl, tetrahydroisoquinolinyl, quinolinyl and isoquinolinyl, wherein each is optionally substituted with one to five groups independently selected from halo, —NH$_2$, —OH, —CN, —CF$_3$, (C$_1$–C$_6$)alkylamino, oxo, (C$_1$–C$_6$)alkoxy, (C$_2$–C$_6$)alkenyl, (C$_2$–C$_6$)alkynyl, di(C$_1$–C$_6$)alkylamino, —C(O)R$^8$, —COOR$^8$, —C(O)NR$^8$R$^{8'}$, —NR$^8$C(O)R$^{8'}$, and (C$_1$–C$_6$)alkyl, aryl, heteroaryl, cycloalkyl and heterocyclyl, each of which is optionally substituted with one to three groups independently selected from halo, —NH$_2$, —OH, —CN, —CF$_3$, (C$_1$–C$_6$)alkylamino, halo(C$_1$–C$_6$)alkyl, oxo, (C$_1$–C$_6$)alkoxy, (C$_1$–C$_6$)alkoxy(C$_1$–C$_6$)alkyl, (C$_1$–C$_6$)alkyl, (C$_2$–C$_6$)alkenyl, (C$_2$–C$_6$)alkynyl, di(C$_1$–C$_6$)alkylamino, —C(O)R$^8$, —COOR$^8$, —C(O)NR$^8$R$^{8'}$, and —NR$^8$C(O)R$^{8'}$.

The invention also relates to compounds of Formula VI wherein R is selected from 1,2,3,4-tetrahydronaphth-1-yl, 1,2,3,4-tetrahydronaphth-2-yl, indan-1-yl and indan-2-yl, chroman-4-yl, and 2,2-dioxo-3,4-dihydro-1H-2, 1-benzothiazin-4-yl.

The invention also relates to compounds of Formula VI wherein R$^a$ is selected from H, or (C$_1$–C$_2$)alkyl, such as methyl; or phenyl, each of which is optionally substituted with one or two groups independently selected from H and C$_{1-4}$-alkyl, or aryl optionally substituted with one to three groups selected from halo, —NH$_2$, —OH, —CN, —CF$_3$, (C$_1$–C$_6$)alkylamino, halo(C$_1$–C$_6$)alkyl, oxo, (C$_1$–C$_6$)alkoxy, (C$_1$–C$_6$)alkoxy(C$_1$–C$_6$)alkyl, (C$_1$–C$_6$)alkyl, (C$_2$–C$_6$)alkenyl, (C$_2$–C$_6$)alkynyl, di(C$_1$–C$_6$)alkylamino, —C(O)R$^8$, —COOR$^8$, —C(O)NR$^8$R$^{8'}$, and —NR$^8$C(O)R$^{8'}$.

The invention also relates to compounds of Formula I'

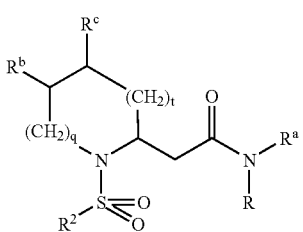

I' wherein q is 0–3;
wherein t is 0–2, provided that when t is 2, q is not 3;
wherein R is a 9–11 membered fused bicyclic carbocyclic or heterocyclic ring substituted with one to three basic moieties, and optionally substituted with one to three groups independently selected from halo, —NH$_2$, —OH, —CN, —CF$_3$, (C$_1$–C$_6$)alkylamino, oxo, (C$_1$–C$_6$)alkoxy, (C$_2$–C$_6$)alkenyl, (C$_2$–C$_6$)alkynyl, di(C$_1$–C$_6$)alkylamino, —C(O)R$^8$, —COOR$^8$, —C(O)NR$^8$R$^{8'}$, —NR$^8$C(O)R$^{8'}$, and (C$_1$–C$_6$)alkyl, aryl, heteroaryl, cycloalkyl or heterocyclyl, each of which is optionally substituted with one to three groups independently selected from halo, —NH$_2$, —OH, —CN, —CF$_3$, (C$_1$–C$_6$)alkylamino, halo (C$_1$–C$_6$)alkyl, oxo, (C$_1$–C$_6$)alkoxy, (C$_1$–C$_6$)alkoxy (C$_1$–C$_6$)alkyl, (C$_1$–C$_6$)alkyl, (C$_2$–C$_6$)alkenyl, (C$_2$–C$_6$)alkynyl, di(C$_1$–C$_6$)alkylamino, —C(O)R$^8$, —COOR$^8$, —C(O)NR$^8$R$^{8'}$, and —NR$^8$C(O)R$^{8'}$;

wherein R$^8$ and R$^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

wherein R$^2$ is selected from arylalkenyl, aryl, and heterocyclyl selected from thienyl, imidazolyl and benzofused heteroaryl, wherein R$^2$ is optionally substituted with one to five groups independently selected from halo, —NH$_2$, —OH, —CN, —CF$_3$, (C$_1$–C$_6$)alkylamino, oxo, (C$_1$–C$_6$)alkoxy, haloalkoxy, (C$_2$–C$_6$)alkenyl, (C$_2$–C$_6$)alkynyl, di(C$_1$–C$_6$)alkylamino, —C(O)R$^8$, —COOR$^8$, —C(O)NR$^8$R$^{8'}$, —NR$^8$C(O)R$^{8'}$, and (C$_1$–C$_6$)alkyl, aryl, heteroaryl, cycloalkyl and heterocyclyl, each of which is optionally substituted with one to three groups independently selected from halo, —NH$_2$, —OH, —CN, —CF$_3$, (C$_1$–C$_6$)alkylamino, halo (C$_1$–C$_6$)alkyl, oxo, (C$_1$–C$_6$)alkoxy, (C$_1$–C$_6$)alkoxy (C$_1$–C$_6$)alkyl, (C$_1$–C$_6$)alkyl, (C$_2$–C$_6$)alkenyl, (C$_2$–C$_6$)alkynyl, di(C$_1$–C$_6$)alkylamino, —C(O)R$^8$, —COOR8, —C(O)NR$^8$R$^{8'}$, and —NR$^8$C(O)R$^{8'}$;

wherein R$^a$ is independently selected from H and C$_{1-4}$-alkyl, and aryl optionally substituted with one to three groups independently selected from halo, —NH$_2$, —OH, —CN, —CF$_3$, (C$_1$–C$_6$)alkylamino, halo(C$_1$–C$_6$)alkyl, oxo, (C$_1$–C$_6$)alkoxy, (C$_1$–C$_6$)alkoxy(C$_1$–C$_6$)alkyl, (C$_1$–C$_6$)alkyl, (C$_2$–C$_6$)alkenyl, (C$_2$–C$_6$)alkynyl, di(C$_1$–C$_6$)alkylamino, —C(O)R$^8$, —COOR$^8$, —C(O)NR$^8$R$^{8'}$, and —NR$^8$C(O)R$^{8'}$;

wherein each R$^b$ is independently selected from H, oxo, hydroxy, benzyloxy and C$_{1-2}$-alkyl;
wherein R$^c$ is independently selected from H and C$_{1-2}$-alkyl; or wherein R$^b$ and R$^c$ together with the carbon atoms to which they are attached form a 6-membered aryl or heteroaryl ring optionally substituted with one to three groups independently selected from halo, —NH$_2$, —OH, —CN, —CF$_3$, (C$_1$–C$_6$)alkylamino, oxo, (C$_1$–C$_6$)alkoxy, (C$_1$–C$_6$)alkenyl, (C$_2$–C$_6$)alkynyl, di(C$_1$–C$_6$)alkylamino, —C(O)R$^8$, —COOR$^8$, —C(O)NR$^8$R$^{8'}$, —NR$^8$C(O)R$^{8'}$, and (C$_1$–C$_6$)alkyl, aryl, heteroaryl, cycloalkyl and heterocyclyl, each of which is optionally substituted with one to three groups independently selected from halo, —NH$_2$, —OH, —CN, —CF$_3$, (C$_1$–C$_6$)alkylamino, halo (C$_1$–C$_6$)alkyl, oxo, (C$_1$–C$_6$)alkoxy, (C$_1$–C$_6$)alkoxy (C$_1$–C$_6$)alkyl, (C$_1$–C$_6$)alkyl, (C$_2$–C$_6$)alkenyl, (C$_2$–C$_6$)alkynyl, di(C$_1$–C$_6$)alkylamino, —C(O)R$^8$, —COOR$^8$, —C(O)NR$^8$R$^{8'}$, and —NR$^8$C(O)R$^{8'}$;

and pharmaceutically acceptable derivatives thereof;

provided the basic moiety is not 2-oxo-piperazin-4-ylmethyl.

The invention also relates to compounds of Formula I wherein R is a partially unsaturated carbocyclic ring; in conjunction with any of the above or below embodiments.

The invention also relates to compounds of Formula I' wherein R is 1,2,3,4-tetrahydronaphthyl; in conjunction with any of the above or below embodiments.

The invention also relates to compounds of Formula I' wherein R is indanyl; in conjunction with any of the above or below embodiments.

The invention also relates to compounds of Formula I' wherein R is selected from 1,2,3,4-tetrahydronaphth-1-yl, 1,2,3,4-tetrahydronaphth-2-yl, indan-1-yl and indan-2-yl; in conjunction with any of the above or below embodiments.

The invention also relates to compounds of Formula I' wherein R is partially unsaturated heterocyclyl; in conjunction with any of the above or below embodiments.

The invention also relates to compounds of Formula I' wherein R is chroman; in conjunction with any of the above or below embodiments.

The invention also relates to compounds of Formula I' wherein R is 2,2-dioxo-3,4-dihydro-1H-2,1-benzothiazinyl; in conjunction with any of the above or below embodiments.

The invention also relates to compounds of Formula I' wherein R is chroman-4-yl, 5,6,7,8-tetrahydro-quinazolin-5-yl, 5,6,7,8-tetrahydro-[1,6]naphthyridin-4-yl or 2,2-dioxo-3,4-dihydro-1H-2,1-benzothiazin-4-yl; in conjunction with any of the above or below embodiments.

The invention also relates to compounds of Formula I' wherein q is 1 or 2; t is 0 or 1;

wherein each $R^2$ is selected from phenyl-CH=CH—, tetrahydronaphthyl, naphtho[2.3-d]dioxolyl, benzofuranyl, benzoxadiazolyl, benzothiadiazolyl, benzothiazolyl, 1H-pyrazolyl, thienyl, isoxazolthienyl, benzothienyl, thieno[3,2-c]pyridinyl, naphthyl, phenyl, pyridinyl, tetrahydroisoquinolinyl, quinolinyl and isoquinolinyl;

wherein $R^2$ is optionally substituted with one to five groups independently selected from halo, —$NH_2$, —OH, —CN, —$CF_3$, ($C_1$–$C_6$)alkylamino, oxo, ($C_1$–$C_6$)alkoxy, ($C_2$–$C_6$) alkenyl, ($C_2$–$C_6$)alkynyl, di($C_1$–$C_6$)alkylamino, —C(O)$R^8$, —COOR$^8$, —C(O)NR$^8$R$^{8'}$, —NR$^8$C(O)R$^{8'}$, and ($C_1$–$C_6$)alkyl, aryl, heteroaryl, cycloalkyl or heterocyclyl, each of which is optionally substituted with one to three groups independently selected from halo, —$NH_2$, —OH, —CN, —$CF_3$, ($C_1$–$C_6$)alkylamino, halo ($C_1$–$C_6$)alkyl, oxo, ($C_1$–$C_6$)alkoxy, ($C_1$–$C_6$)alkoxy ($C_1$–$C_6$)alkyl, ($C_1$–$C_6$)alkyl, ($C_2$–$C_6$)alkenyl, ($C_2$–$C_6$) alkynyl, di($C_1$–$C_6$)alkylamino, —C(O)$R^8$, —COOR$^8$, —C(O)NR$^8$R$^{8'}$, and —NR$^8$C(O)R$^{8'}$;

wherein $R^a$ is selected from H and $C_{1-2}$-alkyl;
wherein $R^b$ and $R^c$ are H;
wherein the basic substituent on R is selected from cycloalkylamino($C_1$–$C_6$)alkyl, cycloalkyl($C_1$–$C_6$)alkylamino ($C_1$–$C_6$)alkyl,

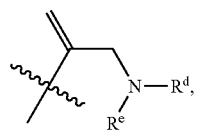

heteroarylamino($C_1$–$C_6$)alkyl, heteroaryl($C_1$–$C_6$)alkylamino($C_1$–$C_6$)alkyl, arylamino($C_1$–$C_6$)alkyl, alkoxyalkylaminoalkyl, hydroxyalkylaminoalkyl, alkenylalkylamnioalkyl, aminocarbonylalkylaminoalkyl, carboxyalkylaminoalkyl, aryl($C_1$–$C_6$)alkylamino ($C_1$–$C_6$)alkyl, $C_{1-6}$-alkylamino–$C_{1-6}$-alkoxy, haloalkylaminoalkyl, amino($C_1$–$C_6$)alkyl, ($C_1$–$C_6$)alkylamino ($C_1$–$C_6$)alkyl, 5–8 membered nitrogen-containing heterocyclyl, 5–7 membered nitrogen-containing heterocyclyl-alkylaminoalkyl and 5–7 membered heterocyclyl-alkyl; and wherein each of said basic substituents is optionally substituted with one to three groups independently selected from halo, —$NH_2$, —OH, —CN, —$CF_3$, ($C_1$–$C_6$)alkylamino, oxo, ($C_1$–$C_6$) alkoxy, ($C_2$–$C_6$)alkenyl, ($C_2$–$C_6$)alkynyl, di($C_1$–$C_6$) alkylamino, —C(O)$R^8$, —COOR$^8$, —C(O)NR$^8$R$^{8'}$, —NR$^8$C(O)R$^{8'}$, and ($C_1$–$C_6$)alkyl, aryl, heteroaryl, cycloalkyl or heterocyclyl, each of which is optionally substituted with one to three groups independently selected from halo, —$NH_2$, —OH, —CN, —$CF_3$, ($C_1$–$C_6$)alkylamino, halo ($C_1$–$C_6$)alkyl, oxo, ($C_1$–$C_6$)alkoxy, ($C_1$–$C_6$)alkoxy ($C_1$–$C_6$)alkyl, ($C_1$–$C_6$)alkyl, ($C_2$–$C_6$)alkenyl, ($C_2$–$C_6$) alkynyl, di($C_1$–$C_6$)alkylamino, —C(O)$R^8$, —COOR$^8$, —C(O)NR$^8$R$^{8'}$, and —NR$^8$C(O)R$^{8'}$; and wherein $R^d$ is selected from alkyl, cycloalkyl, cycloalkylalkyl, hydroxyalkyl, alkoxyalkyl, and H;
wherein $R^e$ is H; or where $R^d$ and $R^e$ together with the nitrogen atom to which they are attached form a heterocyclic ring;

and pharmaceutically acceptable derivatives thereof; in conjunction with any of the above or below embodiments.

The invention also relates to compounds of Formula I' wherein $R^2$ is selected from phenyl-CH=CH—, tetrahydronaphthyl, naphtho[2.3-d]dioxol-6-yl, 1-benzofur-2-yl, 2,1,3-benzoxadiazol-4-yl, 2,1,3-benzothiadiazol-4-yl, 1,3-benzothiazol-2-yl, 1H-pyrazol-4-yl, thien-2-yl, 5-isoxazolthien-2-yl, benzothien-2-yl, benzothien-3-yl, thieno[3,2-c]pyridin-2-yl, naphthyl, phenyl, 3-pyridyl, tetrahydroisoquinolyl, quinol-8-yl and isoquinolyl; and
wherein each $R^2$ is said optionally substituted;
wherein $R^a$ is H; and
wherein the basic substituent on R is selected from —$NH_2$,

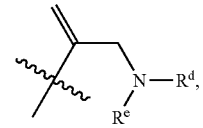

$C_{3-6}$-cycloalkyl($C_1$–$C_2$)alkylamino($C_1$–$C_2$)alkyl, $C_{3-6}$-cycloalkylamino($C_1$–$C_2$)alkyl, ($C_1$–$C_2$)alkoxy($C_1$–$C_2$)alkylamino($C_1$–$C_2$)alkyl, mono-$C_{2-4}$-alkenylamino-$C_{1-4}$-alkyl, di-$C_{2-4}$-alkenylamino-$C_{1-4}$-alkyl, hydroxy-$C_{1-4}$-alkylamino-$C_{1-4}$-alkyl, aminocarbonyl-$C_{1-4}$-alkylamino-$C_{1-2}$-alkyl, mono-$C_{1-6}$-alkylamino-$C_{1-4}$-alkyl, di-$C_{1-4}$-alkylamino-$C_{1-4}$-alkyl and 5–8 membered heterocyclyl-$C_{1-4}$-alkyl;

wherein each is optionally substituted with one to three groups independently selected from halo,
—$NH_2$, —OH, —CN, —$CF_3$, ($C_1$–$C_6$)alkylamino, oxo, ($C_1$–$C_6$)alkoxy, ($C_2$–$C_6$)alkenyl, ($C_2$–$C_6$)alkynyl, di($C_1$–$C_6$)alkylamino, —C(O)$R^8$, —COOR$^8$, —C(O) NR$^8$R$^{8'}$, —NR$^8$C(O)R$^{8'}$, and ($C_1$–$C_6$)alkyl, aryl, heteroaryl, cycloalkyl or heterocyclyl, each of which is optionally substituted with one to three groups independently selected from halo, —$NH_2$, —OH, —CN, —$CF_3$, ($C_1$–$C_6$)alkylamino, halo($C_1$–$C_8$)alkyl, oxo, ($C_1$–$C_6$)alkoxy, ($C_1$–$C_6$)alkoxy($C_1$–$C_6$)alkyl, ($C_1$–$C_6$) alkyl, ($C_2$–$C_6$)alkenyl, ($C_2$–$C_6$)alkynyl, di($C_1$–$C_6$)alkylamino, —C(O)$R^8$, —COOR$^8$, —C(O)NR$^8$R$^{8'}$, and —NR$^8$C(O)R$^{8'}$;

wherein $R^d$ is selected from $C_{1-5}$-alkyl, $C_{3-6}$-cycloalkyl, $C_{3-6}$-cycloalkyl-$C_{1-4}$-alkyl, $C_{1-4}$-hydroxyalkyl, $C_{1-3}$-alkoxy-$C_{1-3}$-alkyl and H; and wherein $R^e$ is H; or where $R^d$ and $R^e$ together with the nitrogen atom to which they are attached form a 4–8 membered nitrogen-containing heterocyclic ring;

and pharmaceutically acceptable derivatives thereof; in conjunction with any of the above or below embodiments.

The invention also relates to compounds of Formula I' wherein $R^a$ is H; in conjunction with any of the above or below embodiments.

The invention also relates to compounds of Formula I' wherein the basic substituent on R is selected from —$NH_2$, aminomethyl, aminoethyl, aminopropyl, isopropylaminomethyl, t-butylaminomethyl, iso-butylaminomethyl, 1-methylpropylaminomethyl, 2-methylbutylaminomethyl, 2,2'-dimethylpropylamnomethyl, 2,2',3-trimethylpropylaminomethyl, allyl-aminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl; in conjunction with any of the above or below embodiments.

The invention also relates to compounds of Formula I' wherein $R^b$ and $R^c$ are joined to form a phenyl ring; and wherein q is 2; in conjunction with any of the above or below embodiments.

The invention also relates to compounds of Formula II'

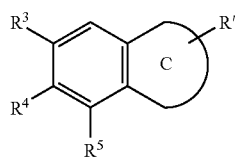

II' wherein the C ring is a 4- to 7-membered saturated carbocyclic or heterocyclic moiety;

wherein R' is selected from

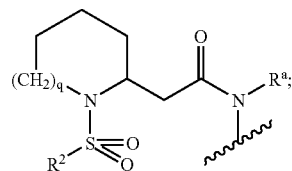

wherein q is 0–3;

wherein $R^2$ is selected from arylalkenyl, aryl, and heterocyclyl selected from thienyl, imidazolyl and benzofused heteroaryl, wherein $R^2$ is optionally substituted with one to five groups independently selected from halo, —$NH_2$, —OH, —CN, —$CF_3$, ($C_1$–$C_6$)alkylamino, oxo, ($C_1$–$C_6$)alkoxy, haloalkoxy, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, —N$R^8$C(O)$R^{8'}$, and ($C_1$–$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$–$C_6$)alkylamino, halo ($C_1$–$C_6$)alkyl, oxo, ($C_1$–$C_6$)alkoxy, ($C_1$–$C_6$)alkoxy ($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, and —N$R^8$C(O)$R^{8'}$;

wherein $R^a$ is independently selected from H and $C_{1-4}$-alkyl, or aryl optionally substituted with one to three groups selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, and —N$R^8$C(O)$R^{8'}$;

wherein $R^3$, $R^4$ and $R^5$ are the same or different and represent H, halo, —$NH_2$, —OH, —CN, —$CF_3$, ($C_1$–$C_6$)alkylamino, oxo, ($C_1$–$C_6$)alkoxy, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, —N$R^8$C(O)$R^{8'}$, a basic moiety, or ($C_1$–$C_2$)alkyl, aryl, heteroaryl, cycloalkyl or heterocyclyl, each of which is optionally substituted with one to three groups independently selected from halo, —$NH_2$, —OH, —CN, —$CF_3$, ($C_1$–$C_6$)alkylamino, halo ($C_1$–$C_6$)alkyl, oxo, ($C_1$–$C_6$)alkoxy, ($C_1$–$C_6$)alkoxy ($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, and —N$R^8$C(O)$R^{8'}$; and wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

provided at least one of $R^3$, $R^4$ and $R^5$ is a basic moiety;

and pharmaceutically acceptable derivatives thereof.

The invention also relates to compounds of Formula II' wherein $R^3$ and $R^5$ are H; and wherein $R^4$ is selected from —$NH_2$, aminomethyl, aminoethyl, aminopropyl, isopropylaminomethyl, t-butylaminomethyl, iso-butylaminomethyl, 1-methylpropylaminomethyl, 2-methylbutylaminomethyl, 2,2'-dimethylpropylamnomethyl, 2,2',3-trimethylpropylaminomethyl, allyl-aminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl; in conjunction with any of the above or below embodiments.

The invention also relates to compounds of Formula II' wherein $R^4$ and $R^5$ are H; and wherein $R^3$ is selected from —NH$_2$, aminomethyl, aminoethyl, aminopropyl, isopropylaminomethyl, t-butylaminomethyl, iso-butylaminomethyl, 1-methylpropylaminomethyl, 2-methylbutylaminomethyl, 2,2'-dimethylpropylamnomethyl, 2,2',3-trimethylpropylaminomethyl, allyl-aminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl; in conjunction with any of the above or below embodiments.

The invention also relates to compounds of Formula II' wherein $R^3$ and $R^4$ are H; and wherein $R^5$ is selected from —NH$_2$, aminomethyl, aminoethyl, aminopropyl, isopropylaminomethyl, t-butylaminomethyl, iso-butylaminomethyl, 1-methylpropylaminomethyl, 2-methylbutylaminomethyl, 2,2'-dimethylpropylamnomethyl, 2,2',3-trimethylpropylaminomethyl, allyl-aminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl; in conjunction with any of the above or below embodiments.

The invention also relates to compounds of Formula II' wherein the C ring is selected from

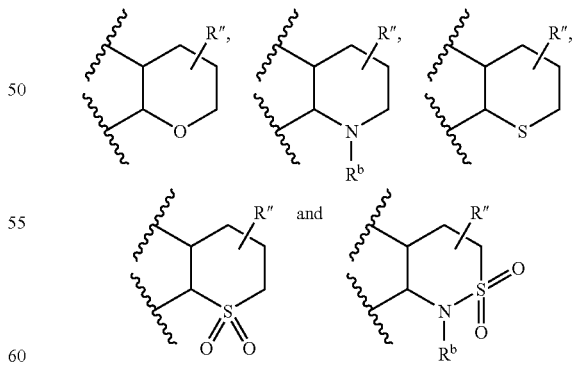

wherein $R^b$ is independently selected from R', H and $C_{1-2}$-alkyl; and wherein R" is R' when $R^b$ is hydrogen or $C_{1-2}$alkyl, or R" is hydrogen when $R^b$ is R'; in conjunction with any of the above or below embodiments.

The invention also relates to compounds of Formula II' wherein the C ring is

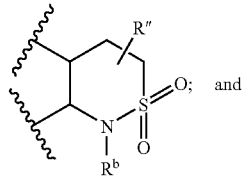

wherein $R^b$ is R'.

The invention also relates to compounds of Formula II' wherein $R^2$ is selected from phenyl-CH=CH—, tetrahydronaphthyl, naphtho[2.3-d]dioxol-6-yl, 1-benzofuran-2-yl, 2,1,3-benzoxadiazol-4-yl, 2,1,3-benzothiadiazol-4-yl, 1,3-benzothiazol-2-yl, 1H-pyrazol-4-yl, thien-2-yl, 5-isoxazolthien-2-yl, benzothien-2-yl, benzothien-3-yl, thieno[3,2-c]pyridin-2-yl, naphthyl, phenyl, 3-pyridyl, tetrahydroisoquinolinyl, quinolinyl and isoquinolinyl;

wherein each $R^2$ is optionally substituted with one to five groups independently selected from halo, —NH$_2$, —OH, —CN, —CF$_3$, (C$_1$–C$_6$)alkylamino, oxo, (C$_1$–C$_6$)alkoxy, (C$_2$–C$_6$)alkenyl, (C$_2$–C$_6$)alkynyl, di(C$_1$–C$_6$)alkylamino, —C(O)R$^8$, —COOR$^8$, —C(O)NR$^8$R$^{8'}$, —NR$^8$C(O)R$^{8'}$, and (C$_1$–C$_6$)alkyl, aryl, heteroaryl, cycloalkyl and heterocyclyl, each of which is optionally substituted with one to three groups independently selected from halo, —NH$_2$, —OH, —CN, —CF$_3$, (C$_1$–C$_6$)alkylamino, halo(C$_1$–C$_6$)alkyl, oxo, (C$_1$–C$_6$)alkoxy, (C$_1$–C$_6$)alkoxy (C$_1$–C$_6$)alkyl, (C$_1$–C$_6$)alkyl, (C$_2$–C$_6$)alkenyl, (C$_2$–C$_6$) alkynyl, di(C$_1$–C$_6$)alkylamino, —C(O)R$^8$, —COOR$^8$, —C(O)NR$^8$R$^{8'}$, or —NR$^8$C(O)R$^{8'}$; in conjunction with any of the above or below embodiments.

The invention also relates to compounds of Formula II' wherein $R^2$ is selected from 2-naphthyl, 1-naphthyl, phenyl, 3-chlorophenyl, 4-chlorophenyl, 3,5-dichlorophenyl, 3,4-dichlorophenyl, 2,4,6-trichlorophenyl, 3-fluorophenyl, 3-methoxyphenyl, 4-methoxyphenyl, 3-biphenyl, 4'-chlorophenyl-3-phenyl, 3-methylphenyl, 3-trifluoromethylphenyl, 2-chlorobenzothien-3-yl, and 3-pyridyl; in conjunction with any of the above or below embodiments.

The invention also relates to compounds of Formula II' wherein $R^a$ is H; in conjunction with any of the above or below embodiments.

The invention also relates to compounds of Formula II' wherein $R^2$ is 2-naphthyl; in conjunction with any of the above or below embodiments.

The invention also relates to compounds of Formula II' wherein $R^2$ is 3,4-dichlorophenyl; in conjunction with any of the above or below embodiments.

The invention also relates to compounds of Formula II' wherein $R^2$ is 3-trifluoromethylphenyl; in conjunction with any of the above or below embodiments.

The invention also relates to compounds of Formula III'

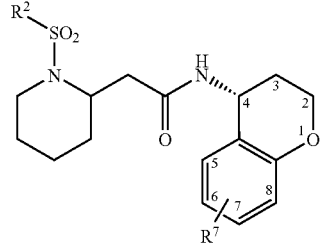

wherein $R^2$ is selected from naphthyl, phenyl, pyridinyl, benzothienyl, quinolinyl and isoquinolinyl, and wherein each is optionally substituted with one to three substituents selected from chloro, fluoro, methoxy, methyl, trifluoromethyl, and phenyl; and
wherein $R^7$ is selected from

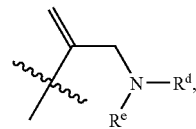

C$_{3-6}$-cycloalkyl(C$_1$–C$_2$)alkylamino(C$_1$–C$_2$)alkyl, C$_{3-6}$-cycloalkylamino(C$_1$–C$_2$)alkyl, (C$_1$–C$_2$)alkoxy(C$_1$–C$_2$) alkylamino(C$_1$–C$_2$)alkyl, mono-C$_{2-4}$-alkenylamino-C$_{1-4}$-alkyl, di-C$_{2-4}$-alkenylamino-C$_{1-4}$-alkyl, hydroxy-C$_{1-4}$-alkylamino-C$_{1-4}$-alkyl, aminocarbonyl-C$_{1-4}$-alkylamino-C$_{1-2}$-alkyl, mono-C$_{1-6}$-alkylamino-C$_{1-4}$-alkyl, di-C$_{1-4}$-alkylamino-C$_{1-4}$-alkyl and 5–8 membered heterocyclyl-C$_{1-4}$-alkyl; wherein the 5–8 membered heterocyclyl-(CH$_2$)$_p$— optionally substituted with one to three groups independently selected from halo, —NH$_2$, —OH, —CN, —CF$_3$, (C$_1$–C$_6$) alkylamino, oxo, (C$_1$–C$_6$)alkoxy, (C$_2$–C$_6$)alkenyl, (C$_2$–C$_6$)alkynyl, di(C$_1$–C$_6$)alkylamino, —C(O)R$^8$, —COOR$^8$, —C(O)NR$^8$R$^{8'}$, —NR$^8$C(O)R$^{8'}$, =NCN;
wherein $R^d$ is selected from C$_{1-5}$-alkyl, C$_{3-6}$-cycloalkyl, C$_{3-6}$-cycloalkyl-C$_{1-4}$-alkyl, C$_{1-4}$-hydroxyalkyl, C$_{1-3}$-alkoxy-C$_{1-3}$-alkyl and H; and
wherein $R^e$ is H; or where $R^d$ and $R^e$ together with the nitrogen atom form a 4–8 membered nitrogen-containing heterocyclic ring;
wherein $R^7$ is at position 6, 7 or 8; and
wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

and pharmaceutically acceptable derivatives thereof.

The invention also relates to compounds of Formula III' $R^7$ is selected from aminomethyl, aminoethyl, aminopropyl, isopropylaminomethyl, t-butylaminomethyl, isobutylaminomethyl, 1-methylpropylaminomethyl, 2-methylbutylaminomethyl, 2,2'-dimethylpropylamnomethyl, 2,2',3-trimethylpropylaminomethyl, allyl-aminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl; in conjunction with any of the above or below embodiments.

The invention also relates to compounds of Formula III' wherein $R^7$ is at position 7; in conjunction with any of the above or below embodiments.

The invention also relates to compounds of Formula III' wherein $R^2$ is 2-naphthyl, 3,4-dichlorophenyl or 3-trifluoromethylphenyl; in conjunction with any of the above or below embodiments.

The invention also relates to compounds of Formula IV'

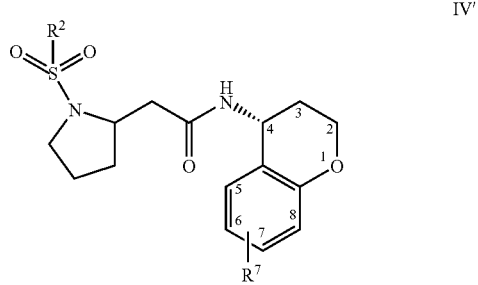

IV' wherein $R^2$ is selected from naphthyl, phenyl, pyridinyl, benzothienyl, quinolinyl and isoquinolinyl, and wherein each is optionally substituted with one to three substituents selected from chloro, fluoro, methoxy, methyl, trifluoromethyl, and phenyl; and
wherein $R^7$ is selected from

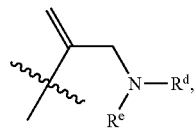

$C_{3-6}$-cycloalkyl$(C_1-C_2)$alkylamino$(C_1-C_2)$alkyl, $C_{3-6}$-cycloalkylamino$(C_1-C_2)$alkyl, $(C_1-C_2)$alkoxy$(C_1-C_2)$alkylamino$(C_1-C_2)$alkyl, mono-$C_{2-4}$-alkenylamino-$C_{1-4}$-alkyl, di-$C_{2-4}$-alkenylamino-$C_{1-4}$-alkyl, hydroxy-$C_{1-4}$-alkyl, aminocarbonyl-$C_{1-4}$-alkyl, aminocarbonyl-$C_{1-4}$-alkylamino-$C_{1-2}$-alkyl, mono-$C_{1-6}$-alkylamino-$C_{1-4}$-alkyl, di-$C_{1-4}$-alkylamino-$C_{1-4}$-alkyl and 5–8 membered heterocyclyl-$C_{1-4}$-alkyl; wherein the 5–8 membered heterocyclyl-$(CH_2)_p$— optionally substituted with one to three groups independently selected from halo, —$NH_2$, —OH, —CN, —$CF_3$, $(C_1-C_6)$alkylamino, oxo, $(C_1-C_6)$alkoxy, $(C_2-C_6)$alkenyl, $(C_2-C_6)$alkynyl, di$(C_1-C_6)$alkylamino, —C(O)$R^8$, —COOR$^8$, —C(O)NR$^8$R$^{8'}$, —NR$^8$C(O)R$^{8'}$, =NCN;

wherein $R^d$ is selected from $C_{1-5}$-alkyl, $C_{3-6}$-cycloalkyl, $C_{3-6}$-cycloalkyl-$C_{1-4}$-alkyl, $C_{1-4}$-hydroxyalkyl, $C_{1-3}$-alkoxy-$C_{1-3}$-alkyl and H; and wherein $R^e$ is H; or where $R^d$ and $R^e$ together with the nitrogen atom to which they are attached form a 4–8 membered nitrogen-containing heterocyclic ring;

wherein $R^7$ is at position 6, 7 or 8; and wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

wherein each $(C_1-C_6)$alkyl, aryl, heteroaryl, cycloalkyl and heterocyclyl, each of which is optionally substituted with one to three groups independently selected from halo, —$NH_2$, —OH, —CN, —$CF_3$, $(C_1-C_6)$alkylamino, halo$(C_1-C_6)$alkyl, oxo, $(C_1-C_6)$alkoxy, $(C_1-C_6)$alkoxy$(C_1-C_6)$alkyl, $(C_1-C_6)$alkyl, $(C_2-C_6)$alkenyl, $(C_2-C_6)$alkynyl, di$(C_1-C_6)$alkylamino, —C(O)$R^8$, —COOR$^8$, —C(O)NR$^8$R$^{8'}$, and —NR$^8$C(O)R$^{8'}$;

and pharmaceutically acceptable derivatives thereof.

The invention also relates to compounds of Formula IV' wherein $R^7$ is selected from aminomethyl, aminoethyl, aminopropyl, isopropylaminomethyl, t-butylaminomethyl, isobutylaminomethyl, 1-methylpropylaminomethyl, 2-methylbutylaminomethyl, 2,2'-dimethylpropylamnomethyl, 2,2',3-trimethylpropylaminomethyl, allyl-aminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl; in conjunction with any of the above or below embodiments.

The invention also relates to compounds of Formula IV' wherein R is at position 7; in conjunction with any of the above or below embodiments.

The invention also relates to compounds of Formula IV' wherein $R^2$ is 2-naphthyl, 3,4-dichlorophenyl or 3-trifluoromethylphenyl; in conjunction with any of the above or below embodiments.

The invention also relates to compounds of Formula V'

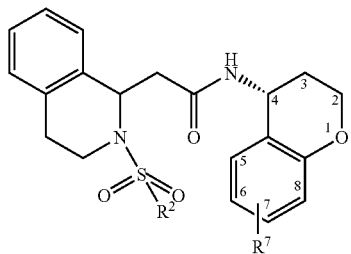

wherein $R^2$ is selected from naphthyl, phenyl, pyridinyl, benzothienyl, quinolinyl and isoquinolinyl, and wherein each is optionally substituted with one to three substituents selected from chloro, fluoro, methoxy, methyl, trifluoromethyl, and phenyl; and
wherein $R^7$ is selected from

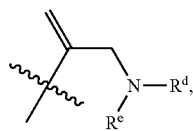

$C_{3-6}$-cycloalkyl($C_1$–$C_2$)alkylamino($C_1$–$C_2$)alkyl, $C_{3-6}$-cycloalkylamino($C_1$–$C_2$)alkyl, ($C_1$–$C_2$)alkoxy($C_1$-$c_2$) alkylamino($C_1$–$C_2$)alkyl, mono-$C_{2-4}$-alkenylamino-$C_{1-4}$- alkyl, di-$C_{2-4}$-alkenylamino-$C_{1-4}$-alkyl, hydroxy-$C_{1-4}$- alkylamino-$C_{1-4}$-alkyl, aminocarbonyl-$C_{1-4}$-alkylamino-$C_{1-2}$-alkyl, mono-$C_{1-6}$-alkylamino-$C_{1-4}$-alkyl, di-$C_{1-4}$-alkylamino-$C_{1-4}$-alkyl and 5–8 membered heterocyclyl-$C_{1-4}$-alkyl; wherein the 5–8 membered heterocyclyl-$(CH_2)_p$— optionally substituted with one to three groups independently selected from halo, —$NH_2$, —OH, —CN, —$CF_3$, ($C_1$–$C_6$)alkylamino, oxo, ($C_1$–$C_6$)alkoxy, ($C_2$–$C_6$)alkenyl, ($C_2$–$C_6$)alkynyl, di($C_1$–$C_6$)alkylamino, —C(O)$R^8$, —COO$R^8$, —C(O)NR$^8$R$^{8'}$, —NR$^8$C(O)R$^{8'}$, =NCN;
wherein $R^d$ is selected from $C_{1-5}$-alkyl, $C_{3-6}$-cycloalkyl, $C_{3-6}$-cycloalkyl-$C_{1-4}$-alkyl, $C_{1-4}$-hydroxyalkyl, $C_{1-3}$-alkoxy-$C_{1-3}$-alkyl and H; and
wherein $R^e$ is H; or where $R^d$ and $R^e$ together with the nitrogen atom to which they are attached form a 4–8 membered nitrogen-containing heterocyclic ring;
wherein $R^7$ is at position 6, 7 or 8; and
wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;
wherein each ($C_1$–$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$–$C_6$)alkylamino, halo ($C_1$–$C_6$)alkyl, oxo, ($C_1$–$C_6$)alkoxy, ($C_1$–$C_6$)alkoxy ($C_1$–$C_6$)alkyl, ($C_1$–$C_6$)alkyl, ($C_2$–$C_6$)alkenyl, ($C_2$–$C_6$) alkynyl, di($C_1$–$C_6$)alkylamino, —C(O)$R^8$, —COO$R^8$, —C(O)NR$^8$R$^{8'}$, and —NR$^8$C(O)R$^{8'}$;
and pharmaceutically acceptable derivatives thereof.

The invention also relates to compounds of Formula V' wherein $R^7$ is selected from aminomethyl, aminoethyl, aminopropyl, isopropylaminomethyl, t-butylaminomethyl, isobutylaminomethyl, 1-methylpropylaminomethyl, 2-methylbutylaminomethyl, 2,2'-dimethylpropylamnomethyl, 2,2',3-trimethylpropylaminomethyl, allyl-aminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di (isopropyl)aminomethyl, N,N-dimethylaminomethyl, N,N-diethylaminomethyl, N,N-di(t-butyl)-aminomethyl, N,N-di (allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1] heptyl, piperazin-1-ylmethyl, 4-methylpiperazin-1-ylmethyl, and 1-pyrrolidinylethylaminomethyl; in conjunction with any of the above or below embodiments.

The invention also relates to compounds of Formula V' wherein R is at position 7; in conjunction with any of the above or below embodiments.

The invention also relates to compounds of Formula V' wherein $R^2$ is 2-naphthyl, 3,4-dichlorophenyl or 3-trifluoromethylphenyl; in conjunction with any of the above or below embodiments.

A family of specific compounds of particular interest within Formula I consists of compounds and pharmaceutically-acceptable salts thereof as follows:
N-(7-Piperidin-1-ylmethyl-chroman-4-(R)-yl)-2-[1-(3-trifluoromethyl-benzenesulfonyl)-piperidin-2-yl]-acetamide;
2-[1-(Naphthalene-2-sulfonyl)-piperidin-2-yl]-N-(7-piperidin-1-ylmethyl-chroman-4-(R)-yl)-acetamide; and
2-[1-(Naphthalene-2-sulfonyl)-pyrrolidin-2-(L)-yl]-N-(7-piperidin-1-ylmethyl-chroman-4-(R)-yl)-acetamide.

A family of specific compounds of particular interest within Formula I consists of compounds and pharmaceutically-acceptable salts thereof as follows:
N-(7-Piperidin-1-ylmethyl-chroman-4-(R)-yl)-2-[1-(3-trifluoromethyl-benzenesulfonyl)-piperidin-2-yl]-acetamide;
2-[1-(Naphthalene-2-sulfonyl)-piperidin-2-yl]-N-(7-piperidin-1-ylmethyl-chroman-4-(R)-yl)-acetamide;

2-[1-(Naphthalene-2-sulfonyl)-pyrrolidin-2-(L)-yl]-N-(7-piperidin-1-ylmethyl-chroman-4-(R)-yl)-acetamide;

N-((1R)-6-(1-piperidinylmethyl)-1,2,3,4-tetrahydro-1-naphthalenyl)-2-((2S)-1-((3-(trifluoromethyl)phenyl)sulfonyl)-2;

N-((1R)-6-(((1,1-dimethylethyl)amino)methyl)-1,2,3,4-tetrahydro-1-naphthalenyl)-2-((2S)-1-((3-(trifluoromethyl)phenyl)sulfonyl)-2-piperidinyl)acetamide;

N-((1R)-6-(((1,1-dimethylethyl)amino)methyl)-1,2,3,4-tetrahydro-1-naphthalenyl)-2-((2S)-1-((4-methylphenyl)sulfonyl)-2-piperidinyl)acetamide;

2-((2S)-1-((3-chloro-4-methylphenyl)sulfonyl)-2-piperidinyl)-N-((1R)-6-(((1,1-dimethylethyl)amino)methyl)-1,2,3,4-tetrahydro-1-naphthalenyl)acetamide;

2-((2S)-1-((2,4,6-trimethylphenyl)sulfonyl)-2-piperidinyl)-N-((1R)-6-(((1,1-dimethylethyl)amino)methyl)-1,2,3,4-tetrahydro-1-naphthalenyl)acetamide;

N-((1R)-6-(1-piperidinylmethyl)-1,2,3,4-tetrahydro-1-naphthalenyl)-2-((2S)-1-((2,4,6-trimethylphenyl)sulfonyl)-1,2,3,4-tetrahydro-2-quinolinyl)acetamide;

2-((2S)-1-((3,4-dichlorophenyl)sulfonyl)-2-piperidinyl)-N-((1R)-6-(((1,1-dimethylethyl)amino)methyl)-1,2,3,4-tetrahydro-1-naphthalenyl)acetamide;

N-((1R)-6-(1-piperidinyl)methyl)-1,2,3,4-tetrahydro-1-naphthalenyl)-2-((2S)-1-((3-(trifluoromethyl)phenyl)sulfonyl)-2-piperidinyl)acetamide;

N-((1R)-6-((cyclobutylamino)methyl)-1,2,3,4-tetrahydro-1-naphthalenyl)-2-((2S)-1-((3-(trifluoromethyl)phenyl)sulfonyl)-2-piperidinyl)acetamide;

N-methyl-N-((4R)-7-(1-piperidinylmethyl)-3,4-dihydro-2H-chromen-4-yl)-2-((2S)-1-((3-(trifluoromethyl)phenyl)sulfonyl)-2-piperidinyl)acetamide;

N-((1R)-6-(((1,1-dimethylethyl)amino)methyl)-1,2,3,4-tetrahydro-1-naphthalenyl)-2-((2S)-1-((4-(1,1-dimethylethyl)phenyl)sulfonyl)-2-piperidinyl)acetamide;

N-((1R)-6-(((1,1-dimethylethyl)amino)methyl)-1,2,3,4-tetrahydro-1-naphthalenyl)-2-((2S)-1-((4-(1,1-dimethylethyl)phenyl)sulfonyl)-2-piperidinyl)acetamide;

N-((1R)-6-((diethylamino)methyl)-1,2,3,4-tetrahydro-1-naphthalenyl)-2-((2S)-1-((3-(trifluoromethyl)phenyl)sulfonyl)-2-piperidinyl)acetamide;

N-((1R)-6-(((isobutylamino)methyl)-1,2,3,4-tetrahydro-1-naphthalenyl)-2-((2S)-1-((3-(trifluoromethyl)phenyl)sulfonyl)-2-piperidinyl)acetamide;

N-((1R)-6-(((1,1-dimethylethyl)amino)methyl)-1,2,3,4-tetrahydro-1-naphthalenyl)-2-((2S)-1-((4-methyl-3-(trifluoromethyl)phenyl)sulfonyl)-2-piperidinyl)acetamide;

N-((1R)-6-((cyclopropylamino)methyl)-1,2,3,4-tetrahydro-1-naphthalenyl)-2-((2S)-1-((3-(trifluoromethyl)phenyl)sulfonyl)-2-piperidinyl)acetamide;

N-((1R)-6-(((2-methylbutyl)amino)methyl)-1,2,3,4-tetrahydro-1-naphthalenyl)-2-((2S)-1-((3-(trifluoromethyl)phenyl)sulfonyl)-2-piperidinyl)acetamide;

N-((1R)-6-(((2-(methyloxy)ethyl)amino)methyl)-1,2,3,4-tetrahydro-1-naphthalenyl)-2-((2S)-1-((3-(trifluoromethyl)phenyl)sulfonyl)-2-piperidinyl)acetamide;

N-((1R)-6-(((cyclopropylmethyl)amino)methyl)-1,2,3,4-tetrahydro-1-naphthalenyl)-2-((2S)-1-((3-(trifluoromethyl)phenyl)sulfonyl)-2-piperidinyl)acetamide;

N-((1R)-6-(((isopropylmethyl)amino)methyl)-1,2,3,4-tetrahydro-1-naphthalenyl)-2-((2S)-1-((3-(trifluoromethyl)phenyl)sulfonyl)-2-piperidinyl)acetamide;

N-((1R)-6-((4-fluoro-1-piperidinyl)methyl)-1,2,3,4-tetrahydro-1-naphthalenyl)-2-((2S)-1-((3-(trifluoromethyl)phenyl)sulfonyl)-2-piperidinyl)acetamide;

N-((1R)-6-(((1,1-dimethylethyl)amino)methyl)-1,2,3,4-tetrahydro-1-naphthalenyl)-2-((2R/S)-1-((3-(trifluoromethyl)phenyl)sulfonyl)-1,2,3,4-tetrahydro-2-quinolinyl)acetamide;

N-((1R)-6-((4-fluoro-1-piperidinyl)methyl)-1,2,3,4-tetrahydro-1-naphthalenyl)-2-((2R/S)-1-((3-(trifluoromethyl)phenyl)sulfonyl)-1,2,3,4-tetrahydro-2-quinolinyl)acetamide;

N-((1R)-6-((((cyclopropylmethyl)amino)methyl)-1,2,3,4-tetrahydro-1-naphthalenyl)-2-((2R/S)-1-((3-(trifluoromethyl)phenyl)sulfonyl)-1,2,3,4-tetrahydro-2-quinolinyl)acetamide;

N-((1R)-6-(((isopropylmethyl)amino)methyl)-1,2,3,4-tetrahydro-1-naphthalenyl)-2-((2R/S)-1-((3-(trifluoromethyl)phenyl)sulfonyl)-1,2,3,4-tetrahydro-2-quinolinyl)acetamide;

N-((1R)-6-(((isobutylmethyl)amino)methyl)-1,2,3,4-tetrahydro-1-naphthalenyl)-2-((2R/S)-1-((3-(trifluoromethyl)phenyl)sulfonyl)-1,2,3,4-tetrahydro-2-quinolinyl)acetamide;

N-((1R)-6-(((diethylamino)methyl)-1,2,3,4-tetrahydro-1-naphthalenyl)-2-((2R/S)-1-((3-(trifluoromethyl)phenyl)sulfonyl)-1,2,3,4-tetrahydro-2-quinolinyl)acetamide;

N-((1R)-6-((4-fluoro-1-piperidinyl)methyl)-1,2,3,4-tetrahydro-1-naphthalenyl)-2-((2R)-1-((4-methylphenyl)sulfonyl)-1,2,3,4-tetrahydro-2-quinolinyl)acetamide;

2-((2R/S)-1-((4-methylphenyl)sulfonyl)-1,2,3,4-tetrahydro-2-quinolinyl)-N-((1R)-6-(((2-methylpropyl)amino)methyl)-1,2,3,4-tetrahydro-1-naphthalenyl)acetamide;

N-((1R)-6-(((2,2-dimethylpropyl)amino)methyl)-1,2,3,4-tetrahydro-1-naphthalenyl)-2-((2S)-1-((3-(trifluoromethyl)phenyl)sulfonyl)-2-piperidinyl)acetamide;

2-((2S)-1-(1-benzothien-3-ylsulfonyl)-2-piperidinyl)-N-((1R)-6-(((1,1-dimethylethyl)amino)methyl)-1,2,3,4-tetrahydro-1-naphthalenyl)acetamide;

2-((2S)-1-(1-benzothien-3-ylsulfonyl)-2-piperidinyl)-N-((1R)-6-(((2,2-dimethylpropyl)amino)methyl)-1,2,3,4-tetrahydro-1-naphthalenyl)acetamide;

1-(((5R)-5-((((2S)-1-((3-(trifluoromethyl)phenyl)sulfonyl)-2-piperidinyl)acetyl)amino)-5,6,7,8-tetrahydro-2-naphthalenyl)methyl)-3-piperidinecarboxamide;

N-((4R)-7-(4-morpholinylmethyl)-3,4-dihydro-2H-chromen-4-yl)-2-((1S)-2-((3-(trifluoromethyl)phenyl)sulfonyl)-1,2,3,4-tetrahydro-1-isoquinolinyl)acetamide;

N-((4R)-7-(7-azabicyclo[2.2.1]hept-7-ylmethyl)-3,4-dihydro-2H-chromen-4-yl)-2-((1S)-2-((3-(trifluoromethyl)phenyl) sulfonyl)-1,2,3,4-tetrahydro-1-isoquinolinyl)acetamide;

N-((4R)-7-(1-Piperidinylmethyl)-3,4-dihydro-2H-chromen-4-yl)-2-((1R)-2-((3-(trifluoromethyl)phenyl)sulfonyl)-1,2,3,4-tetrahydro-1-isoquinolinyl)acetamide;

N-((4R)-7-((4-Fluoro-1-piperidinyl)methyl)-3,4-dihydro-2H-chromen-4-yl)-2-((2S)-1-((3-(trifluoromethyl)phenyl)sulfonyl)-2-pyrrolidinyl)acetamide;

N-((4R)-7-((4,4-Difluoro-1-piperidinyl)methyl)-3,4-dihydro-2H-chromen-4-yl)-2-((2S)-1-((3-(trifluoromethyl)phenyl) sulfonyl)-2-pyrrolidinyl)acetamide;

2-((2S)-1-(2-Naphthalenylsulfonyl)-2-piperidinyl)-N-((4R)-7-(1-piperidinylmethyl)-3,4-dihydro-2H-chromen-4-yl)acetamide;

N-((4R)-6-chloro-7-(1-piperidinylmethyl)-3,4-dihydro-2H-chromen-4-yl)-2-((2S)-1-((3-(trifluoromethyl)phenyl) sulfonyl)-2-pyrrolidinyl)acetamide;

N-((4R)-7-(1-Piperidinylmethyl)-3,4-dihydro-2H-chromen-4-yl)-2-((3R)-2-((3-(trifluoromethyl)phenyl)sulfonyl)-1,2,3,4-tetrahydro-3-isoquinolinyl)acetamide;

N-((4R)-7-(1-Piperidinylmethyl)-3,4-dihydro-2H-chromen-4-yl)-2-((1S)-2-((3-(trifluoromethyl)phenyl)sulfonyl)-1,2,3,4-tetrahydro-1-isoquinolinyl)acetamide;

N-((4R)-7-(4-Morpholinylmethyl)-3,4-dihydro-2H-chromen-4-yl)-2-((1S)-2-((3-(trifluoromethyl)phenyl)sulfonyl)-1,2,3,4-tetrahydro-1-isoquinolinyl)acetamide;

N-((4R)-7-(7-Azabicyclo[2.2.1]hept-7-ylmethyl)-3,4-dihydro-2H-chromen-4-yl)-2-((1S)-2-((3-(trifluoromethyl)phenyl)sulfonyl)-1,2,3,4-tetrahydro-1-isoquinolinyl)acetamide;

N-((4R)-7-(1-Piperidinylmethyl)-3,4-dihydro-2H-chromen-4-yl)-2-((2S)-1-((3-(trifluoromethyl)phenyl)sulfonyl)-2-piperidinyl)acetamide;

N-((4R)-7-(1-Piperidinylmethyl)-3,4-dihydro-2H-chromen-4-yl)-2-((2R)-1-((3-(trifluoromethyl)phenyl)sulfonyl)-2-piperidinyl)acetamide;

N-((1R)-6-((1S)-1-methyl-2-(1-piperidinyl)ethyl)-1,2,3,4-tetrahydro-1-naphthalenyl)-2-((2S)-1-((3-(trifluoromethyl)phenyl)sulfonyl)-2-piperidinyl)acetamide; and N-((1R)-6-(1-(1-piperidinylmethyl)ethenyl)-1,2,3,4-tetrahydro-1-naphthalenyl)-2-((2S)-1-((3-(trifluoromethyl)phenyl)sulfonyl)-2-piperidinyl)acetamide.

Indications

The present invention also provides methods of using the compounds in for the treatment of a disorder such as acute pain, dental pain, back pain, lower back pain, pain from trauma, surgical pain, pain resulting from amputation or abscess, causalgia, fibromyalgia, demyelinating diseases, trigeminal neuralgia, cancer, chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, tension headache, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, sympathetically maintained pain, deafferentation syndromes, asthma, vasomotor or allergic rhinitis, epithelial tissue damage or dysfunction, herpes simplex, post-herpetic neuralgia, disturbances of visceral motility at respiratory, genitourinary, gastrointestinal or vascular regions, wounds, burns, allergic skin reactions, pruritis, vitiligo, general gastrointestinal disorders, colitis, inflammatory bowel disease, gastric ulceration, duodenal ulcers, thalamic pain syndrome, diabetes, toxins and chemotherapy, septic shock, and bronchial disorders.

The invention also provides for the use of the compounds of the present invention for the prevention or for the treatment of a disorder such as acute pain, dental pain, back pain, lower back pain, pain from trauma, surgical pain, pain resulting from amputation or abscess, causalgia, fibromyalgia, demyelinating diseases, trigeminal neuralgia, cancer, chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, tension headache, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, sympathetically maintained pain, deafferentation syndromes, asthma, vasomotor or allergic rhinitis, epithelial tissue damage or dysfunction, herpes simplex, post-herpetic neuralgia, disturbances of visceral motility at respiratory, genitourinary, gastrointestinal or vascular regions, wounds, burns, allergic skin reactions, pruritis, vitiligo, general gastrointestinal disorders, colitis, inflammatory bowel disease, gastric ulceration, duodenal ulcers, thalamic pain syndrome, diabetes, toxins and chemotherapy, septic shock, and bronchial disorders.

Accordingly, the present invention also relates to the use of one or more of the compounds of the present invention in the manufacture of a medicament for the treatment of a disorder such as acute pain, dental pain, back pain, lower back pain, pain from trauma, surgical pain, pain resulting from amputation or abscess, causalgia, fibromyalgia, demyelinating diseases, trigeminal neuralgia, cancer, chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, tension headache, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, sympathetically maintained pain, deafferentation syndromes, asthma, vasomotor or allergic rhinitis, epithelial tissue damage or dysfunction, herpes simplex, post-herpetic neuralgia, disturbances of visceral motility at respiratory, genitourinary, gastrointestinal or vascular regions, wounds, burns, allergic skin reactions, pruritis, vitiligo, general gastrointestinal disorders, colitis, inflammatory bowel disease, gastric ulceration, duodenal ulcers, thalamic pain syndrome, diabetes, toxins and chemotherapy, septic shock, and bronchial disorders.

The compounds of this invention may also act as inhibitors of other receptors or kinases, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

DEFINITIONS

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective pain therapeutic agents relieve the pain sensation of the patient. Alternatively, effective therapeutic agents for the treatment of inflammation minimize the damage from the inflammation, and the like.

The term "treatment" includes therapeutic treatment as well as prophylactic treatment (either preventing the onset of disorders altogether or delaying the onset of a preclinically evident stage of disorders in individuals).

The term "H" denotes a single hydrogen atom. This radical may be attached, for example, to an oxygen atom to form a hydroxyl radical.

Where the term "alkyl" is used, either alone or within other terms such as "haloalkyl", "cyanoalkyl" and "alkylamino", it embraces linear or branched radicals having one to about twenty carbon atoms or, preferably, one to about twelve carbon atoms, or as otherwise indicated. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. Even more preferred are lower alkyl radicals having one to four carbon atoms. The term "alkylenyl" embraces bridging divalent alkyl radicals such as methylenyl and ethyleneyl.

The term "alkenyl" embraces linear or branched radicals having at least one carbon-carbon double bond of two to about twenty carbon atoms or, preferably, two to about twelve carbon atoms, or as otherwise indicated. More preferred alkenyl radicals are "lower alkenyl" radicals having two to about four carbon atoms. Examples of alkenyl radicals include ethenyl, 2-propenyl, allyl, butenyl and 4-methylbutenyl. The terms "alkenyl" and "lower alkenyl", embrace radicals having "cis" and "trans" orientations, or alternatively, "E" and "Z" orientations.

The term "alkynyl" embraces linear or branched radicals having at least one carbon-carbon triple bond of two to about twenty carbon atoms or, preferably, two to about twelve carbon atoms, or as otherwise indicated. More preferred alkynyl radicals are "lower alkynyl" radicals having two to about four carbon atoms. Examples of alkynyl radicals include ethynyl, 2-propynyl, and 4-methylbutynyl.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. The "alkoxy" radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy, and fluoropropoxy.

The term "alkoxyalkyl" embraces linear or branched alkyl radicals having one to about ten carbon atoms any one of which may be substituted with one or more alkoxyl radicals. More preferred alkoxyalkyl radicals are "lower alkoxyalkyl" radicals repectively having one to six carbon atoms. Examples of such radicals include methoxymethyl, methoxyethyl, and the like. Even more preferred are lower alkoxyalkyl radicals respectivly having one to three carbon atoms alkyl radicals.

The term "aryl", alone or in combination, means a carbocyclic aromatic system containing one or two rings wherein such rings may be attached together in a pendent manner or may be fused. The term "aryl" embraces aromatic radicals such as phenyl, naphthyl, tetrahydronaphthyl, indane and biphenyl. More preferred aryl is phenyl. Said "aryl" group may have 1 to 3 substituents such as lower alkyl, hydroxyl, halo, haloalkyl, nitro, cyano, alkoxy, and lower alkylamino. Benzodioxolyl is considered aryl.

The term "heterocyclyl" embraces saturated, partially saturated and unsaturated heteroatom-containing ring radicals, where the heteroatoms may be selected from nitrogen, sulfur and oxygen. It does not include rings containing —O—O— or —S—S— portions. Said "heterocyclyl" group may have 1 to 3 substituents such as hydroxyl, halo, haloalkyl, cyano, lower alkyl, lower aralkyl, oxo, lower alkoxy, amino, and lower alkylamino.

Examples of saturated heterocyclic radicals include saturated 3 to 8-membered heteromonocyclic group containing 1 to 4 nitrogen atoms [e.g. pyrrolidinyl, imidazolidinyl, piperidino, piperazinyl]; saturated 3 to 8-membered heteromonocyclic group containing 1 to 2 oxygen atoms and 1 to 3 nitrogen atoms [e.g. morpholinyl]; saturated 3 to 8-membered heteromonocyclic group containing 1 to 2 sulfur atoms and 1 to 3 nitrogen atoms [e.g., thiazolidinyl]. Examples of partially saturated heterocyclyl radicals include dihydrothiophene, dihydropyran, dihydrofuran and dihydrothiazole.

Examples of unsaturated heterocyclic radicals, also termed "heteroaryl" radicals, include unsaturated 5 to 6 membered heteromonocyclyl groups containing 1 to 4 nitrogen atoms, for example, pyrrolyl, pyrrolinyl, imidazolyl, pyrazolyl, 2-pyridinyl, 3-pyridinyl, 4-pyridinyl, pyrimidinyl, pyrazinyl, pyridazinyl, triazolyl [e.g., 4H-1,2,4-triazolyl, 1H-1,2,3-triazolyl, 2H-1,2,3-triazolyl]; unsaturated 3 to 6-membered heteromonocyclic group containing an oxygen atom, for example, pyranyl, 2-furyanl, 3-furyanl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolinyl, isoindolinyl, indolizinyl, benzimidazolyl, quinolinyl, isoquinolinyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl].

The term also includes bridged, spiro and oxo-containing heterocyclic rings, such as 1,4-dioxa-8-aza-spiro[4.5]decyl, phthalimidyl, 1,4-dioxa-8-aza-spiro[4.5]decyl, and (1-azabicyclo[2.2.2]oct-3-yl).

Preferred heterocyclic radicals include five to ten membered fused or unfused radicals. More preferred examples of heteroaryl radicals include quinolinyl, isoquinolinyl, imidazolyl, pyridinyl, thienyl, thiazolyl, oxazolyl, furanyl, and pyrazinyl. Even more preferred heteroaryl radicals are 5- or 6-membered heteroaryl, containing one or two heteroatoms selected from sulfur, nitrogen and oxygen, selected from thienyl, furanyl, pyrrolyl, thiazolyl, oxazolyl, imidazolyl, pyrazolyl, isoxazolyl, isothiazolyl, pyridinyl, piperidinyl and pyrazinyl.

The term "sulfonyl", whether used alone or linked to other terms such as alkylsulfonyl, denotes respectively divalent radicals —$SO_2$—.

The terms "sulfamyl," "aminosulfonyl" and "sulfonamidyl," whether alone or used with terms such as "N-alkylaminosulfonyl", "N-arylaminosulfonyl", "N,N-dialkylaminosulfonyl" and "N-alkyl-N-arylaminosulfonyl", denotes a sulfonyl radical substituted with an amine radical, forming a sulfonamide (—$SO_2NH_2$).

The term "cycloalkylaminoalkyl" includes "N-cycloalkylaminoalkyl" and "N,N-dicycloalkylaminoalkyl" where alkyl radicals are independently substituted, respectively, with one cycloalkyl radical, or two cycloalkyl radicals. More preferred cycloalkylaminoalkyl radicals are "lower cycloalkylaminoalkyl" radicals having alkyl radicals with one to six carbon atoms. Even more preferred are lower cycloalkylaminoalkyl radicals having alkyl radicals with one to three carbon atoms. Examples of such lower alkylaminosulfonyl radicals include N-cyclohexylaminomethyl, and N-cyclopentylaminoethyl.

The term "cycloalkyl-alkylaminoalkyl" embraces cycloalkyl radicals as described above, attached to an alkylaminoalkyl radical. More preferred are lower cycloalkylalkylaminoalkyl radicals independently having alkyl radicals of one to three carbon atoms.

The term "N-arylaminoalkyl" denotes alkyl radicals substituted with an aryl radical. More preferred arylaminoalkyl radicals are "lower N-arylaminoalkyl" radicals having alkyl radicals of one to six carbon atoms. Even more preferred are phenylaminoalkyl radicals having one to three carbon atoms. Examples of such radicals include N-phenylaminomethyl and N-phenylaminoethyl.

The term "aralkylaminoalkyl" embraces aralkyl radicals as described above, attached to an aminoalkyl radical. More preferred are lower arylalkylaminoalkyl radicals independently having alkyl radicals of one to three carbon atoms.

The term "heterocyclylaminoalkyl" embraces heterocyclyl radicals as described above, attached to an aminoalkyl radical.

The term "heteroarylalkylaminoalkyl" embraces heteroarylalkyl radicals as described above, attached to an aminoalkyl radical. More preferred are lower heteroarylalkylaminoalkyl radicals having, independently, alkyl radicals of one to three carbon atoms.

The terms "carboxy" or "carboxyl", whether used alone or with other terms, such as "carboxyalkyl", denotes —$CO_2H$.

The term "carbonyl", whether used alone or with other terms, such as "aminocarbonyl", denotes —(C=O)—.

The terms "alkylcarbonyl" denotes carbonyl radicals which have been substituted with an alkyl radical. More preferred are "lower alkylcarbonyl" having lower alkyl radicals as described above attached to a carbonyl radical.

The terms "arylcarbonyl" denotes carbonyl radicals substituted with an aryl radical. More preferred are "optionally substituted phenylcarbonyl" radicals.

The terms "cycloalkylcarbonyl" denotes carbonyl radicals substituted with an cycloalkyl radical. More preferred are "optionally substituted cycloalkylcarbonyl" radicals, even more preferably containing $C_{3-6}$ cycloalkyl.

The terms "heterocyclylcarbonyl" denotes carbonyl radicals substituted with an heterocyclyl radical. More preferred are "optionally substituted 5–6 membered heterocyclylcarbonyl" radicals.

The term "aminocarbonyl" when used by itself or with other terms such as "aminocarbonylalkyl", "N-alkylaminocarbonyl", "N-arylaminocarbonyl", "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula $H_2NC(=O)$—.

The terms "N-alkylaminocarbonyl", and "N,N-dialkylaminocarbonyl" denote aminocarbonyl radicals which have been substituted with one alkyl radical and independently with two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces aminoalkyl radicals having the nitrogen atom independently substituted with an alkyl radical. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "heterocyclylalkyl" embraces heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkyl radicals having alkyl portions of one to three carbon atoms. Examples include such radicals as pyridinylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are lower aralkyl radicals phenyl attached to alkyl portions having one to three carbon atoms. Examples of such radicals include benzyl, diphenylmethyl and phenylethyl. The aryl in said aralkyl may be additionally substituted with halo, alkyl, alkoxy, haloalkyl and haloalkoxy.

The term "arylalkenyl" embraces aryl-substituted alkenyl radicals. Preferable arylalkenyl radicals are "lower arylalkenyl" radicals having aryl radicals attached to alkenyl radicals having two to six carbon atoms. Examples of such radicals include phenylethenyl. The aryl in said arylalkenyl may be additionally substituted with halo, alkyl, alkoxy, haloalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, ($CH_3S$—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylsulfinyl" embraces radicals containing a linear or branched alkyl radical, of one to ten carbon atoms, attached to a divalent —S(=O)— atom. More preferred are lower alkylsulfinyl radicals having one to three carbon atoms.

The term "arylsulfinyl" embraces radicals containing an aryl radical, attached to a divalent —S(=O)— atom. Even more preferred are optionally substituted phenylsulfinyl radicals.

The term "haloalkylsulfinyl", embraces radicals containing a haloalkyl radical, of one to ten carbon atoms, attached to a divalent —S(=O)— atom. Even more preferred are lower haloalkylsulfinyl radicals having one to three carbon atoms.

The term "alkylamino" denotes amino groups which have been substituted with one alkyl radical and with two alkyl radicals, including terms "N-alkylamino" and "N,N-dialkylamino". More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable "alkylamino" may be mono or dialkylamino such as N-methylamino, N-ethylamino, N,N-dimethylamino, N,N-diethylamino and the like.

The term "arylamino" denotes amino groups which have been substituted with one or two aryl radicals, such as N-phenylamino. The "arylamino" radicals may be further substituted on the aryl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "aralkylamino" denotes amino groups which have been substituted with one or two aralkyl radicals. More preferred are phenyl-$C_1$–$C_3$-alkylamino radicals, such as N-benzylamino. The "aralkylamino" radicals may be further substituted on the aryl ring portion of the radical.

The term "alkylaminoalkylamino" denotes alkylamino groups which have been substituted with one or two alkylamino radicals. More preferred are $C_1$–$C_3$-alkylamino–$C_1$–$C_3$-alkylamino radicals.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals independently having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminoethoxymethoxy, N,N-dimethylaminoethoxymethoxy, N,N-diethylaminomethoxymethoxy, and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "aminoalkoxy" embraces alkoxy radicals substituted with an amino radical. More preferred aminoalkoxy radicals are "lower aminoalkoxy" radicals having alkoxy radicals of one to six carbon atoms. Suitable aminoalkoxy radicals may be aminoethoxy, aminomethoxy, aminopropoxy and the like.

The terms "N-aralkyl-N-alkylamino" and "N-alkyl-N-arylamino" denote amino groups which have been substituted with one aralkyl and one alkyl radical, or one aryl and one alkyl radical, respectively, to an amino group.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$–$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heterocyclyloxy" embraces optionally substituted heterocyclyl radicals, as defined above, attached to an oxygen atom. Examples of such radicals include piperidyloxy.

The term "heterocyclylalkoxy" embraces oxy-containing heterocyclylalkyl radicals attached through an oxygen atom to other radicals. More preferred heterocyclylalkoxy radicals are "lower heteroarylalkoxy" radicals having optionally substituted heteroaryl radicals attached to lower alkoxy radical as described above.

The term "heterocyclyloxyalkyl" embraces heteroaryl radicals attached through an ether oxygen atom to an alkyl radical. More preferred heterocyclyloxyalkyl radicals are "lower heteroaryloxyalkyl" radicals having optionally substituted heteroaryl radicals attached to an —O—$C_{1-6}$ alkyl radical.

The term "cycloalkyl" includes saturated carbocyclic groups. Preferred cycloalkyl groups include $C_3$–$C_6$ rings. More preferred compounds include cyclopentyl, cyclopropyl, and cyclohexyl.

The term "cycloalkenyl" includes carbocyclic groups have one or more carbon-carbon double bonds. "Cycloalkenyl" and "cycloalkyldienyl" compounds are included. Preferred cycloalkenyl groups include $C_3$–$C_6$ rings. More preferred compounds include, for example, cyclopentenyl, cyclopentadienyl, cyclohexenyl and cycloheptadienyl.

The term "basic moiety" or "basic moieties" means a chemical moiety that has a measured or calculated $pK_a$ of from about 7 to about 13. The term also can include a chemical moiety that is protonable, to some extent, between a pH range of from about 7 to about 10. Examples of basic moieties include, but are not limited to, cycloalkylaminoalkyl, cycloalkylalkylaminoalkyl, heteroarylaminoalkyl, heteroarylalkylaminoalkyl, arylaminoalkyl, arylalkylaminoalkyl, $C_{1-6}$-alkylamino-$C_{1-6}$-alkoxy, $C_{1-6}$-alkylamino-$C_{1-6}$-alkoxy-$C_{1-6}$-alkoxy, aminoalkoxy, aminoalkyl, alkylaminoalkyl, 5–6 membered heterocyclyloxy, 5–6 membered nitrogen-containing heterocyclyl, 5–7 membered nitrogen-containing heterocyclyl-alkyl, $NH_2$; and more preferably aminomethyl, isopropylaminomethyl, t-butylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, 1-piperidinylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl and 4-methylpiperazin-1-ylmethyl. Each basic moiety can be optionally substituted with one to three groups independently selected from halo, —$NH_2$, —OH, —CN, —$CF_3$, ($C_1$–$C_6$)alkylamino, haloalkyl, oxo, ($C_1$–$C_6$)alkoxy, ($C_1$–$C_6$)alkoxyalkyl, ($C_2$–$C_6$)alkenyl, ($C_2$–$C_6$)alkynyl, di($C_1$–$C_6$)alkylamino, —C(O)$R^8$, —COO$R^8$, —C(O)$NR^8R^{8'}$, —$NR^8C(O)R^{8'}$, =NCN; and ($C_1$–$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$–$C_6$)alkylamino, haloalkyl, oxo, ($C_1$–$C_6$)alkoxy, ($C_1$–$C_6$)alkoxyalkyl, ($C_1$–$C_6$)alkyl, ($C_2$–$C_6$)alkenyl, ($C_2$–$C_6$)alkynyl, di($C_1$–$C_6$)alkylamino, —C(O)$R^8$—COO$R^8$, —C(O)$NR^8R^{8'}$, and —$NR^8C(O)R^{8'}$.

The term "comprising" is meant to be open ended, including the indicated component but not excluding other elements.

The present invention preferably includes compounds that antagonize bradykinin 1.

The present invention also comprises the use of a compound of the invention, or pharmaceutically acceptable salt thereof, in the manufacture of a medicament for the treatment either acutely or chronically of pain or an inflammation mediated disease state, including those described previously. The compounds of the present invention are also useful in the manufacture of an anti-inflmmatory medicament. The compounds of the present invention are also useful in the manufacture of a medicament to attenuate or prevent disorders through inhibition of bradykinin 1. The compounds of the present invention are also useful in the manufacture of a medicament to treat pain.

The present invention comprises a pharmaceutical composition comprising a therapeutically-effective amount of a compound of Formulas I–VI in association with at least one pharmaceutically-acceptable carrier, adjuvant or diluent.

COMBINATIONS

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

The present compounds may also be used in combination therapies with opioids and other anti-pain analgesics, including narcotic analgesics, Mu receptor antagonists, Kappa receptor antagonists, non-narcotic (i.e. non-addictive) analgesics, monoamine uptake inhibitors, adenosine regulating agents, cannabinoid derivatives, Substance P antagonists, neurokinin-1 receptor antagonists, COX-2 inhibitors such as celecoxib, rofecoxib, valdecoxib, parecoxib, and darecoxib, NSAID's, and sodium channel blockers, among others. More preferred would be combinations with compounds selected from morphine, meperidine, codeine, pentazocine, buprenorphine, butorphanol, dezocine, meptazinol, hydrocodone, oxycodone, methadone, tetrahydrocannibinol, pregabalin, Tramadol [(+) enantiomer], DuP 747, Dynorphine A, Enadoline, RP-60180, HN-11608, E-2078, ICI-204448, acetominophen (paracetamol), propoxyphene, nalbuphine, E-4018, filenadol, mirtentanil, amitriptyline, DuP631, Tramadol [(−) enantiomer], GP-531, acadesine, AKI-1, AKI-2, GP-1683, GP-3269, 4030W92, tramadol racemate, Dynorphine A, E-2078, AXC3742, SNX-111, ADL2-1294, ICI-204448, CT-3, CP-99,994, and CP-99,994.

Alternatively, the present compounds may also be used in co-therapies with other treatments for inflammation, e.g. steroids, NSAIDs, iNOS inhibitors, p38 inhibitors, TNF inhibitors, 5-lipoxygenase inhibitors, $LTB_4$ receptor antagonists and $LTA_4$ hydrolase inhibitors.

The present invention comprises a process for the preparation of a compound of Formula I–VI and I'–VI'.

Compounds of the present invention can possess, in general, one or more asymmetric carbon atoms and are thus capable of existing in the form of optical isomers as well as in the form of racemic or non-racemic mixtures thereof. Unless otherwise indicated, the compounds of the present invention, as depicted or named, may exist as the racemate, a single enantiomer, or any uneven (i.e. non 50/50) mixture of enantiomers. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column, such as, for example, a CHIRAL-AGP column, optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

Compounds of the present invention can possess, in general, tautomeric forms, which are included in the family of compounds in Formula I–VI and I'–VI'.

Also included in the family of compounds of Formula I–VI are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I–VI and I'–VI' may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxyethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of Formula I–VI and I'–VI' include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethylmorpholine, piperazine, piperidine, triethylamine, trimethylamine. All of these salts may be prepared by conventional means from the corresponding compound of the invention by reacting, for example, the appropriate acid or base with the compound of Formula I–VI.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as HCl, $H_2SO_4$ and $H_3PO_4$ and such organic acids as oxalic acid, maleic acid, succinic acid and citric acid. Other examples include salts with alkali metals or alkaline earth metals, such as sodium, potassium, calcium or magnesium or with organic bases.

GENERAL SYNTHETIC PROCEDURES

The compounds of the invention can be synthesized according to the following procedures of Schemes 1–8, wherein the substituents are as defined for Formulas I–VI and I'–VI', above, except where further noted.

The following abbreviations are used:

| | |
|---|---|
| AcOH, HOAc | acetic acid |
| $CH_3CN$ | acetonitrile |
| $NH_3$ | ammonia |
| $NH_4Cl$ | ammonium chloride |
| $NH_4OH$ | ammonium hydroxide |
| $(PPh_3)_2NiBr_2$ | bis(triphenylphosphine)nickel(II) bromide |
| $BH_3$ | borane |
| $BH_3DMS$ | borane dimethylsulfide complex |
| $Br_2$ | bromine |
| BMS | borane-methyl sulfide complex |
| $BH_3$-$SMe_2$ | borane-methyl sulfide complex |
| Boc | N-tert-butoxycarbonyl |
| $Boc_2O$ | Boc anhydride |
| $CHCl_3$ | chloroform |
| CBS | (R)-2-methyl-CBS-oxazaborolidine |
| DBU | 1,8-diazabicyclo[5.4.0]undec-7-ene |
| DEAD | diethyl azodicarboxylate |
| DIAD | diisopropyl azodicarboxylate |
| $CH_2Cl_2$ | dichloromethane |
| $Et_2O$ | diethyl ether |
| DMAP | 4-(dimethylamino)pyridine |
| DIPEA, DIEA | diisopropylethylamine |
| DIBALH | diisobutylaluminum hydride |
| $Me_2NH$ | dimethylamine |
| DPPA, dppa | diphenylphosphoryl azide |
| DMF | dimethylformamide |
| DMSO | dimethyl sulfoxide (also known as methyl sulfoxide) |
| EtOAc | ethyl acetate |
| EDC, EDCI | (3-dimethylamino-propyl)-ethyl carbodiimide-HCl salt |
| EtOH | ethanol |
| HCOOH | formic acid |
| g | gram |
| h | hour |
| HATU | O-(7-azabenzotriazol-1-yl)-N,N,N',N'-tetramethyluronium hexafluorophosphate |
| HCl | hydrochloric acid |
| $H_2$ | hydrogen |
| HOBt | 1-hydroxybenzotriazole |
| $NH_2OH$ | hydroxylamine |
| $H_3PO_4$ | phosphoric acid |
| $H_2SO_4$ | sulfuric acid |
| IPrOH, IPA | isopropanol |
| $K_2CO_3$ | potassium carbonate |
| LAH | lithium aluminum hydride |
| $LiBH_4$ | lithium borohydride |

| | |
|---|---|
| LDA | lithium diisopropylamide |
| MnO2 | manganese oxide |
| MeOH | methanol |
| MsCl | mesyl chloride |
| Ms$_2$O | methanesulfonic anhydride |
| MeMgBr | methylmagnesium bromide |
| MeAlClNH$_2$ | methylchloroaluminum amide |
| mL | milliliter |
| min | minutes |
| MgSO$_4$ | magnesium sulfate |
| MeI | methyliodide |
| Ni—Al | Raney nickel |
| N$_2$ | nitrogen |
| NMM | N-methylmorpholine |
| NMO | 4-methylmorpholine N-oxide |
| OsO$_4$ | osmium tetroxide |
| Pd/C | palladium on carbon |
| Pd(OH)$_2$ | paladdium hydroxide |
| Pd$_2$(dba)$_3$ | tris(dibenzylideneacetone)dipalladium |
| KCN | potassium cyanide |
| KOH | potassium hydroxide |
| RT | room temperature |
| SiO$_2$ | silica |
| NaOAc | sodium acetate |
| NaN$_3$ | sodium azide |
| NaHCO$_3$ | sodium bicarbonate |
| NaBH$_4$ | soduim borohydride |
| NaIO$_4$ | sodium periodate |
| NaH | sodium hydride |
| Na$_2$CO$_3$ | sodium carbonate |
| NaBH(OAc)$_3$ | sodium triacetoxyborohydride |
| NaOH | sodium hydroxide |
| SOCl$_2$ | thionyl chloride |
| TBDPSCl | tert-butyldiphenylchlorosilane |
| TBAF | tetrabutylammonium fluoride |
| Tf$_2$O | trifluoromethanesulfonic anhydride |
| TFA | trifluoroacetic acid |
| THF | tetrahydrofuran |
| TEA, Et$_3$N | triethylamine |
| Me$_3$Al | trimethylaluminum |
| PPh$_3$ | triphenylphosphine |
| TBu3P | tri(tert-butyl)phosphine |
| H$_2$O | water |

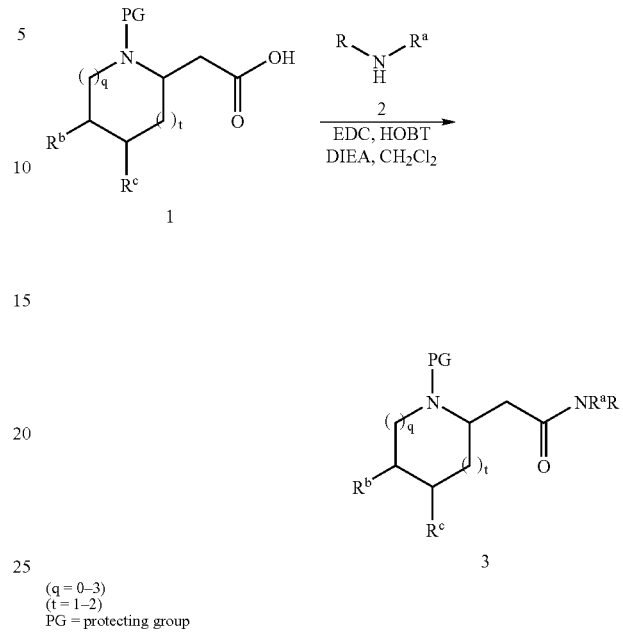

Scheme 1

(q = 0–3)
(t = 1–2)
PG = protecting group

Compounds of Formula I may be prepared in a convergent manner as described in Scheme 1. Acids 1 are coupled with the substituted amine 2 using standard peptide coupling conditions, such as with HOBT, EDC, and DIEA in a solvent, such as CH$_2$Cl$_2$, and reacted at RT, to afford the substituted amide 3. The acids 1 are commercially available or may be prepared by literature methods (for example, by the method described by Dieter et. al., Liebigs Annalen/ Recueil, 4:699–706; 1997). Similarly, substituted amine 2 are either commercially available, can be prepared via literature methods, or may be prepared following literature methods described for analogous compounds. Some of these methods are illustrated in the subsequent schemes. Alternatively, substituted amide 3 is an intermediate to the compounds of Formula I. Protective groups employed in compounds 3 can be removed to provide deprotected compounds of Formula I.

Scheme 2

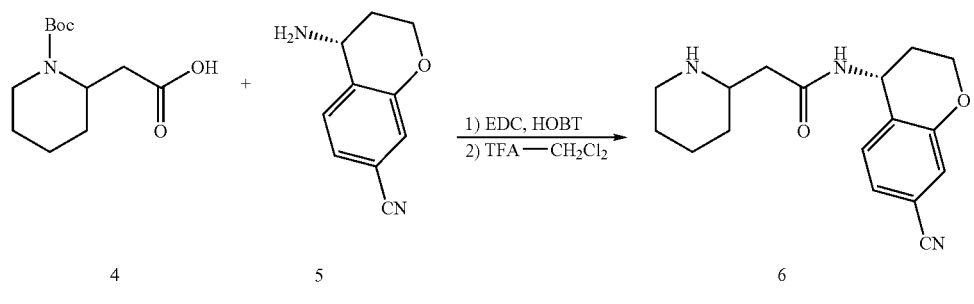

-continued

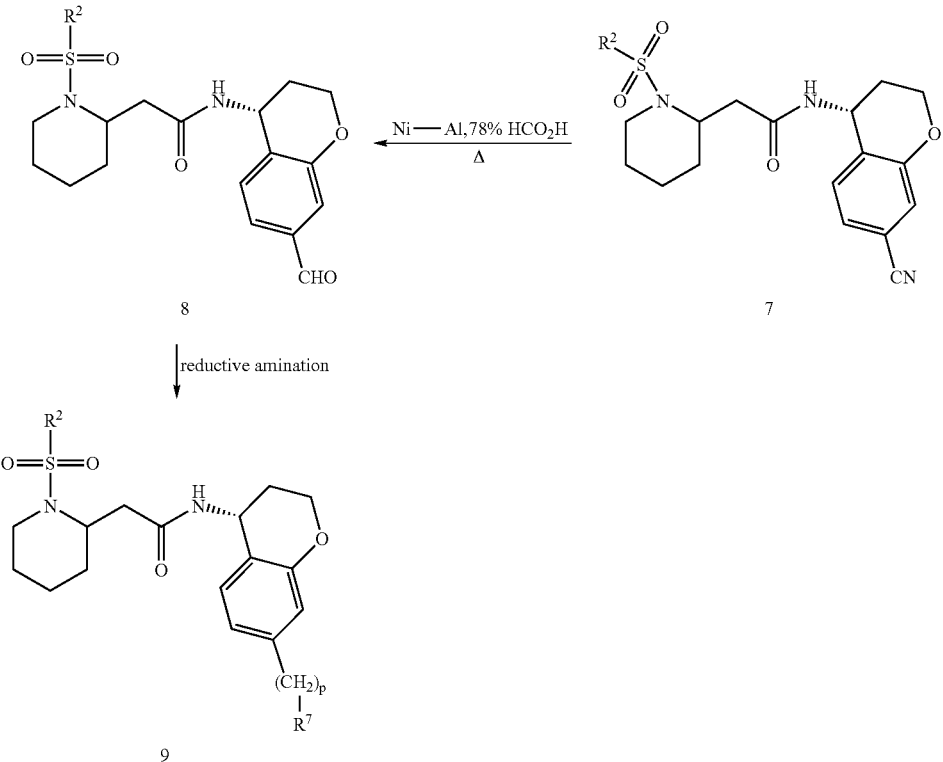

Compounds of Formula III may be prepared as described in Scheme 2. Piperidyl acids 4 are coupled with the substituted chroman amine 5 using standard peptide coupling conditions, such as with HOBT, EDC, and DIEA in a solvent, such as $CH_2Cl_2$, and reacted at RT, to afford the substituted amide 6. Acetamide 6 was reacted with an active sulfonyl compound, such as a substituted sulfonyl chloride, in the presence of base, preferably an organic base such as DIEA, in a solvent such as $CH_2Cl_2$ to form the substituted sulfonyl piperid-2-yl acetamide 7. The reaction was kept at a temperature above about 0° C., preferably at about RT. The formyl chroman 8 was formed from the cyano derivative 7 by oxidation, such as with formic acid in the presence of a catalyst, such as Raney-Nickel, at a temperature above about RT, preferably above about 50° C., even more preferably at about 100° C. Reductive amination of 9, such as in the presence of $NaBH(OAc)_3$ and substitutd amine, yields the compound of Formula III.

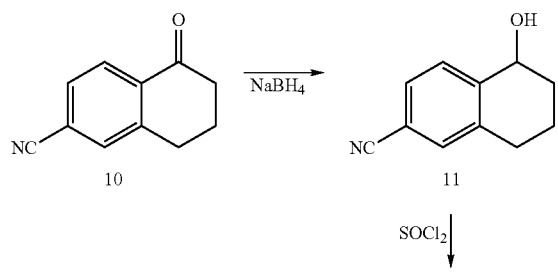

Scheme 3

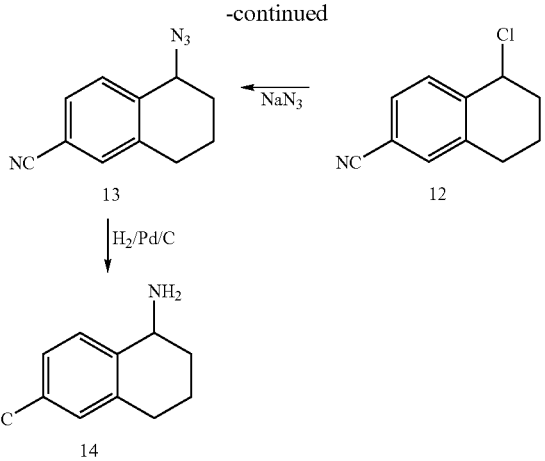

Cyano substituted bicylic amines 14 may be prepared as described in Scheme 3. 5-Oxo-5,6,7,8-tetrahydro-naphth-2-yl carbonitrile 10 is reduced, such as with $NaBH_4$, in a solvent such as THF and MeOH at a temperature between about 0° C. and about 30° C., preferably about RT, to form the 5-hydroxy-5,6,7,8-tetrahydro-naphth-2-yl carbonitrile 11. The alcohol 11 is converted to the halide 12, such as the chloride, such as by treatment with $SOCl_2$ in a solvent such as $CH_2Cl_2$, at a temperature between about 0° C. and about 30° C., preferably about RT. The 5-chloro-5,6,7,8-tetrahydro-naphth-2-yl carbonitrile 12 is treated with $NaN_3$ in a solvent such as dry DMF, at a temperature above RT, preferably above about 50° C., even more preferably at about 75° C., to form the 5-azido-5,6,7,8-tetrahydro-naphth-2-yl carbonitrile 13. The azide is hydrogenated, such as with H₂ in the presence of a catalyst, such as Pd/C, in the presence of solvent, such as in EtOAc, to form the amine 14. These steps can be used to form analogous cyano substituted bicyclic amines.

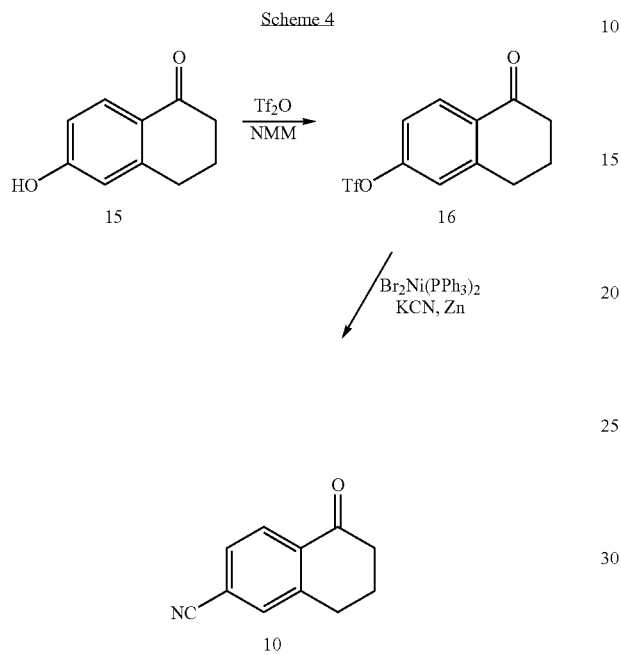

5-Oxo-5,6,7,8-tetrahydro-naphth-2-yl carbonitrile 10 can be prepared from corresponding alcohols by the methods described in Scheme 4. 6-Hydroxy-3,4-dihydro-2H-naphthalen-1-one 15 is converted to the triflate 16 by treatment with trifluoro-methanesulfonic anhydride in a solvent such as CH₂Cl₂, in the presence of base, such as NMM, and DMAP, and at a temperature below RT, preferably at a temperature at about 0° C. The triflate 16 is reacted with KCN in the presence of PPh₃ and (PPh₃)₂NiBr₂ in a solvent such as degassed CH₃CN, a temperature above RT, preferably above about 50° C., even more preferably at about 60° C., to form the cyano compound 10. These steps can be used to form analogous oxo substituted bicyclic carbonitriles.

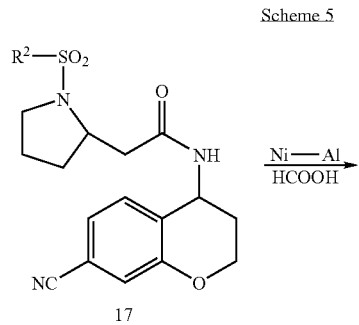

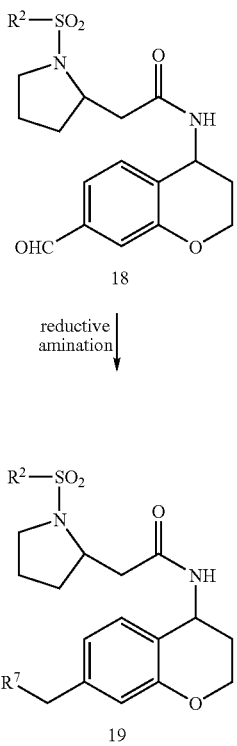

Compounds of Formula I may be prepared as described in Scheme 5. Cyano chromans 17 are reduced, such as with Raney nickel in the presence of formic acid, a temperature above RT, preferably above about 75° C., even more preferably at about 100° C., to form the formyl compounds 18. Reductive amination of the formyl compounds 18, such as with NaBH(OAc)₃ and an amine, provides the aminomethyl compounds 19 (where Rz is H or alkyl or together with the amine forms a cyclic compound). The compounds can be isolated as a salt or as the free base. These steps can be used to form analogous compounds.

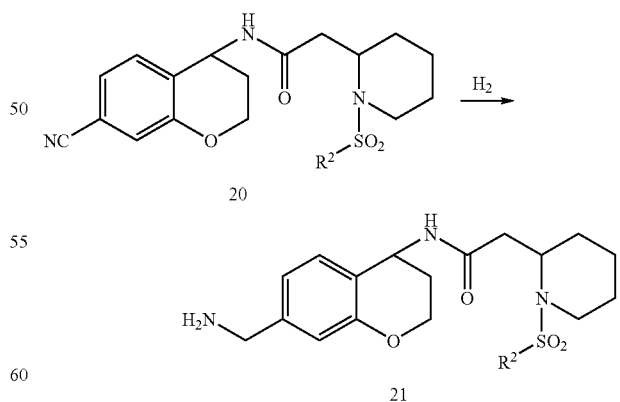

Compounds of Formula I may be prepared as described in Scheme 6. Cyano chromans 20 are reduced, such as with hydrogen in the presence of a catalyst such as Pd(OH)₂, in a solvent, such as MeOH, to form the corresponding aminomethyl compounds 21.

Scheme 7

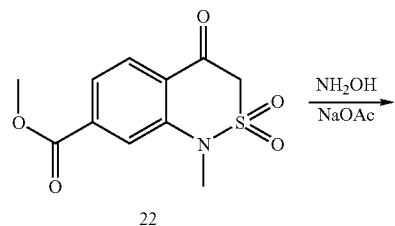

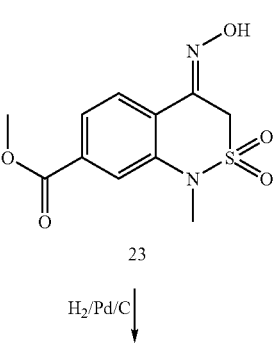

Scheme 8

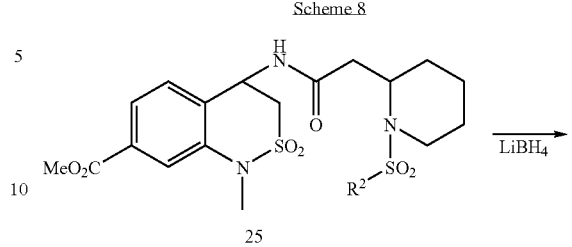

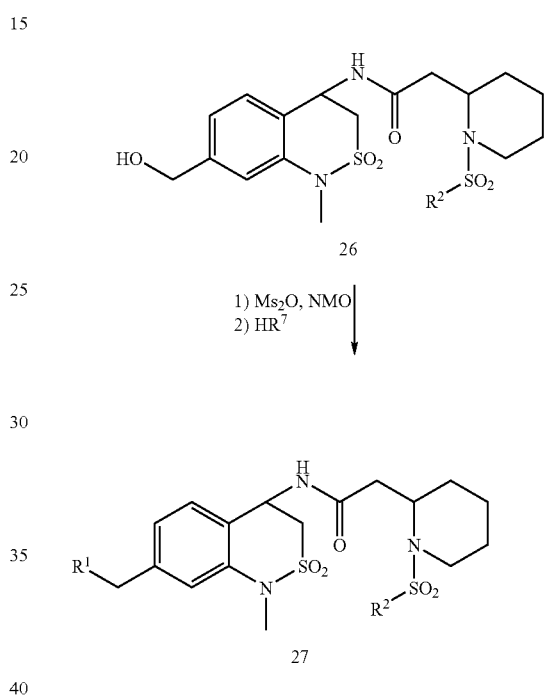

Amino compounds 24 are prepared from the corresponding ketones 22 by the method described in Scheme 7. Treatment of the ketones 22 with hydroxylamine in a solvent such as NaOAc, at a temperature above RT, preferably above about 75° C., even more preferably at reflux, provides the oxime 23. Hydrogenation of the oxime 23, such as in the presence of a catalyst such as Pd/C, provides the amine 24.

Compounds of Formula I may be prepared as described in Scheme 8. Esters 24 are reduced to the corresponding alcohols 25, such as in the presence of LiBH$_4$, at a temperature above RT, preferably above about 50° C. Derivatization to the mesylate and treatment with an amine provides compounds 26.

Scheme 9

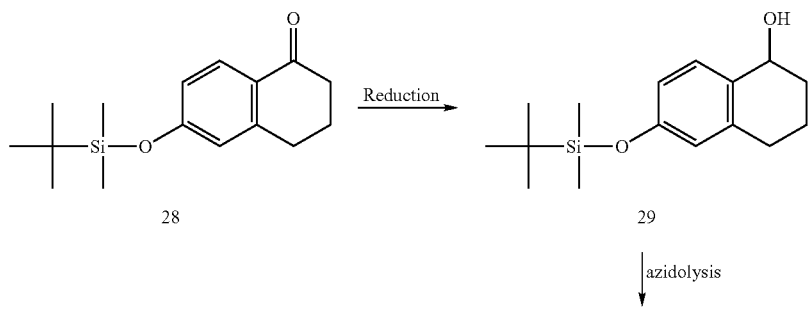

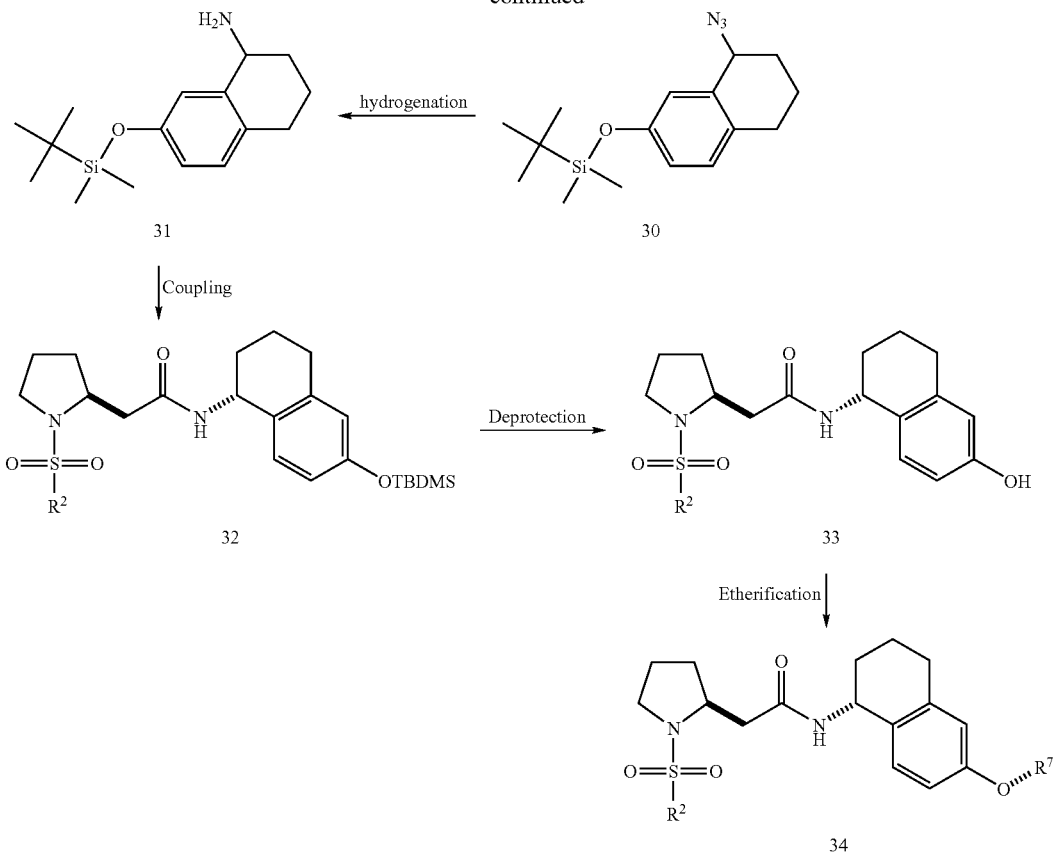

In addition, ether linked chroman, indane and tetraline linked analogs may be prepared as depicted in Scheme 9. Following silyl protection of the phenolic hydroxyl moiety, the ketone 28 is reduced using the CBS asymmetric reduction protocol. Similar to that described in Scheme 3, the resulting alcohol 29 is converted the azide 30 then reduced, such as with $H_2$ in the presence of Pd catalyst (e.g. palladium ethylenedamine complex) to afford the protected aminophenol 31. Amine 31 is converted to 32 as described in Scheme 1 then deprotected to yield the free phenol 33. Mitsunobu etherification followed by deprotection (if necessary) yields the compound 34.

Sulfonyl chlorides useful in preparing compounds of formula I may either be commercially available or prepared from aromatic amines similar to that described in Scheme 10.

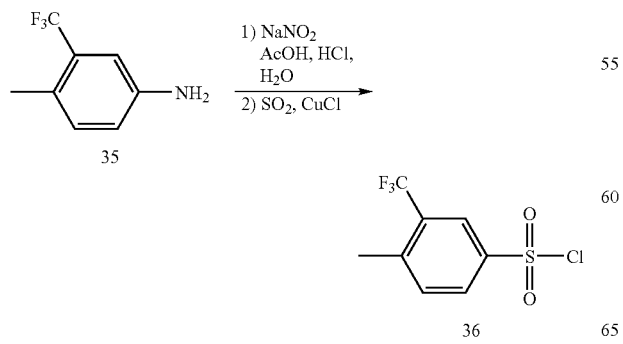

Scheme 10

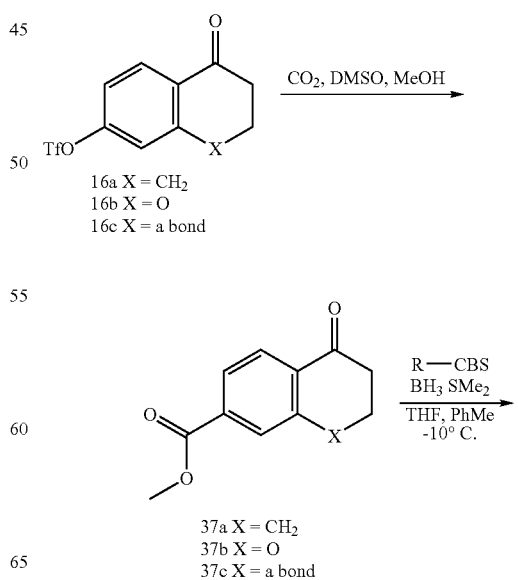

Scheme 11

-continued

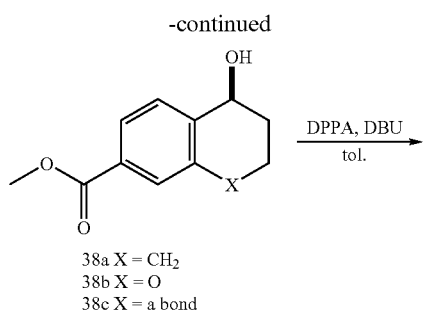

38a X = CH₂
38b X = O
38c X = a bond

DPPA, DBU
tol.

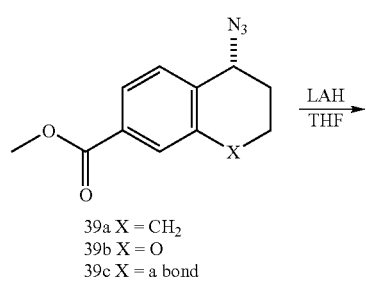

39a X = CH₂
39b X = O
39c X = a bond

LAH
THF

-continued

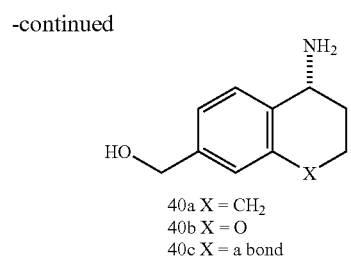

40a X = CH₂
40b X = O
40c X = a bond

In addition compounds of Formula I can be prepared in diasteromerically pure forms using the method described in Scheme 11. Ketotrifalates 16a–c are subjected to Pd mediated carbonylation in a mixture of DMSO and alcohol, such as MeOH to afford the ketoesters 37a–c. Enantioselective reduction of the ketone moieties, for example using the CBS (E. J. Corey et al., J. Am. Chem. Soc., 109:5551 (1987)) or Noyori. (T. Noyori, et al., J. Am. Chem. Soc., 117:2675–2676 (1995)) protocols affords either enantiomer of the alcohols 38a–c with an enantiomeric excess of >99%. Either the R or S enantiomer of the alcohol may be prepared by using either of the enantioselective reduction protocols. Azidation of the resulting secondary alcohol, for example using a method described by Thompson et al. (Journal of Org. Chem., 58(22):5886–5888 (1993))and LAH reduction affords the enantiopure amino alcohols 40a–c in high yield.

Scheme 12

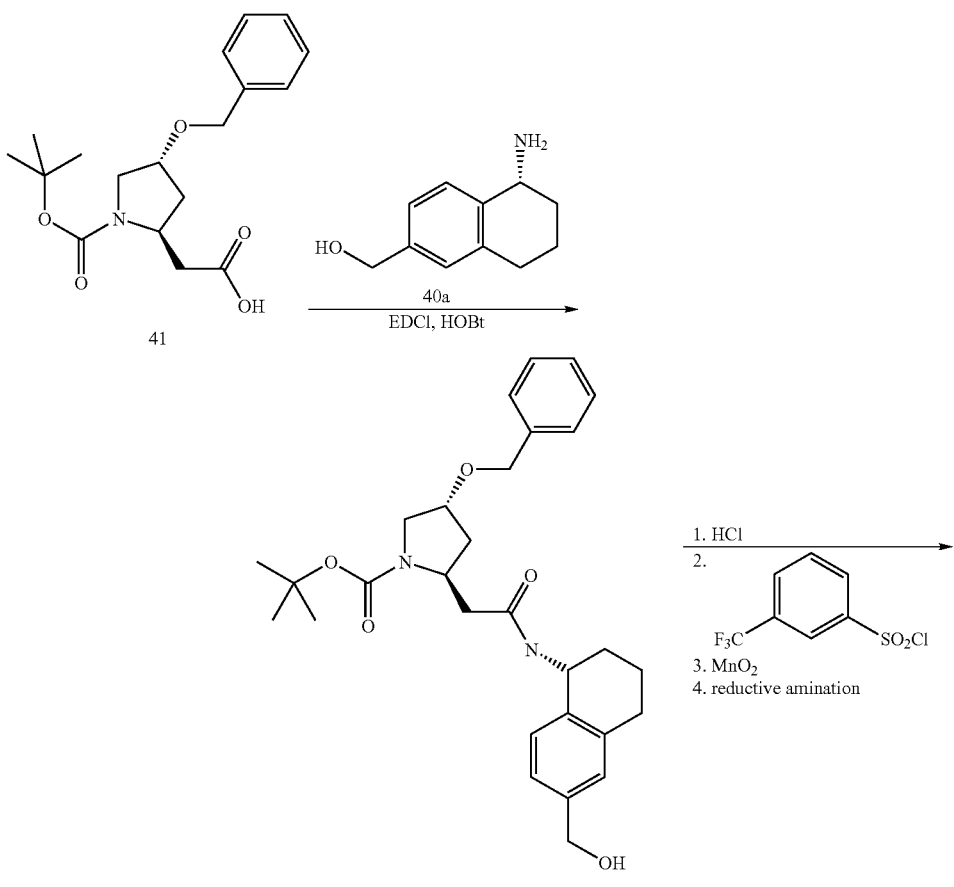

-continued
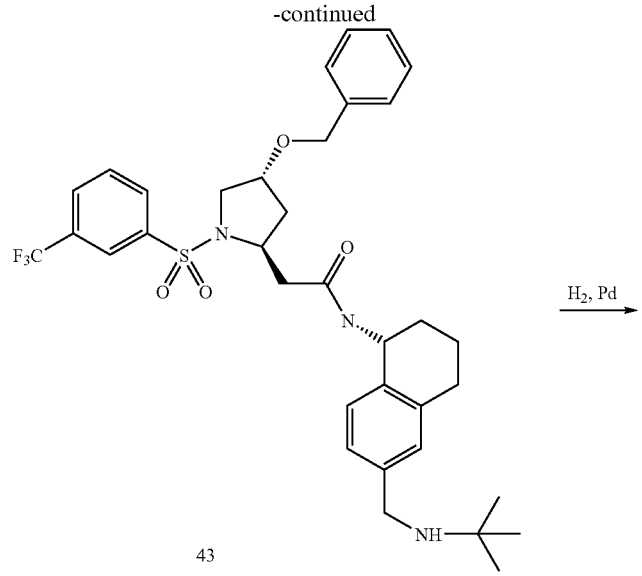
43
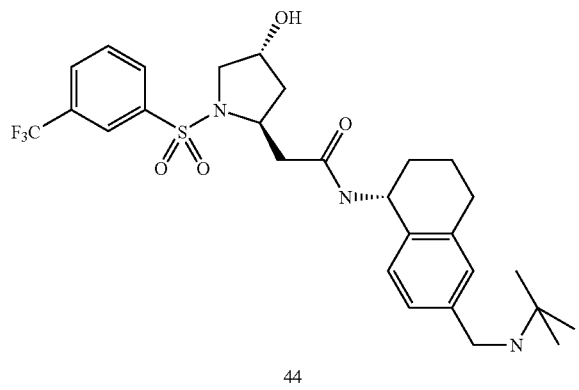
44
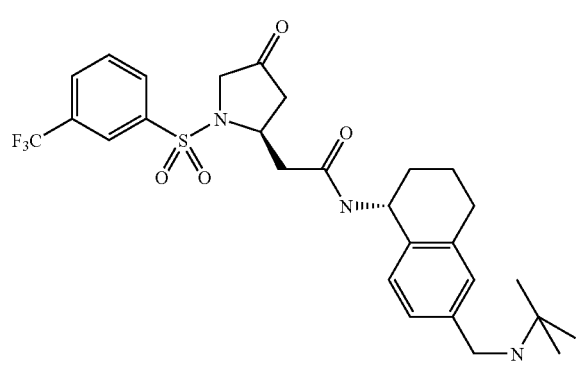
45
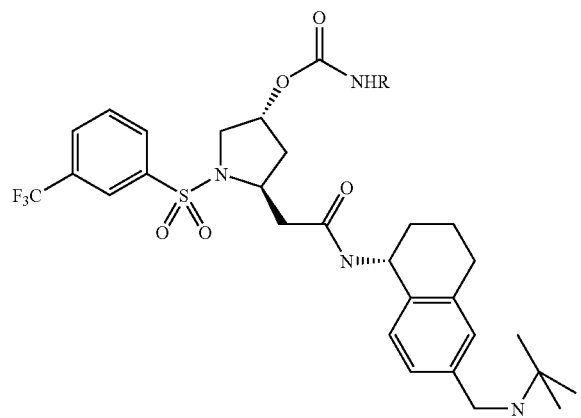
46

Compounds of the invention can be prepared as described in Scheme 12. 4-Benzyloxy-2-carboxymethyl-pyrrolidine-1-carboxylic acid tert-butyl ester 41 was coupled to [4-(1-amino-propyl)-phenyl]-methanol 40a using EDC, HOBt as described earlier to afford the amide 42. Deprotection and coupling using standard procedures provides the sulfonamide 43. Deprotection, such as with catalytic hydrogenation, provides the free alcohol 44. Oxidation of the alcohol 44, such as with MnO₂, yields the pyrrolidone 45. Reductive amination with methyl chloroformate, similar to that previously described, gives the carbamic acid 46.

Scheme 13

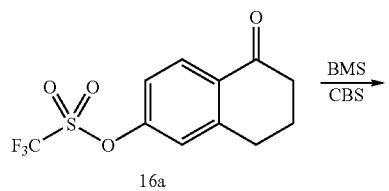

16a

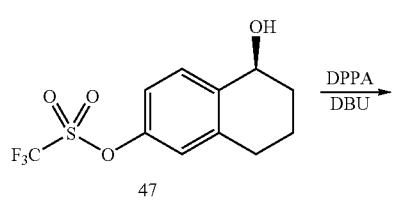

47

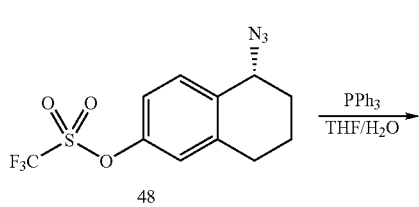

48

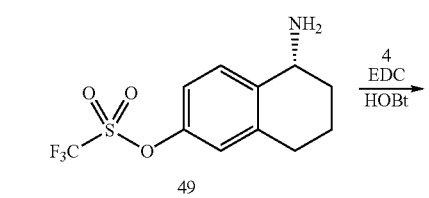

49

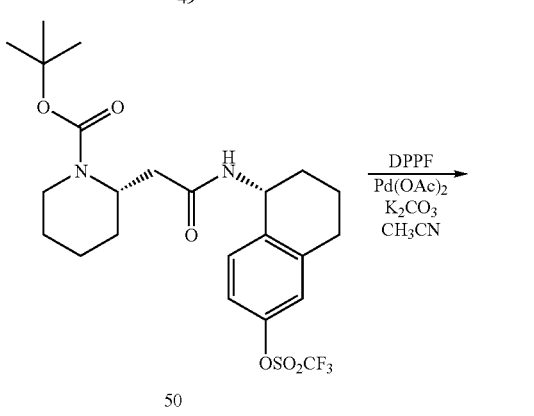

50

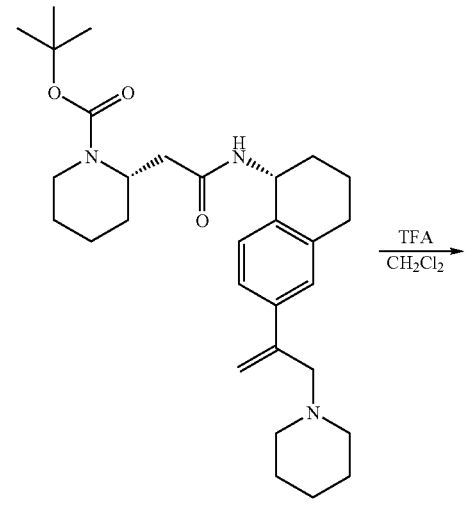

51

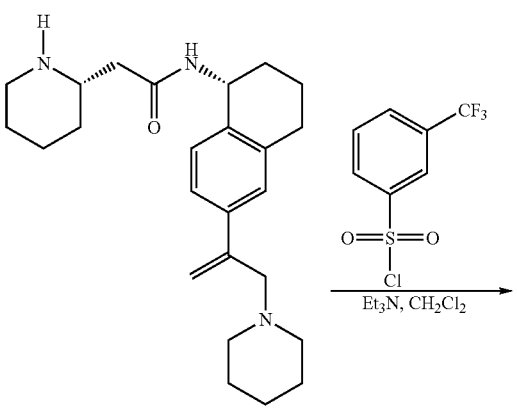

52

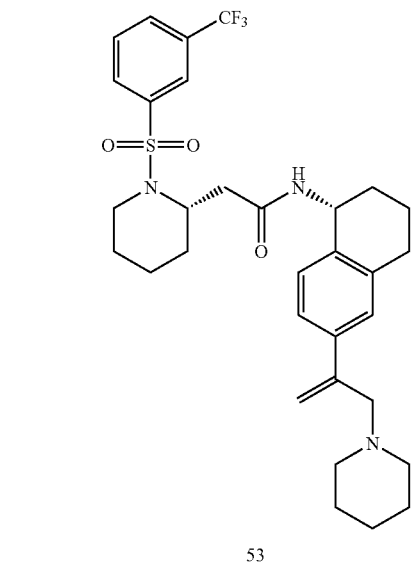

53

Compounds of formula I incorporating allylic amine functionalities may be prepared as depicted in Scheme 14. The amide trifalate 50 is converted to its allylic amine using a Heck cross coupling reaction. Following removal of the-Boc protecting group, the resulting amine is converted to compounds of formula I by sulfonylation.

alcohol 56. The alcohol 56 is oxidized, such as with MnO₂ as previously described, to form the protected ketone 57. The resulting ketone 57 is deprotected such as with HCl to form amines 58.

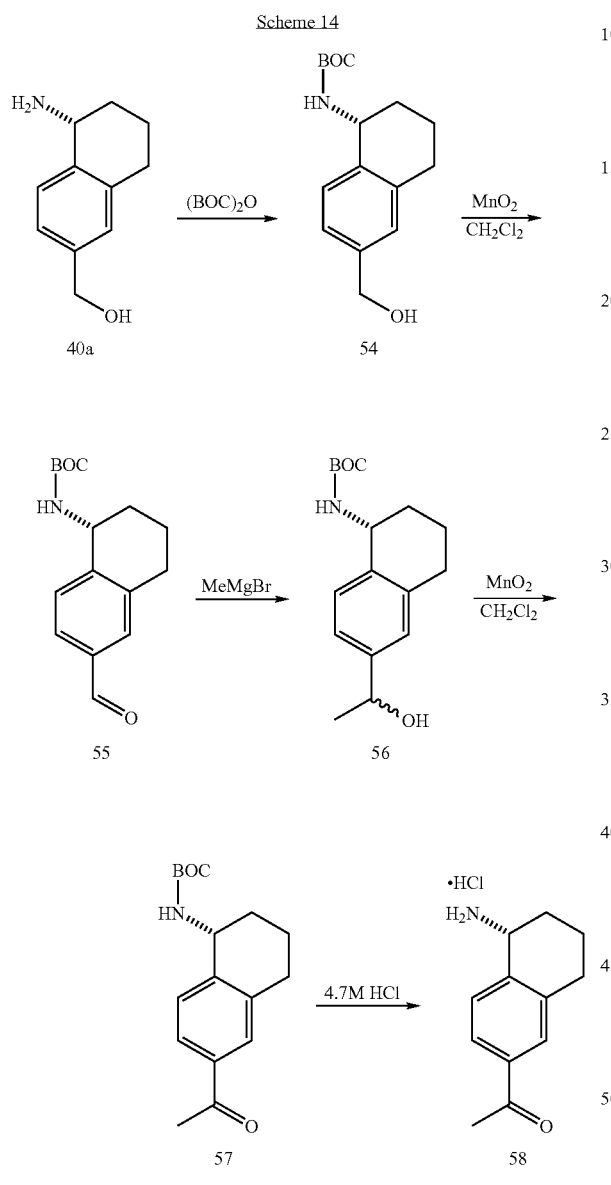

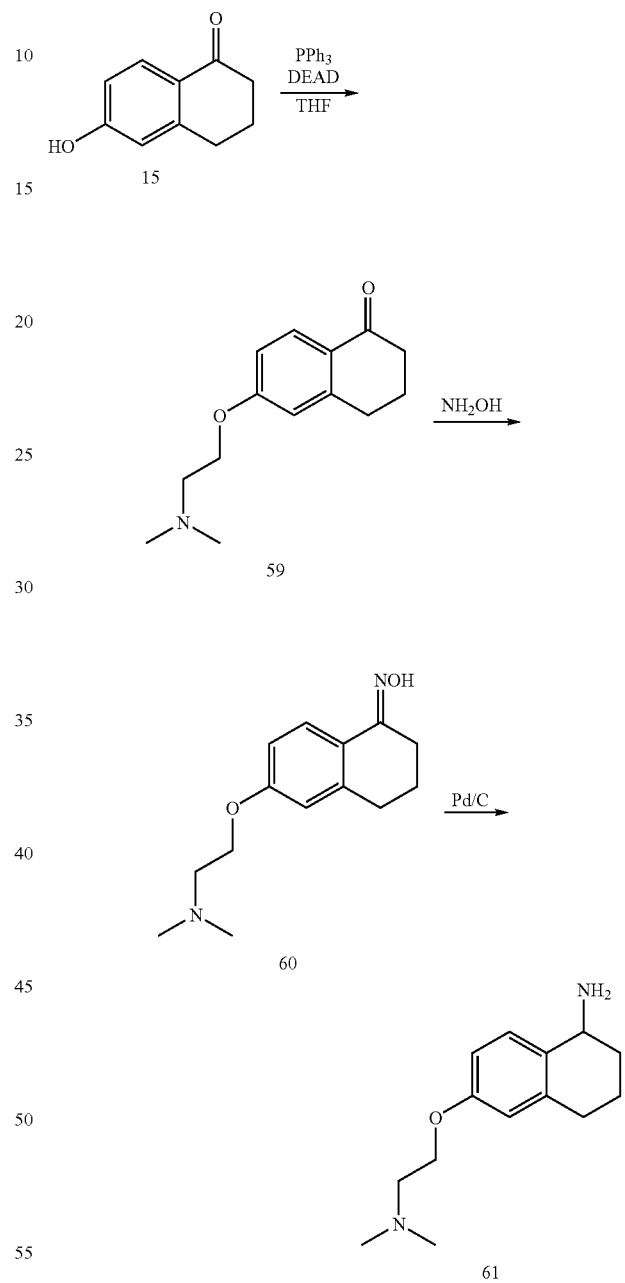

Analogs of compounds of Formula II may be prepared as illustrated in Scheme 14. Following Boc protection, amino alcohol 40a is converted to its methyl ketone 57 by the three step procedure depicted in Scheme 12. Protected 1-amino-6-hydroxymethyl-1,2,3,4-tetrahydro-naphthalene 54 is oxidized, such as with MnO₂ in an organic solvent, such as CH₂Cl₂, preferably at a temperature of about RT, to form the aldehyde 55. The aldehyde is alkylated, such as with a Grignard reagent in a solvent such as THF, at a temperature initially below RT, preferably about −30° C. and more preferably at about −78° C., then at about RT, to form the Ether linked analogs such as 61, are prepared by the convergent synthesis depicted in scheme 15. The 6-hydroxy-1-tetralone 15 is reacted with an amine, such as N,N-dimethylethanolamine, preferably in the presence of PPh₃ and DEAD at a temperature preferably between about 0° C. and about RT to form the 6-(2-dimethylamino-ethoxy)-3,4-dihydro-2H-naphthalen-1-one 59. The 6-(2-dimethylamino-ethoxy)-3,4-dihydro-2H-naphthalen-1-one 59 is reacted with hydroxylamine hydrochloride and base, such as Et₃N.

The reaction is heated above RT, preferably at reflux to form the oxime 60. Hydrogenation of the oxime 60, such as with Pd/C and H$_2$ provides the amine 61.

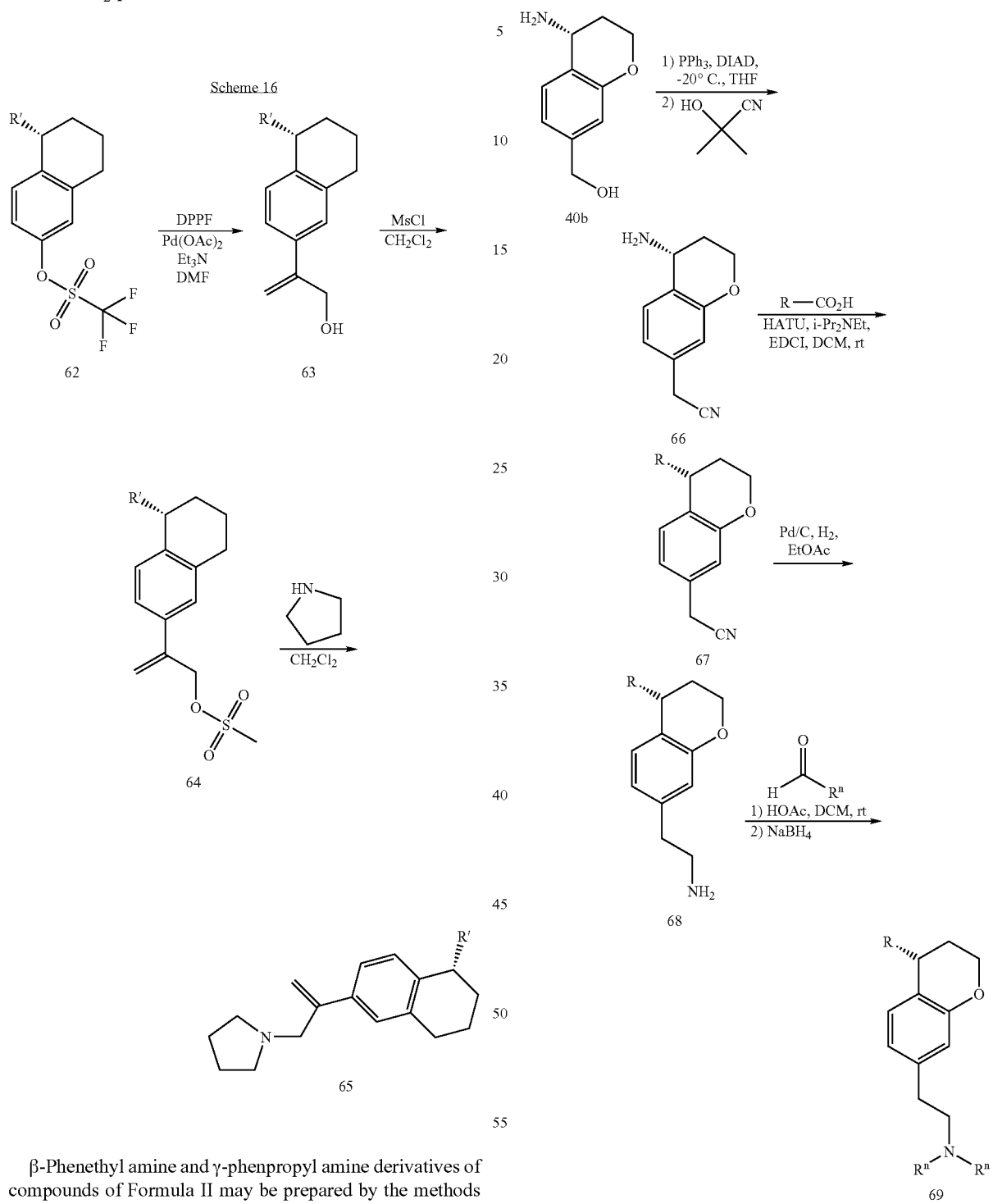

β-Phenethyl amine and γ-phenpropyl amine derivatives of compounds of Formula II may be prepared by the methods illustrated in Scheme 16. Reaction with the amide 62 palladium(II)acetate, dppf, base (e.g. Et$_3$N) and allyl alcohol, heated to a temperature above RT, preferably between about 50 and about 100° C., more preferably at about 80° C. provides the vinyl alcohol 63. Treatment of the 1-hydroxymethyl-vinyl compound 63 with mesyl chloride provides Mesyl derivative 64, which upon treatment with an amine, such as pyrrolidine, provides the vinyl amine 65.

Following the protocols described above the tether length for all of the amino compounds of Formulas I and II may be varied from 1–4 carbons. The alcohol 40b can be converted to the carbonitrile 66 such as with treatment with P(Ph)$_3$, DEAD and acetone cyanohydrin. The nitrile 66 can be coupled with the acid, such as with HATU, EDC and DIEA. The (7-cyanomethyl-4-chroman 67 is hydrogenated, such as with palladium catalyst in an alcohol, e.g. MeOH, to form the alkyl amine 68 of the present invention. The alkyl amine can be substituted using standard methods to make the substituted amines 69 (where R″ is alkyl, substituted alkyl, and the like).

Formation of the 5,6,7,8-tetrahydro-quinazolone 74 is achieved such as by reaction of amidine 72 and 2-dimethylaminomethylene-cyclohexane-1,3-dione 73 at a temperature above RT, preferably above about 50° C. and more preferably at about 80° C. 5,6,7,8-tetrahydro-quinazolone 74 is reduced such as with NaBH$_4$ to give the alcohol 75. The alcohol 75 is treated with DPPA and DBU to form the azide derivative which is reduced to form the amine 77. The amine 77 is deprotected, such as with TBAF to form the desired intermediate 78.

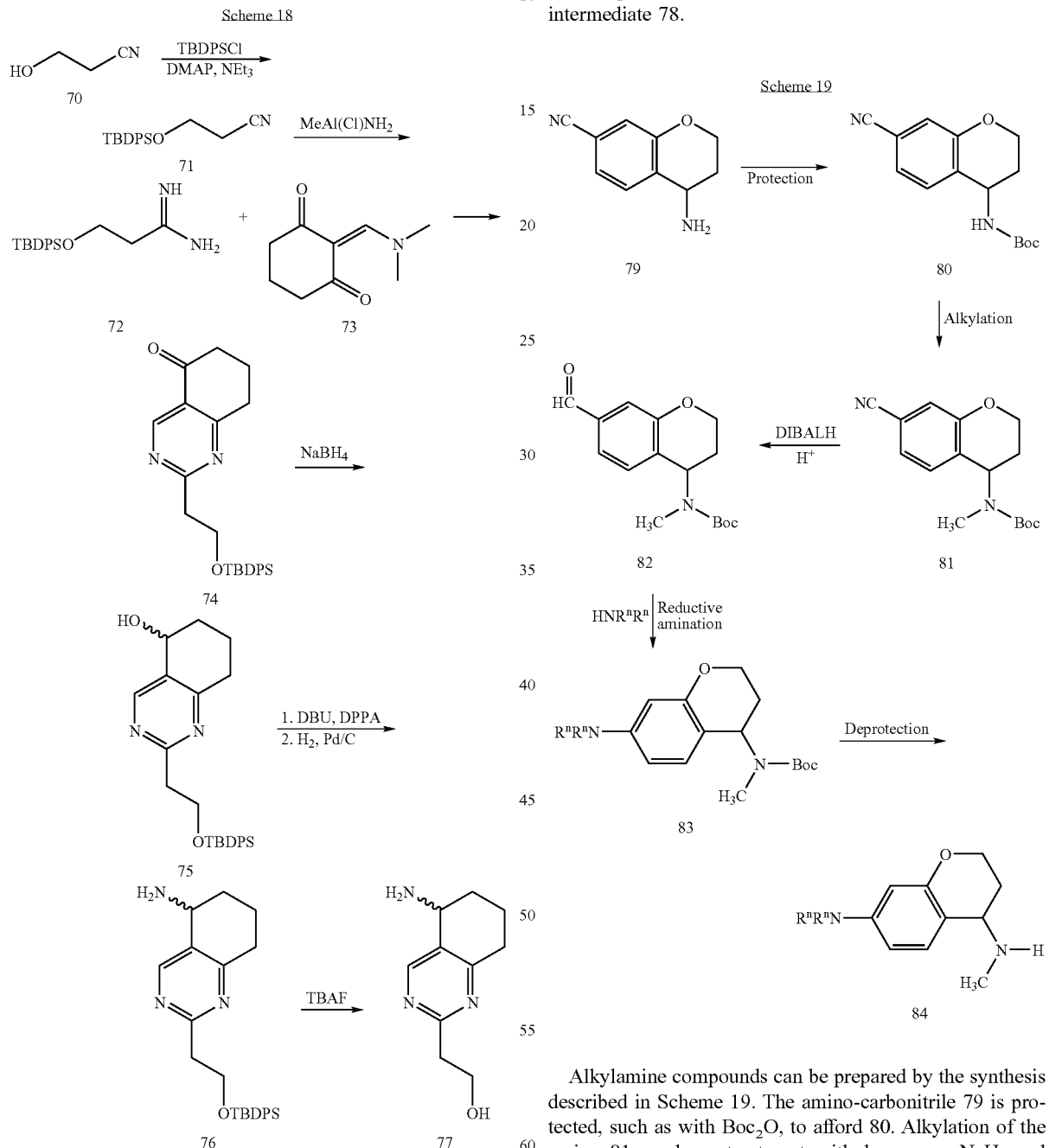

Methods for preparing additional compounds of formulas I and II are illustrated in scheme 18. The cyano alcohol 70 can be treated with DMAP, base (e.g. NEt$_3$), and PBDPSCl to form the protected alcohol 71. The protected alcohol 71 is aminated, such as with Me$_3$Al, at a temperature below RT and preferably at about 0° C., to yield the amidine 72.

Alkylamine compounds can be prepared by the synthesis described in Scheme 19. The amino-carbonitrile 79 is protected, such as with Boc$_2$O, to afford 80. Alkylation of the amine 81, such as treatment with base, e.g. NaH, and iodoaklyl, such as MeI, at a temperature preferably at RT, yields the alkylamine 81. Treatment of 81 with DIBALH and an acid such as glacial HOAc provides the aldehyde 82. Reductive amination, similar to that previously described affords the amine 83, which upon deprotection yields the intermediate 84.

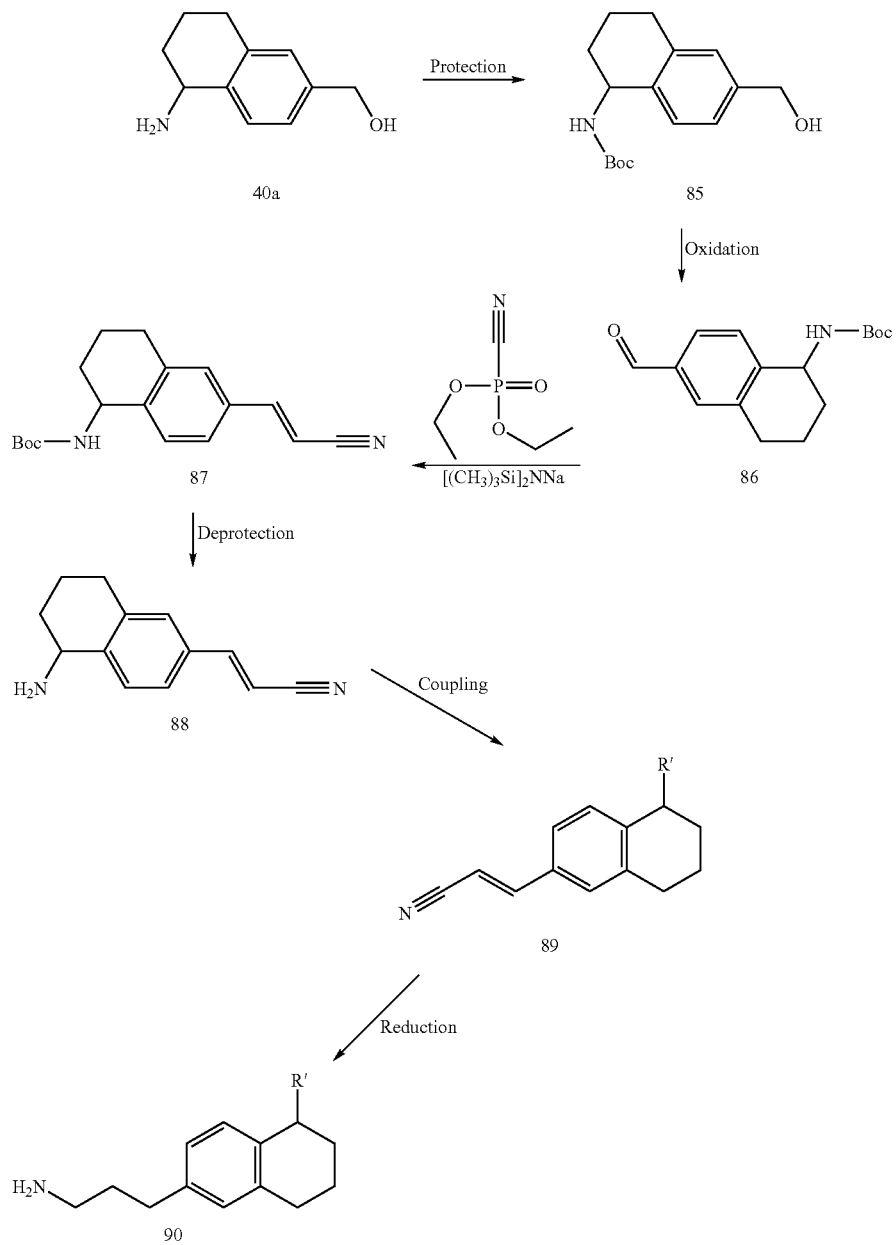

Scheme 20

Alternatively, compounds with longer tethers are prepared by the method described in Scheme 20. (5-Amino-5,6,7,8-tetrahydro-naphthalen-2-yl)-methanol 40a is protected, such as with (Boc)$_2$O to provide 85. The protected amine 85 is oxidized, using methods described in other schemes above, to form the aldehyde 86. The cyano-vinyl compound 87 is prepared via treatment with diethyl cyanophosphate and sodium bis(trimethylsilyl)amide at a temperature between about −78° C. and RT. Deprotection yields the free amine 88 which can be coupled as described above, to provide the intermediate 89. Reduction, such as with Pt catalyzed treatment with H$_2$ yields the aminopropyl compound 90 of the present invention.

If one or more other functional groups, for example carboxy, hydroxy, amino, or mercapto, are or need to be protected in a compound of Formulas I–VI, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, Protective Groups in Organic Chemistry, Plenum Press, London and New York (1973), in T. W. Greene, Protective Groups in Organic Synthesis, Wiley, New York (1981), in The Peptides; Volume 3 (editors: E. Gross and J. Meienhofer), Academic Press, London and New York (1981), in Methoden der Organischen Chemie (Methods of Organic Chemistry), Houben Weyl, $4^{th}$ edition, Volume 15/1, Georg Thieme Verlag, Stuttgart (1974), in H.-D. Jakubke and H. Jescheit, Aminosauren, Peptide, Proteine (Amino Acids, Peptides, Proteins), Verlag Chemie, Weinheim, Deerfield Beach, and Basel (1982), and in Jochen Lehmann, Chemie der Kohlenhydrate: Monosaccharide und Derivate (Chemistry of Carbohydrates: Monosaccharides and Derivatives), Georg Thieme Verlag, Stuttgart (1974).

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of Formula I with a salt-forming group may be prepared in a manner known per se. Acid addition salts of compounds of Formula I may thus be obtained by treatment with an acid or with a suitable anion exchange reagent. A salt with two acid molecules (for example a dihalogenide of a compound of Formula I) may also be converted into a salt with one acid molecule per compound (for example a monohalogenide); this may be done by heating to a melt, or for example by heating as a solid under a high vacuum at elevated temperature, for example from 130–170° C., one molecule of the acid being expelled per molecule of a compound of Formula I.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the $H^+$ form, depending on the type of reaction and/or reactants at reduced, normal, or elevated temperature, for example in the range from about −100° C. to about 190° C., preferably from about −80° C. to about 150° C., for example at about −80 to about 60° C., at RT, at about −20 to about 40° C. or at the boiling point of the solvent used, under atmospheric pressure or in a closed vessel, where appropriate under pressure, and/or in an inert atmosphere, for example, under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include, for example, $H_2O$, esters, typically lower alkyl-lower alkanoates, e.g. EtOAc, ethers, typically aliphatic ethers, e.g. $Et_2O$, or cyclic ethers, e.g. THF, liquid aromatic hydrocarbons, typically benzene or toluene, alcohols, typically MeOH, EtOH or 1-propanol, IPA, nitrites, typically $CH_3CN$, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g. HOAc, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of Formula I–VI, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

The following examples contain detailed descriptions of the methods of preparation of compounds of Formulas I–VI. These detailed descriptions fall within the scope, and serve to exemplify, the above-described General Synthetic Procedures which form part of the invention. These detailed descriptions are presented for illustrative purposes only and are not intended as a restriction on the scope of the invention.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention. The compounds of this invention may also be represented in multiple tautomeric forms, for example, as illustrated below:

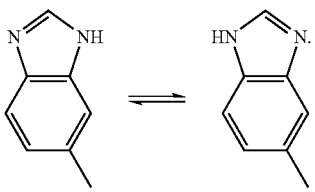

The invention expressly includes all tautomeric forms of the compounds described herein. The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3$^{rd}$ Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Unless otherwise noted, all materials were obtained from commercial suppliers and used without further purification. All parts are by weight and temperatures are in Degrees centigrade unless otherwise indicated. All compounds showed NMR spectra consistent with their assigned structures.

In order that the invention described herein may be more readily understood, the following examples are set forth. It should be understood that these examples are for illustrative purposes only and are not to be construed as limiting this invention in any manner.

The following examples contain detailed descriptions of the methods of preparation of compounds of Formulas I–VI. These detailed descriptions fall within the scope, and serve to exemplify, the above-described General Synthetic Procedures which form part of the invention. These detailed descriptions are presented for illustrative purposes only and are not intended as a restriction on the scope of the invention.

Unless otherwise noted, all materials were obtained from commercial suppliers and used without further purification. All parts are by weight unless otherwise indicated. All compounds showed NMR spectra consistent with their assigned structures. Melting points were determined on a Buchi apparatus and are uncorrected. Mass spectral data was determined by electrospray ionization technique. All examples were purified to >95% purity as determined by high-performance liquid chromatography. Unless otherwise stated, reactions were run at RT.

Preparation I—tert-butyl-(chroman-4-yloxy)-dimethyl-silane tert-Butyl-chloro-dimethyl-silane (10.54 g, 70 mmol) was added to a $CH_2Cl_2$ (200 mL) solution of 4-chromanol (10.00 g, 66.6 mmol), N-methylmorpholine (10.98 mL, 100 mmol) and imidazole (0.20 g, 3 mmol) at 0° C. The mixture was stirred for 3 days at RT. The reaction was diluted with $CH_2Cl_2$ (200 mL), washed with dilute HCl and $H_2O$, dried over $MgSO_4$, filtered, and concentrated in vacuo to provide the title compound.

Preparation II—7-cyano-4-chromanone

7-[[(Trifluoromethyl)sulfonyl]oxy]-4-chromanone (27.8 g, 94 mmol) and $PPh_3$ (2.5g, 9.6 mmol) were dissolved in degassed $CH_3CN$ (350 mL). KCN (6.8 g, 105 mmol), $(PPh_3)_2NiBr_2$ (3.5 g, 4.7 mmol) and acid washed (stirred in 0.5 N HCl 1 min, washed successively with $H_2O$, acetone, and $Et_2O$) zinc dust (2.0 g, 31 mmol) were added and the reaction was purged with $N_2$. The reaction was heated in a 60° C. bath for 6 h. The reaction was cooled, poured into $H_2O$ (400 mL) and extracted with EtOAc (3×300 mL). The organic layers were combined and washed with $H_2O$ (200 mL) and brine (150 mL). The solution was dried over $MgSO_4$, filtered and concentrated in vacuo to provide a residue which was purified on a plug of silica ($CH_2Cl_2$ eluant) to provide the title compound.

Preparation III—7-cyano-4-chromanol

7-Cyano-4-chromanone (7.7 g, 44 mmol) was dissolved in THF (75 mL) and MeOH (150 mL), and cooled to 10° C. $NaBH_4$ (1.9 g, 49 mmol) was added and the reaction was warmed to RT and stirred overnight (14 h). The reaction was quenched with acetone (5 mL) and 2 N HCl (100 mL) was added. The reaction was concentrated in vacuo to approximately 75 mL in volume and the reaction was partitioned between 2 N HCl (200 mL) and EtOAc (400 mL). The layers were separated and the aqueous layer was back extracted with EtOAc (200 mL). The organic layers were combined, washed successively with $H_2O$ (200 mL) and brine (200 mL). The solution was dried over $MgSO_4$, filtered and concentrated in vacuo to provide the title compound which was used without further purification.

Preparation IV—4-chloro-7-cyanochroman

7-Cyano-4-chromanol (8.0 g, 46 mmol) was dissolved in $CH_2Cl_2$ (120 mL) and cooled to 10° C. $SOCl_2$ (5.0 mL, 70 mmol) was added, the reaction was warmed to RT and stirred overnight. The reaction was concentrated in vacuo and azeotroped with $CH_2Cl_2$ (2×50 mL). The residue was dissolved in EtOAc (500 mL), washed with saturated $NaHCO_3$ (250 mL), and with brine (150 mL), dried over $MgSO_4$, filtered and concentrated in vacuo to provide the title compound which was used without further purification.

Preparation V—4-azido-7-cyanochroman

4-Chloro-7-cyanochroman (8.1 g, 42 mmol) was dissolved in dry DMF (90 mL) and $NaN_3$ (4.0 g, 62 mmol) was added and the reaction was heated to 80° C. under $N_2$. After 5 h TLC ($SiO_2$, toluene) showed that no starting chloride was present. The reaction was cooled and partitioned between EtOAc (200 mL) and $H_2O$ (150 mL). The organic phase was washed with $H_2O$ (2×100 mL) and brine (100 mL). The solution was dried over $MgSO_4$, filtered and concentrated in vacuo to provide a residue which was purified by column chromatography ($SiO_2$, 15% EtOAc in hexane) to provide the title compound.

Preparation VI—4-amino-7-cyanochroman

4-Azido-7-cyanochroman (4.3 g, 21 mmol) was dissolved in EtOAc (200 mL) and purged with $N_2$. Pd/C (10%, 0.6 g) was added and the reaction was purged with $N_2$. The reaction was purged with $H_2$ and rapidly stirred under a $H_2$ atmosphere until consumption of starting material was complete by TLC analysis (approximately 1 h). The reaction was purged with $N_2$, and filtered through Celite®. The Celite® was washed with MeOH. The solution was concentrated in vacuo to provide a residue which was purified by column chromatography (silica, 3% MeOH in $CH_2Cl_2$ plus 0.5% $NH_4OH$) to provide the title compound.

Preparation VII—trifluoro-methanesulfonic Acid 1-oxo-indan-4-yl ester

Trifluoro-methanesulfonic acid 1-oxo-indan-4-yl ester was prepared from 4-hydroxy-indan-1-one using essentially the same procedure described in Preparation I yielding a brown oil.

Preparation VIII—1-oxo-indan-4-carbonitrile

1-Oxo-indan-4-carbonitrile was prepared from trifluoro-methanesulfonic acid 1-oxo-indan-4-yl ester using essentially the same procedure described in Preparation II yielding a yellow solid.

Preparation IX—1-hydroxy-indan-4-carbonitrile

1-Hydroxy-indan-4-carbonitrile was prepared from 1-oxo-indan-4-carbonitrile using essentially the same procedure described in Preparation III.

Preparation X—1-azido-indan-4-carbonitrile

1-Azido-indan-4-carbonitrile was prepared in several steps from 1-hydroxy-indan-4-carbonitrile using essentially the same procedure described in Preparation IV–V, yielding a colorless oil.

Preparation XI—1-amino-indan-4-carbonitrile

1-Amino-indan-4-carbonitrile was prepared from 1-azido-indan-4-carbonitrile, using essentially the same procedure described in Preparation VI, yielding a yellow-green solid.

Preparation XII—trifluoro-methanesulfonic acid 1-oxo-indan-5-yl ester

The title compound was prepared from 5-hydroxy-indan-1-one, using essentially the same procedure described in Preparation I yielding a brown oil.

Preparation XIII—1-oxo-indan-5-carbonitrile

The title compound was prepared from trifluoro-methanesulfonic acid 1-oxo-indan-5-yl ester, using essentially the same procedure described in Preparaion II.

Preparation XIV—1-hydroxy-indan-5-carbonitrile

The title compound was prepared from 1-oxo-indan-5-carbonitrile, using essentially the same procedure described in Preparation III, yielding a yellow solid.

Preparation XV—1-azido-indan-5-carbonitrile

The title compound was prepared in several steps from 1-hydroxy-indan-5-carbonitrile, using essentially the same procedure described in Preparations IV–V.

Preparation XVI—1-amino-indan-5-carbonitrile

The title compound was prepared from 1-azido-indan-5-carbonitrile, using essentially the same procedure described in Preparation VI. MS (APCI) m/z 142 $(M+H)^+$.

Preparation XVII—4-(tert-butyl-dimethyl-silanyloxy)-chroman-8-carbaldehyde

Butyllithium was added to an $Et_2O$ (80 mL) solution of tert-butyl-(chroman-4-yloxy)-dimethyl-silane (6.21 g, 23.5 mmol) at −80° C. After stirring the mixture at 3° C. for 15 h, DMF (10 mL) was added at 0° C. Following a 30 min stirring at RT, the reaction was quenched with saturated $NH_4Cl$ solution. The reaction was diluted with $Et_2O$ (200 mL) and washed with brine. The organic phase was dried over $MgSO_4$, filtered, and concentrated in vacuo to provide the crude compound (40% conversion by $^1H$ NMR) which was purified by column chromatography (silica, 0 to 10% ether in hexane) to provide the title compound.

Preparation XVIII—1-[4-(tert-butyl-dimethyl-silanyloxy)-chroman-8-ylmethyl]-piperidine $NaBH(OAc)_3$ (3.86 g, 18.21 mmol) was added to a dichloroethane (30 mL) solution of 4-(tert-butyl-dimethyl-silanyloxy)-chroman-8-carbaldehyde (2.66 g, 9.10 mmol) and piperidine (2.70 mL, 27.31 mmol) at RT. After stirring for 1 h, the reaction was quenched with MeOH (10 mL) while the stirring was continued for 20 more min. The reaction was diluted with $CH_2Cl_2$ (200 mL) and washed with saturated $NaHCO_3$ solution and brine. The organic phase was dried over $MgSO_4$, filtered, and concentrated in vacuo from heptane to provide the title compound.

Preparation XIX—1-(4-azido-chroman-8-ylmethyl)-piperidine

HCl (1.2 mL, 37%) was added to a MeOH (60 mL) solution of 1-[4-(tert-butyl-dimethyl-silanyloxy)-chroman-8-ylmethyl]-piperidine (3.00 g, 8.30 mmol). After stirring for 1 h, the mixture was evaporated to dryness from benzene. The resulting crude alcohol was dissolved in $SOCl_2$ (5 mL) and stirred for 3 days at RT. Following the removal of the excess $SOCl_2$ in vacuo from hexane, the crude chloride was dissolved in DMF (20 mL) and $NaN_3$ (1.618 g, 24.9 mmol) was added. The mixture was stirred at 80° C. for 1 h and, upon cooling, it was diluted with $Et_2O$ (100 mL), hexane (100 mL) and $H_2O$ (100 mL). After separation, the organic phase was washed with brine, dried over $MgSO_4$, filtered, and concentrated in vacuo to provide the title compound. MS (APCI+, m/z): 273 $(M+1)^+$.

Preparation XX—8-piperidin-1-ylmethyl-chroman-4-ylamine bis-hydrochloride 1-(4-Azido-chroman-8-ylmethyl)-piperidine (1.862 g, 6.84 mmol) was hydrogenated over $Pd(OH)_2$ (200 mg, 20% on carbon, Pearlman type) in EtOAc (100 mL) at atmospheric pressure for two days. After filtration of the catalyst and evaporation of the solution, HCl (20 mL, 1 M in THF) was added while stirring vigorously. The precipitated, hygroscopic solid was filtered, washed with $Et_2O$ and dried to furnish the title compound. MS (APCI+, m/z): 247 $(M+1)^+$.

Preparation XXI—chroman-4-one oxime

To a mixture of 4-chromanone (10.00 g, 67.50 mmol) and hydroxylamine hydrochloride (7.04 g, 101 mmol) in EtOH (100 ml) was added a solution of NaOAc (16.61 g, 202.5 mmol) in $H_2O$ (30 mL). The reaction was heated to reflux for 2 h. The mixture was cooled to RT and concentrated in vacuo. The residue was diluted with $H_2O$ and acidified with 1N HCl. The aqueous was extracted with EtOAc until tlc analysis showed no evidence of title compound in the aqueous layer. The combined organics were dried with $MgSO_4$ and concentrated in vacuo to furnish the crude title compound which was used without further purification. MS (APCI pos) 164 (M+H).

Preparation XXII—chroman-4-ylamine

LAH (6.35 g, 167 mmol) was suspended in THF (100 mL) at 0° C. A solution of chroman-4-one oxime (10.92 g, 66.92 mmol) in THF (100 mL) was added dropwise. The mixture was heated slowly to reflux for 4 h. The reaction was cooled to RT and added drop-wise to a stirred saturated solution of Rochelle's salt in $H_2O$. The bi-phasic mixture was stirred rapidly at RT for 1 h. The layers were separated and the aqueous layer was extracted with EtOAc until tlc analysis of the aqueous layer showed no evidence of the title compound. The combined organics were dried over $MgSO_4$ and concentrated in vacuo to furnish the crude material, which was purified by flash column chromatography to afford the title compound. MS (APCI pos) 150 (M+H).

Preparation XXIII—6-bromo-chroman-4-ylamine

A solution of chroman-4-ylamine (2.550 g, 17.09 mmol) in AcOH (50 mL) at RT was treated with $Br_2$ (3.01 g, 0.96 mL, 18.8 mmol) drop-wise. The reaction was stirred at RT until HPLC analysis showed complete consumption of starting material. The mixture was diluted with $H_2O$ (100 mL) and NaOH was added until the solution became basic. The aqueous layer was extracted with EtOAc until tlc analysis of the aqueous layer showed no evidence of the title compound. The combined organics were dried over $MgSO_4$ and concentrated in vacuo to yield the crude compound, which was purified by flash column chromatography to afford the pure title compound. MS (APCI pos) 229 (M+H).

Preparation XXIV—(6-bromo-chroman-4-yl)-carbamic acid tert-butyl ester

To a RT solution of 6-bromo-chroman-4-ylamine (2.270 g, 9.952 mmol) and di-tert-butyl dicarbonate (2.606 g, 11.94 mmol) in $CH_2Cl_2$ (50 mL) was added a solution of $NaHCO_3$ (1.672 g, 19.90 mmol) in $H_2O$ (50 mL). The bi-phasic mixture was rapidly stirred until complete consumption of starting material was observed by HPLC analysis (over night). The reaction was diluted with EtOAc and $H_2O$ and the layers were separated. The organics were dried with $MgSO_4$ and concentrated in vacuo to afford the crude title compound, which was used without further purification.

Preparation XXV—(6-formyl-chroman-4-yl)-carbamic acid tert-butyl ester (6-Bromo-chroman-4-yl)-carbamic acid tert-butyl ester (3.859 g, 11.76 mmol) was dissolved in THF (50 mL) and cooled to −78° C. n-Butyllithium (2.5 M) (11.76 mL, 29.40 mmol) was added drop-wise to the stirred solution. The reaction mixture was stirred at −78° C. for 30 min and DMF (4.55 mL, 58.8 mmol) was added drop-wise and the system was slowly warmed to RT overnight. The reaction was quenched with saturated aqueous $NH_4Cl$ solution and extracted with EtOAc. The combined organics were dried with $MgSO_4$ and concentrated in vacuo to afford the crude compound, which was purified by flash column chromatography to furnish the pure title compound.

Preparation XXVI—trifluoro-methanesulfonic acid 5-oxo-5,6,7,8-tetrahydro-naphthalen-2-yl ester Trifluoro-methanesulfonic anhydride (14.35 mL, 77.3 mmol) was added to a $CH_2Cl_2$ (150 mL) solution of 6-hydroxy-3,4-dihydro-2H-naphthalen-1-one (11.40 g, 70.3 mmol), N-methylmorpholine (8.5 mL, 77.3 mmol) and DMAP (130 mg, 1 mmol) in 5 min at −80° C. The mixture was warmed to 0° C. in 1 h then poured into a cold solution of saturated $NH_4Cl$. The mixture was diluted with $CH_2Cl_2$ (400 mL), washed with $H_2O$, dried over $MgSO_4$, filtered, and concentrated in vacuo to provide the crude compound which was purified by column chromatography (silica, 0 to 60% $CH_2Cl_2$ in hexane) to provide the title compound.

Preparation XXVII—5-oxo-5,6,7,8-tetrahydro-naphthalen-2-carbonitrile

The title compound was prepared from trifluoro-methanesulfonic acid 5-oxo-5,6,7,8-tetrahydro-naphthalen-2-yl ester by a method similar to that described in Preparation II.

Preparaion XXVIII—5-hydroxy-5,6,7,8-tetrahydro-naphthalen-2-carbonitrile

The title compound was prepared from 5-oxo-5,6,7,8-tetrahydro-naphthalen-2-carbonitrile by a method similar to that described in Preparation III.

Preparation XXIX—5-azido-5,6,7,8-tetrahydro-naphthalen-2-carbonitrile

The title compound was prepared from 5-hydroxy-5,6,7,8-tetrahydro-naphthalen-2-carbonitrile via 5-chloro-5,6,7,8-tetrahydro-naphthalen-2-carbonitrile by a method similar to that described in Preparation IV–V. MS (+APCI m/z): 171 $(M-N_2+H)^+$.

Preparation XXX—5-amino-5,6,7,8-tetrahydro-naphthalen-2-carbonitrile

The title compound was prepared from 5-azido-5,6,7,8-tetrahydro-naphthalen-2-carbonitrile by catalytic hydrogenation similar to that described in Preparation VI.

Preparation XXXI—6-bromo-3,4-dihydro-1H-naphthalen-2-one oxime

To a mixture of 6-bromo-3,4-dihydro-1H-naphthalen-2-one (5.370 g, 23.86 mmol) and and hydroxylamine hydrochloride (2.487 g, 35.79 mmol) in EtOH (80 mL) was added a solution of NaOAc (5.871 g, 71.57 mmol) in $H_2O$ (20 mL). The mixture was heated to reflux for 2 h. The reaction was cooled to RT and concentrated in vacuo. The residue was suspended in $H_2O$ and filtered. The pad was washed with $H_2O$ (2×50 mL) and $Et_2O$ (2×50 mL) and the solids were dried in vacuo to furnish the title compound, which was used without further purification. MS (APCI pos) 242 (M+H).

Preparation XXXII—6-bromo-1,2,3,4-tetrahydro-naphthalen-2-ylamine

A solution of $BH_3$-THF complex (1M) (35.9 mL, 35.9 mmol) was added drop-wise to a stirred solution of 6-bromo-3,4-dihydro-1H-naphthalen-2-one oxime (3.450 g, 14.37 mmol) in THF (125 mL) at 0° C. The mixture was warmed to RT and to reflux for 24 h. The reaction was cooled to RT and 1 N aqueous HCl was added carefully until the mixture was acidic and the system was stirred until no further gas was evolved. The solution was made basic by the addition of NaOH and the aqueous layer was extracted with EtOAc. The combined organics were dried over $MgSO_4$ and concentrated in vacuo to afford the crude title compound, which was purified by flash column chromatography to yield the title compound. MS (APCI pos) 228 (M+H).

Preparation XXXIII—(6-bromo-1,2,3,4-tetrahydro-naphthalen-2-yl)-carbamic acid tert-butyl ester Di-tert-butyl dicarbonate (1.030 g, 4.719 mmol) was added to a stirred RT solution of 6-bromo-1,2,3,4-tetrahydro-naphthalen-2-ylamine (0.970 g, 4.290 mmol) in $CH_2Cl_2$ (100 mL). TEA (0.897 mL, 6.435 mmol) was added to the reaction and the mixture was stirred at RT until HPLC analysis showed complete consumption of starting material. The reaction was diluted with $CH_2Cl_2$, washed with saturated aqueous $NaHCO_3$, dried over $MgSO_4$ and concentrated in vacuo to afford the crude material. The crude was purified by flash column chromatography to yield the title compound. MS (APCI pos) 269 (M-t-Bu).

Preparationo XXXIV—(6-formyl-1,2,3,4-tetrahydro-naphthalen-2-yl)-carbamic acid tert-butyl ester (6-Bromo-1,2,3,4-tetrahydro-naphthalen-2-yl)-carbamic acid tert-butyl ester (1.080 g, 3.311 mmol) was dissolved in THF (30 mL) and cooled to −78° C. n-Butyllithium (2.5 M) (3.311 mL, 8.276 mmol) was added drop-wise to the stirred solution. The reaction was stirred at −78° C. for 30 min and DMF (1.282 mL, 16.55 mmol) was added drop-wise and the mixture was slowly warmed to RT overnight. The reaction was quenched with saturated aqueous $NH_4Cl$ solution and extracted with EtOAc. The combined organics were dried over $MgSO_4$ and concentrated in vacuo to afford the crude material, which was purified by flash column chromatography to furnish the pure title compound. MS (APCI pos) 217 (M-t-Bu).

Preparation XXXV—(6-piperidin-1-ylmethyl-1,2,3,4-tetrahydro-naphthalen-2-yl)-carbamic acid tert-butyl ester (6-Formyl-1,2,3,4-tetrahydro-naphthalen-2-yl)-carbamic acid tert-butyl ester (0.090 g, 0.33 mmol) was dissolved in N,N-dimethylacetamide (10 mL). Piperdine (0.162 mL, 1.63 mmol) was added and the mixture was stirred at RT for 30 min. $NaBH(OAc)_3$ (0.173 g, 0.817 mmol) was added in one portion and the reaction was stirred at RT until complete consumption of starting material was observed by HPLC analysis. The reaction was in concentrated in vacuo and the residue was diluted with $CH_2Cl_2$ and $H_2O$ and the aqueous layer was made basic with NaOH. The layers were separated and the organics were dried over $MgSO_4$ and concentrated in vacuo to afford the crude title compound, which was used without further purification. MS (APCI pos) 345 (M+H).

Preparation XXXVI—6-piperidin-1-ylmethyl-1,2,3,4-tetrahydro-naphthalen-2-ylamine (6-Piperidin-1-ylmethyl-1,2,3,4-tetrahydro-naphthalen-2-yl)-carbamic acid tert-butyl ester (0.113 g, 0.327 mmol) was suspended in $CH_2Cl_2$ (2.5 mL) then TFA was added (2.5 mL). The reaction was stirred at RT until complete consumption of starting material was observed by HPLC analysis (2 h). The reaction mixture was concentrated in vacuo to afford the crude title compound as the bis-TFA salt, which was used without further purification. MS (APCI pos) 245 (M+H).

Preparation XXXVII—4-hydroxyimino-1-methyl-2,2-dioxo-1,2,3,4-tetrahydro-$2\lambda^6$-benzo[c][1,2]thiazine-7-carboxylic acid methyl ester NaOAc (3.66 g, 44.5 mmol) was added to an EtOH (100 mL) solution of 1-methyl-2,2,4-trioxo-1,2,3,4-tetrahydro-$2\lambda^6$-benzo[c][1,2]thiazine-7-carboxylic acid methyl ester (4.00 g, 14.8 mmol) and hydroxylamine hydrochloride (1.55 g, 22.3 mmol). After heating at reflux for 4 days, it was evaporated, diluted with $CH_2Cl_2$ (400 mL), washed with $H_2O$, dried over $MgSO_4$, filtered, and concentrated in vacuo. Crystallization from MeOH provided the title compound. MS (−APCI, m/z): 283 (M−H)⁻.

Preparation XXXVIII—4-Amino-1-methyl-2,2-dioxo-1,2,3,4-tetrahydro-$2\lambda^6$-benzo[c][1,2]thiazine-7-carboxylic acid methyl ester 4-Hydroxyimino-1-methyl-2,2-dioxo-1,2,3,4-tetrahydro-$2\lambda^6$-benzo[c][1,2]thiazine-7-carboxylic acid methyl ester (1.50 g, 5.28 mmol) was hydrogenated over $Pd(OH)_2$ (1.30 g, 20% on carbon, wet) in MeOH (100 mL) for 60 h. After filtration and evaporation, chromatography (silica, 0–3% MeOH in $CH_2CL_2$) furnished the title compound. MS (+APCI, m/z): 271 (M+H)⁺, 254 (M−$NH_2$)⁺, MS (−APCI, m/z): 252 (M−$NH_4$)⁻.

Preparation XXXIX—(S)-4-hydroxy-chroman-7-carbonitrile

A ruthenium chiral complex was prepared as follows: (1S,2S)-(+)-N-p-Tosyl-1,2-diphenylethylenediamine (1.10 g, 3.0 mmol, Aldrich) and [$RuCl_2(\kappa^6$-para–cymene)]$_2$ (0.92 g, 1.5 mmol, STREM) were dissolved in 35 mL of i-PrOH and stirred at 80° C. for 1 h. The reaction was concentrated under reduced pressure to ~5 mL. The mixture was cooled to −20° C., and 10 mL of $H_2O$ was added with shaking. The solution was scratched with a spatula until it all solidifies. The solid was filtered and washed with $H_2O$ to provide the desired chiral complex. The complex was dried in vacuo. A 5/2 mixture of formic acid and $Et_3N$ was prepared as follows: A mixture of formic acid (190 mL, 232 g, 5.03 mmol) and $Et_3N$ (280 mL, 203 g, 2.01 mmol) were heated to 100° C. under reduced pressure (~100 mm Hg) to remove volatile chemicals. The residue was used without further purification. 7-Cyanochroman-4-one (10.2 g, 58.9 mmol) and a 5/2 mixture of formic acid and $Et_3N$ (50 mL) were dissolved in $CH_3CN$ (120 ml). The ruthenium chiral complex (S,S-, 0.380 g, 0.589 mmol) was added. The reaction was stirred at RT for 14 h. After the addition of $H_2O$ (100 mL), the mixture was extracted with EtOAc (300 mL, 3×). The organic phases were combined and washed sequentially with a saturated $NaHCO_3$ solution and brine. The organic solution was dried over $MgSO_4$, filtered and concentrated in vacuo to provide a crude brown solid which was purified by flash column chromatography (silica, 50% EtOAc in hexane) to provide the title compound.

Preparation XL—(R)-4-azido-chroman-7-carbonitrile

Azeotropically dried (S)-4-hydroxy-chroman-7-carbonitrile (2.0 g, 11 mmol) was dissolved in dry THF (55 ml). DPPA (3.0 ml, 3.8 g, 14 mmol) was added to the solution at RT and the mixture was stirred for 5 min. The solution was cooled to 0° C. and 1,8-diazabicyclo[5,4,0]undec-7-ene (2.0 mL, 2.1 g, 14 mmol) was added. After stirring for 10 min at 0° C., the reaction was warmed to RT, at which time a white precipitate formed, and was stirred for 14 h. The resulting solution was poured into $H_2O$ (100 mL) and extracted with $Et_2O$ (300 mL, 3×). The organic phases were combined, washed with brine, dried over $MgSO_4$, filtered and concentrated in vacuo to provide a residue which was purified by flash column chromatography (silica, 33% hexane in $CH_2Cl_2$) to provide the title compound.

Preparation XLI—N-(7-Cyano-chroman-4-(R)-yl)-2-piperidin-2-yl-acetamide

2-Carboxymethyl-piperidine-1-carboxylic acid tert-butyl ester (700 mg, 2.9 mmol), 4-(R)-amino-chroman-7-carbonitrile (500 mg, 2.9 mmol), benzotriazol-1-ol (430 mg, 0.32 mmol), and diisopropylethylamine (560 mg, 4.4 mmol) were dissolved in dichloromethane (20 mL) followed by the addition of (3-dimethylamino-propyl)-ethyl-carbodiimide-HCl salt (667 mg, 3.5 mmol) with magnetic stirring. The reaction was kept at 22–25° C. overnight until completed. The reaction solution was washed with dilute (~5%) $NaHCO_3$—$H_2O$ and $H_2O$, and the solution was dried over magnesium sulfate, filtered and concentrated in vacuo. The crude product was purified by column chromatography (silica gel, 25% hexane in ethyl acetate) to provide the desired coupling product (970 mg, 79%), which was followed by deprotection with trifluoroacetic acid (4.0 mL) in dichloromethane (2.0 mL) solution overnight until completed. The reaction solution was poured into ethyl ether (50 mL) and the compound precipitated as a salt, then filtered to provide a white solid of the title compound as a mixture of diastereomers (ca. 1:1 by $^1$H NMR). MS (ESI) 300 (M+H)$^+$.

Preparation XLII—N-(7-Cyano-chroman-4-(R)-yl)-2-[1-(3-trifluoromethyl-benzenesulfonyl)-piperidin-2-yl]-acetamide N-(7-Cyano-chroman-4-(R)-yl)-2-piperidin-2-yl-acetamide (200 mg, 0.67 mmol) and DIEA (170 mg, 1.4 mmol) were dissolved in $CH_2Cl_2$ (4.0 mL), followed by the addition of 3-trifluoromethyl-benzenesulfonyl chloride (165 mg, 0.67 mmol) with magnetic stirring. The reaction was kept at 22–25° C. overnight until completed. The reaction solution was washed with dilute (~5%) $NaHCO_3$—$H_2O$ and $H_2O$, and the solution was dried over $MgSO_4$, filtered and concentrated in vacuo to provide a residue which was purified by column chromatography (silica gel, 20% hexane in EtOAc) to provide the title compound as a mixture of diastereomers (ca. 1:1 by $^1$H NMR). MS (ESI) 508 (M+H)$^+$.

Preparation XLIII—N-(7-Formyl-chroman-4-(R)-yl)-2-[1-(3-trifluoromethyl-benzenesulfonyl)-piperidin-2-yl]-acetamide N-(7-Cyano-chroman-4-(R)-yl)-2-[1-(3-trifluoromethyl-benzenesulfonyl)-piperidin-2-yl]-acetamide (230 mg, 0.45 mmol) and 230 mg Raney-Nickel were added to 3.0 mL of 78% formic acid-$H_2O$ solution, and the reaction solution was heated at 101° C. overnight until the reaction was complete. The reaction solution was filtered and poured into 40 mL ice-water. The compound was extracted with $CH_2Cl_2$ (2×30 mL), and the organic solution was washed with dilute $NaHCO_3$—$H_2O$ and $H_2O$, and dried over $MgSO_4$. After filtration and concentration in vacuo, the compound was purified by column chromatography (silica gel, EtOAc: $Et_2O$=2:1, v/v) to provide the title compound as a mixture of diastereomers (ca. 1:1 by $^1$H NMR). MS (ESI) 511 (M+H)$^+$.

Preparation XLIV—6-(tert-Butyl-dimethyl-silanyloxy)-3,4-dihydro-2H-naphthalen-1-one.

To a 250 mL round-bottomed flask equipped with magnetic stirring were added 6-hydroxy-1-tetralone (5.7 g, 35 mmol, Aldrich), imidazole (6 g, 88 mmol, Aldrich), and chloro-tert-butyldimethylsilane (6.3 g, 42 mmol, Aldrich) in DMF (40 mL). After stirring for ca. 18 h at RT, ether (500 mL) was added, and the organic layer was washed with 1 M HCl and brine (4×), dried over $MgSO_4$, filtered and concentrated in vacuo. The crude was purified on a Biotage silica gel column using 20:1 hexane-EtOAc as the eluant. The desired compound was isolated as a tan oil (ESI-MS, + ion, m/z=277 (MH$^+$)).

Preparation XLV-6-(tert-Butyl-dimethyl-silanyloxy)-1S,2,3,4-tetrahydro-naphthalen-1-ol.

To a flame-dried 50 mL round-bottomed flask equipped with a pressure-equalized addition funnel, magnetic stirring and argon inlet/outlet were added 6-(tert-butyl-dimethyl-silanyloxy)-3,4-dihydro-2H-naphthalen-1-one (1 g, 3.6 mmol) and (3aR)-tetrahydro-1-methyl-3,3-diphenyl-1H,3H-pyrrolo[1,2-c][1,3,2]oxazaborole ((R)-Me-CBS, 0.36 mL of a 1 M solution in toluene, 0.36 mmol, Aldrich) in 3 mL of $CH_2Cl_2$. After cooling in a −25° C. bath (dry ice in $CCl_4$), borane-dimethyl sulfide complex (0.36 mL, 3.8 mmol, Aldrich) in 3 mL of $CH_2Cl_2$ was added in small portions through the addition funnel over 4.5 h. After the addition of borane was completed, the sample was placed in a −15° C. freezer overnight. The next morning, 2 mL of the reaction mixture was removed and quenched with 18 mg of solid citric acid, and the mixture was stirred at RT for 20 min. Toluene was added, and the lower boiling solvents were removed in vacuo. EtOAc was added, and the organic layer was washed with 10% citric acid, sat'd $NaHCO_3$, and brine. The organic layers were dried over $MgSO_4$, filtered and concentrated in vacuo to give (ESI-MS, m/z=261 (MH–$H_2O$)) the desired compound with minor impurities, but sufficiently pure for the next step. The remaining material from the reaction mixture was quenched with 90 mg of solid citric acid and worked-up by the same method as described above. This material was purified on a Biotage silica gel column using 3:1 hexane-ether as the eluant to give the purified compound as a colorless oil. (ESI-MS, + ion, m/z=261 (MH–$H_2O$)).

Preparation LXVI—(5R-Azido-5,6,7,8-tetrahydro-naphthalen-2-yloxy)-tert-butyl-dimethyl-silane.

To a 100 mL round-bottomed flask equipped with magnetic stirring and argon inlet/outlet was added 6-(tert-butyldimethyl-silanyloxy)-1S,2,3,4-tetrahydro-naphthalen-1-ol (460 mg, 1.65 mmol) in 7 mL of toluene. The flask was cooled in a −25° C. bath (dry ice in CCl$_4$), and DPPA (540 mg, 1.98 mmol, Aldrich) and 1,8-diaza-7-bicyclo[5.4.0]undecene (300 mg, 1.98 mmol) were added. Toluene (1 mL) was used to aid in the transfer of these last two reagents. The reaction was warmed to RT overnight, and was quenched with 10% citric acid the next day. The aqueous layer was extracted with Et$_2$O (3×), and the combined organic extracts were washed with sat'd NaHCO$_3$ and brine, dried over MgSO$_4$, filtered and concentrated in vacuo. The crude was purified on a Biotage 40S silica gel column using 2% EtOAc-hexane as the eluant. Desired material was isolated as a clear oil.

Preparation LXVII—6-(tert-Butyl-dimethyl-silanyloxy)-1R,2,3,4-tetrahydro-naphthalen-1-ylamine.

To a 10 mL round-bottomed flask containing magnetic stirring was added (5R-azido-5,6,7,8-tetrahydro-naphthalen-2-yloxy)-tert-butyl-dimethylsilane (198 mg, 0.65 mmol) in 2.5 mL of MeOH. Palladium ethylenediamine complex (23 mg, prepared by the method of Sajiki et al., see J. Org. Chem., 63:7990 (1998)) was added. The flask was purged with H$_2$ and fitted with a balloon full of H$_2$ (ca. 1 L). After ca. 4 h, the mixture was poured through a pad of Celite®, the pad was washed with MeOH, and the filtrate was concentrated in vacuo to give the desired compound as a clear oil.

Preparation LXVII—4-Methyl-3-trifluoromethyl-benzenesulfonyl chloride.

Following the method described by R. V. Hoffman (Org. Syn. Coll. 7:508), HCl (12 M, 10 mL), acetic acid (3 mL), and 4-amino-2-trifluoromethyltoluene (5 g, 29 mmol, Lancaster) were added to a 50 mL round bottomed flask equipped with magnetic stirring and an internal temperature probe. The viscous mixture was cooled in a dry-ice/EtOH bath, and sodium nitrite (2.2 g, 32 mmol, Aldrich) in 3 mL of water was added over 10 min at such a rate that the internal temperature was maintained between −5 and −15° C. Into a separate round-bottomed flask was added 30 mL of HOAc, and sulfur dioxide gas (Aldrich) was bubbled into this solution for 20 min. Copper(I)chloride (720 mg, 7.3 mmol, Aldrich) was added to this solution, and sulfur dioxide was bubbled into this solution for another 20 min. This cuprous solution was cooled in an ice bath, and the diazonium salt from above was added in small portions over 30 min. Gas evolution occurred. After complete addition of the diazonium salt, the mixture stirred for another 15 min in the ice bath. The contents were then added to a 1:1 mixture of water/ice (100 mL) affording a yellow solid, which was set aside. The remaining solution was extracted with ether (3×). These ether layers were combined and used to dissolve the yellow solid previously set aside. This combined organic layer was washed with sat'd NaHCO$_3$ (2×, caution! vigorous gas evolution), water, and brine, dried over MgSO$_4$, filtered, and concentrated in vacuo. The desired material was isolated as a brown oil. The compound did not ionize well, but an aliquot, when treated with dimethylamine, provided the dimethyl-arylsulfonamide adduct with a ESI-MS, + ion, m/z=268 (MH$^+$).

Preparation LXVIII—4-Chloro-3-trifluoromethyl-benzenesulfonyl chloride.

Following the procedure of N. Ikemoto et al. (Tetrahedron, 59:1317 (1998)), 3-chloro-4-trifluoromethylaniline (890 mg, 4.6 mmol, Ryan Scientific) in CH$_3$CN (37 mL) was added to a 250 mL round-bottomed flask. The flask was cooled in an ice bath, and HOAc (3.7 mL) and HCl (12 M, 1.8 mL) were added. Sodium nitrite (380 mg, 5.5 mmol, Aldrich) in 0.77 mL of H$_2$O was added in 0.15 mL portions every 2 min until all of the solution had been added (total time ca. 9 min). After 25 min, sulfur dioxide (Aldrich) was bubbled into the reaction mixture for 1.25 h. Copper(II) chloride (780 mg, 5.8 mmol, Aldrich) in 1.5 mL of water was then added to the reaction mixture. Gas evolution occurred, and the reaction was warmed to RT and stirred overnight. After the lower boiling solvents were removed in vacuo, water was added, and the mixture was extracted with CH$_2$Cl$_2$ (3×). The combined organic layers were washed with water, dried over MgSO$_4$, filtered and concentrated in vacuo to give the crude material as a brownish oil with solid in it. The compound did not ionize well, but an aliquot, when treated with propylamine, provided the propylarylsulfonamide adduct with a ESI-MS, −ion, m/z=300.2 (M−1).

EXAMPLE 1

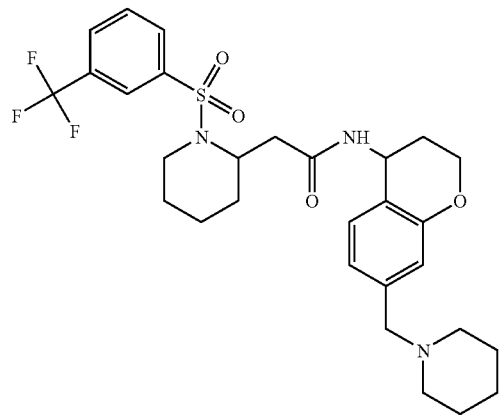

N-(7-Piperidin-1-ylmethyl-chroman-4-(R)-yl)-2-[1-(3-trifluoromethyl-benzenesulfonyl)-piperidin-2-yl]-acetamide N-(7-Formyl-chroman-4-(R)-yl)-2-[1-(3-trifluoromethyl-benzenesulfonyl)-piperidin-2-yl]-acetamide (135 mg, 0.26 mmol) and piperidine (28 mg, 0.33 mmol) were added to N,N-dimethyl-acetamide (1.5 mL) solution, followed by NaBH(OAc)$_3$ (115 mg, 0.52 mmol) and the reaction was stirred overnight (14 h). The reaction was quenched with dilute NaHCO$_3$—H$_2$O (10 mL), and the mixture was extracted with CH$_2$Cl$_2$ (2×10 mL), and the organic phase was washed with dilute NaHCO$_3$—H$_2$O and H$_2$O, and dried over MgSO$_4$. After filtration and concentration in vacuo, the crude was purified by precipitation and crystallization as the HCl salt in Et$_2$O to provide a white solid (of the title compound as a mixture of diastereomers (ca. 1:1 by $^1$H NMR). MS (ESI) 580 (M+H)$^+$.

EXAMPLE 2

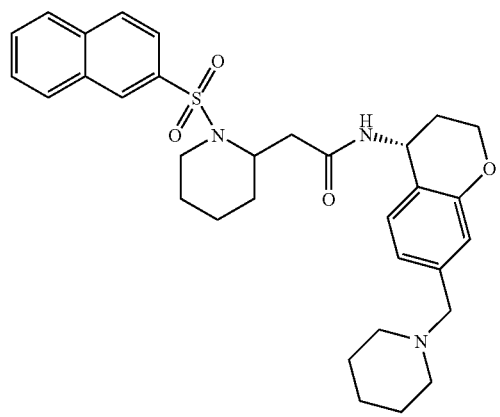

2-[1-(Naphthalene-2-sulfonyl)-piperidin-2-yl]-N-(7-piperidin-1-ylmethyl-chroman-4-(R)-yl)-acetamide The synthetic procedure was essentially the same as preparation of the compound of Example 1 to provide the title compound as a mixture of diastereomers (ca. 2:3 by $^1$H NMR). MS (ESI) 562 (M+H)$^+$.

EXAMPLE 3

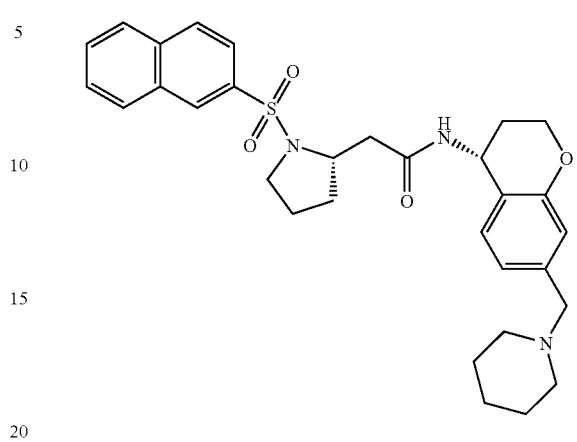

2-[1-(Naphthalene-2-sulfonyl)-pyrrolidin-2-(L)-yl]-N-(7-piperidin-1-ylmethyl-chroman-4-(R)-yl)-acetamide The example was prepared from (S)-2-carboxymethyl-pyrrolidine-1-carboxylic acid tert-butyl ester using a synthetic procedure similar to that found in Example 1.

The following compounds can be prepared by methods similar to that described above:

| Example | Structure | M + H | MASS |
|---|---|---|---|
| a | 2-((2S)-1-(2,1,3-benzoxadiazol-4-ylsulfonyl)-2-pyrrolidinyl)-N-((4R)-7-(((1,1-dimethylethyl)amino)methyl)-3,4-dihydro-2H-chromen-4-yl)acetamide $C_{26}H_{33}N_5O_5S$ | 528.3 | 527.22 |

-continued

| Example | Structure | | M + H | MASS |
|---|---|---|---|---|
| b | N-((4R)-7-(((1,1-dimethylethyl)amino)methyl)-3,4-dihydro-2H-chromen-4-yl)-2-((2S)-1-((4-(1,1-dimethylethyl)phenyl)sulfonyl)-2-pyrrolidinyl)acetamide | $C_{30}H_{43}N_3O_4S$ | 542.5 | 541.30 |
| c | 2-((2S)-1-((2,4-dichlorophenyl)sulfonyl)-2-pyrrolidinyl)-N-((4R)-7-(((1,1-dimethylethyl)amino)methyl)-3,4-dihydro-2H-chromen-4-yl)acetamide | $C_{26}H_{33}Cl_2N_3O_4S$ | 554.2 | 553.16 489.24 |
| d | N-((4R)-7-(((1,1-dimethylethyl)amino)methyl)-3,4-dihydro-2H-chromen-4-yl)-2-((2S)-1-((1-methyl-1H- | $C_{24}H_{35}N_5O_4S$ | 490.4 | |

-continued

| Example | Structure | | M + H | MASS |
|---|---|---|---|---|
| | imidazol-4-yl)sulfonyl)-2-pyrrolidinyl)acetamide | | | |
| e | 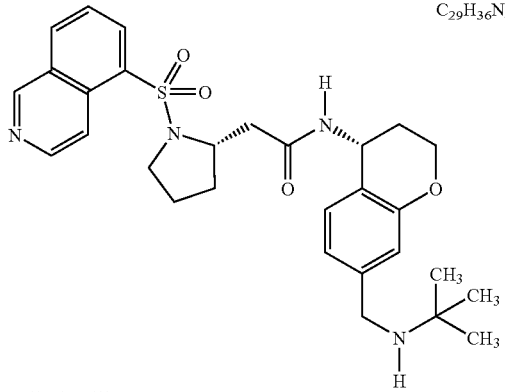 N-((4R)-7-(((1,1-dimethylethyl)amino)methyl)-3,4-dihydro-2H-chromen-4-yl)-2-((2S)-1-(5-isoquinolinylsulfonyl)-2-pyrrolidinyl)acetamide | $C_{29}H_{36}N_4O_4S$ | 537.2 | 536.25 |
| f | 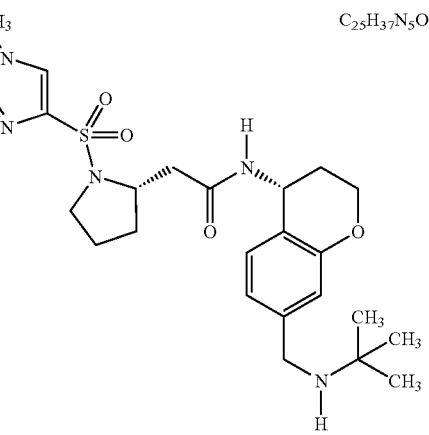 N-((4R)-7-(((1,1-dimethylethyl)amino)methyl)-3,4-dihydro-2H-chromen-4-yl)-2-((2S)-1-((1,2-dimethyl-1H-imidazol-4-yl)sulfonyl)-2-pyrrolidinyl)acetamide | $C_{25}H_{37}N_5O_4S$ | 504.3 | 503.26 |
| g | 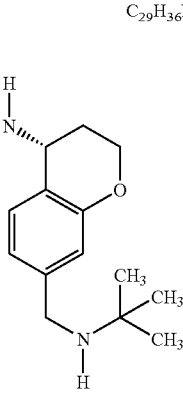 N-((4R)-7-(((1,1-dimethylethyl)amino)methyl)-3,4-dihydro-2H-chromen-4-yl)-2-((2S)-1-(8- | $C_{29}H_{36}N_4O_4S$ | 536.4 | 536.25 |

| Example | Structure | | M + H | MASS |
|---|---|---|---|---|
| | quinolinylsulfonyl)-2-pyrrolidinyl)acetamide | | | |
| h | 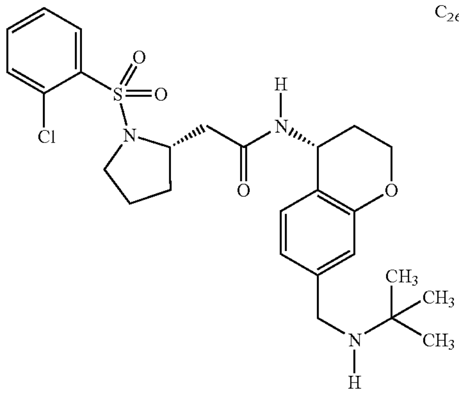 | C₂₆H₃₄ClN₃O₄S | 520.1 | 519.20 |
| | 2-((2S)-1-((2-chloro-5-(trifluoromethyl)phenyl)sulfonyl)-2-pyrrolidinyl)-N-((4R)-7-(((1,1-dimethylethyl)amino)methyl)-3,4-dihydro-2H-chromen-4-yl)acetamide | | | |
| i | 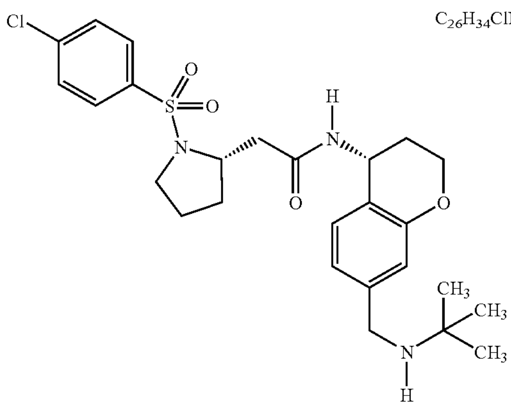 | C₂₆H₃₄ClN₃O₄S | 520.3 | 519.20 |
| | 2-((2S)-1-((2,4-dichlorophenyl)sulfonyl)-2-pyrrolidinyl)-N-((4R)-7-(((1,1-dimethylethyl)amino)methyl)-3,4-dihydro-2H-chromen-4-yl)acetamide | | | |

-continued
| Example | Structure | | M + H | MASS |
|---|---|---|---|---|
| j | 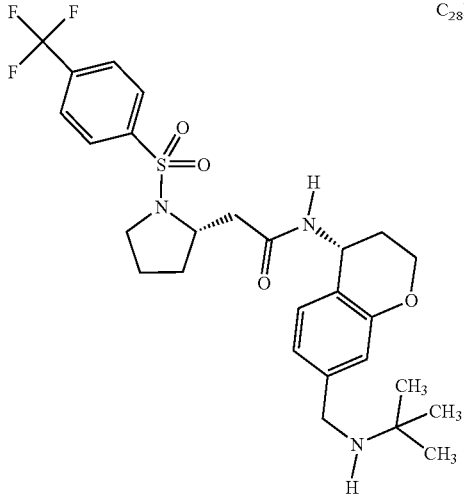 N-((4R)-7-(((1,1-dimethylethyl)amino)methyl)-3,4-dihydro-2H-chromen-4-yl)-2-((2S)-1-((4-(trifluoromethyl)phenyl)sulfonyl)-2-pyrrolidinyt)acetamide | $C_{28}H_{38}F_3N_3O_4S$ | 570.3 | 569.25 |
| k | 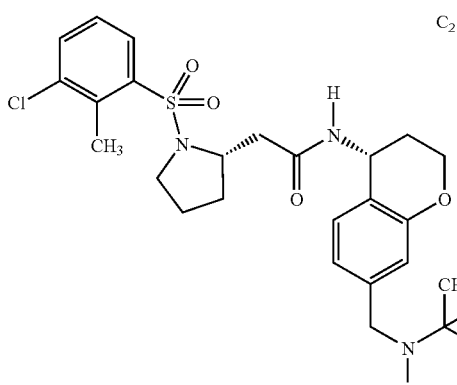 2-((2S)-1-((3-chloro-2-methylphenyl)sulfonyl)-2-pyrrolidinyl)-N-((4R)-7-(((1,1-dimethylethyl)amino)methyl)-3,4-dihydro-2H-chromen-4-yl)acetamide | $C_{27}H_{36}ClN_3O_4S$ | 534.3 | 533.21 |
| l | 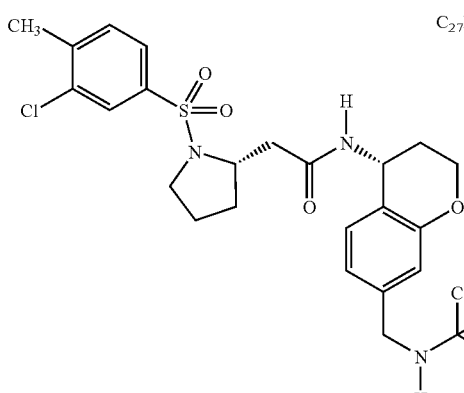 2-((2S)-1-((3-chloro-4-methylphenyl)sulfonyl)-2-pyrrolidinyl)-N-((4R)-7-(((1,1- | $C_{27}H_{36}ClN_3O_4S$ | 534.4 | 533.21 |

-continued

| Example | Structure | | M + H | MASS |
|---|---|---|---|---|
| m | N-((4R)-7-(((1,1-dimethylethyl)amino)methyl)-3,4-dihydro-2H-chromen-4-yl)-2-((2S)-1-((4-fluoro-3-(trifluoromethyl)phenyl)sulfonyl)-2-pyrrolidinyl)acetamide | C₂₇H₃₃F₄N₃O₄S | 572.2 | 571.21 |
| n | 2-((2S)-1-((5-chloro-2,4-difluorophenyl)sulfonyl)-2-pyrrolidinyl)-N-((4R)-7-(((1,1-dimethylethyl)amino)methyl)-3,4-dihydro-2H-chromen-4-yl)acetamide | C₂₆H₃₂ClF₂N₃O₄S | 556.3 | 555.18 |
| o | 2-((2S)-1-((3-chloro-4-fluorophenyl)sulfonyl)-2-pyrrolidinyl)-N-((4R)-7-(((1,1- | C₂₆H₃₃ClFN₃O₄S | 538.3 | 537.19 |

-continued

| Example | Structure | | M + H | MASS |
|---------|-----------|---|-------|------| dimethylethyl)amino)methyl)-3,4-dihydro-2H-chromen-4-yl)acetamide p 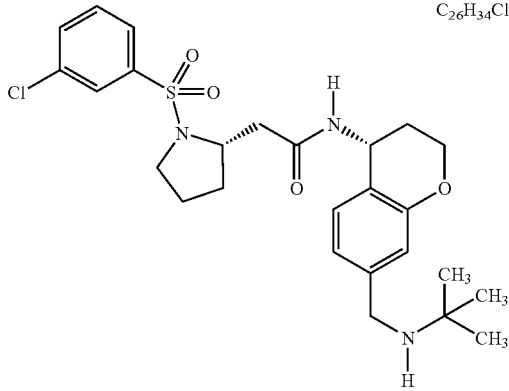 C₂₆H₃₄ClN₃O₄S 520.2 519.20

2-((2S)-1-((3-chlorophenyl)sulfonyl)-2-pyrrolidinyl)-N-((4R)-7-(((1,1-dimethylethyl)amino)methyl)-3,4-dihydro-2H-chromen-4-yl)acetamide q 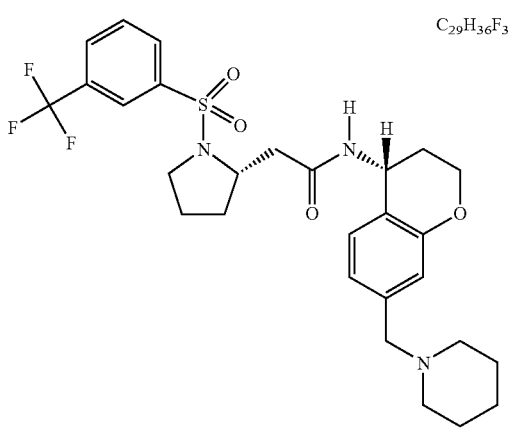 C₂₉H₃₆F₃N₃O₃S 563.4 563.24

N-((1R)-6-(1-piperidinylmethyl)-1,2,3,4-tetrahydro-1-naphthalenyl)-2-((2S)-1-((3-(trifluoromethyl)phenyl)sulfonyl)-2-pyrrolidinyl)acetamide r 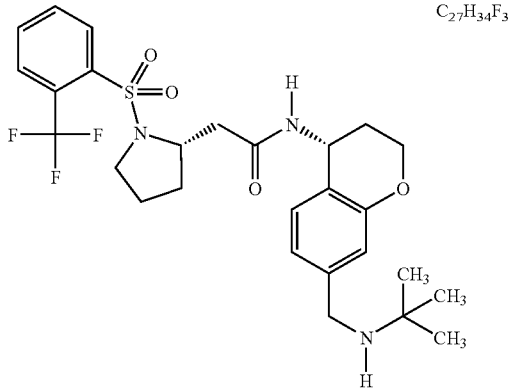 C₂₇H₃₄F₃N₃O₄S 554.3 553.22

N-((4R)-7-(((1,1-dimethylethyl)amino)methyl)-3,4-dihydro-2H-chromen-4-yl)-2-((2S)-1-((2-

-continued

| Example | Structure | | M + H | MASS |
|---|---|---|---|---|
| | (trifluoromethyl)phenyl)sulfonyl)-2-pyrrolidinyl)acetamide | | | |
| s | [Structure diagram] N-((4R)-7-(1-piperidinylmethyl)-3,4-dihydro-2H-chromen-4-yl)-2-((2S)-1-((2,4,6-trimethylphenyl)sulfonyl)-2-pyrrolidinyl)acetamide | C₃₀H₄₁N₃O₄S | 539.4 | 539.28 |
| t | [Structure diagram] 2-((2S)-1-((5-chloro-2-thienyl)sulfonyl)-2-pyrrolidinyl)-N-((4R)-7-(1-piperidinylmethyl)-3,4-dihydro-2H-chromen-4-yl)acetamide | C₂₅H₃₂ClN₃O₄S₂ | 538.3 | 537.15 |
| v | [Structure diagram] N-((1R)-6-(((1,1-dimethylethyl)amino)methyl)- | C₂₉H₃₈F₃N₃O₃S | 566.4 | 565.26 |

-continued

| Example | Structure | | M + H | MASS |
|---|---|---|---|---|
| | 1,2,3,4-tetrahydro-1-naphthalenyl)-2-((2S)-1-((3-(trifluoromethyl)phenyl)sulfonyl)-2-piperidinyl)acetamide | | | |
| v | [structure] | C$_{29}$H$_{41}$N$_3$O$_3$S | 552 | 511.29 |
| | N-((1R)-6-(((1,1-dimethylethyl)amino)methyl)-1,2,3,4-tetrahydro-1-naphthalenyl)-2-((2S)-1-((4-methylphenyl)sulfonyl)-2-piperidinyl)acetamide | | | |
| w | [structure] | C$_{28}$H$_{38}$ClN$_3$O$_3$S | 532.4 | 531.23 |
| | N-((1R)-6-(((1,1-dimethylethyl)amino)methyl)-1,2,3,4-tetrahydro-1-naphthalenyl)-2-((2S)-1-((4-chlorophenyl)sulfonyl)-2-piperidinyl)acetamide | | | |
| x | [structure] | C$_{29}$H$_{41}$N$_3$O$_4$S | 528.6 | 527.28 |

| Example | Structure | | M + H | MASS |
|---|---|---|---|---|
| | N-((1R)-6-(((1,1-dimethylethyl)amino)methyl)-1,2,3,4-tetrahydro-1-naphthalenyl)-2-((2S)-1-((4-methoxyphenyl)sulfonyl)-2-piperidinyl)acetamide | | | |
| y | 2-((2S)-1-((3-chloro-4-methylphenyl)sulfonyl)-2-piperidinyl)-N-((1R)-6-(((1,1-dimethylethyl)amino)methyl)-1,2,3,4-tetrahydro-1-naphthalenyl)acetamide | $C_{29}H_{40}ClN_3O_3S$ | 546.5 | 545.25 |
| z | 2-((2S)-1-((2,4,6-trimethylphenyl)sulfonyl)-2-piperidinyl)-N-((1R)-6-(((1,1-dimethylethyl)amino)methyl)-1,2,3,4-tetrahydro-1-naphthalenyl)acetamide | $C_{31}H_{45}N_3O_3S$ | 539.4 | 539.32 |

-continued

| Example | Structure | | M + H | MASS |
|---|---|---|---|---|
| aa | 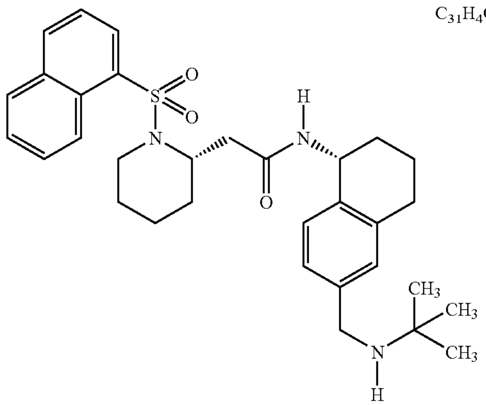 | C₃₁H₄ON₄O₃S | 548.3 | 548.28 |
| | N-((1R)-6-(((1,1-dimethylethyl)amino)methyl)-1,2,3,4-tetrahydro-1-naphthalenyl)-2-((2S)-1-(8-quinolinylsulfonyl)-2-piperidinyl)acetamide | | | |
| ab | 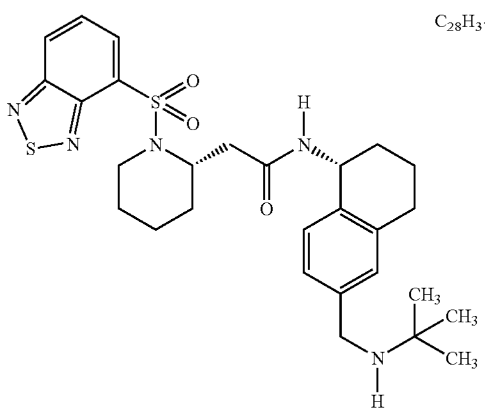 | C₂₈H₃₇N₅O₃S₂ | 556.4 | 555.23 |
| | 2-((2S)-1-(2,1,3-benzothiadiazol-4-ylsulfonyl)-2-piperidinyl)-N-((1R)-6-(((1,1-dimethylethyl)amino)methyl)-1,2,3,4-tetrahydro-1-naphthalenyl)acetamide | | | |

| Example | Structure | M + H | MASS |
|---------|-----------|-------|------|
| ac | 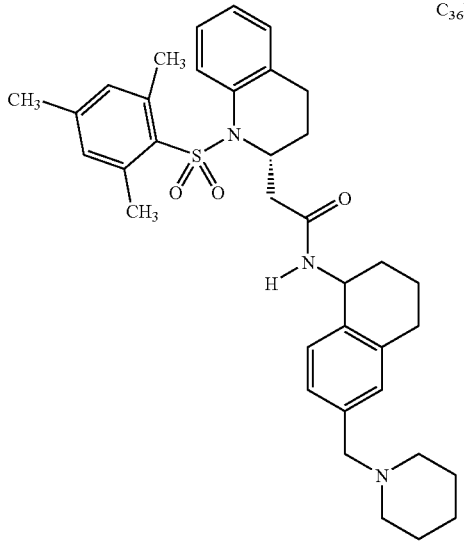 C₃₆H₄₅N₃O₃S<br>N-((1R)-6-(1-piperidinylmethyl)-1,2,3,4-tetrahydro-1-naphthalenyl)-2-((2S)-1-((2,4,6-trimethylphenyl)sulfonyl)-1,2,3,4-tetrahydro-2-quinolinyl)acetamide | 600.3 | 599.32 |
| ad | 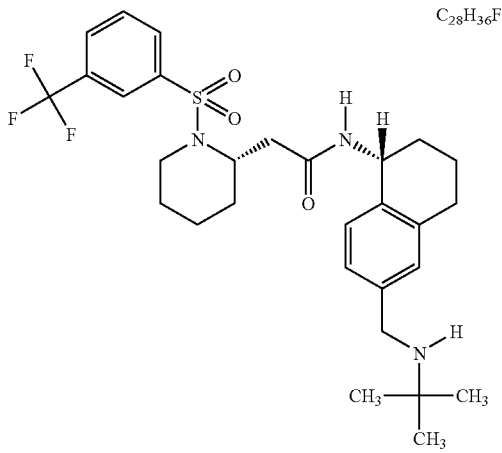 C₂₈H₃₆F₃N₃O₄S<br>N-((4R)-7-(((1,1-dimethylethyl)amino)methyl)-3,4-dihydro-2H-chromen-4-yl)-2-((2S)-1-((3-(trifluoromethyl)phenyl)sulfonyl)-2-piperidinyl)acetamide | 568.4 | 567.24 |

-continued
| Example | Structure | | M + H | MASS |
|---|---|---|---|---|
| ae | 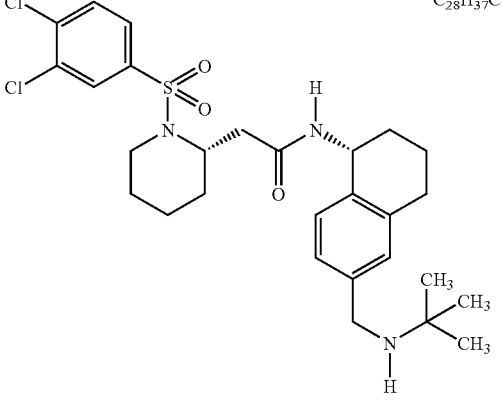  2-((2S)-1-((3,4-dichlorophenyl)sulfonyl)-2-piperidinyl)-N-((1R)-6-(((1,1-dimethylethyl)amino)methyl)-1,2,3,4-tetrahydro-1-naphthalenyl)acetamide | $C_{28}H_{37}Cl_2N_3O_3S$ | 566.3 | 565.19 |
| af | 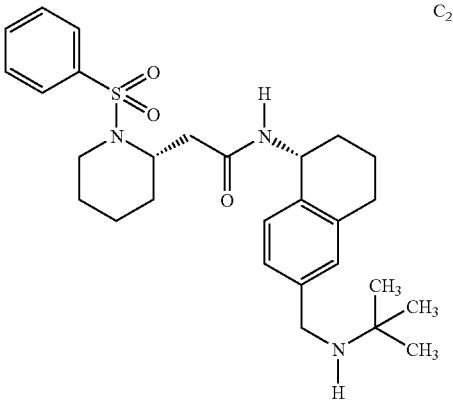  N-((1R)-6-(((1,1-dimethylethyl)amino)methyl)-1,2,3,4-tetrahydro-1-naphthalenyl)-2-((2S)-1-phenyl)sulfonyl)-2-piperidinyl)acetamide | $C_{28}H_{39}N_3O_3S$ | 498.1 | 497.27 |

| Example | Structure | | M + H | MASS |
|---|---|---|---|---|
| ag | 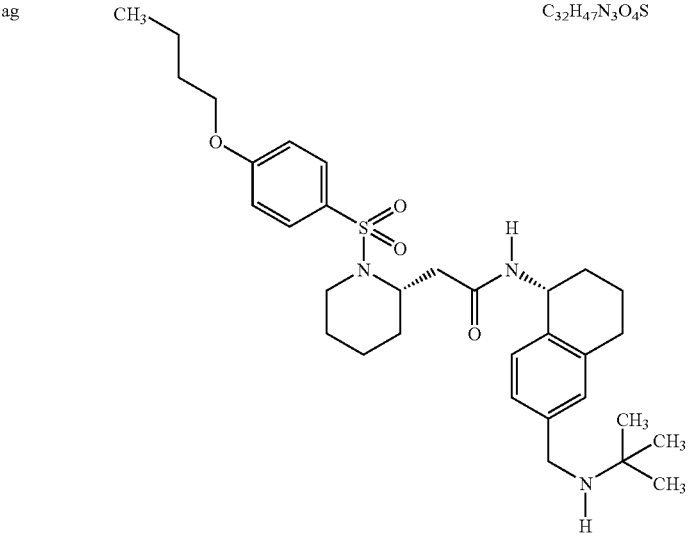<br>2-((2S)-1-((4-(butyloxy)phenyl)sulfonyl)-2-piperidinyl)-N-((1R)-6-(((1,1-dimethylethyl)amino)methyl)-1,2,3,4-tetrahydro-1-naphthalenyl)acetamide | $C_{32}H_{47}N_3O_4S$ | 570.6 | 569.33 |
| ah | 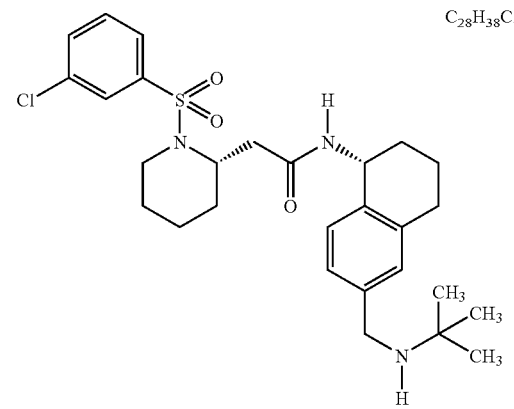<br>2-((2S)-1-((3-chlorophenyl)sulfonyl)-2-piperidinyl)-N-((1R)-6-(((1,1-dimethylethyl)amino)methyl)-1,2,3,4-tetrahydro-1-naphthalenyl)acetamide | $C_{28}H_{38}ClN_3O_3S$ | 532 | 531.23 |

-continued
| Example | Structure | | M + H | MASS |
|---|---|---|---|---|
| ai | 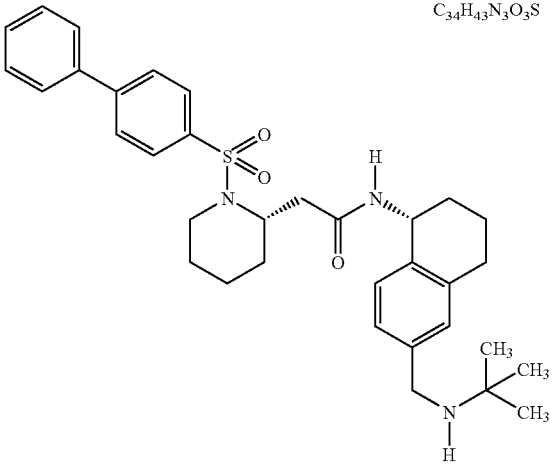 2-((2S)-1-((3-biphenyl)sulfonyl)-2-piperidinyl)-N-((1R)-6-(((1,1-dimethylethyl)amino)methyl)-1,2,3,4-tetrahydro-1-naphthalenyl)acetamide | $C_{34}H_{43}N_3O_3S$ | 574.6 | 573.30 |
| aj | 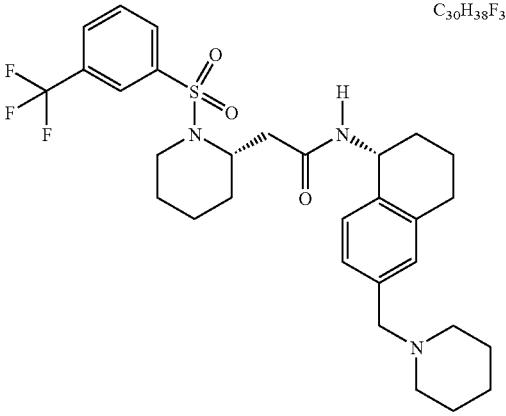 N-((1R)-6-(1-piperidinyl)methyl)-1,2,3,4-tetrahydro-1-naphthalenyl)-2-((2S)-1-((3-(trifluoromethyl)phenyl)sulfonyl)-2-piperidinyl)acetamide | $C_{30}H_{38}F_3N_3O_3S$ | 577.1 | 577.26 |
| ak | 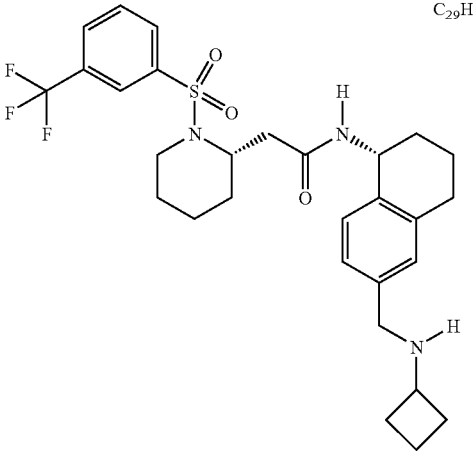 N-((1R)-6-((cyclobutylamino)methyl)- | $C_{29}H_{36}F_3N_3O_3S$ | 564.4 | 563.24 |

-continued

| Example | Structure | | M + H | MASS |
|---|---|---|---|---|
| | 1,2,3,4-tetrahydro-1-naphthalenyl)-2-((2S)-1-((3-(trifluoromethyl)phenyl)sulfonyl)-2-piperidinyl)acetamide | | | |
| al | 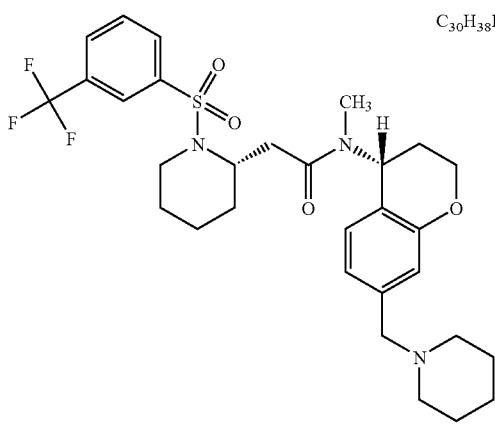<br>N-methyl-N-((4R)-7-(1-piperidinylmethyl)-3,4-dihydro-2H-chromen-4-yl)-2-((2S)-1-((3-(trifluoromethyl)phenyl)sulfonyl)-2-piperidinyl)acetamide | $C_{30}H_{38}F_3N_3O_4S$ | 594.6 | 593.25 |
| am | 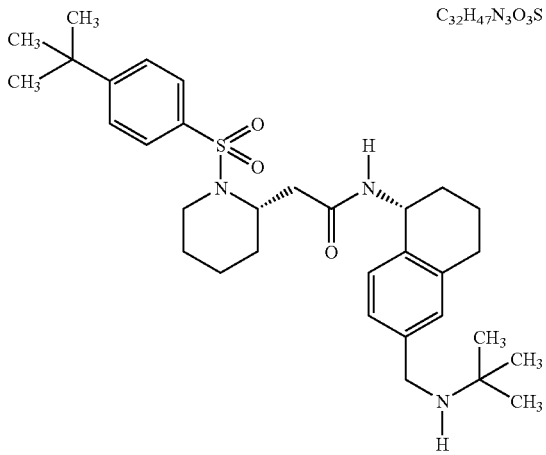<br>N-((1R)-6-(((1,1-dimethylethyl)amino)methyl)-1,2,3,4-tetrahydro-1-naphthalenyl)-2-((2S)-1-((4-(1,1-dimethylethyl)phenyl)sulfonyl)-2-piperidinyl)acetamide | $C_{32}H_{47}N_3O_3S$ | 554 | 553.33 |

-continued

| Example | Structure | | M + H | MASS |
|---|---|---|---|---|
| an | 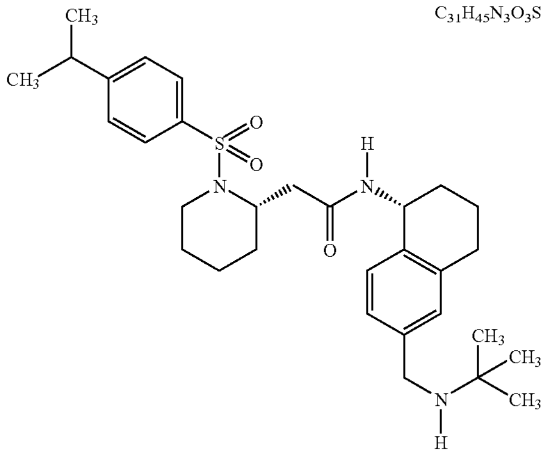 | C₃₁H₄₅N₃O₃S | 540.1566 | 539.32 |
| | N-((1R)-6-(((1,1-dimethylethyl)amino)methyl)-1,2,3,4-tetrahydro-1-naphthalenyl)-2-((2S)-1-((4-(1,1-dimethylethyl)phenyl)sulfonyl)-2-piperidinyl)acetamide | | | |
| ao | 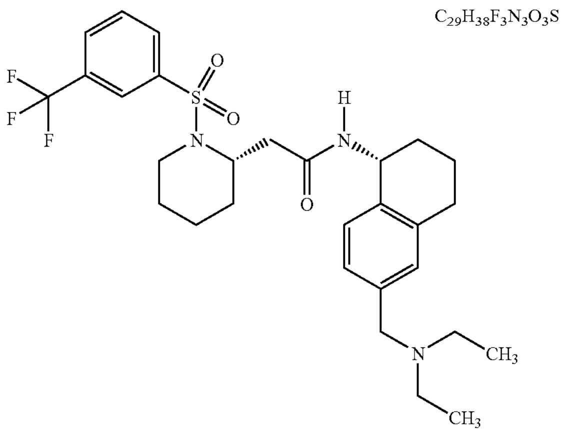 | C₂₉H₃₈F₃N₃O₃S | | 565.26 |
| | N-((1R)-6-((diethylamino)methyl)-1,2,3,4-tetrahydro-1-naphthalenyl)-2-((2S)-1-((3-(trifluoromethyl)phenyl)sulfonyl)-2-piperidinyl)acetamide | | | |
| ap | 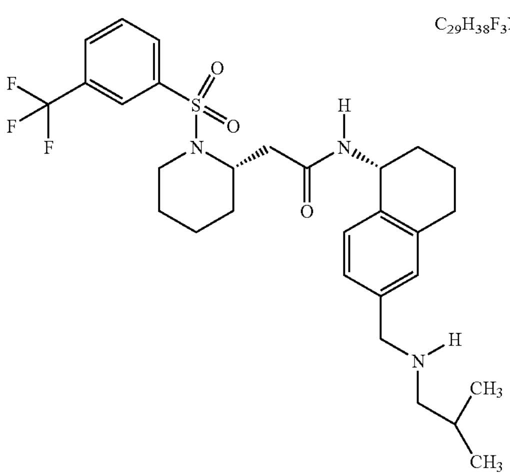 | C₂₉H₃₈F₃N₃O₃S | 566.7 | 565.26 |

| Example | Structure | | M + H | MASS |
|---|---|---|---|---|
| | N-((1R)-6-(((isobutylamino)methyl)-1,2,3,4-tetrahydro-1-naphthalenyl)-2-((2S)-1-((3-(trifluoromethyl)phenyl)sulfonyl)-2-piperidinyl)acetamide | | | |
| aq | 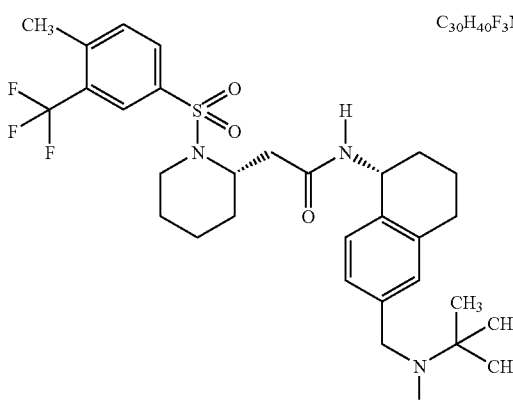 N-((1R)-6-(((1,1-dimethylethyl)amino)methyl)-1,2,3,4-tetrahydro-1-naphthalenyl)-2-((2S)-1-((4-methyl-3-(trifluoromethyl)phenyl)sulfonyl)-2-piperidinyl)acetamide | C₃₀H₄₀F₃N₃O₃S | 580.4 | 579.27 |
| ar |  N-((1R)-6-(((1,1-dimethylethyl)amino)methyl)-1,2,3,4-tetrahydro-1-naphthalenyl)-2-((2S)-1-(5-isoquinolinylsulfonyl)-2-piperidinyl)acetamide | C₃₁H₄₀N₄O₃S | 550.1 | 548.28 |

| Example | Structure | | M + H | MASS |
|---|---|---|---|---|
| as | 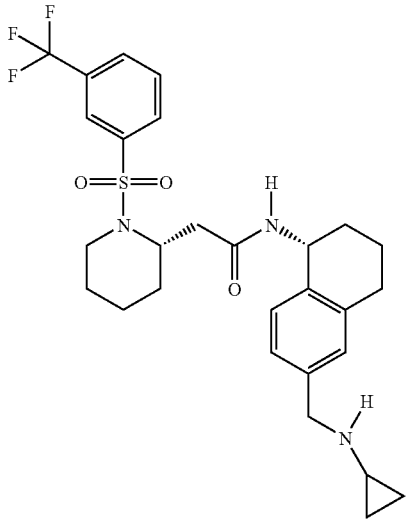<br>N-((1R)-6-((cyclopropylamino)methyl)-1,2,3,4-tetrahydro-1-naphthalenyl)-2-((2S)-1-((3-(trifluoromethyl)phenyl)sulfonyl)-2-piperidinyl)acetamide | $C_{28}H_{34}F_3N_3O_3S$ | 550.2 | 549.23 |
| at | 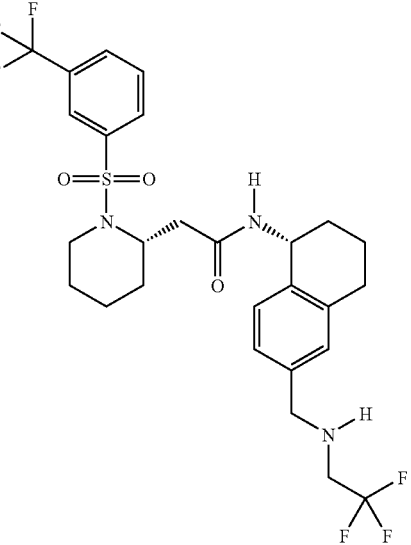<br>N-((1R)-6-(((2,2,2-trifluoroethyl)amino)methyl)-1,2,3,4-tetrahydro-1-naphthalenyl)-2-((2S)-1-((3-(trifluoromethyl)phenyl)sulfonyl)-2-piperidinyl)acetamide | $C_{27}H_{31}F_6N_3O_3S$ | 592.3 | 591.20 |

-continued
| Example | Structure | | M + H | MASS |
|---|---|---|---|---|
| au | 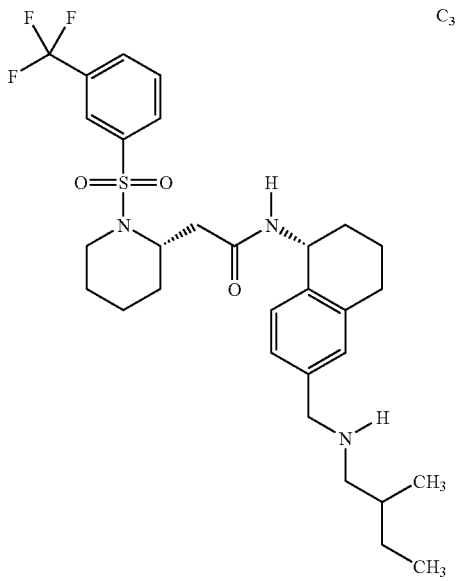 N-((1R)-6-(((2-methylbutyl)amino)methyl)-1,2,3,4-tetrahydro-1-naphthalenyl)-2-((2S)-1-((3-(trifluoromethyl)phenyl)sulfonyl)-2-piperidinyl)acetamide | $C_{30}H_{40}F_3N_3O_3S$ | 580.4 | 579.27 |
| av | 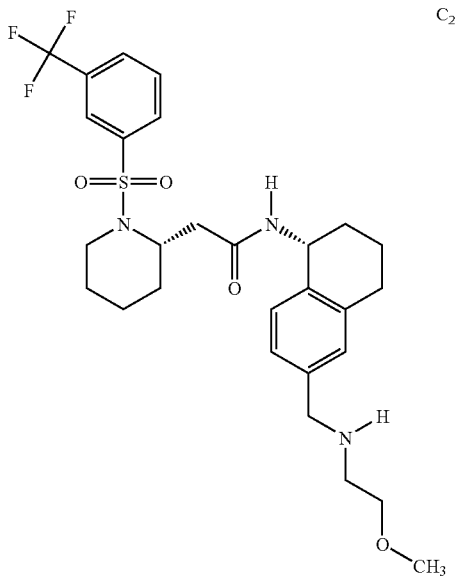 N-((1R)-6-(((2-(methyloxy)ethyl)amino)methyl)-1,2,3,4-tetrahydro-1-naphthalenyl)-2-((2S)-1-((3-(trifluoromethyl)phenyl)sulfonyl)-2-piperidinyl)acetamide | $C_{28}H_{36}F_3N_3O_4S$ | 568 | 567.24 |

-continued

| Example | Structure | | M + H | MASS |
|---|---|---|---|---|
| aw | 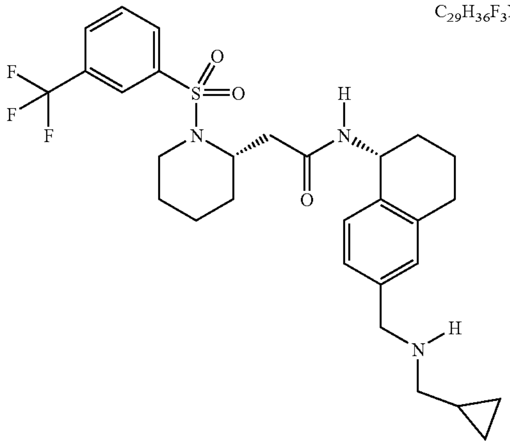 | $C_{29}H_{36}F_3N_3O_3S$ | 564 | 563.24 |
| | N-((1R)-6-(((cyclopropylmethyl)amino)methyl)-1,2,3,4-tetrahydro-1-naphthalenyl)-2-((2S)-1-((3-(trifluoromethyl)phenyl)sulfonyl)-2-piperidinyl)acetamide | | | |
| ax | 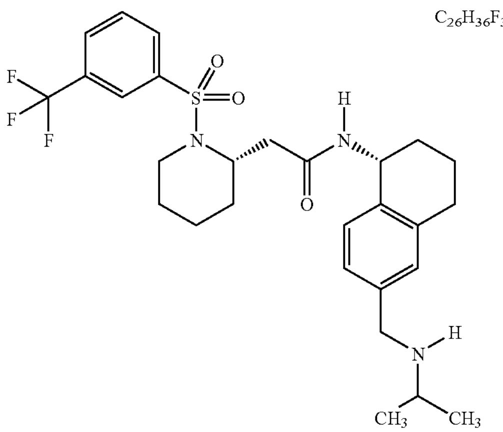 | $C_{26}H_{36}F_3N_3O_3S$ | 552.1 | 551.24 |
| | N-((1R)-6-(((isopropylmethyl)amino)methyl)-1,2,3,4-tetrahydro-1-naphthalenyl)-2-((2S)-1-((3-(trifluoromethyl)phenyl)sulfonyl)-2-piperidinyl)acetamide | | | |
| ay | 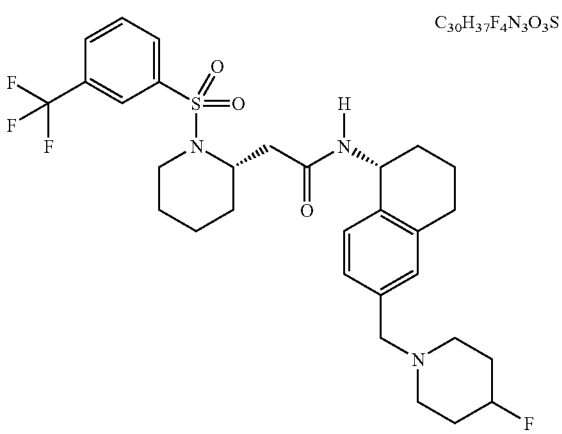 | $C_{30}H_{37}F_4N_3O_3S$ | 596.5 | 595.25 |
| | N-((1R)-6-((4-fluoro-1-piperidinyl)methyl)-1,2,3,4- | | | |

-continued

| Example | Structure | | M + H | MASS |
|---|---|---|---|---|
| | tetrahydro-1-naphthalenyl)-2-((2S)-1-((3-(trifluoromethyl)phenyl)sulfonyl)-2-piperidinyl)acetamide | | | |
| az | N-((1R)-6-(1-azetidinylmethyl)-1,2,3,4-tetrahydro-1-naphthalenyl)-2-((2S)-1-((3-(trifluoromethyl)phenyl)sulfonyl)-2-piperidinyl)acetamide | $C_{28}H_{34}F_3N_3O_3S$ | 550.1 | 549.23 |
| ba | N-((1R)-6-(((1,1-dimethylethyl)amino)methyl)-1,2,3,4-tetrahydro-1-naphthalenyl)-2-((2R/S)-1-((3-(trifluoromethyl)phenyl)sulfonyl)-1,2,3,4-tetrahydro-2-quinolinyl)acetamide | $C_{33}H_{38}F_3N_3O_3S$ | 614.5 | 613.26 |

-continued

| Example | Structure | M + H | MASS |
|---|---|---|---|
| bb | $C_{34}H_{37}F_4N_3O_3S$<br><br>N-((1R)-6-((4-fluoro-1-piperidinyl)methyl)-1,2,3,4-tetrahydro-1-naphthalenyl)-2-((2R/S)-1-((3-(trifluoromethyl)phenyl)sulfonyl)-1,2,3,4-tetrahydro-2-quinolinyl)acetamide | 644.4 | 643.25 |
| bc | $C_{32}H_{41}F_4N_3O_3S$<br><br>N-((1R)-6-(3-(4-fluoro-1-piperidinyl)propyl)-1,2,3,4-tetrahydro-1-naphthalenyl)-2-((2S)-1-((4-(trifluoromethyl)phenyl)sulfonyl)-2-piperidinyl)acetamide | 624 | 623.28 |

-continued
| Example | Structure | M + H | MASS |
|---|---|---|---|
| bd | 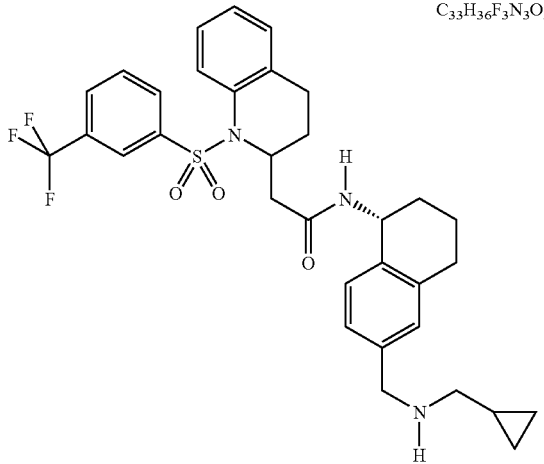 $C_{33}H_{36}F_3N_3O_3S$<br><br>N-((1R)-6-(((cyclopropylmethyl)amino)methyl)-1,2,3,4-tetrahydro-1-naphthalenyl)-2-((2R/S)-1-((3-(trifluoromethyl)phenyl)sulfonyl)-1,2,3,4-tetrahydro-2-quinolinyl)acetamide | 612.5 | 611.24 |
| be | 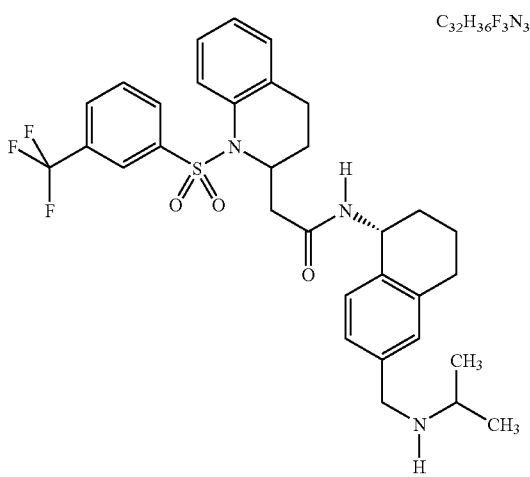 $C_{32}H_{36}F_3N_3O_3S$<br><br>N-((1R)-6-(((isopropylmethyl)amino)methyl)-1,2,3,4-tetrahydro-1-naphthalenyl)-2-((2R/S)-1-((3-(trifluoromethyl)phenyl)sulfonyl)-1,2,3,4-tetrahydro-2-quinolinyl)acetamide | 600 | 599.24 |

-continued

| Example | Structure | | M + H | MASS |
|---|---|---|---|---|
| bf | N-((1R)-6-(((isobutylmethyl)amino)methyl)-1,2,3,4-tetrahydro-1-naphthalenyl)-2-((2R/S)-1-((3-(trifluoromethyl)phenyl)sulfonyl)-1,2,3,4-tetrahydro-2-quinolinyl)acetamide | $C_{33}H_{38}F_3N_3O_3S$ | 614.4 | 613.26 |
| bg | N-((1R)-6-(((diethylamino)methyl)-1,2,3,4-tetrahydro-1-naphthalenyl)-2-((2R/S)-1-((3-(trifluoromethyl)phenyl)sulfonyl)-1,2,3,4-tetrahydro-2-quinolinyl)acetamide | $C_{33}H_{38}F_3N_3O_3S$ | 614.5 | 613.26 |
| bh | 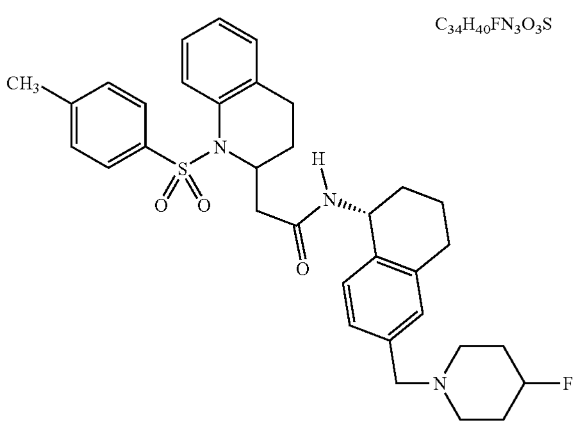 | $C_{34}H_{40}FN_3O_3S$ | 590.3 | 589.28 |

| Example | Structure | | M + H | MASS |
|---|---|---|---|---|
| | N-((1R)-6-((4-fluoro-1-piperidinyl)methyl)-1,2,3,4-tetrahydro-1-naphthalenyl)-2-((2R)-1-((4-methylphenyl)sulfonyl)-1,2,3,4-tetrahydro-2-quinolinyl)acetamide | | | |
| bi | 2-((2R/S)-1-((4-methylphenyl)sulfonyl)-1,2,3,4-tetrahydro-2-quinolinyl)-N-((1R)-6-(((2-methylpropyl)amino)methyl)-1,2,3,4-tetrahydro-1-naphthalenyl)acetamide | $C_{33}H_{41}N_3O_3S$ | 560.2 | 559.29 |
| bj | N-((1R)-6-(((2,2-dimethylpropyl)amino)methyl)-1,2,3,4-tetrahydro-1-naphthalenyl)-2-((2S)-1-((3-(trifluoromethyl)phenyl)sulfonyl)-2-piperidinyl)acetamide | $C_{30}H_{40}F_3N_3O_3S$ | 580.7 | 579.27 |

| Example | Structure | | M + H | MASS |
|---|---|---|---|---|
| bk | 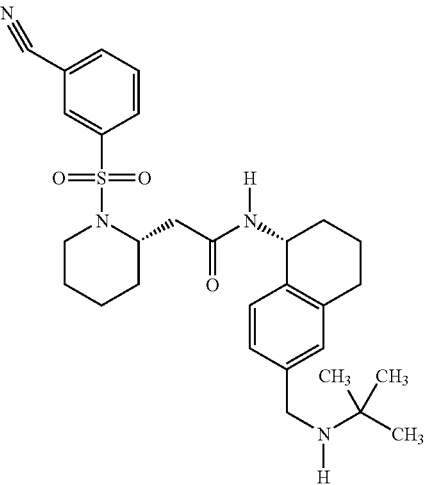 2-((2S)-1-((3-cyanophenyl)sulfonyl)-2-piperidinyl)-N-((1R)-6-(((1,1-dimethylethyl)amino)methyl)-1,2,3,4-tetrahydro-1-naphthalenyl)acetamide | $C_{29}H_{38}N_4O_3S$ | 523 | 522.27 |
| bl | 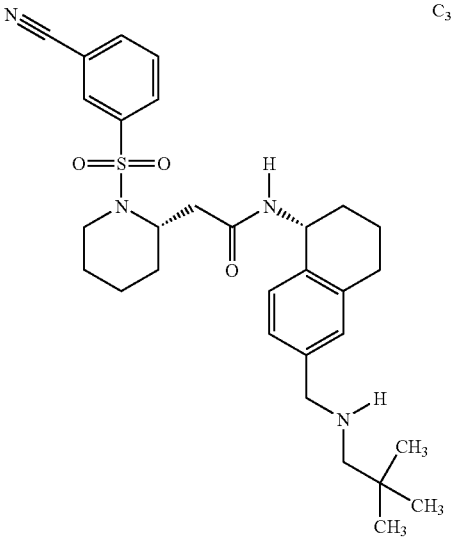 2-((2S)-1-((3-cyanophenyl)sulfonyl)-2-piperidinyl)-N-((1R)-6-(((2,2-dimethylpropyl)amino)methyl)-1,2,3,4-tetrahydro-1-naphthalenyl)acetamide | $C_{30}H_{40}N_4O_3S$ | 536.6 | 536.28 |

-continued
| Example | Structure | | M + H | MASS |
|---|---|---|---|---|
| bm | 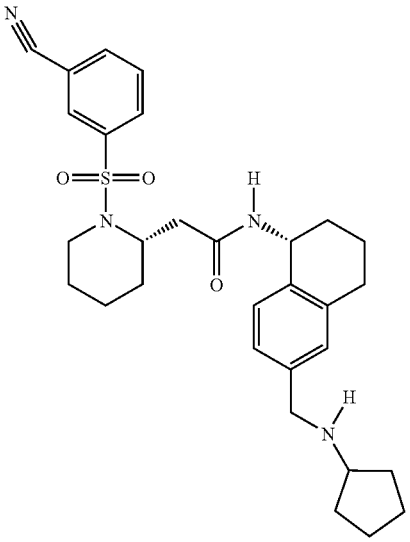<br>2-((2S)-1-((3-cyanophenyl)sulfonyl)-2-piperidinyl)-N-((1R)-6-((cyclopentylamino)methyl)-1,2,3,4-tetrahydro-1-naphthalenyl)acetamide | $C_{30}H_{38}N_4O_3S$ | 535 | 534.27 |
| bn | 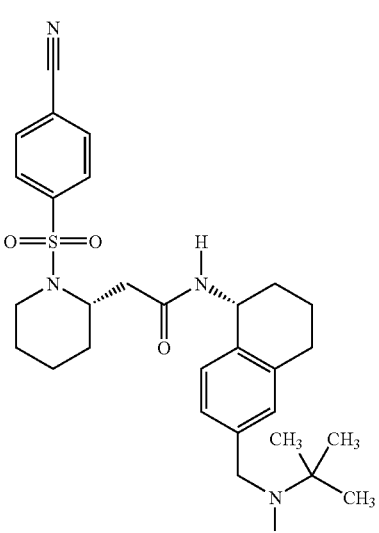<br>2-((2S)-1-((4-cyanophenyl)sulfonyl)-2-piperidinyl)-N-((1R)-6-(((1,1-dimethylethyl)amino)methyl)-1,2,3,4-tetrahydro-1-naphthalenyl)acetamide | $C_{29}H_{38}N_4O_3S$ | 523.4 | 522.27 |

-continued

| Example | Structure | | M + H | MASS |
|---|---|---|---|---|
| bo | 2-((2S)-1-((4-cyanophenyl)sulfonyl)-2-piperidinyl)-N-((1R)-6-(((2,2-dimethylpropyl)amino)methyl)-1,2,3,4-tetrahydro-1-naphthalenyl)acetamide | $C_{30}H_{40}N_4O_3S$ | 537 | 536.28 |
| bp | 2-((2S)-1-((4-cyanophenyl)sulfonyl)-2-piperidinyl)-N-((1R)-6-((cyclopentylamino)methyl)-1,2,3,4-tetrahydro-1-naphthalenyl)acetamide | $C_{30}H_{38}N_4O_3S$ | 534 | 534.27 |

-continued

| Example | Structure | | M + H | MASS |
|---|---|---|---|---|
| bq | 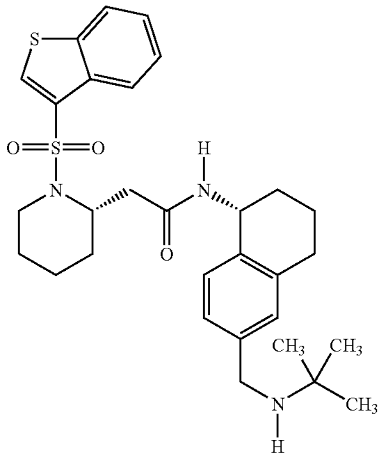 | $C_{30}H_{39}N_3O_3S_2$ | 554 | 553.24 |
| | 2-((2S)-1-(1-benzothien-3-ylsulfonyl)-2-piperidinyl)-N-((1R)-6-(((1,1-dimethylethyl)amino)methyl)-1,2,3,4-tetrahydro-1-naphthalenyl)acetamide | | | |
| br | 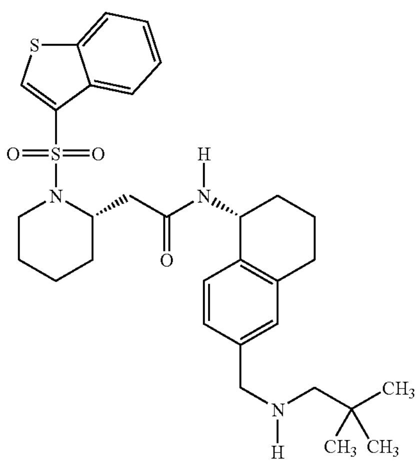 | $C_{31}H_{41}N_3O_3S_2$ | 568.2 | 567.26 |
| | 2-((2S)-1-(1-benzothien-3-ylsulfonyl)-2-piperidinyl)-N-((1R)-6-(((2,2-dimethylpropyl)amino)methyl)-1,2,3,4-tetrahydro-1-naphthalenyl)acetamide | | | |
| bs | 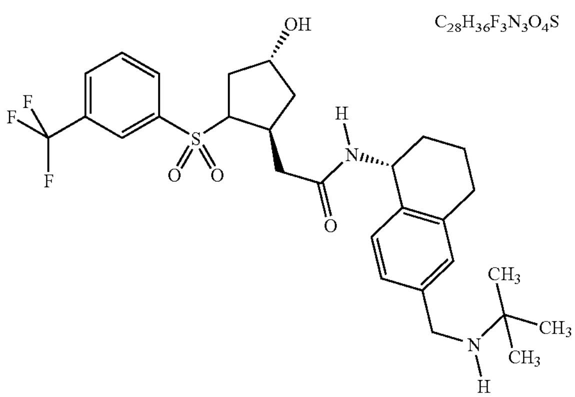 | $C_{28}H_{36}F_3N_3O_4S$ | 568.1 | 567.24 |
| | N-((1R)-6-(((1,1-dimethylethyl)amino)methyl)-1,2,3,4-tetrahydro-1- | | | |

-continued

| Example | Structure | | M + H | MASS |
|---|---|---|---|---|
| | naphthalenyl)-2-((2S,4R)-4-hydroxy-1-((3-(trifluoromethyl)phenyl)sulfonyl)-2-pyrrolidinyl)acetamide | | | |
| bt | 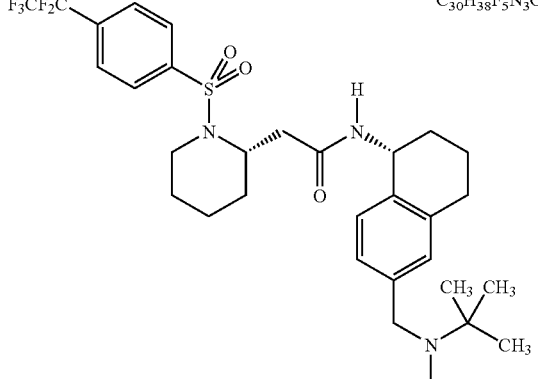<br>N-((1R)-6-(((1,1-dimethylethyl)amino)methyl)-1,2,3,4-tetrahydro-1-naphthalenyl)-2-((2S)-1-((4-(pentafluoroethyl)phenyl)sulfonyl)-2-piperidinyl)acetamide | $C_{30}H_{38}F_5N_3O_3S$ | 166 | 615.26 |
| bu | 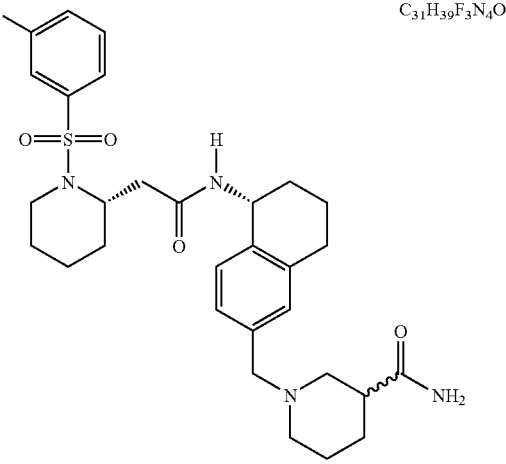<br>1-(((5R)-5-((((2S)-1-((3-(trifluoromethyl)phenyl)sulfonyl)-2-piperidinyl)acetyl)amino)-5,6,7,8-tetrahydro-2-naphthalenyl)methyl)-3-piperidinecarboxamide | $C_{31}H_{39}F_3N_4O_4S$ | 621 | 620.26 |

-continued

| Example | Structure | | M + H | MASS |
|---|---|---|---|---|
| bv | 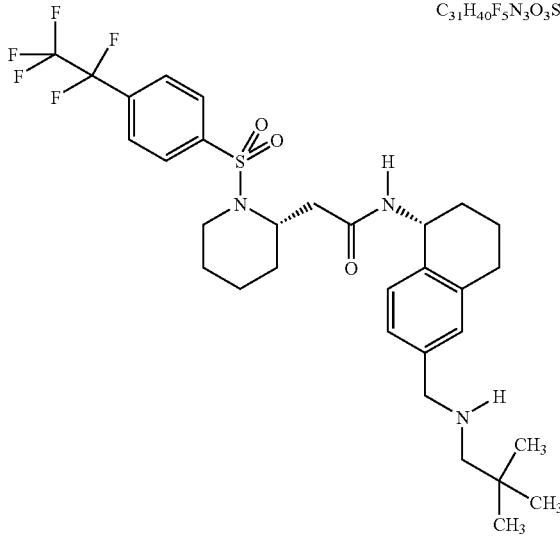 N-((1R)-6-(((2,2-dimethylpropyl)amino)methyl)-1,2,3,4-tetrahydro-1-naphthalenyl)-2-((2S)-1-((4-(pentafluoroethyl)phenyl)sulfonyl)-2-piperidinyl)acetamide | C₃₁H₄₀F₅N₃O₃S | 630.4 | 629.27 |

Other compounds included in this invention are set forth in Tables 1–10 below and Examples 326–354.

TABLE 1

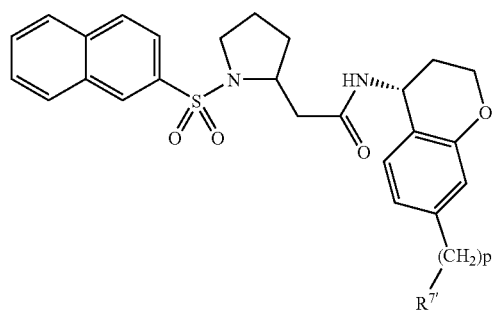

| # | R⁷ | p |
|---|---|---|
| 4. | piperdin-1-yl | 2 |
| 5. | (CH₃)₂N— | 1 |
| 6. | piperazin-1-yl | 1 |
| 7. | 4-CH₃-piperazin-1-yl | 1 |
| 8. | (Et₂)N— | 1 |
| 9. | (CH₃)(Et)N— | 2 |
| 10. | piperazin-1-yl | 2 |

TABLE 2

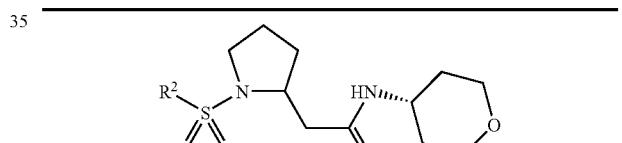

| # | R² |
|---|---|
| 11. | 5,6,7,8-tetrahydronaphth-2-yl |
| 12. | 2,4-dichloro-3-methylphenyl |
| 13. | 2-quinolyl |
| 14. | phenyl |
| 15. | 2-chlorophenyl |
| 16. | 3-chlorophenyl |
| 17. | 4-chlorophenyl |
| 18. | 4-methoxyphenyl |
| 19. | 3,5-dichlorophenyl |
| 20. | 3-methoxyphenyl |
| 21. | 3-fluorophenyl |
| 22. | 3-biphenyl |
| 23. | 4-biphenyl |
| 24. | 3-methylphenyl |
| 25. | 3-CF₃-phenyl |
| 26. | 2,4,6-trichlorphenyl |
| 27. | 2,3,4-trichlorphenyl |
| 28. | 2,4,5-trichlorphenyl |
| 29. | 3,4-dichlorophenyl |
| 30. | 1-naphthyl |

TABLE 2-continued

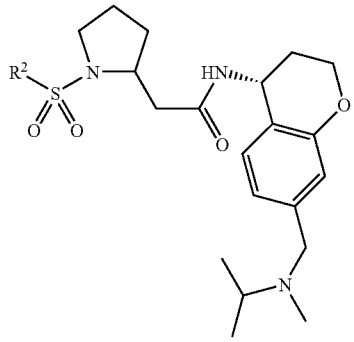

| # | R² |
|---|---|
| 31. | phenyl-ethenyl |
| 32. | benzo[1,2,5]oxadiazol-5-yl |
| 33. | 5-(dimethylamino)naphth-1-yl |
| 34. | 5-chloro-3-methylphenyl |
| 35. | benzothiazol-2-yl |
| 36. | 2,3,4,5,6-pentamethylphenyl |
| 37. | 6-methoxy-2-naphthyl |
| 38. | 4-t-butylphenyl |
| 39. | 3-chloro-4-methylphenyl |
| 40. | 5-methoxy-3-methylbenzothien-2-yl |
| 41. | 6-methoxy-3-methylbenzothien-2-yl |
| 42. | 5-chloro-3-methylbenzothien-2-yl |
| 43. | 3-methylbenzothien-2-yl |
| 44. | 2,4-dichloro-5-methylphenyl |
| 45. | 7-methoxy-2-naphthyl |
| 46. | 6-fluoroethoxy-2-naphthyl |
| 47. | 3-methyl-5-trifluoromethoxybenzofur-2-yl |
| 48. | 3-methyl-5-methoxybenzofur-2-yl |
| 49. | 5-chloro-benzo[1,2,5]oxadiazol-4-yl |
| 50. | 3-methyl-5-trifluoromethoxybenzothien-2-yl |
| 51. | 6-ethoxy-2-naphthyl |
| 52. | 2-Cl-4-CF₃-phenyl |
| 53. | 6-bromonaphthyl |
| 54. | 3-methylbenzofur-2-yl |
| 55. | 3-chlorobenzothien-2-yl |
| 56. | 5-chloro-benzo[1,2,5]thiadiazol-4-yl |
| 57. | 5-chloro-1,3-dimethyl-1H-pyrazol-4-yl |
| 58. | 2,3-dichlorothien-5-yl |
| 59. | 2,5-dichlorothien-3-yl |
| 60. | 5-chloro-2-naphthyl |
| 61. | 4-butoxyphenyl |
| 62. | 3,5-di(trifluoromethyl)phenyl |
| 63. | 5-(isoxazol-3-yl)thien-2-yl |
| 64. | 2-chlorothien-5-yl |
| 65. | 4-chloro-benzo[1,2,5]oxadiazol-7-yl |
| 66. | 2,4-dichloro-6-methylphenyl |
| 67. | 2,4,6-trimethylphenyl |
| 68. | 4-chloro-2,5-dimethylphenyl |
| 69. | 2,5-dichlorophenyl |
| 70. | 3,4-difluorophenyl |
| 71. | 3-chloro-4-fluorophenyl |
| 72. | 4-methylcyclohexyl |
| 73. | 3,5-dimethylbenzothien-2-yl |
| 74. | 5-fluoro-3-methylbenzothien-2-yl |
| 75. | 5-methylbenzothien-2-yl |
| 76. | 5-chloro-3-methylbenzofur-2-yl |
| 77. | 3-pyridyl |

TABLE 3

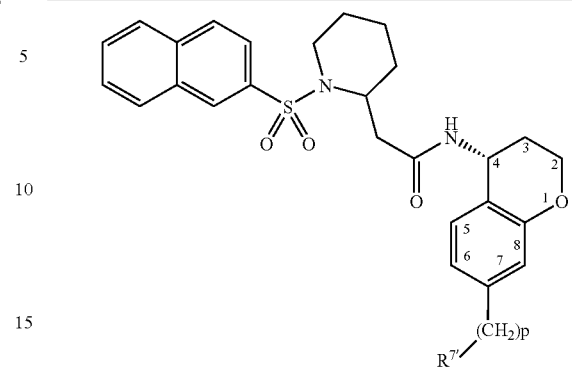

| # | R⁷ | p |
|---|---|---|
| 78. | piperdin-1-yl | 2 |
| 79. | (CH₃)₂N— | 1 |
| 80. | piperazin-1-yl | 1 |
| 81. | 4-CH₃-piperazin-1-yl | 1 |
| 82. | (Et₂)N— | 1 |
| 83. | (CH₃)(Et)N— | 2 |
| 84. | piperazin-1-yl | 2 |

TABLE 4

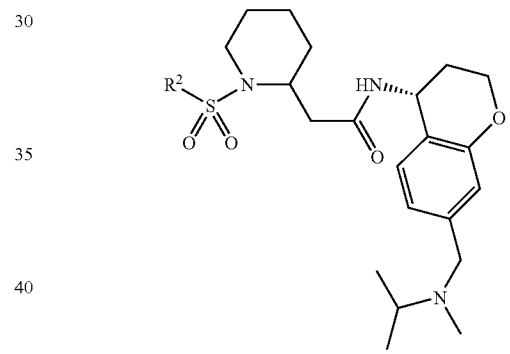

| # | R² |
|---|---|
| 85. | 5,6,7,8-tetrahydronaphth-2-yl |
| 86. | 2,4-dichloro-3-methylphenyl |
| 87. | 2-quinolyl |
| 88. | phenyl |
| 89. | 2-chlorophenyl |
| 90. | 3-chlorophenyl |
| 91. | 4-chlorophenyl |
| 92. | 4-methoxyphenyl |
| 93. | 3,5-dichlorophenyl |
| 94. | 3-methoxyphenyl |
| 95. | 3-fluorophenyl |
| 96. | 3-biphenyl |
| 97. | 4-biphenyl |
| 98. | 3-methylphenyl |
| 99. | 3-CF₃-phenyl |
| 100. | 2,4,6-trichlorphenyl |
| 101. | 2,3,4-trichlorphenyl |
| 102. | 2,4,5-trichlorphenyl |
| 103. | 3,4-dichlorophenyl |
| 104. | 1-naphthyl |
| 105. | phenyl-ethenyl |
| 106. | benzo[1,2,5]oxadiazol-5-yl |
| 107. | 5-(dimethylamino)naphth-1-yl |
| 108. | 5-chloro-3-methylphenyl |
| 109. | benzothiazol-2-yl |
| 110. | 2,3,4,5,6-pentamethylphenyl |
| 111. | 6-methoxy-2-naphthyl |

TABLE 4-continued

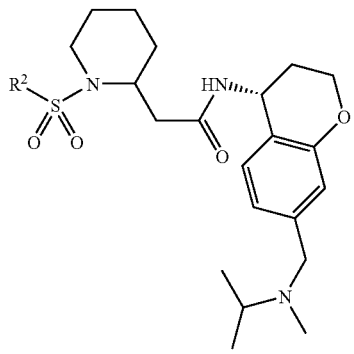

| # | R² |
|---|---|
| 112. | 4-t-butylphenyl |
| 113. | 3-chloro-4-methylphenyl |
| 114. | 5-methoxy-3-methylbenzothien-2-yl |
| 115. | 6-methoxy-3-methylbenzothien-2-yl |
| 116. | 5-chloro-3-methylbenzothien-2-yl |
| 117. | 3-methylbenzothien-2-yl |
| 118. | 2,4-dichloro-5-methylphenyl |
| 119. | 7-methoxy-2-naphthyl |
| 120. | 6-fluoroethoxy-2-naphthyl |
| 121. | 3-methyl-5-trifluoromethoxybenzofur-2-yl |
| 122. | 3-methyl-5-methoxybenzofur-2-yl |
| 123. | 5-chloro-benzo[1,2,5]oxadiazol-4-yl |
| 124. | 3-methyl-5-trifluoromethoxybenzothien-2-yl |
| 125. | 6-ethoxy-2-naphthyl |
| 126. | 2-Cl-4-CF₃-phenyl |
| 127. | 6-bromonaphthyl |
| 128. | 3-methylbenzofur-2-yl |
| 129. | 3-chlorobenzothien-2-yl |
| 130. | 5-chloro-benzo[1,2,5]thiadiazol-4-yl |
| 131. | 5-chloro-1,3-dimethyl-1H-pyrazol-4-yl |
| 132. | 2,3-dichlorothien-5-yl |
| 133. | 2,5-dichlorothien-3-yl |
| 134. | 5-chloro-2-naphthyl |
| 135. | 4-butoxyphenyl |
| 136. | 3,5-di(trifluoromethyl)phenyl |
| 137. | 5-(isoxazol-3-yl)thien-2-yl |
| 138. | 2-chlorothien-5-yl |
| 139. | 4-chloro-benzo[1,2,5]oxadiazol-7-yl |
| 140. | 2,4-dichloro-6-methylphenyl |
| 141. | 2,4,6-trimethylphenyl |
| 142. | 4-chloro-2,5-dimethylphenyl |
| 143. | 2,5-dichlorophenyl |
| 144. | 3,4-difluorophenyl |
| 145. | 3-chloro-4-fluorophenyl |
| 146. | 4-methylcyolohexyl |
| 147. | 3,5-dimethylbenzothien-2-yl |
| 148. | 5-fluoro-3-methylbenzothien-2-yl |
| 149. | 5-methylbenzothien-2-yl |
| 150. | 5-chloro-3-methylbenzofur-2-yl |
| 151. | 3-pyridyl |

TABLE 5

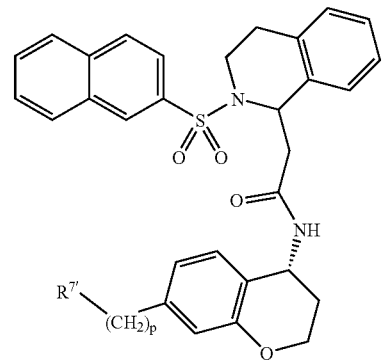

| # | R⁷" | p |
|---|---|---|
| 152. | piperdin-1-yl | 1 |
| 153. | (CH₃)₂N— | 1 |
| 154. | piperazin-1-yl | 1 |
| 155. | 4-CH₃-piperazin-1-yl | 1 |
| 156. | (Et₂)N— | 1 |
| 157. | (CH₃)(Et)N— | 2 |
| 158. | piperazin-1-yl | 2 |

TABLE 6

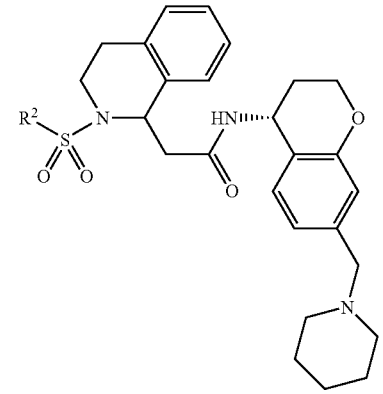

| # | R² |
|---|---|
| 159. | 5,6,7,8-tetrahydronaphth-2-yl |
| 160. | 2,4-dichloro-3-methylphenyl |
| 161. | 2-quinolyl |
| 162. | phenyl |
| 163. | 2-chlorophenyl |
| 164. | 3-chlorophenyl |
| 165. | 4-chlorophenyl |
| 166. | 4-methoxyphenyl |
| 167. | 3,5-dichlorophenyl |
| 168. | 3-methoxyphenyl |
| 169. | 3-fluorophenyl |
| 170. | 3-biphenyl |
| 171. | 4-biphenyl |
| 172. | 3-methylphenyl |
| 173. | 3-CF₃-phenyl |
| 174. | 2,4,6-trichlorphenyl |
| 175. | 2,3,4-trichlorphenyl |
| 176. | 2,4,5-trichlorphenyl |
| 177. | 3,4-dichlorophenyl |
| 178. | 1-naphthyl |
| 179. | phenyl-ethenyl |
| 180. | benzo[1,2,5]oxadiazol-5-yl |
| 181. | 5-(dimethylamino)naphth-1-yl |
| 182. | 5-chloro-3-methylphenyl |
| 183. | benzothiazol-2-yl |

TABLE 6-continued

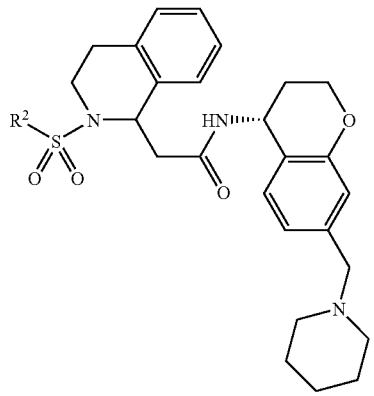

| # | R² |
|---|---|
| 184. | 2,3,4,5,6-pentamethylphenyl |
| 185. | 6-methoxy-2-naphthyl |
| 186. | 4-t-butylphenyl |
| 187. | 3-chloro-4-methylphenyl |
| 188. | 5-methoxy-3-methylbenzothien-2-yl |
| 189. | 6-methoxy-3-methylbenzothien-2-yl |
| 190. | 5-chloro-3-methylbenzothien-2-yl |
| 191. | 3-methylbenzothien-2-yl |
| 192. | 2,4-dichloro-5-methylphenyl |
| 193. | 7-methoxy-2-naphthyl |
| 194. | 6-fluoroethoxy-2-naphthyl |
| 195. | 3-methyl-5-trifluoromethoxybenzofur-2-yl |
| 196. | 3-methyl-5-methoxybenzofur-2-yl |
| 197. | 5-chloro-benzo[1,2,5]oxadiazol-4-yl |
| 198. | 3-methyl-5-trifluoromethoxybenzothien-2-yl |
| 199. | 6-ethoxy-2-naphthyl |
| 200. | 2-Cl-4-CF₃-phenyl |
| 201. | 6-bromonaphthyl |
| 202. | 3-methylbenzofur-2-yl |
| 203. | 3-chlorobenzothien-2-yl |
| 204. | 5-chloro-benzo[1,2,5]thiadiazol-4-yl |
| 205. | 5-chloro-1,3-dimethyl-1H-pyrazol-4-yl |
| 206. | 2,3-dichlorothien-5-yl |
| 207. | 2,5-dichlorothien-3-yl |
| 208. | 5-chloro-2-naphthyl |
| 209. | 4-butoxyphenyl |
| 210. | 3,5-di(trifluoromethyl)phenyl |
| 211. | 5-(isoxazol-3-yl)thien-2-yl |
| 212. | 2-chlorothien-5-yl |
| 213. | 4-chloro-benzo[1,2,5]oxadiazol-7-yl |
| 214. | 2,4-dichloro-6-methylphenyl |
| 215. | 2,4,6-trimethylphenyl |
| 216. | 4-chloro-2,5-dimethylphenyl |
| 217. | 2,5-dichlorophenyl |
| 218. | 3,4-difluorophenyl |
| 219. | 3-chloro-4-fluorophenyl |
| 220. | 4-methylcyclohexyl |
| 221. | 3,5-dimethylbenzothien-2-yl |
| 222. | 5-fluoro-3-methylbenzothien-2-yl |
| 223. | 5-methylbenzothien-2-yl |
| 224. | 5-chloro-3-methylbenzofur-2-yl |
| 225. | 3-pyridyl |

TABLE 7

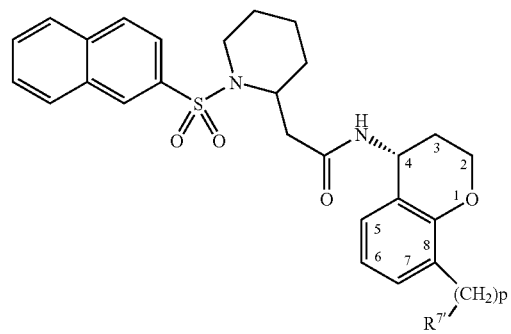

| # | R⁷' | p |
|---|---|---|
| 226. | piperdin-1-yl | 1 |
| 227. | (CH₃)₂N— | 1 |
| 228. | piperazin-1-yl | 1 |
| 229. | 4-CH₃-piperazin-1-yl | 1 |
| 230. | (Et₂)N— | 1 |
| 231. | (CH₃)(Et)N— | 2 |
| 232. | piperazin-1-yl | 2 |

TABLE 8

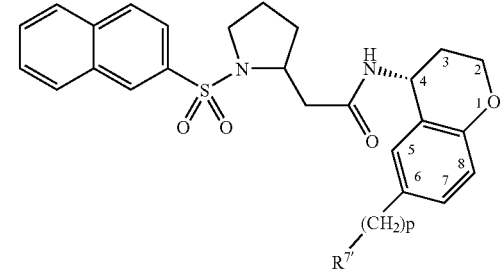

| # | R⁷' | p |
|---|---|---|
| 233. | piperdin-1-yl | 1 |
| 234. | (CH₃)₂N— | 1 |
| 235. | piperazin-1-yl | 1 |
| 236. | 4-CH₃-piperazin-1-yl | 1 |
| 237. | (Et₂)N— | 1 |
| 238. | (CH₃)(Et)N— | 2 |
| 239. | piperazin-1-yl | 2 |

TABLE 9

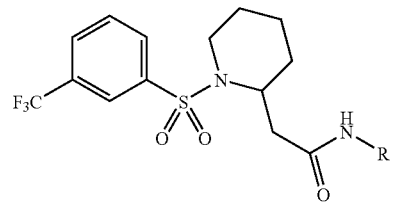

| # | R |
|---|---|
| 240. | 3-isopropyl-7-(1-methylpiperidin-2-yl)chroman-4-yl |
| 241. | 2,2-dimethyl-7-(1-methylpiperidin-2-yl)chroman-4-yl |
| 242. | 7-(piperidin-2-yl)chroman-4-yl |
| 243. | 2,2-dimethyl-7-(methylaminomethyl)chroman-4-yl |
| 244. | 7-(dimethylaminomethyl)-1,2,3,4-tetrahydonaphth-4-yl |
| 245. | 7-(piperidin-1-ylaminomethyl)-1,2,3,4-tetrahydonaphth-2-yl |
| 246. | 5-(piperidin-1-yl)methylindan-1-yl |

TABLE 9-continued

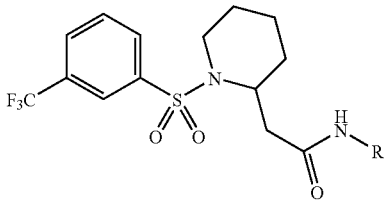

| # | R |
|---|---|
| 247. | 6-(4-methylpiperazin-1-yl)methylindan-1-yl |
| 248. | 4-(piperazin-1-yl)methylindan-1-yl |
| 249. | 2-(di-ethylaminomethyl)-5,6,7,8-tetrahydoquinolin-5-yl |
| 250. | 2-(isopropylaminomethyl)-5,6,7,8-tetrahydoquinolin-8-yl |
| 251. | 2-(t-butylaminomethyl)-5,6,7,8-tetrahydoisoquinolin-8-yl |
| 252. | 7-(morpholin-4-ylmethyl)-quinolin-4-yl |
| 253. | 1-methyl-2-oxo-6-(piperidin-1-yl)methylindol-3-yl |
| 254. | 7-(dimethylaminomethyl)-1,2,3,4-tetrahydonaphth-2-yl |
| 255. | 7-(diethylaminomethyl)-4,5,6,7-tetrahydobenzofur-4-yl |
| 256. | 7-(4-morpholinylmethyl)-4,5,6,7-tetrahydobenzothien-4-yl |
| 257. | 7-(aminomethoxy)chroman-4-yl |
| 258. | methylamino-methoxy |

TABLE 10

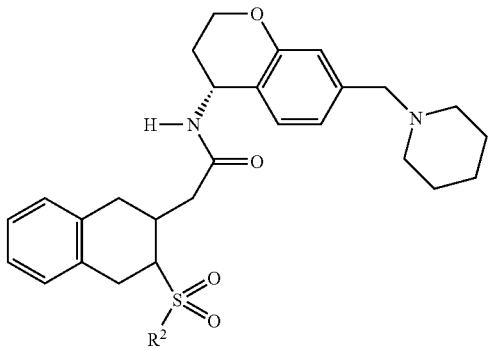

| # | $R^2$ |
|---|---|
| 259. | 5,6,7,8-tetrahydronaphth-2-yl |
| 260. | 2,4-dichloro-3-methylphenyl |
| 261. | 2-quinolyl |
| 262. | phenyl |
| 263. | 2-chlorophenyl |
| 264. | 3-chlorophenyl |
| 265. | 4-chlorophenyl |
| 266. | 4-methoxyphenyl |
| 267. | 3,5-dichlorophenyl |
| 268. | 3-methoxyphenyl |
| 269. | 3-fluorophenyl |
| 270. | 3-biphenyl |
| 271. | 4-biphenyl |
| 272. | 3-methylphenyl |
| 273. | 3-$CF_3$-phenyl |
| 274. | 2,4,6-trichlorphenyl |
| 275. | 2,3,4-trichlorphenyl |
| 276. | 2,4,5-trichlorphenyl |
| 277. | 3,4-dichlorophenyl |
| 278. | 1-naphthyl |
| 279. | phenyl-ethenyl |
| 280. | benzo[1,2,5]oxadiazol-5-yl |
| 281. | 5-(dimethylamino)naphth-1-yl |
| 282. | 5-chloro-3-methylphenyl |
| 283. | benzothiazol-2-yl |
| 284. | 2,3,4,5,6-pentamethylphenyl |
| 285. | 6-methoxy-2-naphthyl |
| 286. | 4-t-butylphenyl |
| 287. | 3-chloro-4-methylphenyl |
| 288. | 5-methoxy-3-methylbenzothien-2-yl |

TABLE 10-continued

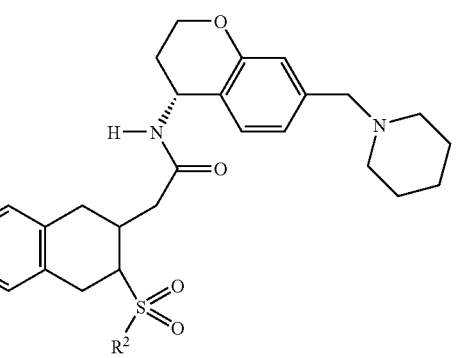

| # | $R^2$ |
|---|---|
| 289. | 6-methoxy-3-methylbenzothien-2-yl |
| 290. | 5-chloro-3-methylbenzothien-2-yl |
| 291. | 3-methylbenzothien-2-yl |
| 292. | 2,4-dichloro-5-methylphenyl |
| 293. | 7-methoxy-2-naphthyl |
| 294. | 6-fluoroethoxy-2-naphthyl |
| 295. | 3-methyl-5-trifluoromethoxybenzofur-2-yl |
| 296. | 3-methyl-5-methoxybenzofur-2-yl |
| 297. | 5-chloro-benzo[1,2,5]oxadiazol-4-yl |
| 298. | 3-methyl-5-trifluoromethoxybenzothien-2-yl |
| 299. | 6-ethoxy-2-naphthyl |
| 300. | 2-Cl-4-$CF_3$-phenyl |
| 301. | 6-bromonaphthyl |
| 302. | 3-methylbenzofur-2-yl |
| 303. | 3-chlorobenzothien-2-yl |
| 304. | 5-chloro-benzo[1,2,5]thiadiazol-4-yl |
| 305. | 5-chloro-1,3-dimethyl-1H-pyrazol-4-yl |
| 306. | 2,3-dichlorothien-5-yl |
| 307. | 2,5-dichlorothien-3-yl |
| 308. | 5-chloro-2-naphthyl |
| 309. | 4-butoxyphenyl |
| 310. | 3,5-di(trifluoromethyl)phenyl |
| 311. | 5-(isoxazol-3-yl)thien-2-yl |
| 312. | 2-chlorothien-5-yl |
| 313. | 4-chloro-benzo[1,2,5]oxadiazol-7-yl |
| 314. | 2,4-dichloro-6-methylphenyl |
| 315. | 2,4,6-trimethylphenyl |
| 316. | 4-chloro-2,5-dimethylphenyl |
| 317. | 2,5-dichlorophenyl |
| 318. | 3,4-difluorophenyl |
| 319. | 3-chloro-4-fluorophenyl |
| 320. | 4-methylcyclohexyl |
| 321. | 3,5-dimethylbenzothien-2-yl |
| 322. | 5-fluoro-3-methylbenzothien-2-yl |
| 323. | 5-methylbenzothien-2-yl |
| 324. | 5-chloro-3-methylbenzofur-2-yl |
|  | 3-pyridyl |

EXAMPLE 326

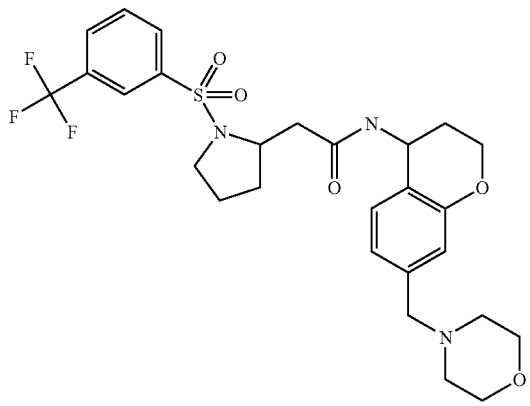

N-((4R)-7-(4-Morpholinylmethyl)-3,4-dihydro-2H-
chromen-4-yl)-2-((2S)-1-((3-(trifluoromethyl)phe-
nyl)sulfonyl)-2-pyrrolidinyl)acetamide

EXAMPLE 327

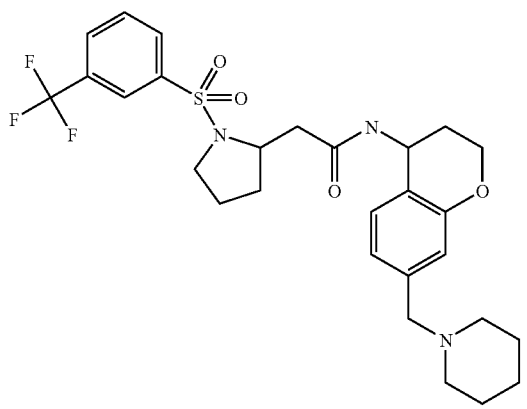

N-((4R)-7-(1-Piperidinylmethyl)-3,4-dihydro-2H-
chromen-4-yl)-2-((2S)-1-((3-(trifluoromethyl)phe-
nyl)sulfonyl)-2-pyrrolidinyl)acetamide

EXAMPLE 328

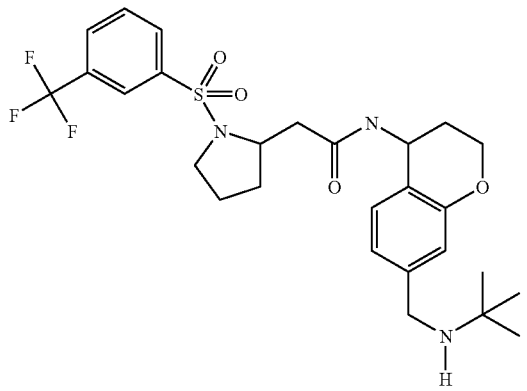

N-((4R)-7-(((1,1-Dimethylethyl)amino)methyl)-3,4-
dihydro-2H-chromen-4-yl)-2-((2S)-1-((3-(trifluo-
romethyl)phenyl)sulfonyl)-2-pyrrolidinyl)acetamide

EXAMPLE 329

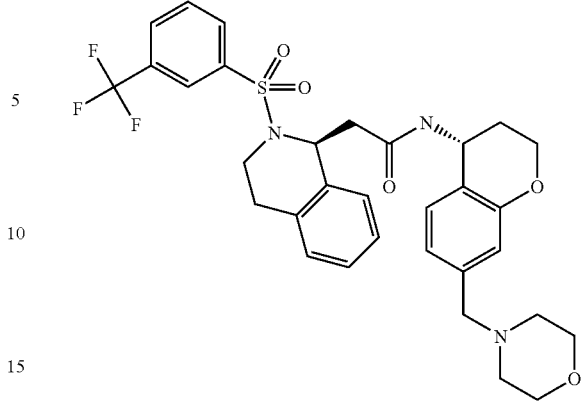

N-((4R)-7-(4-Morpholinylmethyl)-3,4-dihydro-2H-
chromen-4-Yl)-2-((1S)-2-((3-(trifluoromethyl)phe-
nyl)sulfonyl)-1,2,3,4-tetrahydro-1-isoquinolinyl)
acetamide

EXAMPLE 330

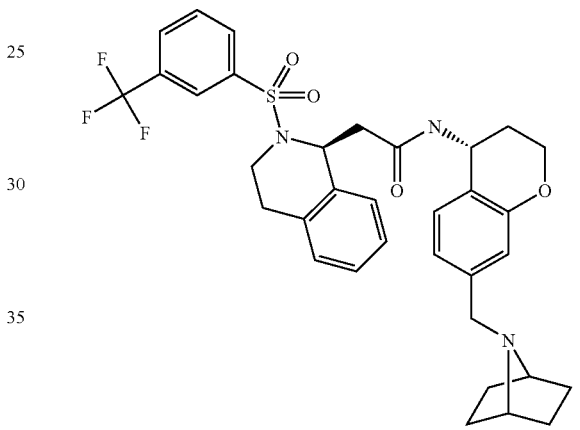

N-((4R)-7-(7-azabicyclo[2.2.1]hept-7-ylmethyl)-3,4-
dihydro-2H-chromen-4-yl)-2-((1S)-2-((3-(trifluo-
romethyl)phenyl)sulfonyl)-1,2,3,4-tetrahydro-1-iso-
quinolinyl)acetamide

EXAMPLE 331

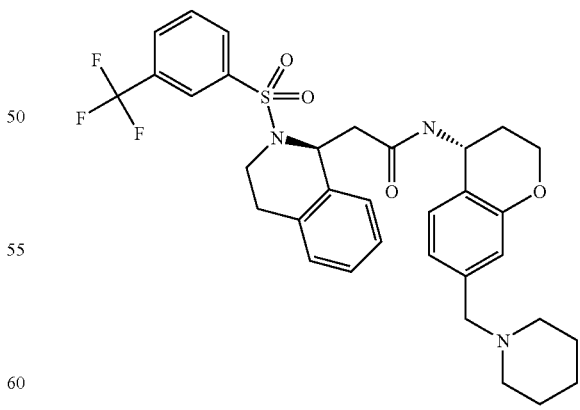

N-((4R)-7-(1-Piperidinylmethyl)-3,4-dihydro-2H-
chromen-4-yl)-2-((1R)-2-((3-(trifluoromethyl)phe-
nyl)sulfonyl)-1,2,3,4-tetrahydro-1-isoquinolinyl)
acetamide

EXAMPLE 332

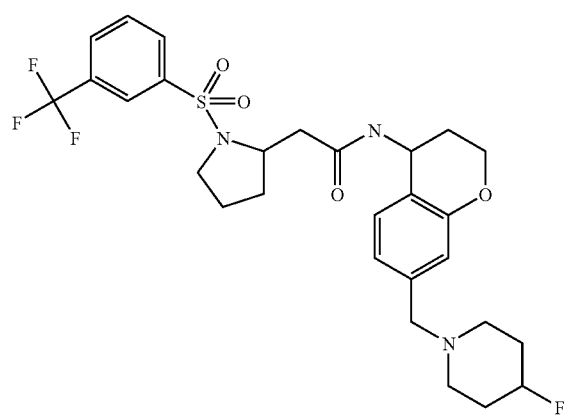

N-((4R)-7-((4-Fluoro-1-piperidinyl)methyl)-3,4-
dihydro-2H-chromen-4-yl)-2-((2S)-1-((3-(trifluo-
romethyl)phenyl)sulfonyl)-2-pyrrolidinyl)acetamide

EXAMPLE 333

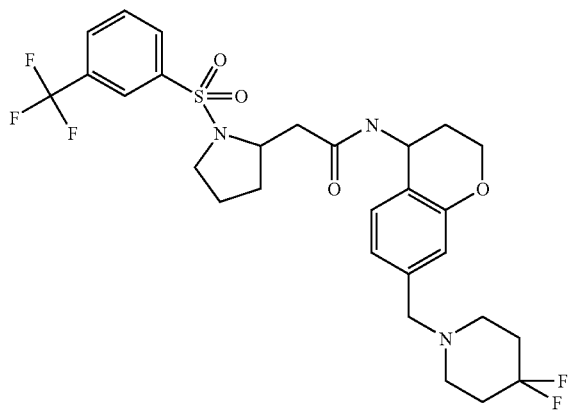

N-((4R)-7-((4,4-Difluoro-1-piperidinyl)methyl)-3,4-
dihydro-2H-chromen-4-yl)-2-((2S)-1-((3-(trifluo-
romethyl)phenyl)sulfonyl)-2-pyrrolidinyl)acetamide

EXAMPLE 334

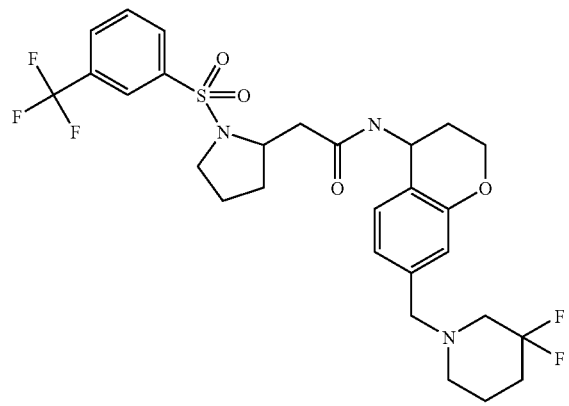

N-((4R)-7-((3,3-Difluoro-1-piperidinyl)methyl)-3,4-
dihydro-2H-chromen-4-yl)-2-((2S)-1-((3-(trifluo-
romethyl)phenyl)sulfonyl)-2-pyrrolidinyl)acetamide

EXAMPLE 335

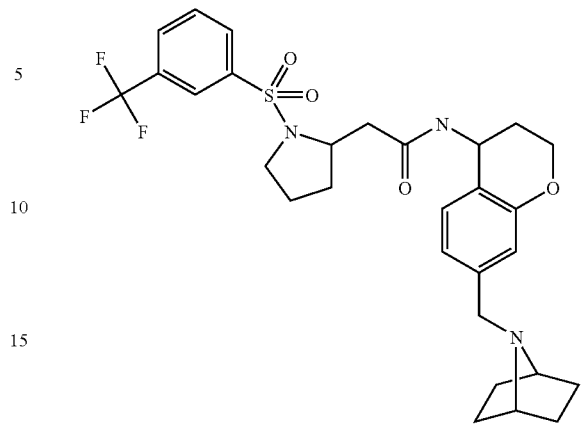

N-((4R)-7-(7-azabicyclo[2.2.1]hept-7-ylmethyl)-3,4-
dihydro-2H-chromen-4-yl)-2-((2S)-1-((3-(trifluo-
romethyl)phenyl)sulfonyl)-2-pyrrolidinyl)acetamide

EXAMPLE 336

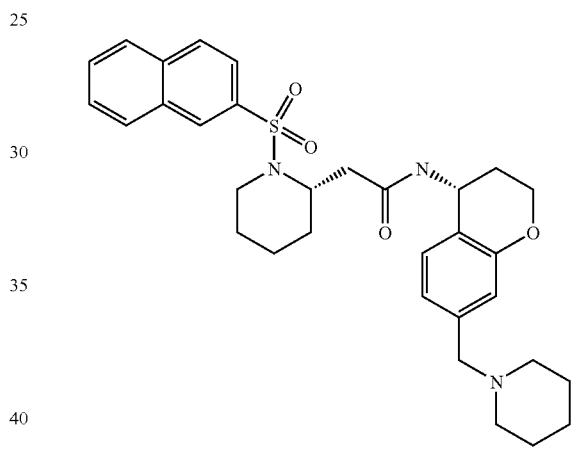

2-((2S)-1-(2-Naphthalenylsulfonyl)-2-piperidinyl)-
N-((4R)-7-(1-piperidinylmethyl)-3,4-dihydro-2H-
chromen-4-yl)acetamide

EXAMPLE 337

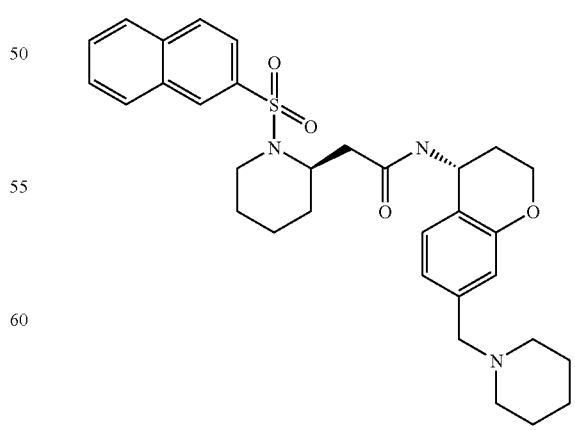

2-((2R)-1-(2-Naphthalenylsulfonyl)-2-piperidinyl)-
N-((4R)-7-(1-piperidinylmethyl)-3,4-dihydro-2H-
chromen-4-yl)acetamide

EXAMPLE 338

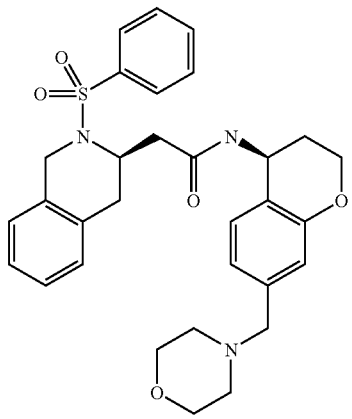

N-((4S)-7-(4-Morpholinylmethyl)-3,4-dihydro-2H-
chromen-4-yl)-2-((3R)-2-(phenylsulfonyl)-1,2,3,4-
tetrahydro-3-isoquinolinyl)acetamide

EXAMPLE 339

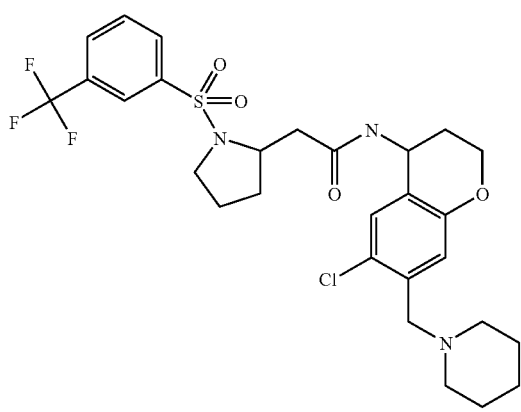

N-((4R)-6-Chloro-7-(1-piperidinylmethyl)-3,4-dihy-
dro-2H-chromen-4-yl)-2-((2S)-1-((3-(trifluorom-
ethyl)phenyl)sulfonyl)-2-pyrrolidinyl)acetamide

EXAMPLE 340

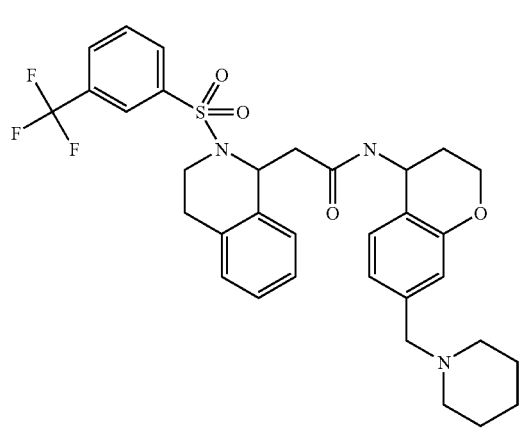

N-((4R)-7-(1-Piperidinylmethyl)-3,4-dihydro-2H-
chromen-4-yl)-2-((3R)-2-((3-(trifluoromethyl)phe-
nyl)sulfonyl)-1,2,3,4-tetrahydro-3-isoquinolinyl)
acetamide

EXAMPLE 341

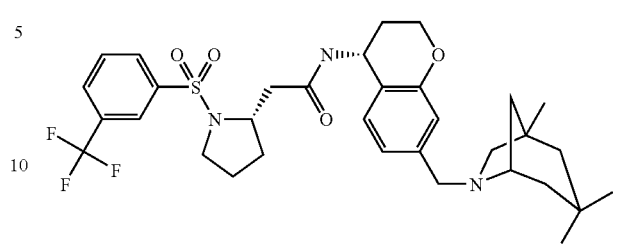

2-((2S)-1-((3-(Trifluoromethyl)phenyl)sulfonyl)-2-
pyrrolidinyl)-N-((4R)-7-((1,3,3-trimethyl-6-azabicy-
clo[3.2.1]oct-6-yl)methyl)-3,4-dihydro-2H-chromen-
4-yl)acetamide

EXAMPLE 342

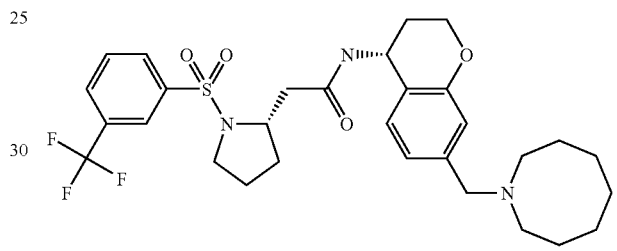

N-((4R)-7-(1-Azocanylmethyl)-3,4-dihydro-2H-
chromen-4-yl)-2-((2S)-1-((3-(trifluoromethyl)phe-
nyl)sulfonyl)-2-pyrrolidinyl)acetamide

EXAMPLE 343

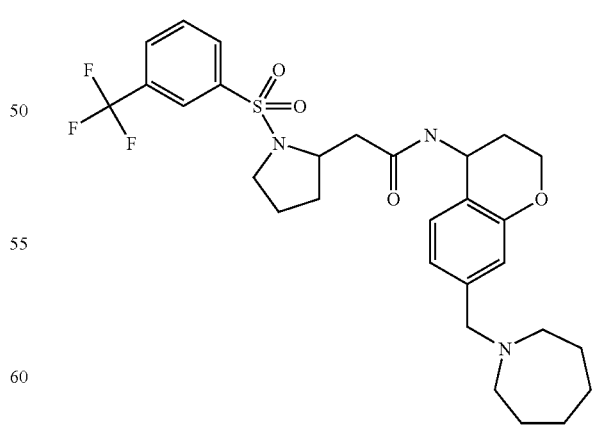

N-((4R)-7-(1-Azepanylmethyl)-3,4-dihydro-2H-
chromen-4-yl)-2-((2S)-1-((3-(trifluoromethyl)phe-
nyl)sulfonyl)-2-pyrrolidinyl)acetamide

EXAMPLE 344

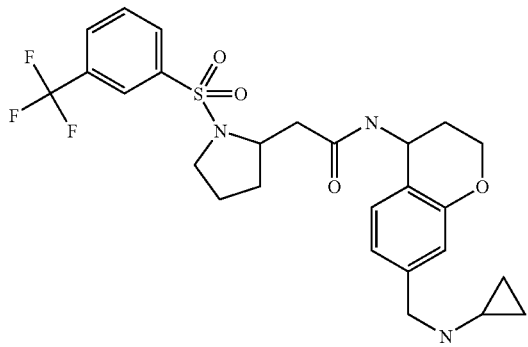

N-((4R)-7-(((Cyclopropylamino)methyl)-3,4-dihydro-2H-chromen-4-yl)-2-((2S)-1-((3-(trifluoromethyl)phenyl)sulfonyl)-2-pyrrolidinyl)acetamide

EXAMPLE 345

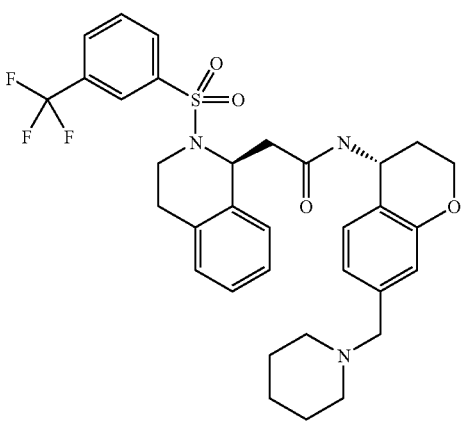

N-((4R)-7-(1-Piperidinylmethyl)-3,4-dihydro-2H-chromen-4-yl)-2-((1S)-2-((3-(trifluoromethyl)phenyl)sulfonyl)-1,2,3,4-tetrahydro-1-isoquinolinyl)acetamide

EXAMPLE 346

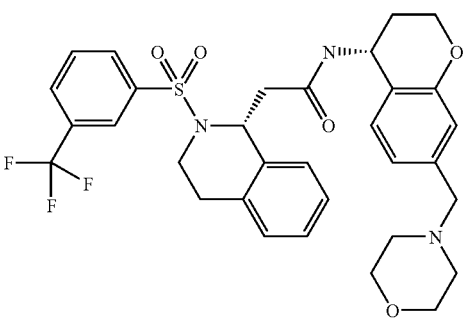

N-((4R)-7-(4-Morpholinylmethyl)-3,4-dihydro-2H-chromen-4-yl)-2-((1R)-2-((3-(trifluoromethyl)phenyl)sulfonyl)-1,2,3,4-tetrahydro-1-isoquinolinyl)acetamide

EXAMPLE 347

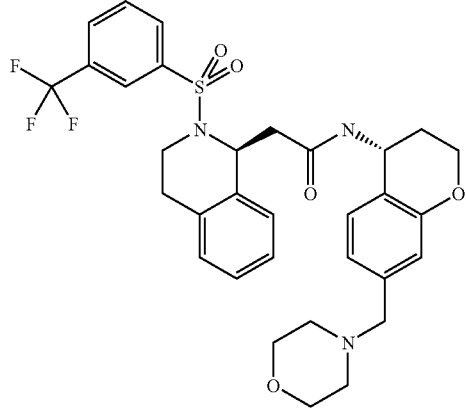

N-((4R)-7-(4-Morpholinylmethyl)-3,4-dihydro-2H-chromen-4-yl)-2-((1S)-2-((3-(trifluoromethyl)phenyl)sulfonyl)-1,2,3,4-tetrahydro-1-isoquinolinyl)acetamide

EXAMPLE 348

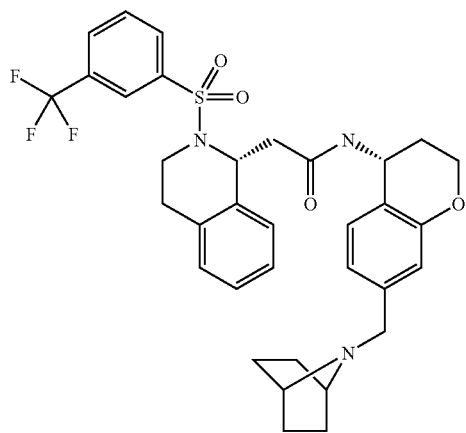

N-((4R)-7-(7-Azabicyclo[2.2.1]hept-7-ylmethyl)-3,4-dihydro-2H-chromen-4-yl)-2-((1R)-2-((3-(trifluoromethyl)phenyl)sulfonyl)-1,2,3,4-tetrahydro-1-isoquinolinyl)acetamide

EXAMPLE 349

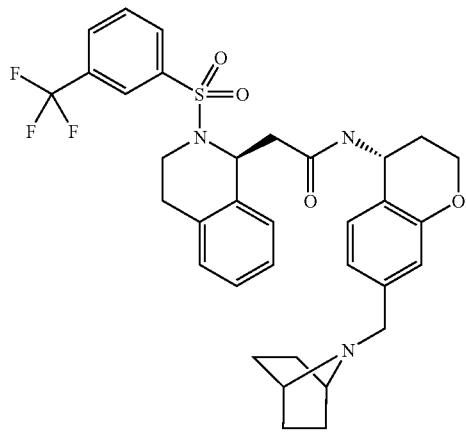

N-((4R)-7-(7-Azabicyclo[2.2.1]hept-7-ylmethyl)-3,4-dihydro-2H-chromen-4-yl)-2-((1S)-2-((3-(trifluoromethyl)phenyl)sulfonyl)-1,2,3,4-tetrahydro-1-isoquinolinyl)acetamide

EXAMPLE 350

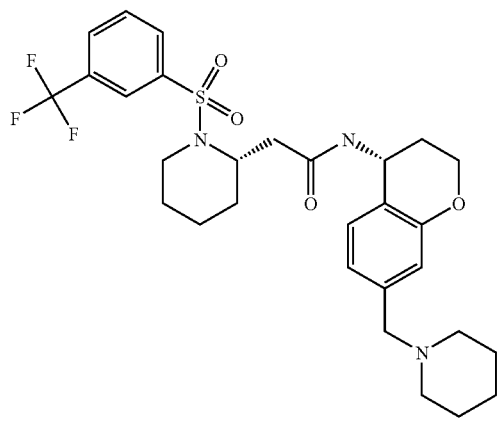

N-((4R)-7-(1-Piperidinylmethyl)-3,4-dihydro-2H-chromen-4-yl)-2-((2S)-1-((3-(trifluoromethyl)phenyl)sulfonyl)-2-piperidinyl)acetamide

EXAMPLE 351

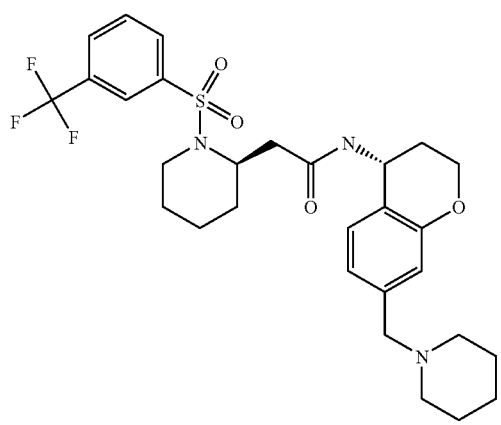

N-((4R)-7-(1-Piperidinylmethyl)-3,4-dihydro-2H-chromen-4-yl)-2-((2R)-1-((3-(trifluoromethyl)phenyl)sulfonyl)-2-piperidinyl)acetamide

EXAMPLE 352

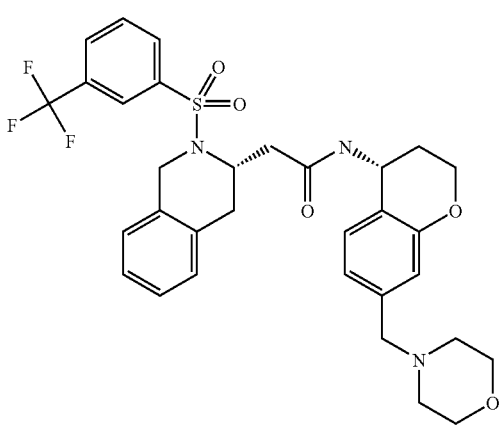

N-((4R)-7-(4-Morpholinylmethyl)-3,4-dihydro-2H-chromen-4-yl)-2-((3S)-2-((3-(trifluoromethyl)phenyl)sulfonyl)-1,2,3,4-tetrahydro-3-isoquinolinyl)acetamide

EXAMPLE 353

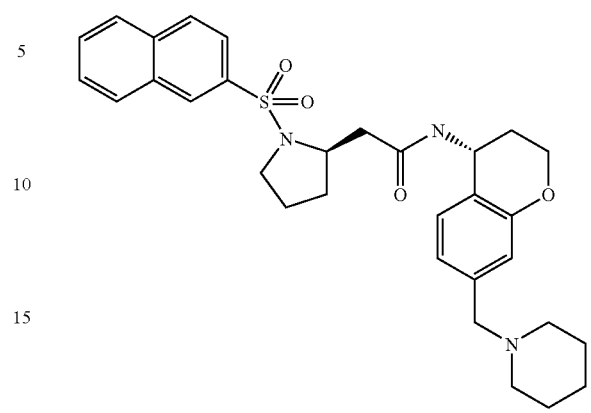

2-((2R)-1-(2-Naphthalenylsulfonyl)-2-pyrrolidinyl)-N-((4R)-7-(1-piperidinylmethyl)-3,4-dihydro-2H-chromen-4-yl)acetamide

EXAMPLE 354

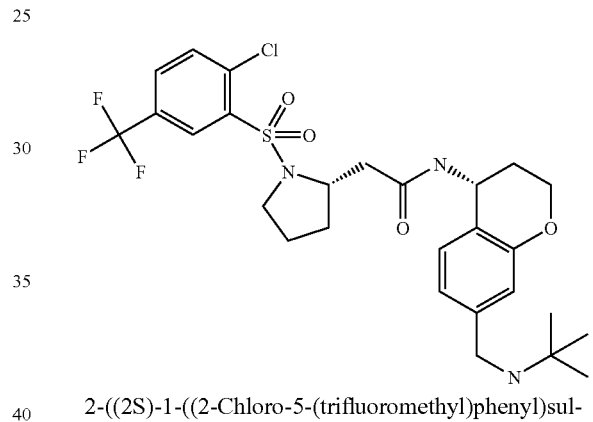

2-((2S)-1-((2-Chloro-5-(trifluoromethyl)phenyl)sulfonyl)-2-pyrrolidinyl)-N-((4R)-7-(((1,1-dimethylethyl)amino)methyl)-3,4-dihydro-2H-chromen-4-yl)acetamide

EXAMPLE 355

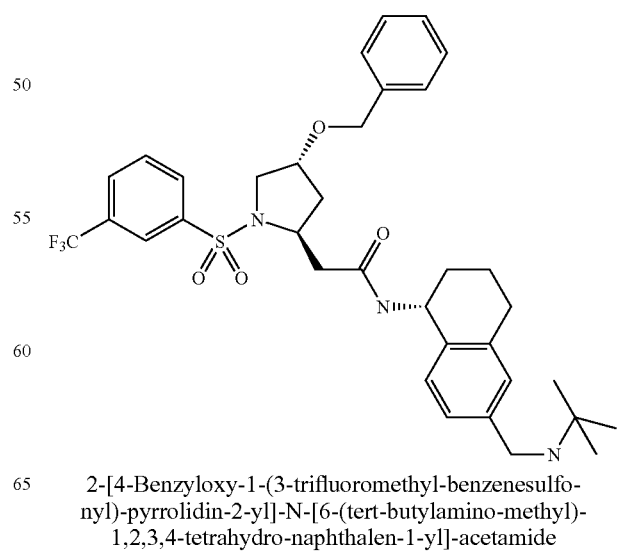

2-[4-Benzyloxy-1-(3-trifluoromethyl-benzenesulfonyl)-pyrrolidin-2-yl]-N-[6-(tert-butylamino-methyl)-1,2,3,4-tetrahydro-naphthalen-1-yl]-acetamide Step a. Preparation of 4-benzyloxy-2-[(6-hydroxymethyl-1,2,3,4-tetrahydro-naphthalen-1-ylcarbamoyl)-methyl]-pyrrolidine-1-carboxylic acid tert-butyl ester 4-Benzyloxy-2-carboxymethyl-pyrrolidine-1-carboxylic acid tert-butyl ester was coupled to [4-(1-aminopropyl)-phenyl]-methanol using EDC and HOBt as described earlier to afford the title compound as a white solid (MS,495, M+H).

Step B. Preparation of 2-(4-benzyloxy-pyrrolidin-2-yl)-N-(6-hydroxymethyl-1,2,3,4-tetrahydro-naphthalen-1-yl)-acetamide.

4-Benzyloxy-2-[(6-hydroxymethyl-1,2,3,4-tetrahydro-naphthalen-1-ylcarbamoyl)-methyl]-pyrrolidine-1-carboxylic acid tert-butyl ester (480 mg. 97 mmol) was dissolved in 25 mL $CH_2Cl_2$ and treated with 10 mL TFA and stirred at RT for 15 min, then concentrated to afford the title compound as a colorless glass. (MS,395, M+H).

Step C. Preparation of 2-[4-benzyloxy-1-(3-trifluoromethyl-benzenesulfonyl)-pyrrolidin-2-yl]-N-(6-hydroxymethyl-1,2,3,4-tetrahydro-naphthalen-1-yl)-acetamide.

The crude product from the above step was dissolved in 20 mL of $CH_2Cl_2$ and treated with 3.0 eq $Et_3N$ followed by 1.0 eq. 3-triflouorlmethlybenzenesulfonyl chloride. After 2 h the reaction solution was washed with water, sat $NaHCO_3$ and brine, then dried over $MgSO_4$ and purified by chromatography on silica to afford the title compound as a white solid (MS,603, M+H).

Step D. Preparation of 2-[4-benzyloxy-1-(3-trifluoromethyl-benzenesulfonyl)-pyrrolidin-2-yl]-N-(6-formyl-1,2,3,4-tetrahydro-naphthalen-1-yl)-acetamide.

The above alcohol was dissolved in 25 mg of anhydrous $CH_2Cl_2$ and treated with activated $MnO_2$ (6 eq.) and stirred overnight at RT, then filtered and evaporated to afford the title compound in quantities yield as a white solid.

Step E. Preparation of 2-[4-Benzyloxy-1-(3-trifluoromethyl-benzenesulfonyl)-pyrrolidin-2-yl]-N-[6-(tert-butylamino-methyl)-1,2,3,4-tetrahydro-naphthalen-1-yl]-acetamide Using the reductive aminations described earlier, gives the title compound as a white solid (MS, 658, M+H).

EXAMPLE 356

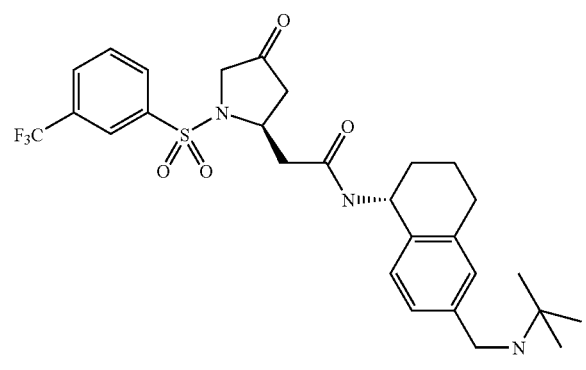

N-[6-(tert-Butylamino-methyl)-1,2,3,4-tetrahydro-naphthalen-1-yl]-2-[4-oxo-1-(3-trifluoromethyl-benzenesulfonyl)-pyrrolidin-2-yl]-acetamide Step A—Preparation of N-[6-(tert-butylamino-methyl)-1,2,3,4-tetrahydro-naphthalen-1-yl]-2-[4-hydroxy-1-(3-trifluoromethyl-benzenesulfonyl)-pyrrolidin-2-yl]-acetamide.

To a solution of 2-[4-benzyloxy-1-(3-trifluoromethyl-benzenesulfonyl)-pyrrolidin-2-yl]-N-[6-(tert-butylamino-methyl)-1,2,3,4-tetrahydro-naphthalen-1-yl]-acetamide (Example 355) in EtOH was treated with 10% Pd/C ((10 wt %) and stirred under an $H_2$ atmosphere for 4 h. The catalyst was removed by filtration affording the title compound as a white solid (MS, 568, M+H).

Step B. Preparation of N-[6-(tert-butylamino-methyl)-1,2,3,4-tetrahydro-naphthalen-1-yl]-2-[4-oxo-1-(3-trifluoromethyl-benzenesulfonyl)-pyrrolidin-2-yl]-acetamide.

N-[6-(tert-Butylamino-methyl)-1,2,3,4-tetrahydro-naphthalen-1-yl]-2-[4-hydroxy-1-(3-trifluoromethyl-benzenesulfonyl)-pyrrolidin-2-yl]-acetamide was oxidized to its ketone using Swern oxidation conditions to afford the title compound as a white solid (MS, 552, M+H).

EXAMPLE 357

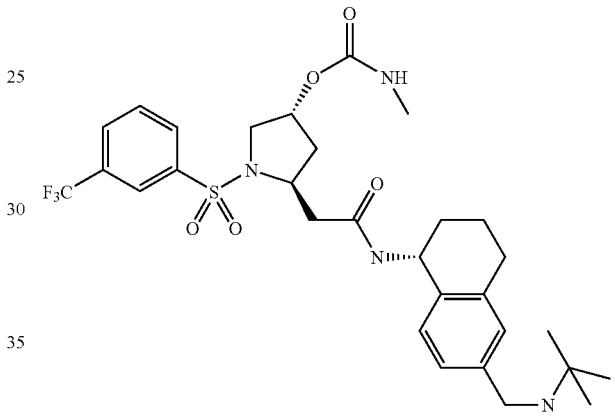

5-{[Methyl-carbamic acid 5-{[6-(tert-butylamino-methyl)-1,2,3,4-tetrahydro-naphthalen-1-ylcarbamoyl]-methyl}-1-(3-trifluoromethyl-benzenesulfonyl)-pyrrolidin-3-yl ester N-[6-(tert-Butylamino-methyl)-1,2,3,4-tetrahydro-naphthalen-1-yl]-2-[4-hydroxy-1-(3-trifluoromethyl-benzenesulfonyl)-pyrrolidin-2-yl]-acetamide was reacted with methyl chloroformate to afford the title compound as a white solid following reverse phase chromatography (MS, 625, M+H).

EXAMPLE 358

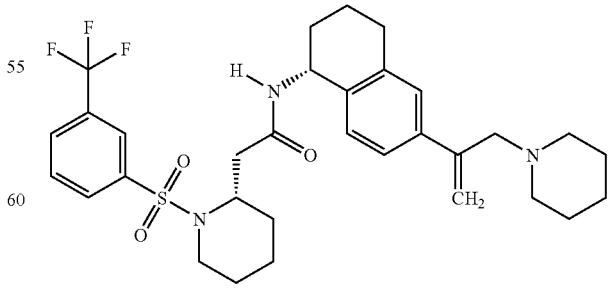

N-((1R)-6-(1-(1-piperidinylmethyl)ethenyl)-1,2,3,4-tetrahydro-1-naphthalenyl)-2-((2S)-1-((3-(trifluoromethyl)phenyl)sulfonyl)-2-piperidinyl)acetamide Step a—Preparation of trifluoro-methanesulfonic acid 5-oxo-5,6,7,8-tetrahydro-naphthalen-2-yl ester To a 1L round-bottomed flask charged with 6-hydroxy-1-tetralone (Aldrich, 21.97 g, 0.136 mol) was added $CH_2Cl_2$ (500 mL) and pyridine (Aldrich, 11 mL, 0.136 mol) at 0° C. Triflic anhydride (Aldrich, 23 mL, 0.136 mol) was added through an additional funnel over 12 min. The reaction was gradually warmed to RT and stirred overnight. The mixture was treated with water. The organic phase was separated, washed with 1N HCl (100 mL×2), saturated $NaHCO_3$, and brine, dried over $Na_2SO_4$, and concentration in vacuo. The crude was purified by flash chromatography (5–11% EtOAc-hexane) to provide the title compound as yellow oil. MS (ESI): 295 $(M+H)^+$.

Step b—Preparation of trifluoro-methanesulfonic acid 5-hydroxy-5,6,7,8-tetrahydro-naphthalen-2-yl ester To a dry three-necked flask containing (R)-2-methyl-CBS-oxazaborolidine (Aldrich, 1.94 mL, 1.0 M in toluene, 1.93 mmol, 0.05 eq) under $N_2$ was added a solution of borane-methylsulfide (BMS) (Aldrich, 3.30 mL, 34.80 mmol, 0.9 eq) in toluene (200 mL) through an additional funnel at RT. After the addition, the reaction was cooled to 0° C. A solution of trifluoro-methanesulfonic acid 5-oxo-5,6,7,8-tetrahydro-naphthalen-2-yl ester (11.37 g, 38.67 mmol, 1.0 eq) in THF (180 mL) was added drop-wise through an additional funnel. Following the addition, the reaction was warmed to RT and stirred for additional 40 min, then quenched with MeOH. The solvent was removed in vacuo. The residue was treated with $H_2O$ (50 mL), and extracted with ether (3×150 mL). The combined organic layers were washed with brine, dried over $Na_2SO_4$, filtered and concentrated in vacuo. The title compound was obtained as an off-white solid after flash chromatography purification (16–22% EtOAc-hexane).

Step c—Preparation of trifluoro-methanesulfonic acid 5-azido-5,6,7,8-tetrahydro-naphthalen-2-yl ester To a solution of trifluoro-methanesulfonic acid 5-hydroxy-5,6,7,8-tetrahydro-naphthalen-2-yl ester (11.2 g, 37.9 mmol, 1.0 eq) in THF (150 mL) at RT was added DPPA (Aldrich, 11.1 mL, 51.6 mmol, 1.36 eq). The resulting mixture was cooled to 0° C., then DBU (Aldrich, 7.7 mL, 51.6 mmol, 1.36 eq) was added slowly through a syringe. The reaction was warmed to RT and stirred over the weekend. The mixture was concentrated in vacuo. The residue was dissolved in EtOAc (400 mL), washed with saturated $NH_4Cl$ (twice), water, and brine, dried over $Na_2SO_4$, and concentrated in vacuo. The crude was purified by flash chromatography (5% EtOAc-hexane) to provide the title compound.

Step d—Preparation of trifluoro-methanesulfonic acid 5-amino-5,6,7,8-tetrahydro-naphthalen-2-yl ester A solution of trifluoro-methanesulfonic acid 5-azido-5,6,7,8-tetrahydro-naphthalen-2-yl ester (10.3 g, 32.1 mmol, 1.0 eq) in THF (70 mL) was added $PPh_3$ (Aldrich, 8.4 g, 32.1 mmol, 1.0 eq), and $H_2O$ (30 mL) at 0° C. The mixture was warmed to RT and stirred overnight. 2N HCl was added until the mixture was acidic (pH ~1–2). The mixture was extracted with toluene (3×100 mL). The aqueous phase was neutralized with 5N NaOH to pH around 12–13, and extracted with ether (3×150 mL). The ether solution was dried over $Na_2SO_4$, filtered and concentrated in vacuo. The crude was purified by flash chromatography (6% MeOH—$CH_2Cl_2$) to provide the title compound.

Step e—Preparation of 2S-[(6-trifluoromethanesulfonyloxy-1,2,3,4-tetrahydro-naphthalen-1R-ylcarbamoyl)-methyl]-piperidine-1-carboxylic acid tert-butyl ester To a 50 mL round bottomed flask equipped with magnetic stirring was added 2S-carboxymethyl-piperidine-1-carboxylic acid tert-butyl ester (Biocatalytics, 0.89 g, 3.7 mmol), HOBt (Aldrich, 0.54 g, 4.0 mmol), and EDC (Aldrich, 0.76 g, 4 mmol) all in 14 mL of 1,2-dichloroethane. After 5 min, 1-trifluoro-methanesulfonic acid 5R-amino-5,6,7,8-tetrahydro-naphthalen-2-yl ester (0.98 g, 3.3 mmol) was added, and the reaction was stirred at RT for ca. 18 h. Water was added, and the aqueous layer was extracted with EtOAc (3×). The organic layers were combined and washed with 1M $H_3PO_4$, water, sat'd $NaHCO_3$, and brine. The organic layers were dried over $MgSO_4$, filtered and concentrated in vacuo. The crude was purified on a Biotage 40M silica gel column using 2:1 hexanes-EtOAc as the eluant. The desired compound was isolated as a clear oil. MS (ESI, + ion) m/z=521 (M+H).

Step f—Preparation of 2-{[6-(1-piperidin-1-ylmethyl-vinyl)-1,2,3,4-tetrahydro-naphthalen-1-ylcarbamoyl]-methyl}-piperidine-1-carboxylic acid tert-butyl ester A solution of 2-[(6-trifluoromethanesulfonyloxy-1,2,3,4-tetrahydro-naphthalen-1-ylcarbamoyl)-methyl]-piperidine-1-carboxylic acid tert-butyl ester (624 mg, 1.19 mmol) in $CH_3CN$ (6 mL) was purged with $N_2$, and then added palladium(II)acetate (Strem Chemicals, 20 mg, 0.09 mmol), 1,1'-bis(diphenylphosphino)ferrocene (Aldrich, 211 mg, 0.38 mmol), $K_2CO_3$ (Aldrich, 299 mg, 2.16 mmol) and 1-allylpiperidine (Lancaster, 904 mg, 7.22 mmol). The mixture was heated to 80° C. overnight, cooled to RT, diluted with water (10 mL), and extracted with ether. The organic solution was dried over $Na_2SO_4$, filtered and concentrated in vacuo. The crude was purified by silica gel chromatography (26% EtOAc-Hexane) to provide the title compound. MS (ESI): 496 $(M+H)^+$.

Step g—Preparation of 2-piperidin-2-yl-N-[6-(1-piperidin-1-ylmethyl-vinyl)-1,2,3,4-tetrahydro-naphthalen-1-yl]-acetamide To a solution of 2-{[6-(1-piperidin-1-ylmethyl-vinyl)-1,2,3,4-tetrahydro-naphthalen-1-ylcarbamoyl]-methyl}-piperidine-1-carboxylic acid tert-butyl ester in $CH_2Cl_2$ (2 mL) was added TFA (2 mL). The mixture was stirred at RT, concentrated in vacuo. The crude was neutralized with 10% $Na_2CO_3$ until the aqueous phase is basic, extracted with $CH_2Cl_2$ three times. The organic solution was dried over $Na_2SO_4$ filtered and concentrated in vacuo to provide the title compound. MS (ESI): 396 $(M+H)^+$.

Preparation VI—N-[6-(1-Piperidin-1-ylmethyl-vinyl)-1,2,3,4-tetrahydro-naphthalen-1-yl]-2-[1-(3-trifluoromethyl-benzenesulfonyl)-piperidin-2-yl]-acetamide To a solution of 2-piperidin-2-yl-N-[6-(1-piperidin-1-ylmethyl-vinyl)-1,2,3,4-tetrahydro-naphthalen-1-yl]-acetamide (155.8 mg, 0.39 mmol) in $CH_2Cl_2$ (2 mL) was added 3-(trifluoromethyl)benzenesulfonyl chloride (Fluka, 0.1 mL, 0.59 mmol) and $Et_3N$ (Aldrich, 0.1 mL, 0.79 mmol). The mixture was stirred at rt overnight, diluted with $CH_2Cl_2$ (30 mL), washed with 10% $Na_2CO_3$ (twice) and brine. The organic solution was dried over $Na_2SO_4$, filtered and concentrated in vacuo. The crude was purified by silica gel chromatography (3%–10% MeOH—$CH_2Cl_2$) to provide the title compound. MS (ESI): 604 $(M+H)^+$. Calc'd for $C_{32}H_{40}F_3N_3O_3S$—603.27.

Example 359 was prepared by a method similar to that described in Example 358.

EXAMPLE 359

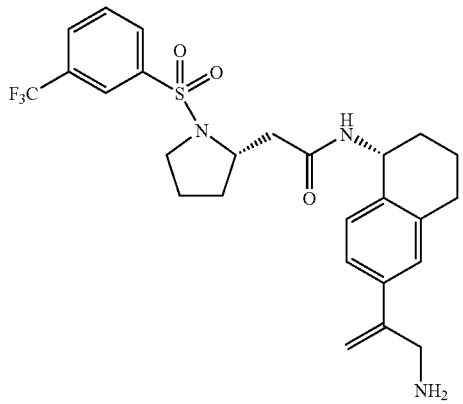

N-[6-(1-Aminomethyl-vinyl)-1,2,3,4-tetrahydro-naphthalen-1-yl]-2-[1-(3-trifluoromethyl-benzenesulfonyl)-pyrrolidin-2-yl]-acetamide Step A—Preparation of trifluoro-methanesulfonic acid 5-{2-[1-(3-trifluoromethyl-benzenesulfonyl)-pyrrolidin-2-yl]-acetylamino}-5,6,7,8-tetrahydro-naphthalen-2-yl ester The desired compound was prepared from [1-(2-trifluoromethyl-benzenesulfonyl)-pyrrolidin-2-yl]-acetic acid by a method similar to that described in Example 358 step e. Exact Mass Calc'd for $C_{24}H_{24}F_6N_2O_6S_2$: 614.10.

Step B—Preparation of [2-(5-{2-[1-(3-trifluoromethyl-benzenesulfonyl)-pyrrolidin-2-yl]-acetylamino}-5,6,7,8-tetrahydro-naphthalen-2-yl)-allyl]-carbamic acid tert-butyl ester A mixture of trifluoro-methanesulfonic acid 5-{2-[1-(3-trifluoromethyl-benzenesulfonyl)-pyrrolidin-2-yl]-acetylamino}-5,6,7,8-tetrahydro-naphthalen-2-yl ester (150 mg, 0.244 mmol, 1.0 eq), allyl carbamic acid tert-butyl ester (230 mg, 1.47 mmol, 6.0 eq), palladium acetate (Strem Chemicals, 3.3 mg, 0.015 mmol, 0.06 eq), DPPF (Aldrich, 36 mg, 0.064 mmol, 0.26 eq) and $K_2CO_3$ (Aldrich, 51 mg, 0.37 mmol, 1.5 eq) in $CH_3CN$ (2 mL) was flushed with $N_2$ for 10 min. The reaction was heated to 80° C. and stirred at 80° C. under $N_2$ for 20 h. The reaction was quenched with $H_2O$ (60 mL), extracted with $CH_2Cl_2$ (60 mL×3). The extract phase was washed with saturated NaCl, dried over $Na_2SO_4$, filtered and concentrated in vacuo. Flash column chromatography (silica gel, 0–4% MeOH—$CH_2Cl_2$) afforded the title compound as a colorless thin film. MS (ESI, pos. ion) m/z: 622 (M+1).

Step C—Preparation of N-[6-(1-aminomethyl-vinyl)-1,2,3,4-tetrahydro-naphthalen-1-yl]-2-[1-(3-trifluoromethyl-benzenesulfonyl)-pyrrolidin-2-yl]-acetamide A solution of [2-(5-{2-[1-(3-trifluoromethyl-benzenesulfonyl)-pyrrolidin-2-yl]-acetylamino}-5,6,7,8-tetrahydro-naphthalen-2-yl)-allyl]-carbamic acid tert-butyl ester (72 mg, 0.12 mmol) in saturated HCl/EtOAc (3 mL) was stirred at RT for 45 min. The solvent was removed with a rotary evaporator. The crude was diluted with saturated $NaHCO_3$ (60 mL) and extracted with $CH_2Cl_2$ (60 mL×3). The extract phase was washed with saturated NaCl, dried over $Na_2SO_4$, filtered and concentrated. Reverse phase liquid chromatography [25–100% $CH_3CN$ (0.1% TFA)-$H_2O$ (0.1% TFA)] afforded the title compound-containing fractional collections. $CH_3CN$ was removed from the combined fractional collections with a rotary evaporator. The aqueous phase was neutralized with saturated with $NaHCO_3$ (40 mL), extracted with $CH_2Cl_2$ (40 mL×3). The extract phase was washed with saturated with NaCl, dried over $Na_2SO_4$, filtered and concentrated. The title compound was obtained as an off-white solid. MS (ESI, pos. ion) m/z: 522 (M+1).

EXAMPLE 360

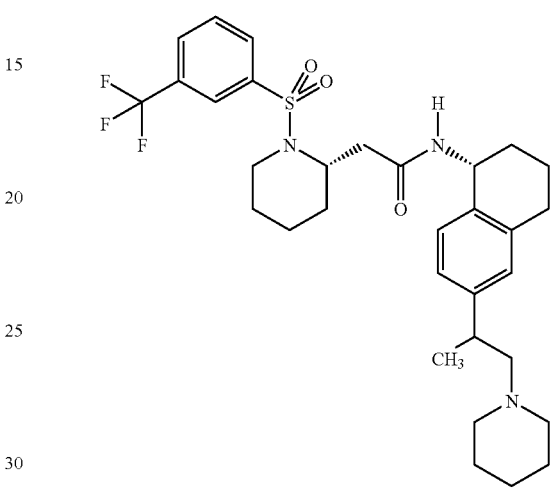

N-((1R)-6-((1S)-1-methyl-2-(1-piperidinyl)ethyl)-1,2,3,4-tetrahydro-1-naphthalenyl)-2-((2S)-1-((3-(trifluoromethyl)phenyl)sulfonyl)-2-piperidinyl)acetamide A mixture of N-[6-(1-piperidin-1-ylmethyl-vinyl)-1,2,3,4-tetrahydro-naphthalen-1-yl]-2-[1-(3-trifluoromethyl-benzenesulfonyl)-piperidin-2-yl]-acetamide (34 mg, 0.05 mmol), EtOH (2 mL), Pd/$Al_2O_3$ (Johnson Matthey, 12 mg, 0.1 eq) was purged with $H_2$ and connected to a $H_2$ balloon for 30 min at RT. The catalyst was filtered through Celite and washed with MeOH. The filtrate was concentrated in vacuo. The crude was purified by silica gel chromatography (7%–10% MeOH—$CH_2Cl_2$) to afford the title compound as a mixture of two diastereomers. MS (ESI): 606 (M+H)$^+$. Calc'd for $C_{32}H_{42}F_3N_3O_3S$—605.29.

Although the pharmacological properties of the compounds of Formula I–VI and I'–VI' vary with structural change, in general, activity possessed by compounds of Formula I–VI may be demonstrated in vivo. The pharmacological properties of the compounds of this invention may be confirmed by a number of pharmacological in vitro assays. The exemplified pharmacological assays which follow have been carried out with the compounds according to the invention and their salts. Compounds of the present invention showed binding $IC_{50}$'s of B1 at doses less than 10 μM.

Biological Testing

Human Bradykinin B1 Receptor and human B2 Receptor In Vitro Binding Assay Supporting Methods:

Preparation of membranes expressing human B1 and human B2 bradykinin receptor. Membranes were prepared from CHO-d⁻AQN cells stably transfected with human bradykinin B1 receptor cDNA. For large-scale production of membranes, cells were grown in 100 L suspension culture to 1.0E8 cells/mL then harvested using the Viafuge at continuous centrifugation of 1000 g. For pilot studies, cells were grown in 2 L spinner culture and harvested by centrifugation (1900 g, 10 min, 4° C.). The cell pellet was washed with PBS, centrifuged (1900 g, 10 min, 4° C.), then the cells resuspended in lysis buffer (25 mM HEPES, pH 7.4, 5 mM EDTA, 5 mM EGTA, 3 mM $MgCl_2$, 10% (w/v) sucrose, Complete Protease Inhibitor tablets (EDTA-free)) to a density of 14% w/v for passage through a microfluidizer (Microfluidics 110S, 3 passes, 6,000 psi). The resulting cell lysate was centrifuged (1900 g, 10 min, 4° C.), and the crude particulate fraction isolated by centrifugation (142,000 g, 1 h, 4° C.) of the low-speed supernatant. The resulting pellet was resuspended in 1/3 the original lysis buffer volume, homogenized, and recentrifuged as above. The membrane pellet was resuspended by homogenization in storage buffer (25 mM HEPES, pH 7.4, 3 mM $MgCl_2$, 10% (w/v) sucrose and Complete Protease Inhibitor tablets (EDTA-free)). Single-use aliquots were made and flash-frozen in liquid $N_2$ prior to storage at −80° C.

Membranes containing human bradykinin B2R were purchased from Receptor Biology (now Perkin Elmer Life Sciences). They were derived from a CHO-K1 line stably expressing the human B2 receptor developed by Receptor Biology and subsequently purchased by Amgen. For some studies, membranes were prepared in-house from this same cell line using the method described for human B1 receptor membranes, except cells were grown in roller bottles and harvested using Cellmate.

Radioligand Binding Assay for human B1 and human B2 bradykinin receptor. Human B1 receptor binding assay was performed in 96-well polypropylene plates (Costar 3365) by adding 50 μl [$^3$H] des-arg$^{10}$ kallidin (NET1064; Perkin Elmer Life Sciences) to 10 μL test compound diluted in 90 μL assay buffer (24 mM TES, pH 6.8, 1 mM 1,10 o-phenanthroline, 0.3% BSA, 0.5 mM Pefabloc SC, 2 ug/ml aprotinin, 5 μg/mL leupeptin, and 0.7 μg/mL pepstatin A). Membranes (50 μL) were added last. [$^3$H] des-arg$^{10}$ kallidin was diluted from stock into assay buffer to yield a final concentration of ~0.3 nM in the assay but was adjusted as needed to ensure a concentration at or below the $K_d$ determined for each batch of receptor membranes. Nonspecific binding was defined with 2 μM des-Arg$^{10}$Leu$^9$ kallidin. Membranes were diluted in assay buffer to yield a final concentration of 0.068 nM hB1 receptor in the assay. Compounds were solubilized in either DMSO or dd$H_2$O, plated into polypropylene plates (Costar 3365), then serially diluted in either DMSO or dilution buffer (20 mM Hepes, pH 7.6, 0.1% BSA) to yield a final concentration of either 5% DMSO or no DMSO in the assay. The assay mixture was incubated with shaking for 1 hr at RT and then filtered through GF/C plates presoaked in 0.5% polyethyleneimine (Unifilter; Perkin Elmer Life Sciences) using a Filtermate 96-well harvester (Perkin Elmer Life Sciences). Filter plates were rapidly washed 6 times with 200 μL ice-cold buffer (50 mM Tris, pH 7.4), dried in a vacuum oven at 55° C. for 15–20 min, backed, and 40 μL per well of Microscint 20 was added. The plates were sealed and activity read on Topcount (Perkin Elmer Life Sciences) using a count time of 3 min per channel.

For human B2 bradykinin receptor, the same procedure was followed with the following exceptions: [$^3$H] bradykinin (NET706; Perkin Elmer Life Sciences) was used at a final concentration of ~0.2 nM and non specific binding was defined with 2 μM bradykinin. Human B2 receptor concentration was 0.068 nM final in the assay.

Data analysis. Data was analyzed in XLFit with the four-parameter logistic $y=A+((B-A)/(1+((C/x)^D)))$ and fit with the Levenburg-Marquardt algorithm. Raw cpm were converted to percent of control values prior to analysis (POC= ((compound cpm−nonspecfic cpm)/(no-compound cpm−nonspecific cpm)*100)). $K_i$ values were determined from the $IC_{50}$ using the Cheng-Prusoff equation and $K_d$ values determined by direct saturation binding of the radioligands.

The compounds of examples 1–3, have binding Ki's to the hB1 receptor at a level below 100 nm. The compounds of examples 1–3, should have binding Ki's to the hB2 receptor at a level above 1 μM.

In vitro B1-Inhibition Activity

A. In vitro Assay of Human B1 Receptor Function Using Calcium Flux:

Activation of the $G_q$ linked B1 receptor results in an increase in intracellular calcium. The calcium sensitive photoprotein aequorin can, therefore, be used as an indicator of B1 receptor activation. Aequorin is a 21-kDa photoprotein that forms a bioluminescent complex when linked to the chromophore cofactor coelenterazine. Following the binding of calcium to this complex, an oxidation reaction of coelenterazine results in the production of apoaequorin, coelenteramide, $CO_2$, and light that can be detected by conventional luminometry.

A stable CHO D-/hB1/Aequorin cell line was established and the cells were maintained in suspension in spinner bottles containing a 1:1 ratio of DMEM and HAM F12 (Gibco 11765-047), high glucose (Gibco 11965-084), 10% Heat Inactivated Dialyzed serum (Gibco 26300-061), 1× Non-Essential Amino Acids (Gibco 11140-050), 1× Glutamine-Pen-Strep (Gibco 10378-016), and Hygromycin, 300 μg/mL (Roche 843555). 15–24 h prior to the luminometer assay, 25,000 cells/well (2.5E6 cells/10 ml/plate) were plated in 96-well black-sided clear bottom assay plates (Costar #3904).

Media was removed from the wells and replaced with 60 μl of serum free HAM's F12 with 30 mM HEPES (pH 7.5) and 15 μM coelenterazine (Coelenterazine h Luciferin #90608 from Assay Designs). The plates were incubated for 1.5–2 h. Ten point $IC_{50}$ compound plates containing 1:3 or 1:5 dilutions of antagonist compounds and an agonist activator plate (20 nM des-Arg10-Kallidin final concentration, $EC_{80}$) were prepared using Ham's F12 with 30 mM HEPES, pH 7.5. Following coelenterazine incubation, an automated flash-luminometer platform was used to dispense the B1 antagonist compounds (dissolved in DMSO and diluted with buffer to the desired concentration (final DMSO concentration <1% DMSO)) to the cell plate, a CCD camera situated underneath the cell plate took 12 images of the cell plate at 5 second intervals to determine if there was any agonist activity with the compounds. The hB1 agonist, des-Arg$_{10}$-Kallidin, was added to the cell plate and another 12 images were recorded to determine the $IC_{50}$ of the antagonist(s). The compounds of examples 1–3, 3q, 3u–3v, 3y–3z, 3ac, 3ae, 3aj–3aq, 3 as, 3au–3ay, 3ba–3bb, 3bd–3bj, 3bq–3br, 3bu, 329–333, 336, 339–340, 345, 347, 349–351, 358 and 360 have binding $IC_{50}$'s to hB1 receptor function at a level below 100 nm.

B. In vitro Assay of hB2 Receptor Function Using Calcium Flux:

The intracellular calcium flux induced by hB2 receptor activation was analyzed using a hB2 recombinant cell line (CHO-K1) purchased from PerkinElmer (Catalog Number: RBHB2C000EA) on a fluorometric imaging plate reader (FLIPR). The cells were cultured in T225 flask containing Ham's F12 Nutrient Mixture (Invitrogen Corp., Cat # 11765-047), 10% Fetal Clone II Bovine Serum (HyClone, Cat # SH3006603), 1 mM Sodium pyruvate (100 mM stock, Invitrogen Corp., Cat# 12454-013), and 0.4 mg/ml Geneticin (G418; 50 mg/mL active geneticin, Invitrogen, Cat# 10131-207). Culture medium was changed every other day. 24 h prior to the FLIPR assay, the hB2/CHO cells were washed once with PBS (Invitrogen, Cat.#) and 10 mL of Versene (1:5000, Invitrogen, Cat# 15040-066) was added to each flask. After 5 min incubation at 37° C., Versene was removed and cells were detached from the flask and resuspended in culture medium. Cells were counted and 25,000 cells/well were plated in 96-well black-sided clear bottom assay plates (Costar #3904). Cells were incubated in a 37° C. $CO_2$ incubator overnight.

The media was aspirated from the cells and replaced with 65 μL of dye-loading buffer. The loading buffer was prepared by diluting a stock solution of 0.5 mM Fluo-4 AM (Molecular Probes, dissolved in DMSO containing 10% [w/v] pluronic acid) to a concentration of 1 μM in Clear Dulbecco's Modified Eagle Medium (DMEM) containing 0.1% BSA, 20 mM HEPES, and 2.5 mM probenecid. The cells were dye-loaded for 1 h at RT. The excess dye was removed by washing the cells 2× with assay buffer. The assay buffer consists of Hank's Balanced Salt Solution (HBSS) containing 20 mM HEPES, 0.1% BSA, and 2.5 mM probenecid. After the wash cycles, a volume of 100 μL was left in each well, and the plate was ready to be assayed in the FLIPR System. Single point (10 μM final concentration) POC antagonist compound plates or ten point $IC_{50}$ compound plates containing 1:3 or 1:5 dilutions of antagonist compounds (dissolved in DMSO and diluted with buffer to the desired concentration (final DMSO concentration <1% DMSO)) and an agonist activator plate (0.3 nM bradykinin final concentration, $EC_{80}$) were prepared using assay buffer. The cell plate and the compound plates were loaded onto the FLIPR and during the assay, fluorescence readings are taken simultaneously from all 96 wells of the cell plate. Ten 1-second readings were taken to establish a stable baseline for each well, then 25 μL from the B1 antagonist plate was rapidly (50 μL/sec.) added. The fluorescence signal was measured in 1-second (1 min) followed by 6-second (2 min) intervals for a total of 3 min to determine if there is any agonist activity with the compounds. The B2 agonist, bradykinin, was added to the cell plate and another 3 min were recorded to determine the percent inhibition at 10 μM (POC plates) or the $IC_{50}$ of the antagonist.

C. Cell and Tissue Based In Vitro Assays of hB1 Receptor Binding:

These studies established the antagonist activity of several compounds at the bradykinin B1 receptors in in vitro cell-based and isolated organ assays.

1. Rabbit endothelial cell B1-specific $PGI_2$ secretion Assay

2. B1 and B2 umblical vein Assay

D. In vitro B1-Inhibition Activity

The effectiveness of the compounds as inhibitors of B1 activity (i.e., B1 "neutralization") can be evaluated by measuring the ability of each compound to block B1 stimulated CGRP and substance P release and calcium signaling in Dorsal Root Ganglion (DRG) neuronal cultures.

Dorsal Root Ganglion Neuronal Cultures. Dorsal root ganglia are dissected one by one under aseptic conditions from all spinal segments of embryonic 19-day old (E19) rats that are surgically removed from the uterus of timed-pregnant, terminally anesthetized Sprague-Dawley rats (Charles River, Wilmington, Mass.). DRG are collected in ice-cold L-15 media (GibcoBRL, Grand Island, N.Y.) containing 5% heat inactivated horse serum (GibcoBRL), and any loose connective tissue and blood vessels are removed. The DRG are rinsed twice in $Ca^{2+}$- and $Mg^{2+}$-free Dulbecco's phosphate buffered saline (DPBS), pH 7.4 (GibcoBRL). The DRG are dissociated into single cell suspension using a papain dissociation system (Worthington Biochemical Corp., Freehold, N.J.). Briefly, DRG are incubated in a digestion solution containing 20 U/mL of papain in Earle's Balanced Salt Solution (EBSS) at 37° C. for 50 min. Cells are dissociated by trituration through fire-polished Pasteur pipettes in a dissociation medium consisting of MEM/Ham's F12, 1:1, 1 mg/ml ovomucoid inhibitor and 1 mg/ml ovalbumin, and 0.005% deoxyribonuclease I (DNase). The dissociated cells are pelleted at 200×g for 5 min and re-suspended in EBSS containing 1 mg/ml ovomucoid inhibitor, 1 mg/mL ovalbumin and 0.005% DNase. Cell suspension is centrifuged through a gradient solution containing 10 mg/mL ovomucoid inhibitor, 10 mg/mL ovalbumin at 200×g for 6 min to remove cell debris, then filtered through a 88-μM nylon mesh (Fisher Scientific, Pittsburgh, Pa.) to remove any clumps. Cell number is determined with a hemocytometer, and cells are seeded into poly-ornithine 100 μg/mL (Sigma, St. Louis, Mo.) and mouse laminin 1 μg/ml (GibcoBRL)-coated 96-well plates at $10 \times 10^3$ cells/well in complete medium. The complete medium consists of minimal essential medium (MEM) and Ham's F12, 1:1, penicillin (100 U/mL), streptomycin (100 μg/mL), and 10% heat inactivated horse serum (GibcoBRL). The cultures are kept at 37° C., 5% $CO_2$ and 100% humidity. For controlling the growth of non-neuronal cells, 5-fluoro-2'-deoxyuridine (75 μM) and uridine (180 μM) are included in the medium. 2 h after plating, cells are treated with recombinant human β-B1 or recombinant rat β-B1 at a concentration of 10 ng/mL (0.38 nM). Positive controls comprising serial-diluted anti-B1 antibody (R&D Systems, Minneapolis, Minn.) are applied to each culture plate. Compounds are added at ten concentrations using 3.16-fold serial dilutions. All samples are diluted in complete medium before being added to the cultures. Incubation time is generally around 40 h prior to measurement of VR1 expression.

Measurement of VR1 Expression in DRG Neurons. Cultures are fixed with 4% paraformaldehyde in Hanks' balanced salt solution for 15 min, blocked with Superblock (Pierce, Rockford, Ill.), and permeabilized with 0.25% Nonidet P-40 (Sigma) in Tris.HCl (Sigma)-buffered saline (TBS) for 1 h at RT. Cultures are rinsed once with TBS containing 0.1% Tween 20 (Sigma) and incubated with rabbit anti-VR1 IgG (prepared at Amgen) for 1.5 h at RT, followed by incubation of Eu-labeled anti-rabbit second antibody (Wallac Oy, Turku, Finland) for 1 h at RT. Washes with TBS (3×five min with slow shaking) are applied after each antibody incubation. Enhance solution (150 μL/well, Wallac Oy) is added to the cultures. The fluorescence signal is measured in a time-resolved fluorometer (Wallac Oy). VR1 expression in samples treated with the compounds is determined by comparing to a standard curve of B1 titration from 0–1000 ng/mL. Percent inhibition (compared to maximum possible inhibition) of B1 effect on VR1 expression in DRG neurons is determined by comparing to controls that are not B1-treated.

In Vivo Antinociceptive Activity in Rat and Monkey Pain Models

A. Rat Neuropathic Pain Model. Male Sprague-Dawley rats (200 g) are anesthetized with isoflurane inhalant anesthesia and the left lumbar spinal nerves at the level of L5 and L6 are tightly ligated (4-0 silk suture) distal to the dorsal root ganglion and prior to entrance into the sciatic nerve, as first described by Kim and Chung (Kim, S. H.; Chung, J. M. An experimental model for peripheral neuropathy produced by segmental spinal nerve ligation in the rat. Pain 50:355–363 (1992)). The incisions are closed and the rats are allowed to recover. This procedure results in mechanical (tactile) allodynia in the left hind paw as assessed by recording the pressure at which the affected paw (ipsilateral to the site of nerve injury) was withdrawn from graded stimuli (von Frey filaments ranging from 4.0 to 148.1 mN) applied perpendicularly to the plantar surface of the paw (between the footpads) through wire-mesh observation cages. A paw withdrawal threshold (PWT) was determined by sequentially increasing and decreasing the stimulus strength and analyzing withdrawal data using a Dixon non-parametric test, as described by Chaplan et al. (Chaplan, S. R.; Bach, F. W.; Pogrel, J. W.; Chung, J. M.; Yaksh, T. L. Quantitative assessment of tactile allodynia in the rat paw. J. Neurosci. Meth, 53:55–63 (1994)).

Normal rats and sham surgery rats (nerves isolated but not ligated) withstand at least 148.1 mN (equivalent to 15 g) of pressure without responding. Spinal nerve ligated rats respond to as little as 4.0 mN (equivalent to 0.41 g) of pressure on the affected paw. Rats are included in the study only if they did not exhibit motor dysfunction (e.g., paw dragging or dropping) and their PWT was below 39.2 mN (equivalent to 4.0 g). At least seven days after surgery rats are treated with compounds (usually a screening dose of 60 mg/kg) or control diluent (PBS) once by s.c. injection and PWT was determined each day thereafter for 7 days.

B. Rat CFA Inflammatory Pain Model. Male Sprague-Dawley rats (200 g) are lightly anesthetized with isoflurane inhalant anesthesia and the left hindpaw is injected with complete Freund's adjuvant (CFA), 0.15 mL. This procedure results in mechanical (tactile) allodynia in the left hind paw as assessed by recording the pressure at which the affected paw is withdrawn from graded stimuli (von Frey filaments ranging from 4.0 to 148.1 mN) applied perpendicularly to the plantar surface of the paw (between the footpads) through wire-mesh observation cages. PWT is determined by sequentially increasing and decreasing the stimulus strength and analyzing withdrawal data using a Dixon non-parametric test, as described by Chaplan et al. (1994). Rats are included in the study only if they do not exhibit motor dysfunction (e.g., paw dragging or dropping) or broken skin and their PWT is below 39.2 mN (equivalent to 4.0 g). At least seven days after CFA injection rats are treated with compounds (usually a screening dose of 60 mg/kg) or control solution (PBS) once by s.c. injection and PWT is determined each day thereafter for 7 days. Average paw withdrawal threshold (PWT) is converted to percent of maximum possible effect (% MPE) using the following formula: % MPE=100*(PWT of treated rats−PWT of control rats)/(15−PWT of control rats). Thus, the cutoff value of 15 g (148.1 mN) is equivalent to 100% of the MPE and the control response is equivalent to 0% MPE.

At the screening dose of 60 mg/kg, compounds in vehicle are expected to produce an antinociceptive effect with a PD relationship.

B. Green Monkey LPS Inflammation Model. The effectiveness of the compounds as inhibitors of B1 activity are evaluated in Male green monkeys (*Cercopithaecus aethiops* St Kitts) challenged locally with B1 agonists essentially as described by deBlois and Horlick (British Journal of Pharmacology. 132:327–335 (2002), which is hereby incorporated by reference in its entirety).

In order to determine whether compounds of the present invention inhibit B1 induced oedema the studies described below are conducted on male green monkeys (*Cercopithaecus aethiops* St Kitts) at the Caribbean Primates Ltd. experimental farm (St Kitts, West Indies). Procedures are reviewed and accepted by the Animal Care Committees of the CR-CHUM (Montreal, Canada) and of Caribbean Primates Ltd. (St Kitts, West Indies). Animals weighing 6.0±0.5 kg (n=67) were anaesthetized (50 mg ketamine $kg^{-1}$) and pretreated with a single intravenous injection of LPS (90 µg $kg^{-1}$) or saline (1 ml) via the saphenous vein.

1. Inflammation Studies

Kinin-induced oedema is evaluated by the ventral skin fold assay (Sciberras et al. (1987)). Briefly, anaesthetized monkeys were injected with captopril (1 mg $kg^{-1}$ 30 min before assay). A single subcutaneous injection of dKD, BK or the vehicle (2 mM amastatin in 100 µL Ringer's lactate) is given in the ventral area and the increase in thickness of skin folds is monitored for 30–45 min using a calibrated caliper. The results are expressed as the difference between the skin fold thickness before and after the subcutaneous injection. Captopril and amastatin are used to reduce degradation of kinins at the carboxyl- and amino-terminus, respectively.

Antagonist Schild Analysis

The dose-response relationship for dKD (1–100 nmol)-induced oedema is determined at 24 h post-LPS in the absence or presence of different concentrations of antagonist. BK (30 nmol) is used as a positive control.

Antagonst Time Course

The time course of inhibition by antagonist is determined at 4, 24 and 48 h, 72 and/or 96 h after single bolus administration. BK (30 nmol) is used as a positive control.

Drugs

Ketamine hydrochloride, LPS, amastatin and captopril are from Sigma (MO, U.S.A.). All peptides are from Phoenix Pharmaceuticals (CA, U.S.A.).

Statistics

Values are presented as mean±standard error of the mean (s. e. mean). In edema studies, the pre-injection thickness of the skin folds was subtracted from the values after subcutaneous challenge. Curve fitting and $EC_{50}$ calculations were obtained using the Delta Graph 4.0 software for Apple Computers. Data were compared by two-way analysis of variance followed by unpaired, one tail Student's t-test with Bonferroni correction. P<0.05 was considered statistically significant.

Formulations

Also embraced within this invention is a class of pharmaceutical compositions comprising the active compounds of Formula I–VI in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg or 5 to 1000 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, preferably between about 0.1 and about 50 mg/kg, and more preferably about 0.1 and about 20 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include DMSO and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

All mentioned references, patents, applications and publications, are hereby incorporated by reference in their entirety, as if here written.

What is claimed is:
1. A compound of Formula I'

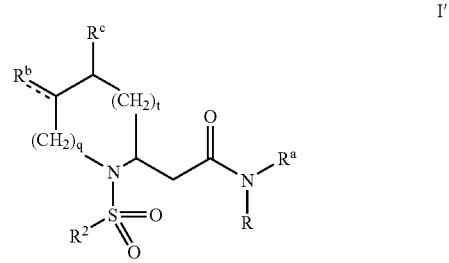

wherein q is 0–3;

wherein t is 0–2, provided that when t is 2, q is not 3;

wherein R is a 9–11 membered fused bicyclic carbocyclic or heterocyclic ring substituted with one to three basic moieties, and optionally substituted with one to three groups independently selected from halo, —$NH_2$, —OH, —CN, —$CF_3$, ($C_1$–$C_6$)alkylamino, oxo, ($C_1$–$C_6$)alkoxy, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, —N$R^8$C(O)$R^{8'}$, and ($C_1$–$C_6$)alkyl, aryl, heteroaryl, cycloalkyl or heterocyclyl, each of which is optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, and —N$R^8$C(O)$R^{8'}$;

wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

wherein $R^2$ is selected from arylalkenyl, aryl, and heterocyclyl selected from thienyl, imidazolyl and benzofused heteroaryl, wherein $R^2$ is optionally substituted with one to five groups independently selected from halo, —$NH_2$, —OH, —CN, —$CF_3$, ($C_1$–$C_6$)alkylamino, oxo, ($C_1$–$C_6$)alkoxy, haloalkoxy, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, —N$R^8$C(O)$R^{8'}$, and ($C_1$–$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, and —N$R^8$C(O)$R^{8'}$;

wherein $R^a$ is independently selected from H and $C_{1-4}$-alkyl, and aryl optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, and —N$R^8$C(O)$R^{8'}$;

wherein each $R^b$ is independently selected from H, hydroxy, benzyloxy and $C_{1-2}$-alkyl, or oxo when ------ is a bond;

wherein $R^c$ is independently selected from H and $C_{1-2}$-alkyl; or wherein $R^b$ and $R^c$ together with the carbon atoms to which they are attached form a 6-membered aryl or heteroaryl ring optionally substituted with one to three groups independently selected from halo, —$NH_2$, —OH, —CN, —$CF_3$, ($C_1$–$C_6$)alkylamino, oxo, ($C_1$–$C_6$)alkoxy, ($C_1$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, —N$R^8$C(O)$R^{8'}$, and ($C_1$–$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, and —N$R^8$C(O)$R^{8'}$;

wherein the one to three basic moieties on R are independently selected from —$NH_2$, cycloalkylamino ($C_1$–$C_6$)alkyl, cycloalkyl($C_1$–$C_6$)alkylamino($C_1$–$C_6$)alkyl,

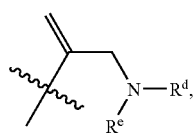

heteroarylamino($C_1$–$C_6$)alkyl, heteroaryl($C_1$–$C_6$)alkylamino($C_1$–$C_6$)alkyl, arylamino($C_1$–$C_6$)alkyl, alkoxyalkylaminoalkyl, hydroxyalkylaminoalkyl, alkenylaminoalkyl, aminocarbonylalkylamino-alkyl, carboxyalkylaminoalkyl, aryl($C_1$–$C_6$)alkylamino ($C_1$–$C_6$)alkyl, $C_{1-6}$-alkylamino-$C_{1-6}$-alkoxy, haloalkylaminoalkyl, amino($C_1$–$C_6$)alkyl, ($C_1$–$C_6$)alkylamino($C_1$–$C_6$)alkyl, 5–8 membered nitrogen-containing heterocyclyl, 5–7 membered nitrogen-containing heterocyclyl-alkylaminoalkyl and 5–8 membered heterocyclyl-alkyl; and wherein each of said basic substituents is optionally substituted with one to three groups independently selected from halo, —$NH_2$, —OH, —CN, —$CF_3$, ($C_1$–$C_6$)alkylamino, oxo, ($C_1$–$C_6$)alkoxy, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, —N$R^8$C(O)$R^{8'}$, and ($C_1$–$C_6$)alkyl, aryl, heteroaryl, cycloalkyl or heterocyclyl, each of which is optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, and —N$R^8$C(O)$R^{8'}$;

and pharmaceutically acceptable derivatives thereof;

provided that the one to three basic moieties on R is not 2-oxo-piperaziny-4-ylmethyl;

further provided wherein $R^b$ and $R^c$ do not form a 6-membered aryl when t is 1 and q is 1;

further provided the basic substituent is not attached to the bicyclic ring via an oxygen atom; provided $R^2$ is not 1-methylimidazol-4-yl.

2. The compound of claim 1 wherein R is a partially unsaturated carbocyclic ring.

3. The compound of claim 2 wherein R is 1,2,3,4-tetrahydronaphthyl.

4. The compound of claim 2 wherein R is indanyl.

5. The compound of claim 2 wherein R is selected from 1,2,3,4-tetrahydronaphth-1-yl, 1,2,3,4-tetrahydronaphth-2-yl, indan-1-yl and indan-2-yl.

6. The compound of claim 1 wherein R is partially unsaturated heterocyclyl.

7. The compound of claim 6 wherein R is chroman.

8. The compound of claim 6 wherein R is 2,2-dioxo-3,4-dihydro-1H-2,1-benzothiazinyl.

9. The compound of claim 1 wherein R is chroman-4-yl, 5,6,7,8-tetrahydro-quinazolin-5-yl, 5,6,7,8-tetrahydro-[1,6]naphthyridin-4-yl or 2,2-dioxo-3,4-dihydro-1H-2,1-benzothiazin-4-yl.

10. The compound of claim 1 wherein q is 1 or 2;

t is 0 or 1;

wherein each $R^2$ is selected from phenyl-CH=CH—, tetrahydronaphthyl, naphtho[2.3-d]dioxolyl, benzofuranyl, benzoxadiazolyl, benzothiadiazolyl, benzothiazolyl, 1H-pyrazolyl, thienyl, isoxazolthienyl, benzothienyl, thieno[3,2-c]pyridinyl, naphthyl, phenyl, pyridinyl, tetrahydroisoquinolinyl, quinolinyl and isoquinolinyl; wherein $R^2$ is optionally substituted with one to five groups independently selected from halo, —$NH_2$, —OH, —CN, —$CF_3$, ($C_1$–$C_6$)alkylamino, oxo, ($C_1$–$C_6$)alkoxy, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, —N$R^8$C(O)$R^{8'}$, and ($C_1$–$C_6$)alkyl, aryl, heteroaryl, cycloalkyl or heterocyclyl, each of which is optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, and —N$R^8$C(O)$R^{8'}$;

wherein $R^a$ is selected from H and $C_{1-2}$-alkyl;

wherein $R^b$ and $R^c$ are H;

and pharmaceutically acceptable derivatives thereof.

11. The compound of claim 1 wherein $R^2$ is selected from phenyl-CH=CH—, tetrahydronaphthyl, naphtho[2.3-d]dioxol-6-yl, 1-benzofur-2-yl, 2,1,3-benzoxadiazol-4-yl, 2,1,3-benzothiadiazol-4-yl, 1,3-benzothiazol-2-yl, 1H-pyrazol-4-yl, thien-2-yl, 5-isoxazolthien-2-yl, benzothien-2-yl, benzothien-3-yl, thieno[3,2-c]pyridin-2-yl, naphthyl, phenyl, 3-pyridyl, tetrahydroisoquinolyl, quinol-8-yl and isoquinolyl; wherein each $R^2$ is said optionally substituted;

wherein $R^a$ is H; and wherein the basic moiety on R is selected from —$NH_2$,

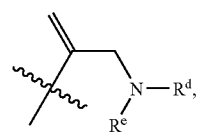

$C_{3-6}$-cycloalkyl($C_1$–$C_2$)alkylamino($C_1$–$C_2$)alkyl, $C_{3-6}$-cycloalkylamino($C_1$–$C_2$)alkyl, ($C_1$–$C_2$)alkoxy (C₁–C₂)alkylamino(C₁–C₂)alkyl, mono-C₂₋₄-alkenylamino-C₁₋₄-alkyl, di-C₂₋₄-alkenylamino-C₁₋₄-alkyl, hydroxy-C₁₋₄-alkylamino-C₁₋₄-alkyl, aminocarbonyl-C₁₋₄-alkylamino-C₁₋₂-alkyl, mono-C₁₋₆-alkylamino-C₁₋₄-alkyl, di-C₁₋₄-alkylamino-C₁₋₄- alkyl and 5–8 membered heterocyclyl-C₁₋₄-alkyl; wherein each is optionally substituted with one to three groups independently selected from halo, —NH₂, —OH, —CN, —CF₃, (C₁–C₆)alkylamino, oxo, (C₁–C₆)alkoxy, (C₂–C₆)alkenyl, (C₂–C₆)alkynyl, di(C₁–C₆)alkylamino, —C(O)R⁸, —COOR⁸, —C(O)NR⁸R⁸′, —NR⁸C(O)R⁸′, and (C₁–C₆)alkyl, aryl, heteroaryl, cycloalkyl or heterocyclyl, each of which is optionally substituted with one to three groups independently selected from halo, —NH₂, —OH, —CN, —CF₃, (C₁–C₆)alkylamino, halo(C₁–C₆)alkyl, oxo, (C₁–C₆)alkoxy, (C₁–C₆)alkoxy(C₁–C₆)alkyl, (C₁–C₆)alkyl, (C₂–C₆)alkenyl, (C₂–C₆)alkynyl, di(C₁–C₆)alkylamino, —C(O)R⁸, —COOR⁸, —C(O)NR⁸R⁸′, and —NR⁸C(O)R⁸′;

wherein $R^d$ is selected from C₁₋₅-alkyl, C₃₋₆-cycloalkyl, C₃₋₆-cycloalkyl-C₁₋₄-alkyl, C₁₋₄-hydroxyalkyl, C₁₋₃-alkoxy-C₁₋₃-alkyl and H; and wherein $R^e$ is H; or where $R^d$ and $R^e$ together with the nitrogen atom to which they are attached form a 4–8 membered nitrogen-containing heterocyclic ring;

and pharmaceutically acceptable derivatives thereof.

12. The compound of claim 1 wherein $R^a$ is H.

13. The compound of claim 1 wherein the basic substituent on R is selected from —NH₂, aminomethyl, aminoethyl, aminopropyl, isopropylaminomethyl, t-butylaminomethyl, iso-butylaminomethyl, 1-methylpropylaminomethyl, 2-methylbutylaminomethyl, 2,2′-dimethylpropylaminomethyl, 2,2′,3-trimethylpropylaminomethyl, allyl-aminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4′-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl.

14. The compound of claim 1 wherein $R^b$ and $R^c$ are joined to form a phenyl ring; and wherein q is 2.

15. A compound of Formula II'

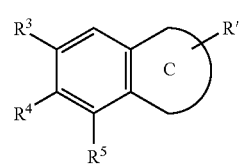

wherein the C ring is a 4- to 7-membered saturated carbocyclic or heterocyclic moiety;

wherein R' is selected from

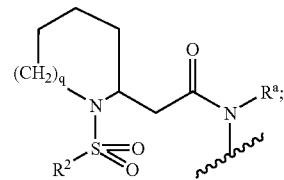

wherein q is 0–3;

wherein $R^2$ is selected from arylalkenyl, aryl, and heterocyclyl selected from thienyl, imidazolyl and benzo-fused heteroaryl, wherein $R^2$ is optionally substituted with one to five groups independently selected from halo, —NH₂, —OH, —CN, —CF₃, (C₁–C₆)alkylamino, oxo, (C₁–C₆)alkoxy, haloalkoxy, (C₂–C₆)alkenyl, (C₂–C₆)alkynyl, di(C₁–C₆)alkylamino, —C(O)R⁸, —COOR⁸, —C(O)NR⁸R⁸′, —NR⁸C(O)R⁸′, and (C₁–C₆)alkyl, aryl, heteroaryl, cycloalkyl and heterocyclyl, each of which is optionally substituted with one to three groups independently selected from halo, —NH₂, —OH, —CN, —CF₃, (C₁–C₆)alkylamino, halo(C₁–C₆)alkyl, oxo, (C₁–C₆)alkoxy, (C₁–C₆)alkoxy(C₁–C₆)alkyl, (C₁–C₆)alkyl, (C₂–C₆)alkenyl, (C₂–C₆)alkynyl, di(C₁–C₆)alkylamino, —C(O)R⁸, —COOR⁸, —C(O)NR⁸R⁸′, and —NR⁸C(O)R⁸′;

wherein $R^a$ is independently selected from H and C₁₋₄-alkyl, or aryl optionally substituted with one to three groups selected from halo, —NH₂, —OH, —CN, —CF₃, (C₁–C₆)alkylamino, halo(C₁–C₆)alkyl, oxo, (C₁–C₆)alkoxy, (C₁–C₆)alkoxy(C₁–C₆)alkyl, (C₁–C₆)alkyl, (C₂–C₆)alkenyl, (C₂–C₆)alkynyl, di(C₁–C₆)alkylamino, —C(O)R⁸, —COOR⁸, —C(O)NR⁸R⁸′, and —NR⁸C(O)R⁸′;

wherein $R^3$, $R^4$ and $R^5$ are the same or different and represent H, halo, —NH₂, —OH, —CN, —CF₃, (C₁–C₆)alkylamino, oxo, (C₁–C₆)alkoxy, (C₂–C₆)alkenyl, (C₂–C₆)alkynyl, di(C₁–C₆)alkylamino, —C(O)R⁸, —COOR⁸, —C(O)NR⁸R⁸′, —NR⁸C(O)R⁸′, a basic moiety, or (C₁–C₂)alkyl, aryl, heteroaryl, cycloalkyl or heterocyclyl, each of which is optionally substituted with one to three groups independently selected from halo, —NH₂, —OH, —CN, —CF₃, (C₁–C₆)alkylamino, halo(C₁–C₆)alkyl, oxo, (C₁–C₆)alkoxy, (C₁–C₆)alkoxy(C₁–C₆)alkyl, (C₁–C₆)alkyl, (C₂–C₆)alkenyl, (C₂–C₆)alkynyl, di(C₁–C₆)alkylamino, —C(O)R⁸, —COOR⁸, —C(O)NR⁸R⁸′, and —NR⁸C(O)R⁸′; and wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

provided at least one of $R^3$, $R^4$ and $R^5$ is a basic moiety selected from —NH$_2$, aminomethyl, aminoethyl, aminopropyl, isopropylaminomethyl, t-butylaminomethyl, iso-butylaminomethyl, 1-methylpropylaminomethyl, 2-methylbutylaminomethyl, 2,2'-dimethylpropylaminomethyl, 2,2', 3-trimethylpropylaminomethyl, allylaminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl;

and pharmaceutically acceptable derivatives thereof.

16. The compound of claim 15 wherein $R^3$ and $R^5$ are H; and wherein $R^4$ is selected from —NH$_2$, aminomethyl, aminoethyl, aminopropyl, isopropylaminomethyl, t-butylaminomethyl, iso-butylaminomethyl, 1-methylpropylaminomethyl, 2-methylbutylaminomethyl, 2,2'-dimethylpropylaminomethyl, 2,2',3-trimethylpropylaminomethyl, allylaminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl;

and pharmaceutically acceptable derivatives thereof.

17. The compound of claim 15 wherein $R^4$ and $R^5$ are H; and wherein $R^3$ is selected from —NH$_2$, aminomethyl, aminoethyl, aminopropyl, isopropylaminomethyl, t-butylaminomethyl, iso-butylaminomethyl, 1-methylpropylaminomethyl, 2-methylbutylaminomethyl, 2,2'-dimethylpropylaminomethyl, 2,2',3-trimethylpropylaminomethyl, allylaminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl;

and pharmaceutically acceptable derivatives thereof.

18. The compound of claim 15 wherein $R^3$ and $R^4$ are H; and wherein $R^5$ is selected from —NH$_2$, aminomethyl, aminoethyl, aminopropyl, isopropylaminomethyl, t-butylaminomethyl, iso-butylaminomethyl, 1-methylpropylaminomethyl, 2-methylbutylaminomethyl, 2,2'-dimethylpropylaminomethyl, 2,2',3-trimethylpropylaminomethyl, allylaminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N- dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl.

19. The compound of claim 15 wherein the C ring is selected from

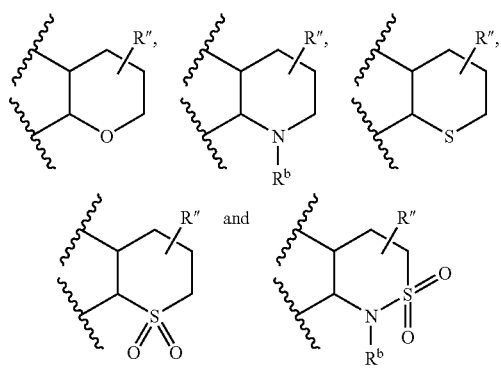

wherein $R^b$ is independently selected from R', H and $C_{1-2}$-alkyl; and wherein R" is R' when $R^b$ is hydrogen or $C_{1-2}$alkyl, or R" is hydrogen when $R^b$ is R'.

20. The compound of claim 19 wherein the C ring is

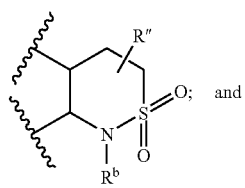

wherein $R^b$ is R'.

21. The compound of claim 15 wherein $R^2$ is selected from phenyl-CH=CH—, tetrahydronaphthyl, naphtho[2.3-d]dioxol-6-yl, 1-benzofuran-2-yl, 2,1,3-benzoxadiazol-4-yl, 2,1,3-benzothiadiazol-4-yl, 1,3-benzothiazol-2-yl, 1H-pyrazol-4-yl, thien-2-yl, 5-isoxazolthien-2-yl, benzothien-2-yl, benzothien-3-yl, thieno[3,2-c]pyridin-2-yl, naphthyl, phenyl, 3-pyridyl, tetrahydroisoquinolinyl, quinolinyl and isoquinolinyl;

wherein each $R^2$ is optionally substituted with one to five groups independently selected from halo, —$NH_2$, —OH, —CN, —$CF_3$, $(C_1-C_6)$alkylamino, oxo, $(C_1-C_6)$alkoxy, $(C_2-C_6)$alkenyl, $(C_2-C_6)$alkynyl, di$(C_1-C_6)$alkylamino, —C(O)$R^8$, —COO$R^8$, —C(O)N$R^8R^{8'}$, —N$R^8$C(O)$R^{8'}$, and $(C_1-C_6)$alkyl, aryl, heteroaryl, cycloalkyl and heterocyclyl, each of which is optionally substituted with one to three groups independently selected from halo, —$NH_2$, —OH, —CN, —$CF_3$, $(C_1-C_6)$alkylamino, halo$(C_1-C_6)$alkyl, oxo, $(C_1-C_6)$alkoxy, $(C_1-C_6)$alkoxy$(C_1-C_6)$alkyl, $(C_1-C_6)$alkyl, $(C_2-C_6)$alkenyl, $(C_2-C_6)$alkynyl, di$(C_1-C_6)$alkylamino, —C(O)$R^8$, —COO$R^8$, —C(O)N$R^8R^{8'}$, or —N$R^8$C(O)$R^{8'}$.

22. The compound of claim 15 wherein $R^2$ is selected from 2-naphthyl, 1-naphthyl, phenyl, 3-chlorophenyl, 4-chlorophenyl, 3,5-dichlorophenyl, 3,4-dichlorophenyl, 2,4,6-trichlorophenyl, 3-fluorophenyl, 3-methoxyphenyl, 4-methoxyphenyl, 3-biphenyl, 4'-chlorophenyl-3-phenyl, 3-methylphenyl, 3-trifluoromethylphenyl, 2-chlorobenzothien-3-yl, and 3-pyridyl; wherein $R^2$ is optionally substituted with one or more groups selected from halo, —$NH_2$, —OH, —$CO_2H$, $(C_1-C_2)$alkylamino, $(C_1-C_2)$alkoxy, $(C_1-C_2)$alkoxy-$(C_1-C_2)$alkyl, $(C_1-C_2)$alkyl, halo$(C_1-C_2)$alkyl, di$(C_1-C_2)$alkylamino, and phenyl.

23. The compound of claim 15 wherein $R^a$ is H.

24. The compound of claim 15 wherein $R^2$ is 2-naphthyl.

25. The compound of claim 15 wherein $R^2$ is 3,4-dichlorophenyl.

26. The compound of claim 15 wherein $R^2$ is 3-trifluoromethylphenyl.

27. The compound of claim 1 and/or pharmaceutically acceptable derivatives thereof selected from N-(7-Piperidin-1-ylmethyl-chroman-4-(R)-yl)-2-[1-(3-trifluoromethyl-benzenesulfonyl)-piperidin-2-yl]-acetamide;

2-[1-(Naphthalene-2-sulfonyl)-piperidin-2-yl]-N-(7-piperidin-1-ylmethyl-chroman-4-(R)-yl)-acetamide; and 2-[1-(Naphthalene-2-sulfonyl)-pyrrolidin-2-(L)-yl]-N-(7-piperidin-1-ylmethyl-chroman-4-(R)-yl)-acetamide.

28. A compound of Formula III'

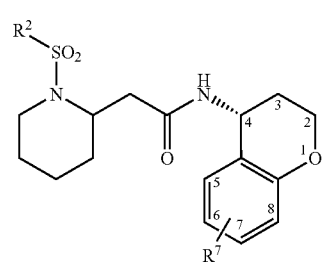

wherein $R^2$ is selected from naphthyl, phenyl, pyridinyl, benzothienyl, quinolinyl and isoquinolinyl, and wherein each is optionally substituted with one to three substituents selected from chloro, fluoro, methoxy, methyl, trifluoromethyl, and phenyl; and wherein R⁷ is selected from

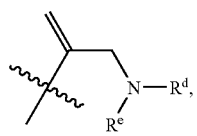

$C_{3-6}$-cycloalkyl($C_1$–$C_2$)alkylamino($C_1$–$C_2$)alkyl, $C_{3-6}$-cycloalkylamino($C_1$–$C_2$)alkyl, ($C_1$–$C_2$)alkoxy($C_1$–$C_2$)alkylamino($C_1$–$C_2$)alkyl, mono-$C_{2-4}$-alkenylamino-$C_{1-4}$-alkyl, di-$C_{2-4}$-alkenylamino-$C_{1-4}$-alkyl, hydroxy-$C_{1-4}$-alkylamino-$C_{1-4}$-alkyl, aminocarbonyl-$C_{1-4}$-alkylamino-$C_{1-2}$-alkyl, mono-$C_{1-6}$-alkylamino-$C_{1-4}$-alkyl, di-$C_{1-4}$-alkylamino-$C_{1-4}$- alkyl and 5–8 membered heterocyclyl-$C_{1-4}$-alkyl; wherein the 5–8 membered heterocyclyl-$(CH_2)_p$-optionally substituted with one to three groups independently selected from halo, —$NH_2$, —OH, —CN, —$CF_3$, ($C_1$–$C_6$)alkylamino, oxo, ($C_1$–$C_6$)alkoxy, ($C_2$–$C_6$)alkenyl, ($C_2$–$C_6$)alkynyl, di($C_1$–$C_6$)alkylamino, —C(O)R⁸, —COOR⁸, —C(O)NR⁸R⁸', —NR⁸C(O)R⁸', =NCN;

wherein R$^d$ is selected from $C_{1-5}$-alkyl, $C_{3-6}$-cycloalkyl, $C_{3-6}$-cycloalkyl-$C_{1-4}$-alkyl, $C_{1-4}$-hydroxyalkyl, $C_{1-3}$-alkoxy-$C_{1-3}$-alkyl and H; and wherein R$^e$ is H; or where R$^d$ and R$^e$ together with the nitrogen atom to which they are attached form a 4–8 membered nitrogen-containing heterocyclic ring;

wherein R⁷ is at position 6, 7 or 8; and wherein R⁸ and R⁸' independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

and pharmaceutically acceptable derivatives thereof.

29. The compound of claim 28 wherein R⁷ is selected from aminomethyl, aminoethyl, aminopropyl, isopropylaminomethyl, t-butylaminomethyl, iso-butylaminomethyl, 1-methylpropylaminomethyl, 2-methylpropylaminomethyl, 2,2'-dimethylpropylaminomethyl, 2,2',3-trimethylpropylaminomethyl, allyl-aminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl;

and pharmaceutically acceptable derivatives thereof.

30. The compound of claim 28 wherein R⁷ is at position 7.

31. The compound of claim 28 wherein R² is 2-naphthyl, 3,4-dichlorophenyl or 3-trifluoromethylphenyl.

32. A compound of Formula IV'

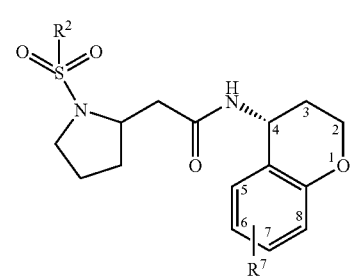

IV' wherein R² is selected from naphthyl, phenyl, pyridinyl, benzothienyl, quinolinyl and isoquinolinyl, and wherein each is optionally substituted with one to three substituents selected from chloro, fluoro, methoxy, methyl, trifluoromethyl, and phenyl; and wherein R⁷ is selected from

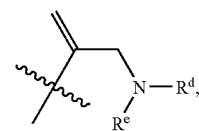

$C_{3-6}$-cycloalkyl($C_1$–$C_2$)alkylamino($C_1$–$C_2$)alkyl, $C_{3-6}$-cycloalkylamino($C_1$–$C_2$)alkyl, ($C_1$–$C_2$)alkoxy($C_1$–$C_2$)alkylamino($C_1$–$C_2$)alkyl, mono-$C_{2-4}$-alkenylamino-$C_{1-4}$-alkyl, di-$C_{2-4}$-alkenylamino-$C_{1-4}$-alkyl, hydroxy-$C_{1-4}$-alkylamino-$C_{1-4}$-alkyl, aminocarbonyl-$C_{1-4}$-alkylamino-$C_{1-2}$-alkyl, mono-$C_{1-6}$-alkylamino-$C_{1-4}$-alkyl, di-$C_{1-4}$-alkylamino-$C_{1-4}$- alkyl and 5–8 membered heterocyclyl-$C_{1-4}$-alkyl; wherein the 5–8 membered heterocyclyl-$(CH_2)_p$— optionally substituted with one to three groups independently selected from halo, —$NH_2$, —OH, —CN, —$CF_3$, ($C_1$–$C_6$)alkylamino, oxo, ($C_1$–$C_6$)alkoxy, ($C_2$–$C_6$)alkenyl, ($C_2$–$C_6$)alkynyl, di($C_1$–$C_6$)alkylamino, —C(O)R⁸, —COOR⁸, —C(O)NR⁸R⁸', —NR⁸C(O)R⁸', =NCN;

wherein R$^d$ is selected from $C_{1-5}$-alkyl, $C_{3-6}$-cycloalkyl, $C_{3-6}$-cycloalkyl-$C_{1-4}$-alkyl, $C_{1-4}$-hydroxyalkyl, $C_{1-3}$-alkoxy-$C_{1-3}$-alkyl and H; and wherein R$^e$ is H; or where R$^d$ and R$^e$ together with the nitrogen atom to which they are attached form a 4–8 membered nitrogen-containing heterocyclic ring;

wherein R⁷ is at position 6, 7 or 8; and wherein R⁸ and R⁸' independently are selected from H, and
lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

and pharmaceutically acceptable derivatives thereof.

33. The compound of claim 32 wherein R⁷ is selected from aminomethyl, aminoethyl, aminopropyl, isopropylaminomethyl, t-butylaminomethyl, iso-butylaminomethyl, 1-methylpropylaminomethyl, 2-methylbutylaminomethyl, 2,2'-dimethylpropylaminomethyl, 2,2',3-trimethylpropylaminomethyl, allyl-aminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl;

and pharmaceutically acceptable derivatives thereof.

34. The compound of claim 32 wherein R is at position 7.

35. The compound of claim 32 wherein R² is 2-naphthyl, 3,4-dichlorophenyl or 3-trifluoromethylphenyl.

36. A compound of Formula V'

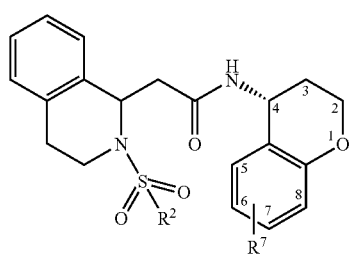

wherein R² is selected from naphthyl, phenyl, pyridinyl, benzothienyl, quinolinyl and isoquinolinyl, and wherein each is optionally substituted with one to three substituents selected from chloro, fluoro, methoxy, methyl, trifluoromethyl, and phenyl; and wherein R⁷ is selected from

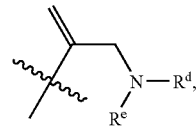

C₃₋₆-cycloalkyl(C₁-C₂)alkylamino(C₁-C₂)alkyl, C₃₋₆-cycloalkylamino(C₁-C₂)alkyl, (C₁-C₂)alkoxy(C₁-C₂)alkylamino(C₁-C₂)alkyl, mono-C₂₋₄-alkenylamino-C₁₋₄-alkyl, di-C₂₋₄-alkenylamino-C₁₋₄-alkyl, hydroxy-C₁₋₄-alkylamino-C₁₋₄-alkyl, aminocarbonyl-C₁₋₄-alkylamino-C₁₋₂-alkyl, mono-C₁₋₆-alkylamino-C₁₋₄-alkyl, di-C₁₋₄-alkylamino-C₁₋₄- alkyl and 5–8 membered heterocyclyl-C₁₋₄-alkyl; wherein the 5–8 membered heterocyclyl-(CH₂)ₚ— optionally substituted with one to three groups independently selected from halo, —NH₂, —OH, —CN, —CF₃, (C₁–C₆)alkylamino, oxo, (C₁–C₆)alkoxy, (C₂–C₆)alkenyl, (C₂–C₆)alkynyl, di(C₁–C₆)alkylamino, —C(O)R⁸, —COOR⁸, —C(O)NR⁸R⁸', —NR⁸C(O)R⁸', =NCN;

wherein R^d is selected from C₁₋₅-alkyl, C₃₋₆-cycloalkyl, C₃₋₆-cycloalkyl-C₁₋₄-alkyl, C₁₋₄-hydroxyalkyl, C₁₋₃-alkoxy-C₁₋₃-alkyl and H; and wherein R^e is H; or where R^d and R^e together with the nitrogen atom to which they are attached form a 4–8 membered nitrogen-containing heterocyclic ring;

wherein R⁷ is at position 6, 7 or 8; and wherein R⁸ and R⁸ independently are selected from H, and
lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

and pharmaceutically acceptable derivatives thereof.

37. The compound of claim 36 wherein R⁷ is selected from aminomethyl, aminoethyl, aminopropyl, isopropylaminomethyl, t-butylaminomethyl, iso-butylaminomethyl, 1-methylpropylaminomethyl, 2-methylbutylaminomethyl, 2,2'-dimethylpropylaminomethyl, 2,2',3-trimethylpropylaminomethyl, allyl-aminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl;

and pharmaceutically acceptable derivatives thereof.

38. The compound of claim 36 wherein R is at position 7.

39. The compound of claim 36 wherein $R^2$ is 2-naphthyl, 3,4-dichlorophenyl or 3-trifluoromethylphenyl.

40. A compound of Formula VI'

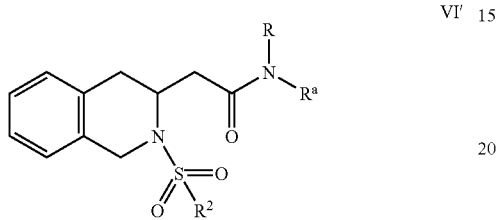

VI' wherein R is a 9–11 membered fused bicyclic carbocyclic or heterocyclic ring substituted with one to three basic moieties, and optionally substituted with one to three groups independently selected from halo, —$NH_2$, —OH, —CN, —$CF_3$, ($C_1$–$C_6$)alkylamino, oxo, ($C_1$–$C_6$)alkoxy, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, —$NR^8$C(O)$R^{8'}$, and ($C_1$–$C_6$)alkyl, aryl, heteroaryl, cycloalkyl or heterocyclyl, each of which is optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, and —$NR^8$C(O)$R^{8'}$;

wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

wherein $R^2$ is selected from arylalkenyl, aryl, and heterocyclyl, wherein $R^2$ is optionally substituted with one to five groups independently selected from halo, —$NH_2$, —OH, —CN, —$CF_3$, ($C_1$–$C_6$)alkylamino, oxo, ($C_1$–$C_6$)alkoxy, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, —$NR^8$C(O)$R^{8'}$, and ($C_1$–$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, and —$NR^8$C(O)$R^{8'}$;

wherein $R^a$ is independently selected from H and $C_{1-4}$-alkyl, and aryl optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, and —$NR^8$C(O)$R^{8'}$; and wherein the one to three basic moieties on R are independently selected from cycloalkylamino $C_{1-6}$-alkyl, cycloalkyl($C_1$–$C_6$)alkylamino $C_{1-6}$-alkyl, heteroarylamino $C_{1-6}$-alkyl, heteroaryl($C_1$–$C_6$)alkylamino $C_{1-6-alkyl}$, arylamino $C_{1-6}$-alkyl, aryl($C_1$–$C_6$)alkylamino $C_{1-6}$alkyl, $C_{1-6}$-alkylamino-$C_{1-6}$-alkoxy, $C_{1-6}$-alkylamino-$C_{1-6}$-alkoxy-$C_{1-6}$-alkoxy, amino $C_{1-6}$-alkoxy, amino $C_{1-6}$-alkyl, alkylamino $C_{1-6}$-alkyl; or 5–6 membered heterocyclyloxy, 5–6 membered nitrogen-containing heterocyclyl or 5–7 membered nitrogen-containing heterocyclyl-$C_{1-6}$-alkyl, each of which is optionally substituted with one to three groups selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$-$C_6$)alkoxyalkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, —$NR^8$C(O)$R^{8'}$, =NCN; or ($C_1$–$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, and —$NR^8$C(O)$R^{8'}$.

41. The compound of claim 40 wherein R is selected from 1,2,3,4-tetrahydronaphth-1-yl, 1,2,3,4-tetrahydronaphth-2-yl, indan-1-yl and indan-2-yl, chroman-4-yl, and 2,2-dioxo-3,4-dihydro-1H-2, 1-benzothiazin-4-yl.

42. The compound of claim 40 $R^a$ is selected from H and ($C_1$–$C_2$)alkyl.

43. A compound of Formula I

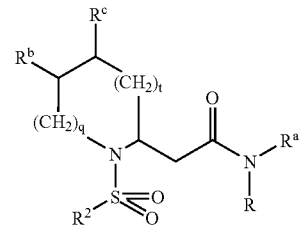

I wherein q is 0–3;

wherein t is 0–2, provided that when t is 2, q is not 3;

wherein R is a 9–11 membered fused bicyclic carbocyclic or heterocyclic ring substituted with one to three basic moieties, and optionally substituted with one to three groups independently selected from halo, —$NH_2$, —OH, —CN, —$CF_3$, ($C_1$–$C_6$)alkylamino, oxo, ($C_1$–$C_6$)alkoxy, ($C_2$–$C_6$)alkenyl, ($C_2$–$C_6$)alkynyl, di($C_1$–$C_6$)alkylamino, —C(O)$R^8$, —COO$R^8$, —C(O)N$R^8R^{8'}$, —$NR^8$C(O)$R^{8'}$, and ($C_1$–$C_6$)alkyl, aryl, heteroaryl, cycloalkyl or heterocyclyl, each of which is optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COOR8, —C(O)$NR^8R^{8'}$, and —$NR^8$C(O)$R^{8'}$;

wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

wherein $R^2$ is selected from arylalkenyl, aryl, and heterocyclyl, wherein $R^2$ is optionally substituted with one to five groups independently selected from halo, —$NH_2$, —OH, —CN, —$CF_3$, ($C_1$–$C_6$)alkylamino, oxo, ($C_1$–$C_6$)alkoxy, ($C_2$–$C_6$)alkenyl, ($C_2$–$C_6$)alkynyl, di($C_1$–$C_6$)alkylamino, —C(O)$R^8$, —COO$R^8$, —C(O)$NR^8R^{8'}$, —$NR^8$C(O)$R^{8'}$, and ($C_1$–$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_3$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)$NR^8R^{8'}$, and —$NR^8$C(O)$R^{8'}$;

wherein $R^a$ is independently selected from H and $C_{1-4}$-alkyl, and aryl optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)$NR^8R^{8'}$, and —$NR^8$C(O)$R^{8'}$;

wherein $R^b$ is independently selected from H and $C_{1-2}$-alkyl; and wherein $R^c$ is independently selected from H and $C_{1-2}$-alkyl; or wherein $R^b$ and $R^c$ may be joined to form a 6-membered aryl or heteroaryl ring optionally substituted with one to three groups independently selected from halo, —$NH_2$, —OH, —CN, —$CF_3$, ($C_1$–$C_6$)alkylamino, oxo, ($C_1$–$C_6$)alkoxy, ($C_1$–$C_6$)alkenyl, ($C_2$–$C_6$)alkynyl, di($C_1$–$C_6$)alkylamino, —C(O)$R^8$, —COO$R^8$, —C(O)$NR^8R^{8'}$, —$NR^8$C(O)$R^{8'}$, and ($C_1$–$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$–$C_6$)alkylamino, halo($C_1$–$C_6$)alkyl, oxo, ($C_1$–$C_6$)alkoxy, ($C_1$–$C_6$)alkoxy($C_1$–$C_6$)alkyl, ($C_1$–$C_6$)alkyl, ($C_2$–$C_6$)alkenyl, ($C_2$–$C_6$)alkynyl, di($C_1$–$C_6$)alkylamino, —C(O)$R^8$, —COO$R^8$, —C(O)$NR^8R^{8'}$, and —$NR^8$C(O)$R^{8'}$;

wherein the one to three basic moieties on R are independently selected from cycloalkylamino $C_{1-6}$-alkyl, cycloalkyl($C_1$–$C_6$)alkylamino $C_{1-6}$-alkyl, heteroarylamino $C_{1-6}$-alkyl, heteroaryl($C_1$–$C_6$)alkylamino $C_{1-6-alkyl,}$ $_{arylamino}$ $_{C1-6}$-alkyl, aryl($C_1$–$C_6$)alkylamino $C_{1-6}$alkyl, $C_{1-6}$-alkylamino-$C_{1-6}$-alkoxy, $C_{1-6}$-alkylamino-$C_{1-6}$-alkoxy-$C_{1-6}$-alkoxy, amino $C_{1-6}$-alkoxy, amino $C_{1-6}$-alkyl, alkylamino $C_{1-6}$-alkyl; or 5–6 membered heterocyclyloxy, 5–6 membered nitrogen-containing heterocyclyl or 5–7 membered nitrogen-containing heterocyclyl-$C_{1-6}$-alkyl, each of which is optionally substituted with one to three groups selected from halo, —$NH_2$, —OH, —CN, —$CF_3$, ($C_1$–$C_6$)alkylamino, halo($C_1$–$C_6$)alkyl, oxo, ($C_1$-$C_6$)alkoxy, ($C_1$-$C_6$)alkoxyalkyl, ($C_2$–$C_6$) alkenyl , ($C_2$–$C_6$)alkynyl, di($C_1$–$C_6$)alkylamino, —C(O)$R^8$, —COO$R^8$, —C(O)$NR^8R^{8'}$, —$NR^8$C(O) $R^{8'}$, =NCN; or ($C_1$–$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$–$C_6$) alkylamino, halo($C_1$–$C_6$)alkyl, oxo, ($C_1$–$C_6$) alkoxy, ($C_1$–$C_6$)alkoxy($C_1$–$C_6$)alkyl, ($C_1$–$C_6$) alkyl, ($C_2$–$C_6$)alkenyl, ($C_2$–$C_6$)alkynyl, di($C_1$–$C_6$) alkylamino, —C(O)$R^8$, —COO$R^8$, —C(O) $NR^8R^{8'}$, and —$NR^8$C(O)$R^{8'}$;

and pharmaceutically acceptable derivatives thereof;

provided the basic moiety is not 2-oxo-piperaziny-4-ylmethyl.

44. The compound of claim 1 and/or pharmaceutically acceptable derivatives thereof selected from N-(7-Piperidin-1-ylmethyl-chroman-4-(R)-yl)-2-[1-(3-trifluoromethyl-benzenesulfonyl)-piperidin-2-yl]-acetamide;

2-(1-(Naphthalene-2-sulfonyl)-piperidin-2-yl]-N-(7-piperidin-1-ylmethyl-chroman-4-(R)-yl)-acetamide;

2-[1-(Naphthalene-2-sulfonyl)-pyrrolidin-2-(L)-yl]-N-(7-piperidin-1-ylmethyl-chroman-4-(R)-yl)-acetamide;

N-((1R)-6-(1-piperidinylmethyl)-1,2,3,4-tetrahydro-1-naphthalenyl)-2-((2S)-1-((3-(trifluoromethyl)phenyl)sulfonyl)-2;

N-((1R)-6-(((1,1-dimethylethyl)amino)methyl)-1,2,3,4-tetrahydro-1-naphthalenyl)-2-((2S)-1-((3-(trifluoromethyl)phenyl)sulfonyl)-2-piperidinyl)acetamide;

N-((1R)-6-(((1,1-dimethylethyl)amino)methyl)-1,2,3,4-tetrahydro-1-naphthalenyl)-2-((2S)-1-((4-methylphenyl)sulfonyl)-2-piperidinyl)acetamide;

2-((2S)-1-((3-chloro-4-methylphenyl)sulfonyl)-2-piperidinyl)-N-((1R)-6-(((1,1-dimethylethyl)amino)methyl)-1,2,3,4-tetrahydro-1-naphthalenyl)acetamide;

2-((2S)-1-((2,4,6-trimethylphenyl)sulfonyl)-2-piperidinyl)-N-((1R)-6-(((1,1-dimethylethyl)amino)methyl)-1,2,3,4-tetrahydro-1-naphthalenyl)acetamide;

N-((1R)-6-(1-piperidinylmethyl)-1,2,3,4-tetrahydro-1-naphthalenyl)-2-((2S)-1-((2,4,6-trimethylphenyl)sulfonyl)-1,2,3,4-tetrahydro-2-quinolinyl)acetamide;

2-((2S)-1-((3,4-dichlorophenyl)sulfonyl)-2-piperidinyl)-N-((1R)-6-(((1,1-dimethylethyl)amino)methyl)-1,2,3,4-tetrahydro-1-naphthalenyl)acetamide;

N-((1R)-6-(1-piperidinyl)methyl)-1,2,3,4-tetrahydro-1-naphthalenyl)-2-((2S)-1-((3-(trifluoromethyl)phenyl)sulfonyl)-2-piperidinyl)acetamide;

N-((1R)-6-((cyclobutylamino)methyl)-1,2,3,4-tetrahydro-1-naphthalenyl)-2-((2S)-1-((3-(trifluoromethyl)phenyl)sulfonyl)-2-piperidinyl)acetamide;

N-methyl-N-((4R)-7-(1-piperidinylmethyl)-3,4-dihydro-2H-chromen-4-yl)-2-((2S)-1-((3-(trifluoromethyl)phenyl)sulfonyl)-2-piperidinyl)acetamide;

N-((1R)-6-(((1,1-dimethylethyl)amino)methyl)-1,2,3,4-tetrahydro-1-naphthalenyl)-2-((2S)-1-((4-(1,1-dimethylethyl)phenyl)sulfonyl)-2-piperidinyl)acetamide;

N-((1R)-6-(((1,1-dimethylethyl)amino)methyl)-1,2,3,4-tetrahydro-1-naphthalenyl)-2-((2S)-1-((4-(1,1-dimethylethyl)phenyl)sulfonyl)-2-piperidinyl)acetamide;

N-((1R)-6-((diethylamino)methyl)-1,2,3,4-tetrahydro-1-naphthalenyl)-2-((2S)-1-((3-(trifluoromethyl)phenyl)sulfonyl)-2-piperidinyl)acetamide;

N-((1R)-6-(((isobutylamino)methyl)-1,2,3,4-tetrahydro-1-naphthalenyl)-2-((2S)-1-((3-(trifluoromethyl)phenyl)sulfonyl)-2-piperidinyl)acetamide;

N-((1R)-6-(((1,1-dimethylethyl)amino)methyl)-1,2,3,4-tetrahydro-1-naphthalenyl)-2-((2S)-1-((4-methyl-3-(trifluoromethyl)phenyl)sulfonyl)-2-piperidinyl)acetamide;

N-((1R)-6-((cyclopropylamino)methyl)-1,2,3,4-tetrahydro-1-naphthalenyl)-2-((2S)-1-((3-(trifluoromethyl)phenyl)sulfonyl)-2-piperidinyl)acetamide;

N-((1R)-6-(((2-methylbutyl)amino)methyl)-1,2,3,4-tetrahydro-1-naphthalenyl)-2-((2S)-1-((3-(trifluoromethyl)phenyl)sulfonyl)-2-piperidinyl)acetamide;

N-((1R)-6-(((2-(methyloxy)ethyl)amino)methyl)-1,2,3,4-tetrahydro-1-naphthalenyl)-2-((2S)-1-((3-(trifluoromethyl)phenyl)sulfonyl)-2-piperidinyl)acetamide;

N-((1R)-6-(((cyclopropylmethyl)amino)methyl)-1,2,3,4-tetrahydro-1-naphthalenyl)-2-((2S)-1-((3-(trifluoromethyl)phenyl)sulfonyl)-2-piperidinyl)acetamide;

N-((1R)-6-(((isopropylmethyl)amino)methyl)-1,2,3,4-tetrahydro-1-naphthalenyl)-2-((2S)-1-((3-(trifluoromethyl)phenyl)sulfonyl)-2-piperidinyl)acetamide;

N-((1R)-6-((4-fluoro-1-piperidinyl)methyl)-1,2,3,4-tetrahydro-1-naphthalenyl)-2-((2S)-1-((3-(trifluoromethyl)phenyl)sulfonyl)-2-piperidinyl)acetamide;

N-((1R)-6-(((1,1-dimethylethyl)amino)methyl)-1,2,3,4-tetrahydro-1-naphthalenyl)-2-((2R/S)-1-((3-(trifluoromethyl)phenyl)sulfonyl)-1,2,3,4-tetrahydro-2-quinolinyl)acetamide;

N-((1R)-6-((4-fluoro-1-piperidinyl)methyl)-1,2,3,4-tetrahydro-1-naphthalenyl)-2-((2R/S)-1-((3-(trifluoromethyl)phenyl)sulfonyl)-1,2,3,4-tetrahydro-2-quinolinyl)acetamide;

N-((1R)-6-(((cyclopropylmethyl)amino)methyl)-1,2,3,4-tetrahydro-1-naphthalenyl)-2-((2R/S)-1-((3-(trifluoromethyl)phenyl)sulfonyl)-1,2,3,4-tetrahydro-2-quinolinyl)acetamide;

N-((1R)-6-(((isopropylmethyl)amino)methyl)-1,2,3,4-tetrahydro-1-naphthalenyl)-2-((2R/S)-1-((3-(trifluoromethyl)phenyl)sulfonyl)-1,2,3,4-tetrahydro-2-quinolinyl)acetamide;

N-((1R)-6-(((isobutylmethyl)amino)methyl)-1,2,3,4-tetrahydro-1-naphthalenyl)-2-((2R/S)-1-((3-(trifluoromethyl)phenyl)sulfonyl)-1,2,3,4-tetrahydro-2-quinolinyl)acetamide;

N-((1R)-6-(((diethylamino)methyl)-1,2,3,4-tetrahydro-1-naphthalenyl)-2-((2R/S)-1-((3-(trifluoromethyl)phenyl)sulfonyl)-1,2,3,4-tetrahydro-2-quinolinyl)acetamide;

N-((1R)-6-((4-fluoro-1-piperidinyl)methyl)-1,2,3,4-tetrahydro-1-naphthalenyl)-2-((2R)-1-((4-methylphenyl)sulfonyl)-1,2,3,4-tetrahydro-2-quinolinyl)acetamide;

2-((2R/S)-1-((4-methylphenyl)sulfonyl)-1,2,3,4-tetrahydro-2-quinolinyl)-N-((1R)-6-(((2-methylpropyl)amino)methyl)-1,2,3,4-tetrahydro-1-naphthalenyl)acetamide;

N-((1R)-6-(((2,2-dimethylpropyl)amino)methyl)-1,2,3,4-tetrahydro-1-naphthalenyl)-2-((2S)-1-((3-(trifluoromethyl)phenyl)sulfonyl)-2-piperidinyl)acetamide;

2-((2S)-1-(1-benzothien-3-ylsulfonyl)-2-piperidinyl)-N-((1R)-6-(((1,1-dimethylethyl)amino)methyl)-1,2,3,4-tetrahydro-1-naphthalenyl)acetamide;

2-((2S)-1-(1-benzothien-3-ylsulfonyl)-2-piperidinyl)-N-((1R)-6-(((2,2-dimethylpropyl)amino)methyl)-1,2,3,4-tetrahydro-1-naphthalenyl)acetamide;

1-(((5R)-5-((((2S)-1-((3-(trifluoromethyl)phenyl)sulfonyl)-2-piperidinyl)acetyl)amino)-5,6,7,8-tetrahydro-2-naphthalenyl)methyl)-3-piperidinecarboxamide;

N-((4R)-7-(4-morpholinylmethyl)-3,4-dihydro-2H-chromen-4-yl)-2-((1S)-2-((3-(trifluoromethyl)phenyl)sulfonyl)-1,2,3,4-tetrahydro-1-isoquinolinyl)acetamide;

N-((4R)-7-(7-azabicyclo[2.2.1]hept-7-ylmethyl)-3,4-dihydro-2H-chromen-4-yl)-2-((1S)-2-((3-(trifluoromethyl)phenyl) sulfonyl)-1,2,3,4-tetrahydro-1-isoquinolinyl)acetamide;

N-((4R)-7-(1-Piperidinylmethyl)-3,4-dihydro-2H-chromen-4-yl)-2-((1R)-2-((3-(trifluoromethyl)phenyl)sulfonyl)-1,2,3,4-tetrahydro-1-isoquinolinyl)acetamide;

N-((4R)-7-((4-Fluoro-1-piperidinyl)methyl)-3,4-dihydro-2H-chromen-4-yl)-2-((2S)-1-((3-(trifluoromethyl)phenyl) sulfonyl)-2-pyrrolidinyl)acetamide;

N-((4R)-7-((4,4-Difluoro-1-piperidinyl)methyl)-3,4-dihydro-2H-chromen-4-yl)-2-((2S)-1-((3-(trifluoromethyl)phenyl) sulfonyl)-2-pyrrolidinyl)acetamide;

2-((2S)-1-(2-Naphthalenylsulfonyl)-2-piperidinyl)-N-((4R)-7-(1-piperidinylmethyl)-3,4-dihydro-2H-chromen-4-yl)acetamide;

N-((4R)-6-chloro-7-(1-piperidinylmethyl)-3,4-dihydro-2H-chromen-4-yl)-2-((2S)-1-((3-(trifluoromethyl)phenyl) sulfonyl)-2-pyrrolidinyl)acetamide;

N-((4R)-7-(1-Piperidinylmethyl)-3,4-dihydro-2H-chromen-4-yl)-2-((3R)-2-((3-(trifluoromethyl)phenyl)sulfonyl)-1,2,3,4-tetrahydro-3-isoquinolinyl)acetamide;

N-((4R)-7-(1-Piperidinylmethyl)-3,4-dihydro-2H-chromen-4-yl)-2-((1S)-2-((3-(trifluoromethyl)phenyl)sulfonyl)-1,2,3,4-tetrahydro-1-isoquinolinyl)acetamide;

N-((4R)-7-(4-Morpholinylmethyl)-3,4-dihydro-2H-chromen-4-yl)-2-((1S)-2-((3-(trifluoromethyl)phenyl)sulfonyl)-1,2,3,4-tetrahydro-1-isoquinolinyl)acetamide;

N-((4R)-7-(7-Azabicyclo(2.2.1]hept-7-ylmethyl)-3,4-dihydro-2H-chromen-4-yl)-2-((1S)-2-((3-(trifluoromethyl)phenyl)sulfonyl)-1,2,3,4-tetrahydro-1-isoquinolinyl)acetamide;

N-((4R)-7-(1-Piperidinylmethyl)-3,4-dihydro-2H-chromen-4-yl)-2-((2S)-1-((3-(trifluoromethyl)phenyl) sulfonyl)-2-piperidinyl)acetamide;

N-((4R)-7-(1-Piperidinylmethyl)-3,4-dihydro-2H-chromen-4-yl)-2-((2R)-1-((3-(trifluoromethyl)phenyl) sulfonyl)-2-piperidinyl)acetamide;

N-((1R)-6-((1S)-1-methyl-2-(1-piperidinyl)ethyl)-1,2,3,4-tetrahydro-1-naphthalenyl)-2-((2S)-1-((3-(trifluoromethyl)phenyl)sulfonyl)-2-piperidinyl)acetamide; and N-((1R)-6-(1-(1-piperidinylmethyl)ethenyl)-1,2,3,4-tetrahydro-1-naphthalenyl)-2-((2S)-1-((3-(trifluoromethyl)phenyl)sulfonyl)-2-piperidinyl)acetamide.

45. A pharmaceutically acceptable salt of a compound of claim 1.

46. A pharmaceutical composition comprising a pharmaceutically acceptable carrier and a compound of claim 1.

47. A method of treating pain comprising administering an effective amount of a compound of claim 1.

48. A pharmaceutical formulation comprising a compound according to claim 1, a pharmaceutically acceptable carrier and, optionally, one or more other pharmacologically active ingredients.

* * * * *